(12) United States Patent
Doerner Barbour et al.

(10) Patent No.: US 12,303,509 B2
(45) Date of Patent: *May 20, 2025

(54) COMPOUNDS FOR THE TREATMENT OF BRAF-ASSOCIATED DISEASES AND DISORDERS

(71) Applicant: Pfizer Inc., New York, NY (US)

(72) Inventors: Patrick Michael Doerner Barbour, Westminster, CO (US); Tanna Marie Bettendorf, Boulder, CO (US); Dean Russell Kahn, Longmont, CO (US); Alex Andrew Kellum, Boulder, CO (US); Ellen Ruth Laird, Longmont, CO (US); David Austin Moreno, Centennial, CO (US); Li Ren, Superior, CO (US)

(73) Assignee: Pfizer Inc., New York, NY (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/338,767

(22) Filed: Jun. 4, 2021

(65) Prior Publication Data

US 2022/0288074 A1 Sep. 15, 2022

Related U.S. Application Data

(60) Provisional application No. 63/175,655, filed on Apr. 16, 2021, provisional application No. 63/116,204, (Continued)

(51) Int. Cl.
*A61K 31/517* (2006.01)
*A61K 31/4184* (2006.01)
(Continued)

(52) U.S. Cl.
CPC ........ *A61K 31/517* (2013.01); *A61K 31/4184* (2013.01); *A61K 31/5377* (2013.01); (Continued)

(58) Field of Classification Search
CPC .............. A61K 31/517; A61K 31/4184; A61K 31/5377; A61K 39/395; A61K 45/06;
(Continued)

(56) References Cited

FOREIGN PATENT DOCUMENTS

| RU | 2678455 | 6/2018 |
|---|---|---|
| WO | 2006/024834 | 3/2006 |

(Continued)

OTHER PUBLICATIONS

Kuske, M., et al (2018) Melanoma Brain Metastases: Local therapies, targeted therapies, immune checkpoint inhibitors and their combinations- chances and challenges Am. J. Clin Dermatol 19; 529-541 (Year: 2018).*

(Continued)

*Primary Examiner* — Scarlett Y Goon
*Assistant Examiner* — Audry L Buttice
(74) *Attorney, Agent, or Firm* — Corey M. Williams

(57) ABSTRACT

Provided herein is a compound of the Formula I:

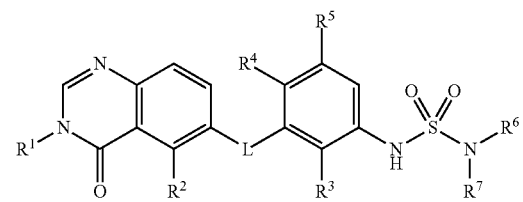

or a pharmaceutically acceptable salt thereof, wherein $R^1$, $R^2$, $R^3$, $R^4$, $R^5$, $R^6$, $R^7$ and L are as defined herein, for the (Continued)

treatment of BRAF-associated diseases and disorders, including BRAF-associated tumors.

16 Claims, 1 Drawing Sheet

Related U.S. Application Data filed on Nov. 20, 2020, provisional application No. 63/036,522, filed on Jun. 9, 2020.

(51) Int. Cl.

| | | |
|---|---|---|
| *A61K 31/5377* | (2006.01) | |
| *A61K 39/395* | (2006.01) | |
| *A61K 45/06* | (2006.01) | |
| *C07D 239/90* | (2006.01) | |
| *C07D 401/12* | (2006.01) | |
| *C07D 403/12* | (2006.01) | |
| *C07D 405/12* | (2006.01) | |
| *C07D 471/08* | (2006.01) | |
| *C07D 487/08* | (2006.01) | |

(52) U.S. Cl.
CPC .......... *A61K 39/3955* (2013.01); *A61K 45/06* (2013.01); *C07D 239/90* (2013.01); *C07D 401/12* (2013.01); *C07D 403/12* (2013.01); *C07D 405/12* (2013.01); *C07D 471/08* (2013.01); *C07D 487/08* (2013.01)

(58) Field of Classification Search
CPC .. C07D 239/90; C07D 401/12; C07D 403/12; C07D 405/12; C07D 471/08; C07D 487/08; A61P 35/00
See application file for complete search history.

(56) References Cited

FOREIGN PATENT DOCUMENTS

| | | |
|---|---|---|
| WO | 2007/113557 | 10/2007 |
| WO | 2007/113558 | 10/2007 |
| WO | 2007/119055 | 10/2007 |
| WO | 2008079903 | 7/2008 |
| WO | 2009/012283 | 1/2009 |
| WO | 2010/010154 | 1/2010 |
| WO | 2011/025927 | 3/2011 |
| WO | 2012/118492 | 9/2012 |
| WO | 2013/070996 | 5/2013 |
| WO | 2019/060611 | 3/2019 |
| WO | 2020/261156 | 12/2020 |
| WO | 2021/116050 A1 | 6/2021 |
| WO | 2021/116055 | 6/2021 |
| WO | 2021/116050 | 7/2021 |

OTHER PUBLICATIONS

Sun, J., et al. (2018) Encorafenib/binimetinib for the treatment of BRAF-mutant advanced, unresectable, or metastatic melanoma: design, development, and potential place in therapy OncoTargets and Therapy 11; 9081-9089 (Year: 2018).*
Peng, S.B., et al (2015) Inhibition of RAF isoforms and active dimers by LY3009120 leads to anti-tumor activities in RAS or BRAF mutant cancers Cancer Cell 28; 384-398 (Year: 2015).*
Choi, et al, "The First Small Molecules Capable of Strongly Suppressing Proliferation of Cancer Cells Harboring BRAF Class I/II/III Mutations" Biochemical and Biophysical Research Communications, 532:315-320 (2020).
Wenglowsky, et al, "Highly Potent and Selective 3-N-methylquinazoline-4(3H)-one base inhibitors of B-Raf V600E Kinase", Bioorganic & Medicinal Chemistry Letters, 24:1923-1927 (2014).
Achrol A.S., et al., Brain metastases, Nature Reviews (2019), 5:5, pp. 1-26.
Behling, F., et al., Frequency of BRAF V600E mutations in 969 central nervous system neoplasms, Diagnostic Pathol 11(1):55, 2016.
Berghoff, AS, Preusser M., Braf alterations in brain tumours: molecular pathology and therapeutic opportunities, Curr Opin Neurol (2014) 27(6):689-696.
Brastianos et al., Exome sequencing identifies BRAF mutations in papillary craniopharyngiomas, Nat Genet 46 (2):161-165, 2014.
Brummer T. and McInnes C., RAF kinase dimerization: implications for drug discovery and clinical outcomes, Oncogene, (2020), 39, pp. 4155 4169 (2020).
Cerami, E., et al., The cBio Cancer Genomics Portal: an Open Platform for Exploring Multidimensional Cancer Genomics Data, Cancer Discov. 2012, 2, 401-404.
Dagogo-Jack, I., et al., Impact of BRAF Mutation Class on Disease Characteristics and Clinical Outcomes in BRAF-Mutant Lung Cancer, Clin Cancer Res. 2018.
Dahlman KB, et al., BRAFL597 Mutations in Melanoma Are Associated with Sensitivity to MEK Inhibitors, Cancer Discov. 2012;2:791-797.
Dankner, et al., Dual MAPK Inhibition Is an Effective Therapeutic Strategy for a Subset of Class II BRAF Mutant Melanomas, Clin. Cancer Research, 2018.
Davies H., et al., Mutations of the BRAF gene in human cancer, Nature 417(6892):949-954, 2002.
Dougherty, M.J., et al., Activating mutations in BRAF characterize a spectrum of pediatric low-grade gliomas, Neuro Oncol, 12(7):621-630, 2010.
Flaherty KT, et al., From genes to drugs: targeted strategies for melanoma, Nat Rev Cancer (2012) 12(5):349-361.
Grisham, R.N., et al., BRAF Mutation is Associated with Early Stage Disease and Improved Outcome in Patients with Low-Grade Serous Ovarian Cancer, Cancer, 2013; 119(3): 548-554.
Johnson, B. E., et al., Mutational Analysis Reveals the Origin and Therapy-driven Evolution of Recurrent Glioma, Science, 343(6167): 189-193 (2014).
Jones JC, et al. Non-V600 BRAF Mutations Define a Clinically Distinct Molecular Subtype of Metastatic Colorectal Cancer, J Clin Oncol. 2017;35:2624-2630.
Kaley, et al., BRAF Inhibition in BRAFV600-Mutant Gliomas: Results From the VE-BASKET Study, J Clin Oncol, vol. 36, No. 35, 2018.
Karoulia, Z, et al., New Perspectives for targeting RAFkinase in human cancer, Nature 17, 676-691 (2017).
Kim, WW et al., Clinical implications of the BRAF mutation in papillary thyroid carcinoma and chronic lymphocytic thyroiditis, J Otolaryngol Head Neck Surg. 2018; 47:4, 1-6.
Lehman, N.L., et al., Morphological and molecular features of astroblastoma, including BRAFV600E mutations, suggest an ontological relationship to other cortical-based gliomas of children and young adults, Neuro Oncol 19 (1):31-42, 2017.
Menzer, C., Non-V600 Clinical Responses to BRAF and or MEK Inhibitors, J. Clin Oncol 2019, 37(33):3142-3151.
Mittapalli, RK, et al., Mechanisms Limiting Distribution of the Threonine-Protein Kinase B-RaFV600E Inhibitor Dabrafenib to the Brain: Implications for the Treatment of Melanoma Brain MetastasessJ Pharmacol. Exp Ther 344:655-664, Mar. 2013.
Mittapalli, RK. et al., Impact of P-Glycoprotein (ABCB1) and Breast Cancer Resistance Protein (ABCG2) on the Brain Distribution of a Novel BRAF Inhibitor: Vemurafenib (PLX4032)J Pharmacol. Exp Ther 342:33-40, Mar. 2012.
Mordechai, O., et al., Metastatic Rhabdoid Meningioma with BRAF V600E Mutation and Good Response to Personalized Therapy: Case Report and Review of the LiteraturePediatr Hematol Oncol 32(3):207-211, 2015.
Myung et al., Analysis of the BRAF V600E Mutation in Central Nervous System Tumors1Transl Oncol 5(6):430-436, 2012.
Oliva I.C.G, et al., Advances in the systemic treatment of melanoma brain metastases, Annals of Oncology, 29: 1509-1520 (2018).

(56) References Cited

OTHER PUBLICATIONS

Paik PK, et al. Clinical characteristics of patients with lung adenocarcinomas harboring BRAF mutations, J Clin Oncol. 2011;29:2046-2051.
Poulikakos et al., RAF inhibitor resistance is mediated by dimerization of aberrantly spliced BRAF(V600E), Nature, 480 (7377):387-390 (2012).
Ross, J.S et al., The distribution of BRAF gene fusions in solid tumors and response to targeted therapy, Int. J. Cancer: 138, 881-890 (2016).
Schindler, G., et al., Analysis of BRAF V600E mutation in 1,320 nervous system tumors reveals high mutation frequencies in pleomorphic xanthoastrocytoma, ganglioglioma and extra-cerebellar pilocytic astrocytoma, Acta Neuropathol 121(3):397-405, 2011.
Schirripa, M., Class 1, 2, and 3 BRAF-mutated Metastatic Colorectal Caner: A Detailed clinical, Pathologic, and Molecular Characterization, Clin Cancer Res., May 2019.
Schreck, et al. BRAF Mutations and the Utility of RAF and MEK Inhibitors in Primary Brain Tumors, Cancers 2019, 11, 1262.
Siroy AE, et al., Beyond BRAF(V600): clinical mutation panel testing by next-generation sequencing in advanced melanoma, J Invest Dermatol. 2015;135:508-515.
Sullivan, R.J., First-in-Class ERK1/2 Inhibitor Ulixertinib (BVD-523) in Patients with MAPK Mutant Advanced solid tumors: results of a Phase I Dose-Escalation and Expansion Study, Cancer Discov Feb. 1, 2018 (8) (2) 184-195.
Sullivan, R.J., Flaherty, K.T., Resistance to BRAF-targeted therapy in melanoma, European Journal of cancer (2013) 49, 1297-1304.
Vido, MJ, et al., BRAF splice variant resistance to RAF inhibitor requires enhanced MEK association, Cell Reports, 25, 1501-1510, 2018.
Wenglowsky, et al., Highly potent and selective 3-N-methylquinazoline-4(3H)-one based inhibitors of B-Raf V600E Kinase, Bioorg Med Chem Lett, 1923-1927, 2014.
Yao, A., et al., BRAF Mutants evade ERK-dependent Feedback by Different Mechanisms that Determine Their sensitivity to Pharmacologic Inhibition, Cancer Cell 28, 370-383, 2015.
Yao, Z., et al., Tumours with class 3 BRAF mutants are sensitive to the inhibition of activated RAS, Nature, vol. 548, 234-248, 2017.
Zhang, C., et al., RAF inhibitors that evade paradoxical MAPK pathway activation, Nature, vol. 526, 583-598, 2015.
International Searching Authority, Search Report mailing date Jul. 22, 2021, PCT/IB2021/054919 Filing date Jun. 4, 2021, Array BioPharma Inc.
El-Husseiny, Walaa M., et al. Synthesis, antitumor activity, and molecular docking study of 2-cyclopentyloxyamsole derivatives: mechanistic study of enzyme inhibition. J Enzyme Inhib Med Chem, 2020; 35(1): 744-758.
Freeman, Burgess B., et al. "Practical approaches to evaluating and optimizing brain exposure in early drug discovery." European Journal of Medicinal Chemistry. 182 (2019) 111643.
Johannessen, Cory M., et al. "COT/MAP3K8 drives resistance to RAF inhibition through MAP kinase pathway reactivation." Nature. Dec. 16, 2010; 468(7326): 968-972 (doi: 10.1038/nature09627).
Summerfield, Scott G., et al. "Free Drug Theory—No Longer Just a Hypothesis?" Pharm. Res. (2022), 39(2), p. 213-222.
Yaeger, Rona, et al. "A next-generation BRAF inhibitor overcomes resistance to BRAF inhibition in patients with BRAF mutant cancers using pharmacokinetics-informed dose escalation." Cancer Discov. (Apr. 30, 2024); DOI: 10.1158/2159-8290.CD-24-0024.

* cited by examiner

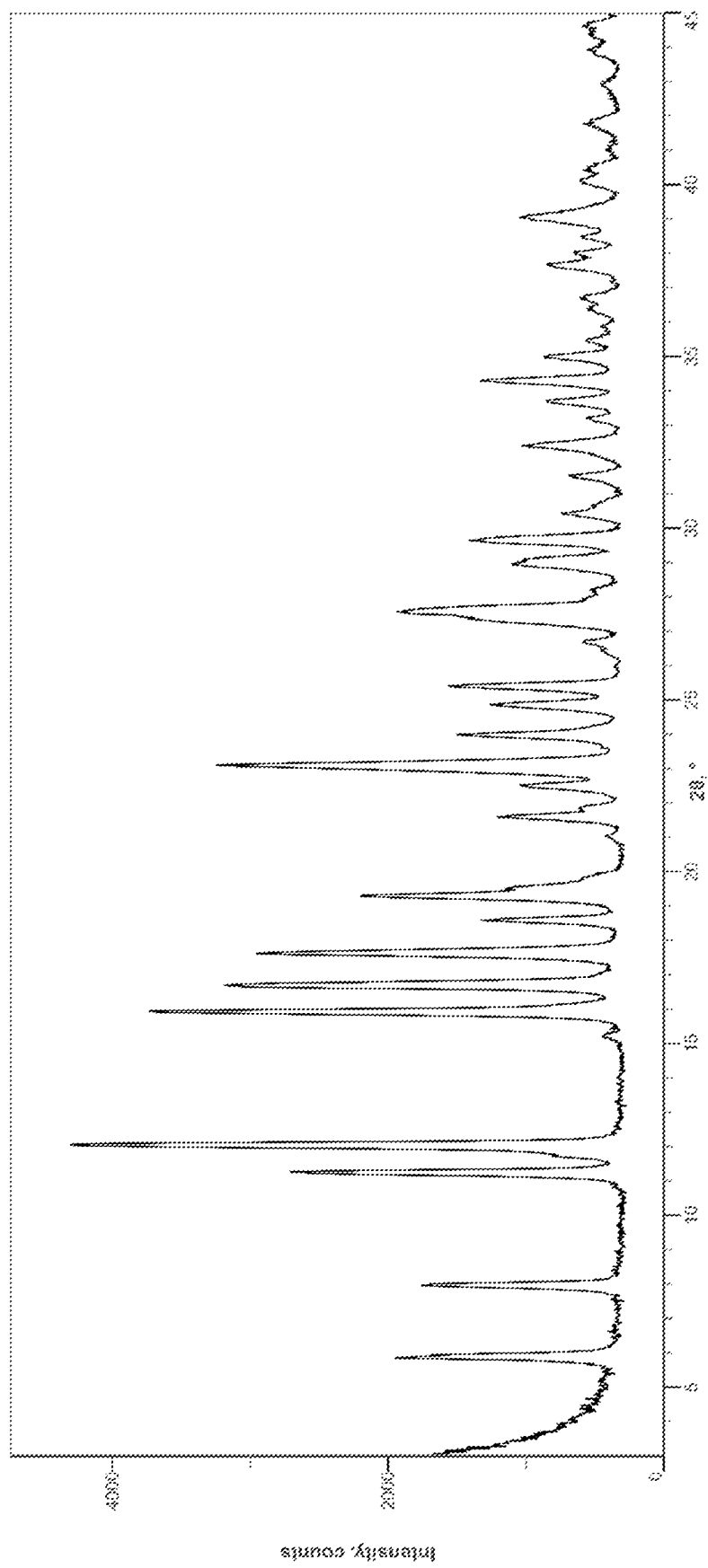

COMPOUNDS FOR THE TREATMENT OF BRAF-ASSOCIATED DISEASES AND DISORDERS

CROSS REFERENCE TO RELATED APPLICATIONS

This application claims priority to U.S. Provisional Application Ser. No. 63/036,522 filed Jun. 9, 2020, and to U.S. Provisional Application Ser. No. 63/116,204 filed Nov. 20, 2020, and to U.S. Provisional Application Ser. No. 63/175,655 filed Apr. 16, 2021, each of which is incorporated herein by reference in its entirety.

FIELD OF THE INVENTION

This disclosure relates to novel quinazolinone compounds or a pharmaceutically acceptable salt thereof, to pharmaceutical compositions comprising such compounds and salts, and to methods of using such compounds, salts, and compositions for the treatment of abnormal cell growth, including cancer, in a subject.

BACKGROUND

The present disclosure relates to quinazolinones for the treatment of BRAF-associated diseases and disorders, including BRAF-associated tumors, including malignant and benign BRAF-associated tumors of the CNS and malignant extracranial BRAF-associated tumors.

BRAF protein, a member of the RAF family of serine/threonine kinases, participates in the cascade of the Ras-Raf-MEK-extracellular signal-regulated kinase (ERK) pathway or mitogen-activated protein kinase (MAPK)/ERK signaling pathway that affects cell division and differentiation. Mutations in the BRAF gene can lead to uncontrolled growth and subsequent tumor formation. Over 100 unique mutations in the BRAF gene have been identified in cancer (Cerami, E., et al., *Cancer Discov.* 2012, 2, 401-404). These mutations lead to ERK activation via different functional mechanisms, and have been grouped into three classes, two of which are referred to as Class I and Class II mutations, based on their dependence on dimerization and on activation by RAS for activity; these properties determine their sensitivity to RAF inhibitors (Yao, A., et al., *Cancer Cell* 2015, 28, 370-383).

Activating Class I BRAF mutations such as V600E and/or V600K have been found human cancers such as melanoma, colorectal cancer, thyroid cancer, non-small cell lung cancer, ovarian cancer, renal cell carcinoma and metastatic cancers thereof, and primary brain tumors. Class I mutations such as BRAF V600 mutants signal as RAS independent active monomers.

Class II BRAF mutations include non-V600 mutations, which activate MEK through dimerization but without a requirement for RAS (Yao, A., et al., *Cancer Cell* 2015, 28, 370-383). These Class II mutations undergo constitutive, RAS-independent dimerization, leading to increased ERK activation with low RAS activity due to negative feedback. Common Class II point mutations include G469A/V/R, K601E/N/T, and L597Q/V. Non-V600 mutants are resistant to Class I BRAF inhibitors such as vemurafenib. Non-V600 BRAF mutants have also been found in many cancers and are more prevalent than V600 mutations in certain tumor types. Non-V600 BRAF mutations are found in 5-16% of melanomas, as well as a variety of other tumor types (Siroy A E, et al., *J Invest Dermatol.* 2015; 135:508-515; Dahlman K B, et al. *Cancer Discov.* 2012; 2:791-797). Approximately 50-80% of BRAF mutations in non-small cell lung cancer and 22-30% in colorectal cancer encode for non-V600 mutations. (Jones J C, et al. *J Clin Oncol.* 2017; 35:2624-2630; Paik P K, et al. *J Clin Oncol.* 2011; 29:2046-2051). Class II BRAF mutations such as G469A, G469R, G469V, K601E, K601N, K601T, L597Q and L597V have been identified in gliomas (Schreck, K. C. et al., *Cancers* (2019) 11:1262) and other tumors such as breast cancer, small cell lung cancer, pancreatic cancer, thyroid cancer, prostate cancer, adenoid cystic carcinoma, appendiceal cancer, small intestine cancer, head and neck squamous cell carcinoma and angiosarcoma (Sullivan, R. J., *Cancer Discov* Feb. 1, 2018 (8) (2) 184-195). Class II BRAF mutations have also been identified in metastatic cancers (Dagogo-Jack, I., *Clin Cancer Res.* September 2018; Schirripa, M., *Clin Cancer Res.*, May 2019; Menzer, C., *J. Clin Oncol* 2019, 37(33): 3142-3151).

Additionally, BRAF in-frame deletions can function as Class II mutations. For example, acquired resistance has been observed in patients treated with BRAF V600 inhibitors. Mechanisms of acquired resistance include alternated splicing. Splice variants of BRAF encode an active kinase, but lack an intact RAS binding domain. Cells resistant to vemurafenib have been found to express variant forms of BRAF V600E that lack exons that encompass the RAS-binding domain, specifically, lacking exons 4-10, exons 4-8, exons 2-8 or exons 2-10 (Poulikakos, P. I, et al., *Nature,* 480(7377):387-390.

Currently, no effective targeted treatments are available for patients harboring non-V600 BRAF alterations or BRAF inhibitor resistance mutations.

Although certain inhibitors of BRAF V600 mutations produce excellent extracranial responses, a cancer may still develop brain metastases during, or subsequent to, therapy with BRAF inhibitors (Oliva I. C. G, et al., *Annals of Oncology,* 29: 1509-1520 (2018)). An estimated 20% of all subjects with cancer will develop brain metastases, with the majority of brain metastases occurring in those with melanoma, colorectal cancer, lung cancer, and renal cell carcinoma (Achrol A. S., et al., *Nature Reviews* (2019), 5:5, pp 1-26). Although these are the most likely types to do so, any type of cancer could spread to the brain. Development of brain metastases remains a substantial contributor to overall cancer mortality in subjects with advance-stage cancer because prognosis remains poor despite multimodal treatments and advances in systemic therapies, which includes combinations of surgery, radiotherapy, chemotherapy, immunotherapy, and/or targeted therapies.

BRAF has also been identified as a potential target for treating primary brain tumors. The prevalence of the BRAF-V600E mutation in primary brain tumors has been reported by Schindler et al. (*Acta Neuropathol* 121(3):397-405, 2011) from the analysis of 1,320 central nervous system (CNS) tumors and by Behling et al. (*Diagn Pathol* 11(1):55, 2016), who analyzed 969 CNS tumors in pediatric and adult populations. These studies, in combination with others, report the presence of BRAF-V600E mutations in various cancers, including papillary craniopharyngiomas, pleomorphic xanthoastrocytomas (PXAs), gangliogliomas, astroblastomas, and others. (Behling et al., *Diagn Pathol* 11(1): 55, 2016; Brastianos et al., *Nat Genet* 46(2):161-165, 2014; Dougherty et al., *Neuro Oncol* 12(7):621-630, 2010; Leh man et al., *Neuro Oncol* 19(1):31-42, 2017; Mordechai et al., *Pediatr Hematol Oncol* 32(3):207-211, 2015; Myung et al., *Transl Oncol* 5(6):430-436, 2012; Schindler et al., *Acta Neuropathol* 121(3):397-405, 2011).

Cancers, including metastatic cancers, having BRAF-fusion proteins have also been described (J. S. Ross, et al., *Int. J. Cancer:* 138, 881-890 (2016)).

Blood-brain interfaces comprise the cerebral microvessel endothelium forming the blood-brain barrier (BBB) and the epithelium of the choroid plexuses forming the blood-CSF barrier (BCSFB). The blood brain barrier (BBB) is a highly selective physical, transport and metabolic barrier that divides the CNS from the blood. The BBB may prevent certain drugs from entering brain tissue and is a limiting factor in the delivery of many peripherally-administered agents to the CNS. Many drugs commonly used to treat cancer are not able to cross the BBB. This means the drugs are not able to penetrate the brain, and therefore cannot effectively kill cancer cells in the brain. Current treatments for subjects with brain tumors include surgical resection, radiotherapy, and/or chemotherapy with agents such as temozolomide and/or bevacizumab. However, treatment of brain cancers by surgery is not always possible or desirable, for example, the tumor may be inaccessible, or the subject may be incapable of withstanding the trauma of neurosurgery. In addition, radiotherapy and treatment with cytotoxic agents are known to have undesirable side effects. For example, there is increasing evidence that the use of temozolomide may itself induce mutations and worsen prognosis in a significant fraction of subjects (B. E. Johnson et al., *Science* 343: 189-193 (2014)), and bevacizumab labeling has boxed warnings for gastrointestinal perforation, surgery and wound healing complications, and hemorrhage. Kinase inhibitors are useful for treating many peripheral cancers. However, due to their structural characteristics, many kinase inhibitors such as BRAF inhibitors (e.g., vemurafenib and dabrafenib) are substrates of active transporters such as P-glycoproteins (P-gp) or breast cancer resistance protein (BCRP). For example, dabrafenib has been reported to have an MDR1 efflux ratio of 11.4, a BCRP efflux ratio of 21.0, and a total brain-to-plasma ratio of 0.023; a free brain-to-plasma ratio was not reported (Mittapalli, R K, et al., *J Pharmacol. Exp Ther* 344:655-664, March 2013), and vemurafenib has been reported to have an MDR1 efflux ratio of 83, a BCRP efflux ratio of 495, and a total brain-to-plasma ratio of 0.004; a free brain-to-plasma ratio was not reported (Mittapalli, R K. et al., *J Pharmacol. Exp Ther* 342:33-40 (March 2012).

Given that both P-gp and BCRP are expressed in the endothelial cells lining the blood brain capillaries, the activity of both P-gp and BCRP in the BBB play a critical role in preventing the distribution of most kinase inhibitors to the brain parenchyma. Therefore, kinase inhibitors are not generally suitable to be used for the treatment of tumors or cancers in the brain, which is protected by the BBB.

Thus, there remains a need for treatment of tumors bearing BRAF mutations, including Class I and Class II mutations, including resistance mutations. In addition, treatments for CNS tumors, including CNS tumors bearing BRAF mutations, including resistance mutations, remain an unmet need.

SUMMARY OF THE INVENTION

Accordingly, provided herein is a compound of the Formula I:

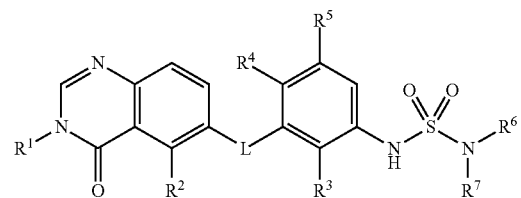

or a pharmaceutically acceptable salt thereof, wherein:

L is NH or O;

$R^1$ is C1-C6 alkyl, C1-C6 deuteroalkyl, C1-C6 fluoroalkyl, C3-C6 cycloalkyl, (C3-C6 cycloalkyl)$CH_2$—, (C1-C6 alkoxy)C1-C6 alkyl-, $Ar^1$, $Ar^1CH_2$—, $hetAr^1$ or $hetCyc^1$;

$Ar^1$ is phenyl which is optionally substituted with 1, 2, 3, 4 or 5 substituents independently selected from halogen and C1-C3 alkyl;

$hetAr^1$ is a 5-6 membered heteroaryl ring having 1 or 2 ring nitrogen atoms and which is optionally substituted with 1, 2 or 3 substituents independently selected from halogen and C1-C3 alkyl;

$hetCyc^1$ is a 4-6 membered saturated monocyclic heterocyclic ring having a ring oxygen atom;

$R^2$ is —$CH_3$, —$CH_2CH_3$, —CH=$CH_2$, F, Cl, Br or CN;

$R^3$ is F or Cl;

$R^4$ is H or F;

$R^5$ is H, F or Cl;

$R^6$ is C1-C6 alkyl, and $R^7$ is C1-C6 alkyl, $hetCyc^2$ or C3-C6 cycloalkyl, or $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —$OCH_3$, —$OCHF_2$, —$OCD_3$, —$CH_3$, —$CH_2CH_3$, —$CH_2OCH_3$, —$CH_2OCH_2F$, —$CH_2OCHF_2$, —$CH_2OCF_3$, —$OCF_3$, —$OCH_2CH_3$, and CN, (ii) a 6-7 membered fused bicyclic ring optionally substituted with 1 or 2 substituents independently selected from F and —$CH_3$, (iii) a 6-7 membered bridged ring, and (iv) a 6-8-membered spirocyclic ring; and $hetCyc^2$ is a 5-6 membered saturated monocyclic heterocyclic ring having 1 or 2 ring heteroatoms independently selected from N and O;

provided that the compound is not:

N-(2-chloro-3-((3,5-dimethyl-4-oxo-3,4-dihydroquinazolin-6-yl)amino)-4-fluorophenyl)pyrrolidine-1-sulfonamide, (R)-N-(2-chloro-3-((3,5-dimethyl-4-oxo-3,4-dihydroquinazolin-6-yl)amino)-4-fluorophenyl)-3-fluoropyrrolidine-1-sulfonamide, or N-(2-chloro-3-((3,5-dimethyl-4-oxo-3,4-dihydroquinazolin-6-yl)amino)-4-fluorophenyl)-N-ethyl-N-methylamino-1-sulfonamide.

Also provided herein is a compound of Formula I-A

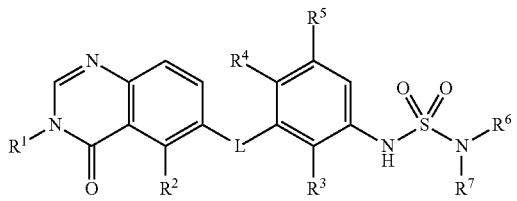

or a pharmaceutically acceptable salt thereof, wherein:
L is NH or O;
R¹ is C1-C6 alkyl, C1-C6 deuteroalkyl, C1-C6 fluoroalkyl, C3-C6 cycloalkyl, (C3-C6 cycloalkyl)CH₂—, (C1-C6 alkoxy)C1-C6 alkyl-, Ar¹, Ar¹CH₂—, hetAr¹ or hetCyc¹;
Ar¹ is phenyl which is optionally substituted with 1, 2, 3, 4 or 5 substituents independently selected from halogen and C1-C3 alkyl;
hetAr¹ is a 5-6 membered heteroaryl ring having 1 or 2 ring nitrogen atoms and which is optionally substituted with 1, 2 or 3 substituents independently selected from halogen and C1-C3 alkyl;
hetCyc¹ is a 4-6 membered saturated monocyclic heterocyclic ring having a ring oxygen atom;
R² is —CH₃, —CH₂CH₃, —CH=CH₂, F, Cl, Br or CN;
R³ is F or Cl;
R⁴ is H or F;
R⁵ is H, F or Cl;
R⁶ is C1-C6 alkyl, and
R⁷ is C1-C6 alkyl, hetCyc² or C3-C6 cycloalkyl,
or R⁶ and R⁷ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH₃, —OCF₂H, —OCD₃, —CH₃ and —CH₂CH₃, (ii) a 6-7 membered fused bicyclic ring optionally substituted with 1 or 2 substituents independently selected from F and —CH₃, (iii) a 6-7 membered bridged ring, and (iv) a 7-membered spirocyclic ring; and
hetCyc² is a 5-6 membered saturated monocyclic heterocyclic ring having 1 or 2 ring heteroatoms independently selected from N and O;
provided that the compound is not:
N-(2-chloro-3-((3,5-dimethyl-4-oxo-3,4-dihydroquinazolin-6-yl)amino)-4-fluorophenyl)pyrrolidine-1-sulfonamide,
(R)-N-(2-chloro-3-((3,5-dimethyl-4-oxo-3,4-dihydroquinazolin-6-yl)amino)-4-fluorophenyl)-3-fluoropyrrolidine-1-sulfonamide, or
N-(2-chloro-3-((3,5-dimethyl-4-oxo-3,4-dihydroquinazolin-6-yl)amino)-4-fluorophenyl)-N-ethyl-N-methylamino-1-sulfonamide.
Also provided herein is a compound of Formula II:

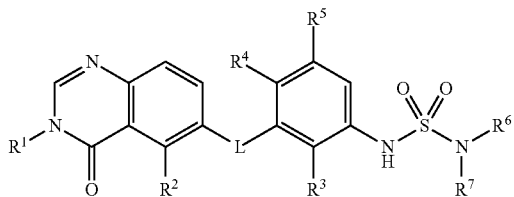

or a pharmaceutically acceptable salt thereof, wherein:
L is NH or O;
R¹ is C1-C6 alkyl or C1-C6 fluoroalkyl;
R² is —CH₃, —CH₂CH₃, —CH=CH₂, F, Cl, Br or CN;
R³ is F or Cl;
R⁴ is H or F;
R⁵ is H, F or Cl;
R⁶ is C1-C6 alkyl, and
R⁷ is C1-C6 alkyl, hetCyc² or C3-C6 cycloalkyl,
or R⁶ and R⁷ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH₃, —OCHF₂, —OCD₃, —CH₃, —CH₂CH₃, —CH₂OCH₃, —CH₂OCH₂F, —CH₂OCHF₂, —CH₂OCF₃, —OCF₃, —OCH₂CH₃, and CN, (ii) a 6-7 membered fused bicyclic ring optionally substituted with 1 or 2 substituents independently selected from F and —CH₃, (iii) a 6-7 membered bridged ring, and (iv) a 6-8-membered spirocyclic ring; and
hetCyc² is a 5-6 membered saturated monocyclic heterocyclic ring having 1 or 2 ring heteroatoms independently selected from N and O;
provided that the compound is not:
N-(2-chloro-3-((3,5-dimethyl-4-oxo-3,4-dihydroquinazolin-6-yl)amino)-4-fluorophenyl)pyrrolidine-1-sulfonamide,
(R)-N-(2-chloro-3-((3,5-dimethyl-4-oxo-3,4-dihydroquinazolin-6-yl)amino)-4-fluorophenyl)-3-fluoropyrrolidine-1-sulfonamide, or
N-(2-chloro-3-((3,5-dimethyl-4-oxo-3,4-dihydroquinazolin-6-yl)amino)-4-fluorophenyl)-N-ethyl-N-methylamino-1-sulfonamide.
Also provided herein is a compound of Formula III

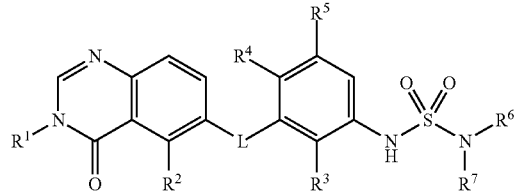

or a pharmaceutically acceptable salt thereof, wherein:
L is NH or O;
R¹ is C1-C6 alkyl, C1-C6 deuteroalkyl, C1-C6 fluoroalkyl, C3-C6 cycloalkyl, (C3-C6 cycloalkyl)CH₂—, (C1-C6 alkoxy)C1-C6 alkyl-, Ar¹, Ar¹CH₂—, hetAr¹ or hetCyc¹;
Ar¹ is phenyl which is optionally substituted with 1, 2, 3, 4 or 5 substituents independently selected from halogen and C1-C3 alkyl;
hetAr¹ is a 5-6 membered heteroaryl ring having 1 or 2 ring nitrogen atoms and which is optionally substituted with 1, 2 or 3 substituents independently selected from halogen and C1-C3 alkyl;
hetCyc¹ is a 4-6 membered saturated monocyclic heterocyclic ring having a ring oxygen atom;
R² is —CH₂CH₃, —CH=CH₂, F, Cl, Br or CN;
R³ is F or Cl;
R⁴ is H or F;
R⁵ is H, F or Cl;

R[6] is C1-C6 alkyl, and

R[7] is C1-C6 alkyl, hetCyc[2] or C3-C6 cycloalkyl, or R[6] and R[7] together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and hetCyc[2] is a 5-6 membered saturated monocyclic heterocyclic ring having 1 or 2 ring heteroatoms independently selected from N and O.

Also provided herein is a compound of Formula IV

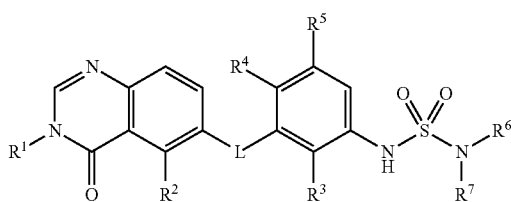

IV or a pharmaceutically acceptable salt thereof, wherein:

L is NH or O;

R[1] is C1-C6 alkyl, C1-C6 deuteroalkyl, C1-C6 fluoroalkyl, C3-C6 cycloalkyl, (C3-C6 cycloalkyl)CH$_2$—, (C1-C6 alkoxy)C1-C6 alkyl-, Ar[1], Ar[1]CH$_2$—, hetAr[1] or hetCyc[1];

Ar[1] is phenyl which is optionally substituted with 1, 2, 3, 4 or 5 substituents independently selected from halogen and C1-C3 alkyl;

hetAr[1] is a 5-6 membered heteroaryl ring having 1 or 2 ring nitrogen atoms and which is optionally substituted with 1, 2 or 3 substituents independently selected from halogen and C1-C3 alkyl;

hetCyc[1] is a 4-6 membered saturated monocyclic heterocyclic ring having a ring oxygen atom;

R[2] is —CH$_3$, —CH$_2$CH$_3$, —CH=CH$_2$, F, Cl, Br or CN;

R[3] is F or Cl;

R[4] is H or F;

R[5] is H, F or Cl;

R[6] is C1-C6 alkyl, and

R[7] is C1-C6 alkyl, hetCyc[2] or C3-C6 cycloalkyl, or R[6] and R[7] together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and hetCyc[2] is a 5-6 membered saturated monocyclic heterocyclic ring having 1 or 2 ring heteroatoms independently selected from N and O;

wherein when R[1] is methyl, L is NH, R[3] is Cl, R[4] is F, R[5] is H, and R[6] is methyl and R[7] is ethyl, or R[6] and R[7] together with the nitrogen atom to which they are attached form a pyrrolidinyl or 3-fluoropyrrolidinyl, then R[2] is —CH$_2$CH$_3$, —CH=CH$_2$, F, C, Br or CN.

Also provided herein is a compound of Formula V

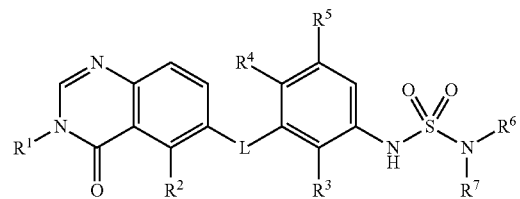

V or a pharmaceutically acceptable salt thereof, wherein:

L is NH;

R[1] is C1-C6 alkyl;

R[2] is F or Cl;

R[3] is Cl;

R[4] is F;

R[5] is H;

R[6] and R[7] together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, and (iii) a 6-7 membered bridged ring.

Also provided herein is a pharmaceutical composition comprising a compound of Formula I, Formula I-A, Formula II, Formula III, Formula IV or Formula V, or a pharmaceutically acceptable salt thereof, and one or more pharmaceutically acceptable carriers.

Also provided herein is a method of treating a BRAF-associated tumor in a subject in need of such treatment, the method comprising administering to the subject a therapeutically effective amount of a compound of Formula I, Formula I-A, Formula II, Formula III, Formula IV, or Formula V, or a pharmaceutically acceptable salt thereof. Compounds of the invention may be administered as single agents or may be administered in combination with other anti-cancer therapies, such as one or more additional anti-cancer therapies independently selected from one or more anticancer agents and/or surgery and/or radiotherapy.

Also provided herein is a method of inhibiting metastasis associated with a BRAF-associated tumor in a subject in need of such treatment, the method comprising administering to the subject a therapeutically effective amount of a compound of Formula I, Formula I-A, Formula II, Formula III, Formula IV, or Formula V, or a pharmaceutically acceptable salt thereof.

Also provided herein is a method of inhibiting BRAF kinase activity, in vitro or in vivo, the method comprising contacting a cell with a therapeutically effective amount of a compound of Formula I, Formula I-A, Formula II, Formula III, Formula IV, or Formula V, or a pharmaceutically acceptable salt thereof.

Also provided herein is a method of inhibiting cell proliferation, in vitro or in vivo, the method comprising contacting a cell with a therapeutically effective amount of a compound of Formula I, Formula I-A, Formula II, Formula III, Formula IV, or Formula V, or a pharmaceutically acceptable salt thereof.

Also provided herein is a compound of Formula I, Formula I-A, Formula II, Formula III, Formula IV, or Formula V, or a pharmaceutically acceptable salt thereof for use in therapy.

Also provided herein is a compound of Formula I, Formula I-A, Formula II, Formula III, Formula IV, or Formula V, or a pharmaceutically acceptable salt thereof for use in the treatment of tumors.

Also provided herein is a compound of Formula I, Formula I-A, Formula II, Formula III, Formula IV, or Formula V, or a pharmaceutically acceptable salt thereof for use in inhibiting metastasis associated with a BRAF-associated tumor.

Also provided herein is a compound of Formula I, Formula I-A, Formula II, Formula III, Formula IV, or Formula V, or a pharmaceutically acceptable salt thereof for use in the inhibition of BRAF kinase activity.

Also provided herein is a compound of Formula I, Formula I-A, Formula II, Formula III, Formula IV, or Formula V, or a pharmaceutically acceptable salt thereof for use in the treatment of a BRAF-associated disease or disorder (e.g., a BRAF-associated tumor).

Also provided herein is the use of a compound of Formula I, Formula I-A, Formula II, Formula III, Formula IV, or Formula V, or a pharmaceutically acceptable salt thereof, as defined herein in the manufacture of a medicament for the treatment of a BRAF-associated tumor (e.g., a BRAF-associated malignant tumor or a BRAF-associated benign tumor).

Also provided herein is the use of a compound of Formula I, Formula I-A, Formula II, Formula III, Formula IV, or Formula V, or a pharmaceutically acceptable salt thereof, as defined herein in the manufacture of a medicament for inhibiting metastasis associated with a BRAF-associated tumor.

Also provided herein is a use of a compound of Formula I, Formula I-A, Formula II, Formula III, Formula IV, or Formula V, or a pharmaceutically acceptable salt thereof, as defined herein in the manufacture of a medicament for the inhibition of BRAF kinase activity.

Also provided herein is the use of a compound of Formula I, Formula I-A, Formula II, Formula III, Formula IV, or Formula V, or a pharmaceutically acceptable salt thereof, as defined herein, in the manufacture of a medicament for the treatment of a BRAF-associated disease or disorder.

Also provided herein is a method for treating a BRAF-associated tumor in a subject in need thereof, the method comprising (a) determining that the tumor is associated with a BRAF mutation; and (b) administering to the subject a therapeutically effective amount of a compound of Formula I, Formula I-A, Formula II, Formula III, Formula IV, or Formula V, or a pharmaceutically acceptable salt thereof, or a pharmaceutical composition thereof.

Also provided herein is a pharmaceutical combination for treating a BRAF-associated tumor in a subject in need thereof, which comprises (a) a compound of Formula I, Formula I-A, Formula II, Formula III, Formula IV, or Formula V, or a pharmaceutically acceptable salt thereof, and (b) an additional anticancer agent, wherein the compound of Formula I, Formula I-A, Formula II, Formula III, Formula IV, or Formula V, or the pharmaceutically acceptable salt thereof, and the additional anticancer agent are formulated as separate compositions or dosages for separate or sequential use for the treatment of the BRAF-associated tumor, wherein the amounts of the compound of Formula I, Formula I-A, Formula II, Formula III, Formula IV, or Formula V, or a pharmaceutically acceptable salt thereof, and of the additional anticancer agent are together effective in treating the BRAF-associated tumor. Also provided herein is the use of such a combination for use in the treatment of a BRAF-associated tumor. Also provided herein is a commercial package or product comprising such a combination as a combined preparation for separate or sequential use in the treatment of a BRAF-associated tumor a subject in need thereof.

Also provided herein are methods of treating a subject with a BRAF-associated tumor that include administering a compound of Formula I, Formula I-A, Formula II, Formula III, Formula IV, or Formula V, or a pharmaceutically acceptable salt thereof, before, during, or after administration of another anticancer therapy (e.g., surgery, radiotherapy and/or another anticancer drug).

Also provided herein is a process for preparing a compound of Formula I, Formula I-A, Formula II, Formula III, Formula IV, or Formula V, or a pharmaceutically acceptable salt thereof.

Also provided herein is a compound of Formula I, Formula I-A, Formula II, Formula III, Formula IV or Formula V, or a pharmaceutically acceptable salt thereof, obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE FIGURES

FIG. 1 illustrates an X-ray powder diffraction (XRPD) pattern of crystalline form (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide Form A.

DETAILED DESCRIPTION OF THE INVENTION

Provided herein is a compound of Formula I:

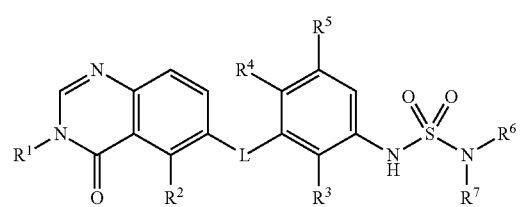

or a pharmaceutically acceptable salt thereof, wherein:
L is NH or O;
R¹ is C1-C6 alkyl, C1-C6 deuteroalkyl, C1-C6 fluoroalkyl, C3-C6 cycloalkyl, (C3-C6 cycloalkyl)CH₂—, (C1-C6 alkoxy)C1-C6 alkyl-, Ar¹, Ar¹CH₂—, hetAr¹ or hetCyc¹;
Ar¹ is phenyl which is optionally substituted with 1, 2, 3, 4 or 5 substituents independently selected from halogen and C1-C3 alkyl;
hetAr¹ is a 5-6 membered heteroaryl ring having 1 or 2 ring nitrogen atoms and which is optionally substituted with 1, 2 or 3 substituents independently selected from halogen and C1-C3 alkyl;
hetCyc¹ is a 4-6 membered saturated monocyclic heterocyclic ring having a ring oxygen atom;
R² is —CH₃, —CH₂CH₃, —CH═CH₂, F, Cl, Br or CN;
R³ is F or Cl;
R⁴ is H or F;
R⁵ is H, F or Cl;
R⁶ is C1-C6 alkyl, and
R⁷ is C1-C6 alkyl, hetCyc² or C3-C6 cycloalkyl,
or R⁶ and R⁷ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH₃, —OCF₂H, —OCD₃, —CH₃, —CH₂CH₃, —CH₂OCH₃, —CH₂OCH₂F, —CH₂OCHF₂, —CH₂OCF₃, —OCF₃, —OCH₂CH₃, and CN, (ii) a 6-7 membered fused bicyclic ring optionally substituted with 1 or 2 substituents independently selected from F and —CH₃, (iii) a 6-7 membered bridged ring, and (iv) a 6-8-membered spirocyclic ring; and
hetCyc² is a 5-6 membered saturated monocyclic heterocyclic ring having 1 or 2 ring heteroatoms independently selected from N and O;
provided that the compound is not:
N-(2-chloro-3-((3,5-dimethyl-4-oxo-3,4-dihydroquinazolin-6-yl)amino)-4-fluorophenyl)pyrrolidine-1-sulfonamide,
(R)-N-(2-chloro-3-((3,5-dimethyl-4-oxo-3,4-dihydroquinazolin-6-yl)amino)-4-fluorophenyl)-3-fluoropyrrolidine-1-sulfonamide, or
N-(2-chloro-3-((3,5-dimethyl-4-oxo-3,4-dihydroquinazolin-6-yl)amino)-4-fluorophenyl)-N-ethyl-N-methylamino-1-sulfonamide.

In one embodiment, provided herein is a compound of Formula I-A

I-A

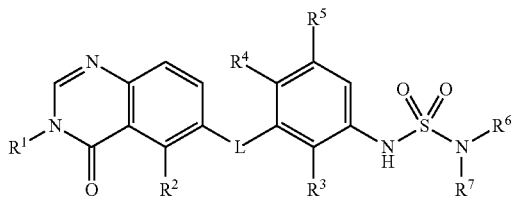

or a pharmaceutically acceptable salt thereof, wherein:
L is NH or O;
R¹ is C1-C6 alkyl, C1-C6 deuteroalkyl, C1-C6 fluoroalkyl, C3-C6 cycloalkyl, (C3-C6 cycloalkyl)CH₂—, (C1-C6 alkoxy)C1-C6 alkyl-, Ar¹, Ar¹CH₂—, hetAr¹ or hetCyc¹;

Ar¹ is phenyl which is optionally substituted with 1, 2, 3, 4 or 5 substituents independently selected from halogen and C1-C3 alkyl;
hetAr¹ is a 5-6 membered heteroaryl ring having 1 or 2 ring nitrogen atoms and which is optionally substituted with 1, 2 or 3 substituents independently selected from halogen and C1-C3 alkyl;
hetCyc¹ is a 4-6 membered saturated monocyclic heterocyclic ring having a ring oxygen atom;
R² is —CH₃, —CH₂CH₃, —CH═CH₂, F, Cl, Br or CN;
R³ is F or Cl;
R⁴ is H or F;
R⁵ is H, F or Cl;
R⁶ is C1-C6 alkyl, and
R⁷ is C1-C6 alkyl, hetCyc² or C3-C6 cycloalkyl,
or R⁶ and R⁷ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH₃, —OCF₂H, —OCD₃, —CH₃ and —CH₂CH₃, (ii) a 6-7 membered fused bicyclic ring optionally substituted with 1 or 2 substituents independently selected from F and —CH₃, (iii) a 6-7 membered bridged ring, and (iv) a 7-membered spirocyclic ring; and
hetCyc² is a 5-6 membered saturated monocyclic heterocyclic ring having 1 or 2 ring heteroatoms independently selected from N and O;
provided that the compound is not:
N-(2-chloro-3-((3,5-dimethyl-4-oxo-3,4-dihydroquinazolin-6-yl)amino)-4-fluorophenyl)pyrrolidine-1-sulfonamide,
(R)-N-(2-chloro-3-((3,5-dimethyl-4-oxo-3,4-dihydroquinazolin-6-yl)amino)-4-fluorophenyl)-3-fluoropyrrolidine-1-sulfonamide, or
N-(2-chloro-3-((3,5-dimethyl-4-oxo-3,4-dihydroquinazolin-6-yl)amino)-4-fluorophenyl)-N-ethyl-N-methylamino-1-sulfonamide.

For complex chemical names employed herein, a substituent group is typically named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The terms "C1-C3 alkyl" and "C1-C6 alkyl" as used herein refer to saturated linear or branched-chain monovalent hydrocarbon radicals of one to three or one to six carbon atoms, respectively. Examples of alkyl groups include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "C1-C6 fluoroalkyl" as used herein refers to a C1-C6 alkyl radical as defined herein, wherein one to three hydrogen atoms is replaced with one to three fluoro atoms, respectively. Examples include, but are not limited to, fluoromethyl, difluoromethyl, trifluoromethyl, 2-fluoroethyl, 2,2-difluoroethyl, 2,2,2- and trifluoroethyl.

The term "C1-C6 deuteroalkyl" as used herein refers to a C1-C6 alkyl radical as defined herein, which is substituted with one to six deuterium atoms. An example includes, but is not limited to, —CD₃.

The term "C3-C6 cycloalkyl" means a saturated carbocyclic ring having from 3-6 ring carbon atoms, for example cyclopropyl, cyclobutyl, cyclopentyl or cyclohexyl The term "C1-C6 alkoxy" as used herein refers to saturated linear or branched-chain monovalent alkoxy radicals of one to six carbon atoms, wherein the radical is on the oxygen atom. Examples of alkoxy groups include methoxy, ethoxy, propoxy, and isopropoxy.

The term "(C1-C6 alkoxy)C1-C6 alkyl" as used herein refer to a C1-C6 alkyl radical as defined herein, wherein one of the carbon atoms is substituted with a C1-C6 alkoxy group. Examples of (C1-C6 alkoxy)C1-C6 alkyl groups include methoxymethyl ($CH_3OCH_2-$) and methoxyethyl ($CH_3OCH_2CH_2-$).

The term "heteroaryl" as used herein refers to an aromatic molecule containing at least one heteroatom as part of the aromatic ring.

The term "heterocycle" as used herein refers to refers to a saturated cycloalkyl group in which one or more of the ring methylene groups (—CH2-) has been replaced with a heteroatom. For example, the term "hetCyc$^1$" as used herein refers to a saturated 4-6 membered monocyclic cycloalkyl ring in which one of the methylene groups has been replaced with —O—, and the term "hetCyc$^2$" as used herein refers to a 5-6 membered saturated monocyclic cycloalkyl ring in which one or two of the methylene groups has been replaced with a group independently selected from —O— and —N—, provided the ring does not contain two adjacent ring heteroatoms.

Throughout the disclosure, it will be understood that the number and nature of optional substituent groups will be limited to the extent that such substitutions make chemical sense.

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

In one embodiment of Formula I, L is NH.
In one embodiment of Formula I, L is O.
In one embodiment of Formula I, $R^1$ is C1-C6 alkyl. Non-limiting examples include methyl, ethyl and isopropyl. In one embodiment of Formula I, $R^1$ is methyl.
In one embodiment of Formula I, $R^1$ is C1-C6 deuteroalkyl. A non-limiting example includes —$CD_3$.
In one embodiment of Formula I, $R^1$ is C1-C6 fluoroalkyl. In one embodiment of Formula I, $R^1$ is fluoromethyl.
In one embodiment of Formula I, $R^1$ is C3-C6 cycloalkyl. Non-limiting examples include cyclopropyl, cyclobutyl and cyclopentyl.
In one embodiment of Formula I, $R^1$ is (C3-C6 cycloalkyl)$CH_2$—. A non-limiting example includes cyclopropylmethyl.
In one embodiment of Formula I, $R^1$ is (C1-C6 alkoxy) C1-C6 alkyl-. A non-limiting example includes methoxyethyl.
In one embodiment of Formula I, $R^1$ is $Ar^1$. In one embodiment, $Ar^1$ is phenyl which is optionally substituted with 1, 2 or 3 substituents independently selected from halogen and C1-C3 alkyl. A non-limiting example of $Ar^1$ is phenyl.
In one embodiment of Formula I, $R^1$ is $Ar^1CH_2$—. In one embodiment, the $Ar^1$ portion is optionally substituted with 1 or 2 substituents independently selected from halogen and C1-C3 alkyl. A non-limiting example of $Ar^1CH_2$— is benzyl (—$CH_2C_6H_5$).
In one embodiment of Formula I, $R^1$ is hetAr$^1$. In one embodiment, hetAr$^1$ is a 5-6 membered heteroaryl ring having 1 or 2 ring nitrogen atoms and which is optionally substituted with 1 or 2 substituents independently selected from halogen and C1-C3 alkyl. In one embodiment, hetAr$^1$ is unsubstituted. A non-limiting example is pyridyl.

In one embodiment of Formula I, $R^1$ is hetCyc$^1$. A non-limiting example includes tetrahydrofuranyl.
In one embodiment of Formula I, $R^2$ is —$CH_3$.
In one embodiment of Formula I, $R^2$ is —$CH_2CH_3$.
In one embodiment of Formula I, $R^2$ is —$CH=CH_2$.
In one embodiment of Formula I, $R^2$ is F.
In one embodiment of Formula I, $R^2$ is Cl.
In one embodiment of Formula I, $R^2$ is Br.
In one embodiment of Formula I, $R^2$ is CN.
In one embodiment of Formula I, $R^2$ is —$CH_3$, F or Cl.
In one embodiment of Formula I, $R^2$ is F or Cl.
In one embodiment of Formula I, $R^3$ is F.
In one embodiment of Formula I, $R^3$ is Cl.
In one embodiment of Formula I, $R^4$ is H.
In one embodiment of Formula I, $R^4$ is F.
In one embodiment of Formula I, $R^5$ is H.
In one embodiment of Formula I, $R^5$ is F.
In one embodiment of Formula I, $R^5$ is Cl.
In one embodiment of Formula I, $R^6$ is C1-C6 alkyl and $R^7$ is C1-C6 alkyl, hetCyc$^2$ or C3-C6 cycloalkyl.
In one embodiment of Formula I, $R^6$ is methyl or ethyl.
In one embodiment of Formula I, $R^7$ is C1-C6 alkyl. In one embodiment, $R^7$ is methyl.
In one embodiment of Formula I, $R^7$ is hetCyc$^2$. In one embodiment, $R^7$ is tetrahydrofuranyl.
In one embodiment of Formula It, $R^7$ is C3-C6 cycloalkyl. In one embodiment, $R^7$ is cyclopropyl or cyclobutyl.
In one embodiment of Formula I, $R^6$ is methyl or ethyl and $R^7$ is methyl, tetrahydrofuranyl, cyclopropyl or cyclobutyl.
In one embodiment of Formula I, $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —$OCH_3$, —$OCHF_2$, —$OCD_3$, —$CH_3$ and —$CH_2CH_3$, (ii) a 6-7 membered fused bicyclic ring optionally substituted with 1 or 2 substituents independently selected from F and —$CH_3$, (iii) a 6-7 membered bridged ring, and (iv) a 6-8-membered spirocyclic ring.

In one embodiment of Formula I, $R^6$ and $R^7$ together with the nitrogen atom to which they are attached form a 4-6 membered monocyclic ring optionally having a second ring heteroatom which is O, wherein said ring is optionally substituted with 1 or 2 substituents independently selected from F, —OH, —$OCH_3$, —$OCF_2H$, —$OCD_3$, —$CH_3$, —$CH_2CH_3$, —$CH_2OCH_3$, —$CH_2OCH_2F$, —$CH_2OCHF_2$, —$CH_2OCF_3$, —$OCF_3$, —$OCH_2CH_3$, and CN. Non-limiting examples include the structures:

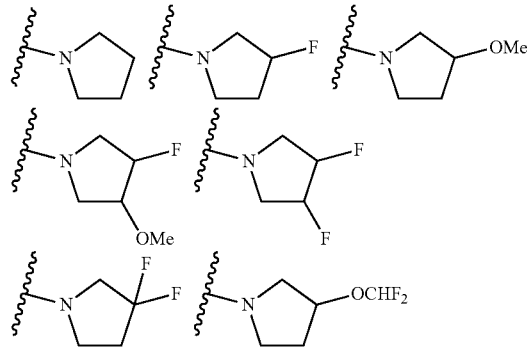

-continued

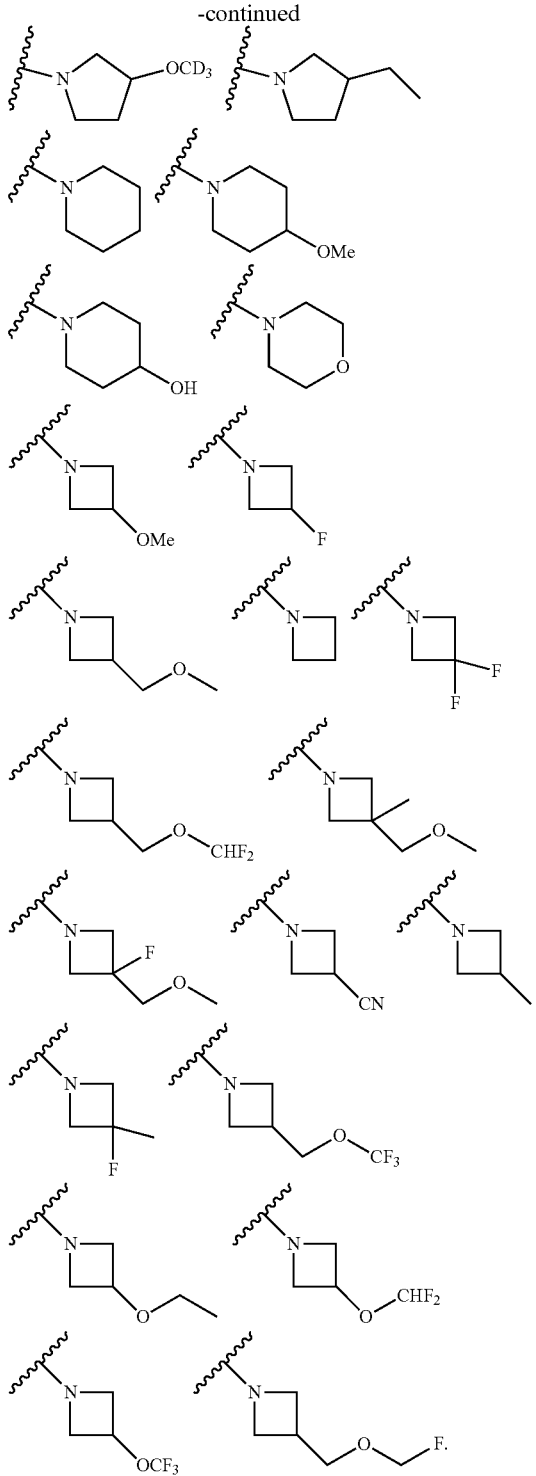

In one embodiment of Formula I, $R^6$ and $R^7$ together with the nitrogen atom to which they are attached form a 4-6 membered monocyclic ring, wherein said ring is substituted a substituent selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN.

In one embodiment of Formula I, $R^6$ and $R^7$ together with the nitrogen atom to which they are attached form a saturated 4-6 membered monocyclic ring substituted with F. Examples include the structures:

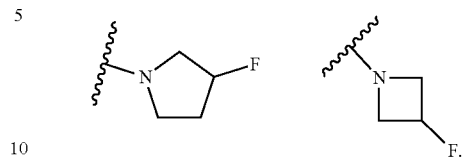

In one embodiment of Formula I, $R^6$ and $R^7$ together with the nitrogen atom to which they are attached form a 6-7 membered fused bicyclic ring optionally substituted with 1 or 2 substituents independently selected from F and —CH$_3$. Non-limiting examples include the structures:

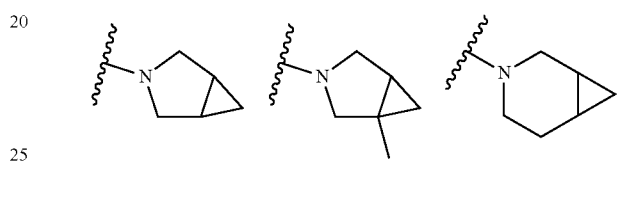

In one embodiment of Formula I, $R^6$ and $R^7$ together with the nitrogen atom to which they are attached form a 6-7 membered bridged ring. Non-limiting examples include the structures:

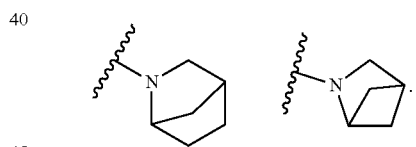

In one embodiment of Formula I, $R^6$ and $R^7$ together with the nitrogen atom to which they are attached form a 6-8-membered spirocyclic ring. A non-limiting example includes the structure:

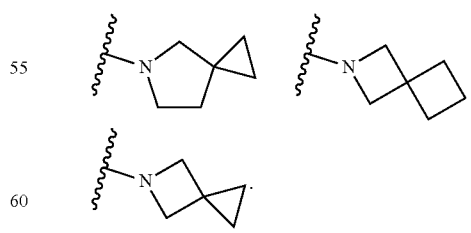

Any of the aforementioned embodiments of Formula I may be combined with each other.

In one embodiment, provided herein is a compound of Formula II

II

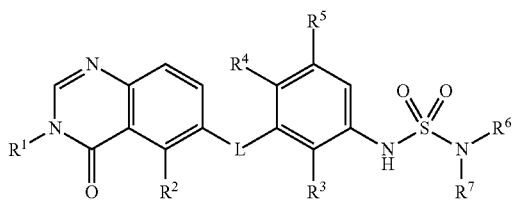

or a pharmaceutically acceptable salt thereof, wherein:
L is NH or O;
$R^1$ is C1-C6 alkyl or C1-C6 fluoroalkyl;
$R^2$ is —CH$_3$, —CH$_2$CH$_3$, —CH═CH$_2$, F, Cl, Br or CN;
$R^3$ is F or Cl;
$R^4$ is H or F;
$R^5$ is H, F or Cl;
$R^6$ is C1-C6 alkyl, and
$R^7$ is C1-C6 alkyl, hetCyc$^2$ or C3-C6 cycloalkyl,
or $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and
hetCyc$^2$ is a 5-6 membered saturated monocyclic heterocyclic ring having 1 or 2 ring heteroatoms independently selected from N and O;
provided that the compound is not: N-(2-chloro-3-((3,5-dimethyl-4-oxo-3,4-dihydroquinazolin-6-yl)amino)-4-fluorophenyl)pyrrolidine-1-sulfonamide,
(R)-N-(2-chloro-3-((3,5-dimethyl-4-oxo-3,4-dihydroquinazolin-6-yl)amino)-4-fluorophenyl)-3-fluoropyrrolidine-1-sulfonamide, or
N-(2-chloro-3-((3,5-dimethyl-4-oxo-3,4-dihydroquinazolin-6-yl)amino)-4-fluorophenyl)-N-ethyl-N-methylamino-1-sulfonamide.

In one embodiment of Formula II, L is NH.
In one embodiment of Formula II, L is O.
In one embodiment of Formula II, $R^1$ is C1-C6 alkyl. Non-limiting examples include methyl, ethyl and isopropyl. In one embodiment of Formula II, $R^1$ is methyl.
In one embodiment of Formula II, $R^1$ is C1-C6 fluoroalkyl. In one embodiment of Formula II, $R^1$ is fluoromethyl.
In one embodiment of Formula II, $R^2$ is —CH$_3$.
In one embodiment of Formula II, $R^2$ is —CH$_2$CH$_3$.
In one embodiment of Formula II, $R^2$ is —CH═CH$_2$.
In one embodiment of Formula II, $R^2$ is F.
In one embodiment of Formula II, $R^2$ is Cl.
In one embodiment of Formula II, $R^2$ is Br.
In one embodiment of Formula II, $R^2$ is CN.
In one embodiment of Formula II, $R^2$ is —CH$_3$, F or Cl.
In one embodiment of Formula II, $R^2$ is F or Cl.
In one embodiment of Formula II, $R^3$ is F.
In one embodiment of Formula II, $R^3$ is Cl.
In one embodiment of Formula II, $R^4$ is H.
In one embodiment of Formula II, $R^4$ is F.
In one embodiment of Formula II, $R^5$ is H.

In one embodiment of Formula II, $R^5$ is F.
In one embodiment of Formula II, $R^5$ is Cl.
In one embodiment of Formula II, $R^6$ is C1-C6 alkyl and $R^7$ is C1-C6 alkyl, hetCyc$^2$ or C3-C6 cycloalkyl.
In one embodiment of Formula II, $R^6$ is methyl or ethyl.
In one embodiment of Formula II, $R^7$ is C1-C6 alkyl. In one embodiment, $R^7$ is methyl.
In one embodiment of Formula II, $R^7$ is hetCyc$^2$. In one embodiment, $R^7$ is tetrahydrofuranyl.
In one embodiment of Formula II, $R^7$ is C3-C6 cycloalkyl. In one embodiment, $R^7$ is cyclopropyl or cyclobutyl.
In one embodiment of Formula II, $R^6$ is methyl or ethyl and $R^7$ is methyl, tetrahydrofuranyl, cyclopropyl or cyclobutyl.
In one embodiment of Formula II, $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$ and —CH$_2$CH$_3$, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring.

In one embodiment of Formula II, $R^6$ and $R^7$ together with the nitrogen atom to which they are attached form a 4-6 membered monocyclic ring optionally having a second ring heteroatom which is O, wherein said ring is optionally substituted with 1 or 2 substituents independently selected from F, —OH, —OCH$_3$, —OCF$_2$H, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN. Non-limiting examples include the structures:

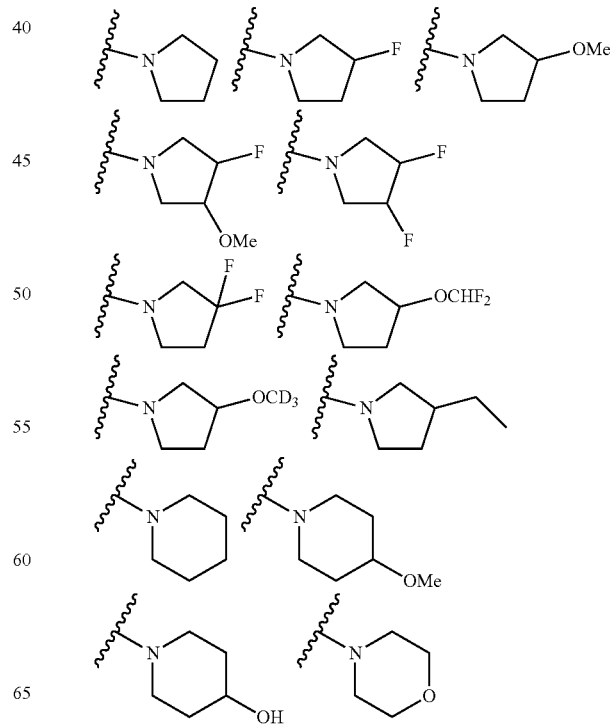

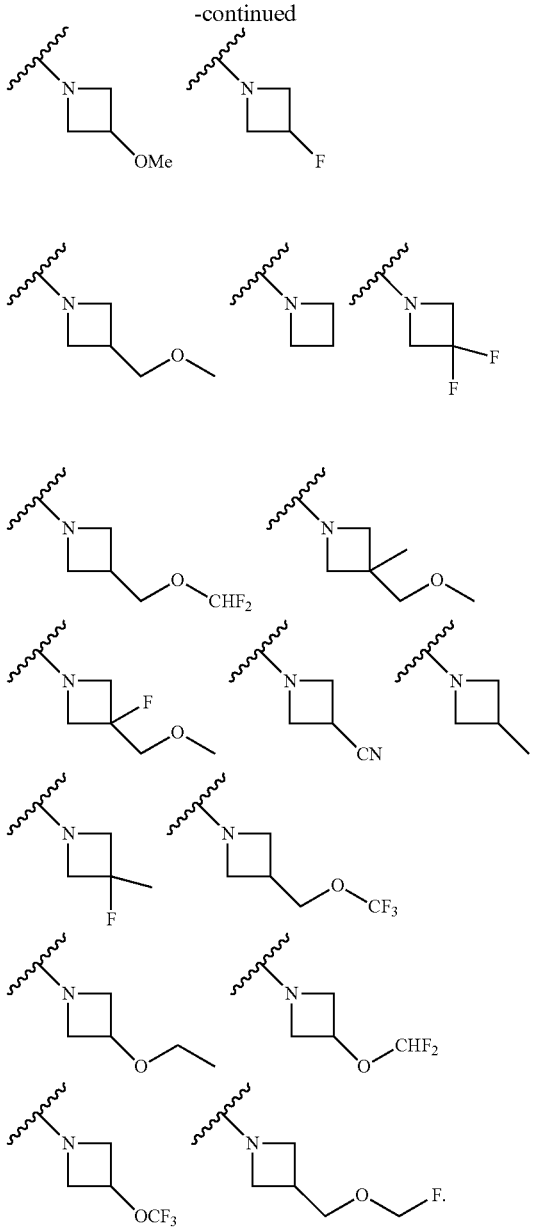

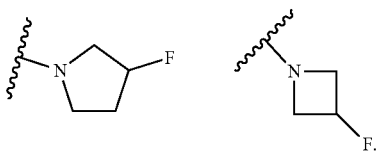 [SMILES: *N1CCC(F)C1 ; *N1CC(F)C1]

In one embodiment of Formula II, R⁶ and R⁷ together with the nitrogen atom to which they are attached form a 6-7 membered fused bicyclic ring optionally substituted with 1 or 2 substituents independently selected from F and —CH₃. Non-limiting examples include the structures:

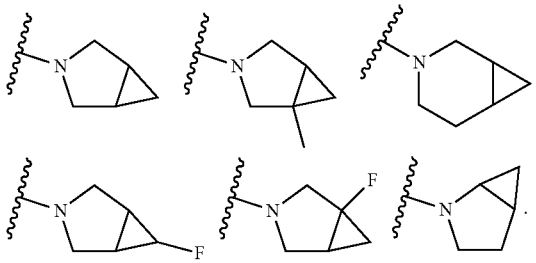

In one embodiment of Formula II, $R^6$ and $R^7$ together with the nitrogen atom to which they are attached form a 6-7 membered bridged ring. Non-limiting examples include the structures:

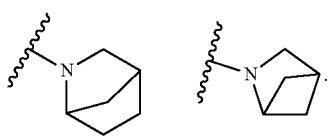 [SMILES: *N1CC2CCC1C2 ; *N1CC2CC1C2]

In one embodiment of Formula II, $R^6$ and $R^7$ together with the nitrogen atom to which they are attached form a 6-8-membered spirocyclic ring. A non-limiting example includes the structure:

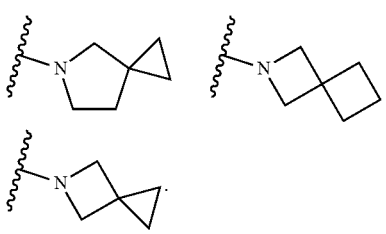

Any of the aforementioned embodiments of Formula II may be combined with each other.

In one embodiment, provided herein is a compound of Formula III:

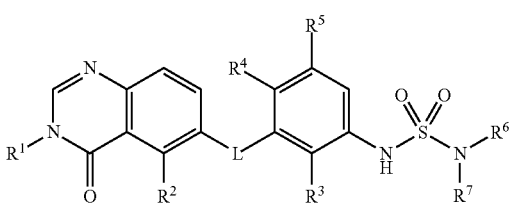

or a pharmaceutically acceptable salt thereof, wherein:
  L is NH or O;
  $R^1$ is C1-C6 alkyl, C1-C6 deuteroalkyl, C1-C6 fluoroalkyl, C3-C6 cycloalkyl, (C3-C6 cycloalkyl)CH₂—, (C1-C6 alkoxy)C1-C6 alkyl-, Ar¹, Ar¹CH₂—, hetAr¹ or hetCyc¹;
  Ar¹ is phenyl which is optionally substituted with 1, 2, 3, 4 or 5 substituents independently selected from halogen and C1-C3 alkyl;

hetAr¹ is a 5-6 membered heteroaryl ring having 1 or 2 ring nitrogen atoms and which is optionally substituted with 1, 2 or 3 substituents independently selected from halogen and C1-C3 alkyl;

hetCyc¹ is a 4-6 membered saturated monocyclic heterocyclic ring having a ring oxygen atom;

$R^2$ is —CH$_2$CH$_3$, —CH=CH$_2$, F, Cl, Br or CN;

$R^3$ is F or Cl;

$R^4$ is H or F;

$R^5$ is H, F or Cl;

$R^6$ is C1-C6 alkyl, and $R^7$ is C1-C6 alkyl, hetCyc² or C3-C6 cycloalkyl, or $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and hetCyc² is a 5-6 membered saturated monocyclic heterocyclic ring having 1 or 2 ring heteroatoms independently selected from N and O.

In one embodiment of Formula III, L is NH.

In one embodiment of Formula III, L is O.

In one embodiment of Formula III, $R^1$ is C1-C6 alkyl or C1-C6 fluoroalkyl.

In one embodiment of Formula III, $R^1$ is C1-C6 alkyl. Non-limiting examples include methyl, ethyl and isopropyl. In one embodiment of Formula II, $R^1$ is methyl.

In one embodiment of Formula III, $R^1$ is C1-C6 fluoroalkyl. In one embodiment of Formula III, $R^1$ is fluoromethyl.

In one embodiment of Formula III, $R^2$ is —CH=CH$_2$.

In one embodiment of Formula III, $R^2$ is F.

In one embodiment of Formula III, $R^2$ is Cl.

In one embodiment of Formula III, $R^2$ is Br.

In one embodiment of Formula III, $R^2$ is CN.

In one embodiment of Formula III, $R^2$ is F or Cl

In one embodiment of Formula III, $R^3$ is F.

In one embodiment of Formula III, $R^3$ is Cl.

In one embodiment of Formula III, $R^4$ is H.

In one embodiment of Formula III, $R^4$ is F.

In one embodiment of Formula III, $R^5$ is H.

In one embodiment of Formula III, $R^5$ is F.

In one embodiment of Formula III, $R^5$ is Cl.

In one embodiment of Formula III, $R^6$ is C1-C6 alkyl and $R^7$ is C1-C6 alkyl, hetCyc² or C3-C6 cycloalkyl.

In one embodiment of Formula III, $R^6$ is methyl or ethyl.

In one embodiment of Formula III, $R^7$ is C1-C6 alkyl. In one embodiment, $R^7$ is methyl.

In one embodiment of Formula III, $R^7$ is hetCyc². In one embodiment, $R^7$ is tetrahydrofuranyl.

In one embodiment of Formula III, $R^7$ is C3-C6 cycloalkyl. In one embodiment, $R^7$ is cyclopropyl or cyclobutyl.

In one embodiment of Formula III, $R^6$ is methyl or ethyl and $R^7$ is methyl, tetrahydrofuranyl, cyclopropyl or cyclobutyl.

In one embodiment of Formula III, $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$ and —CH$_2$CH$_3$, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring.

In one embodiment of Formula III, $R^6$ and $R^7$ together with the nitrogen atom to which they are attached form a 4-6 membered monocyclic ring optionally having a second ring heteroatom which is O, wherein said ring is optionally substituted with 1 or 2 substituents independently selected from F, —OH, —OCH$_3$, —OCF$_2$H, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN. Non-limiting examples include the structures:

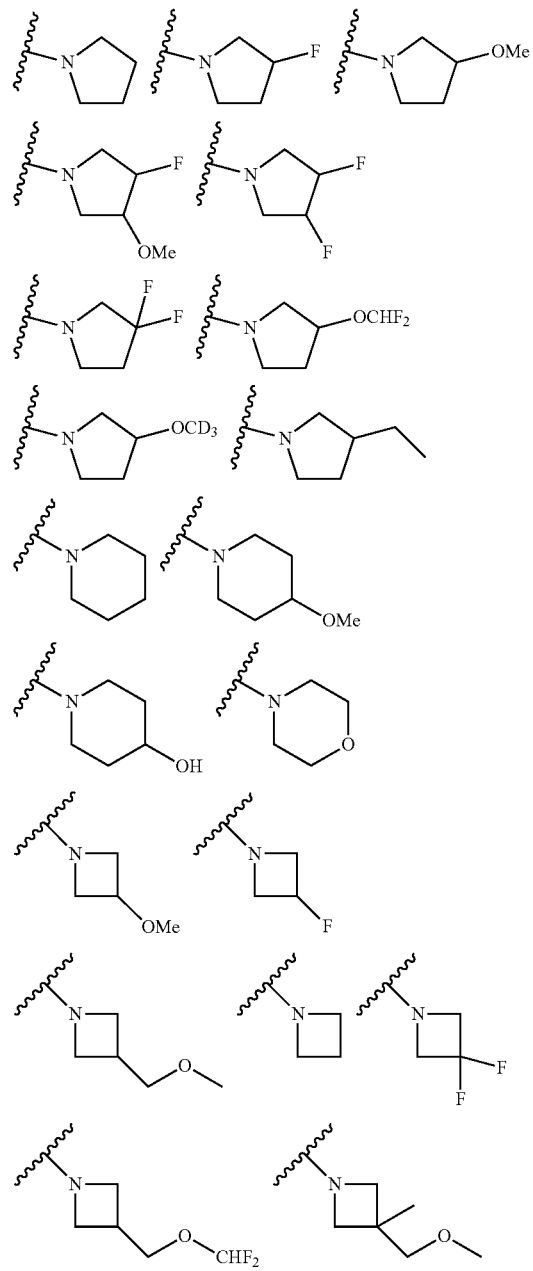

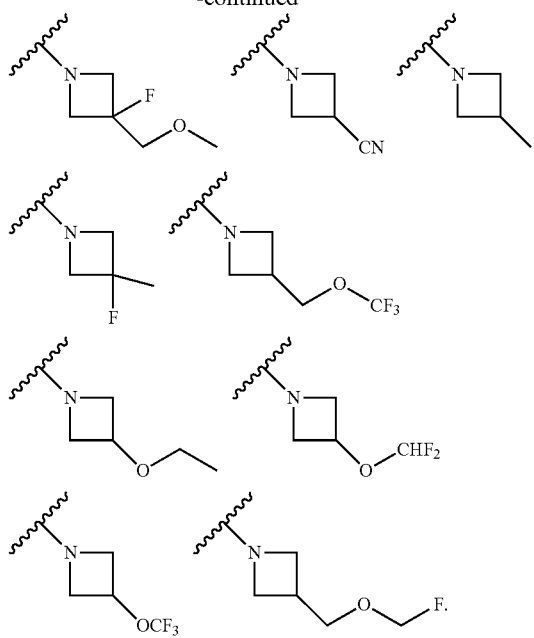

In one embodiment of Formula III, R⁶ and R⁷ together with the nitrogen atom to which they are attached form a saturated 4-6 membered monocyclic ring optionally substituted with F. Examples include the structures:

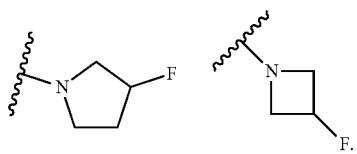 [SMILES: *N1CCC(F)C1 ; *N1CC(F)C1]

In one embodiment of Formula III, R⁶ and R⁷ together with the nitrogen atom to which they are attached form a 6-7 membered fused bicyclic ring optionally substituted with 1 or 2 substituents independently selected from F and —CH₃. Non-limiting examples include the structures:

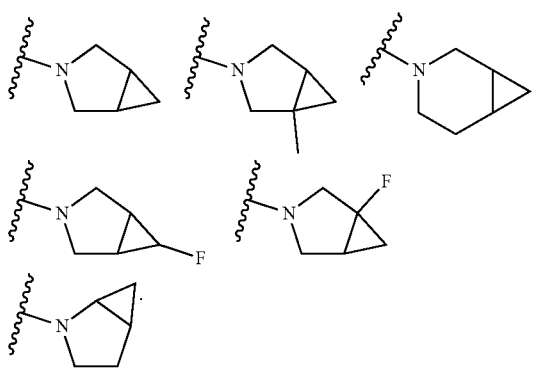

In one embodiment of Formula III, R⁶ and R⁷ together with the nitrogen atom to which they are attached form a 6-7 membered bridged ring. Non-limiting examples include the structures:

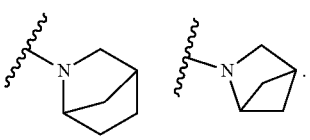

In one embodiment of Formula III, R⁶ and R⁷ together with the nitrogen atom to which they are attached form a 6-8-membered spirocyclic ring. A non-limiting example includes the structure:

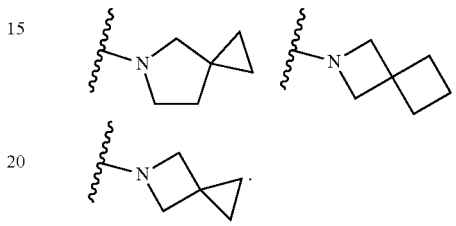

Any of the aforementioned embodiments of Formula III may be combined with each other.

In one embodiment, provided herein is a compound of Formula IV

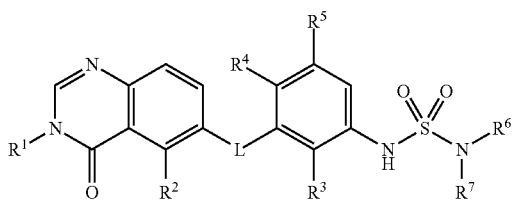

IV or a pharmaceutically acceptable salt thereof, wherein:
L is NH or O;
R¹ is C1-C6 alkyl, C1-C6 deuteroalkyl, C1-C6 fluoroalkyl, C3-C6 cycloalkyl, (C3-C6 cycloalkyl)CH₂—, (C1-C6 alkoxy)C1-C6 alkyl-, Ar¹, Ar¹CH₂—, hetAr¹ or hetCyc¹;
Ar¹ is phenyl which is optionally substituted with 1, 2, 3, 4 or 5 substituents independently selected from halogen and C1-C3 alkyl;
hetAr¹ is a 5-6 membered heteroaryl ring having 1 or 2 ring nitrogen atoms and which is optionally substituted with 1, 2 or 3 substituents independently selected from halogen and C1-C3 alkyl;
hetCyc¹ is a 4-6 membered saturated monocyclic heterocyclic ring having a ring oxygen atom;
R² is —CH₃, —CH₂CH₃, —CH=CH₂, F, Cl, Br or CN;
R³ is F or Cl;
R⁴ is H or F;
R⁵ is H, F or Cl;
R⁶ is C1-C6 alkyl, and
R⁷ is C1-C6 alkyl, hetCyc² or C3-C6 cycloalkyl,
or R⁶ and R⁷ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH₃, —OCHF₂, —OCD₃, —CH₃, —CH₂CH₃, —CH₂OCH₃, —CH₂OCH₂F, —CH₂OCHF₂, —CH₂OCF₃, —OCF₃, —OCH₂CH₃, and CN, (ii) a 6-7 membered fused bicyclic ring optionally substituted with 1 or 2 substituents independently selected from F and —CH₃, (iii) a 6-7 membered bridged ring, and (iv) a 6-8-membered spirocyclic ring; and hetCyc² is a 5-6 membered saturated monocyclic heterocyclic ring having 1 or 2 ring heteroatoms independently selected from N and O;

wherein when R¹ is methyl, L is NH, R³ is Cl, R⁴ is F, R⁵ is H, and R⁶ is methyl and R⁷ is ethyl, or R⁶ and R⁷ together with the nitrogen atom to which they are attached form a pyrrolidinyl or 3-fluoropyrrolidinyl, then R² is —CH₂CH₃, —CH=CH₂, F, Cl, Br or CN.

In one embodiment of Formula IV, L is NH.
In one embodiment of Formula IV, L is O.
In one embodiment of Formula IV, R¹ is C1-C6 alkyl or C1-C6 fluoroalkyl.
In one embodiment of Formula IV, R¹ is C1-C6 alkyl. Non-limiting examples include methyl, ethyl and isopropyl, provided that when R¹ is methyl, L is NH, R³ is Cl, R⁴ is F, R⁵ is H, and R⁶ is methyl and R⁷ is ethyl, or R⁶ and R⁷ together with the nitrogen atom to which they are attached form a pyrrolidinyl or 3-fluoropyrrolidinyl, then R² is —CH₂CH₃, —CH=CH₂, F, Cl, Br or CN. In one embodiment of Formula IV, R¹ is methyl.

In one embodiment of Formula IV, R¹ is C1-C6 fluoroalkyl. In one embodiment of Formula IV, R¹ is fluoromethyl.

In one embodiment of Formula IV, R² is —CH₃.
In one embodiment of Formula IV, R² is —CH₂CH₃.
In one embodiment of Formula IV, R² is —CH=CH₂.
In one embodiment of Formula IV, R² is F.
In one embodiment of Formula IV, R² is Cl.
In one embodiment of Formula IV, R² is Br.
In one embodiment of Formula IV, R² is CN.
In one embodiment of Formula IV, R² is —CH₃, F or Cl.
In one embodiment of Formula IV, R² is F or Cl
In one embodiment of Formula IV, R³ is F.
In one embodiment of Formula IV, R³ is Cl.
In one embodiment of Formula IV, R⁴ is H.
In one embodiment of Formula IV, R⁴ is F.
In one embodiment of Formula IV, R⁵ is H.
In one embodiment of Formula IV, R⁵ is F.
In one embodiment of Formula IV, R⁵ is Cl.
In one embodiment of Formula IV, R⁶ is C1-C6 alkyl and R⁷ is C1-C6 alkyl, hetCyc² or C3-C6 cycloalkyl.
In one embodiment of Formula IV, R⁶ is methyl or ethyl.
In one embodiment of Formula IV, R⁷ is C1-C6 alkyl. In one embodiment, R⁷ is methyl.
In one embodiment of Formula IV, R⁷ is hetCyc². In one embodiment, R⁷ is tetrahydrofuranyl.
In one embodiment of Formula IV, R⁷ is C3-C6 cycloalkyl. In one embodiment, R⁷ is cyclopropyl or cyclobutyl.
In one embodiment of Formula IV, R⁶ is methyl or ethyl and R⁷ is methyl, tetrahydrofuranyl, cyclopropyl or cyclobutyl.

In one embodiment of Formula IV, R⁶ and R⁷ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH₃, —OCHF₂, —OCD₃, —CH₃, —CH₂CH₃, —CH₂OCH₃, —CH₂OCH₂F, —CH₂OCHF₂, —CH₂OCF₃, —OCF₃, —OCH₂CH₃, and CN, (ii) a 6-7 membered fused bicyclic ring optionally substituted with 1 or 2 substituents independently selected from F and —CH₃, (iii) a 6-7 membered bridged ring, and (iv) a 6-8-membered spirocyclic ring.

In one embodiment of Formula IV, R⁶ and R⁷ together with the nitrogen atom to which they are attached form a 4-6 membered monocyclic ring optionally having a second ring heteroatom which is O, wherein said ring is optionally substituted with 1 or 2 substituents independently selected from F, —OH, —OCH₃, —OCF₂H, —OCD₃, —CH₃, —CH₂CH₃, —CH₂OCH₃, —CH₂OCH₂F, —CH₂OCHF₂, —CH₂OCF₃, —OCF₃, —OCH₂CH₃, and CN. Non-limiting examples include the structures:

-continued

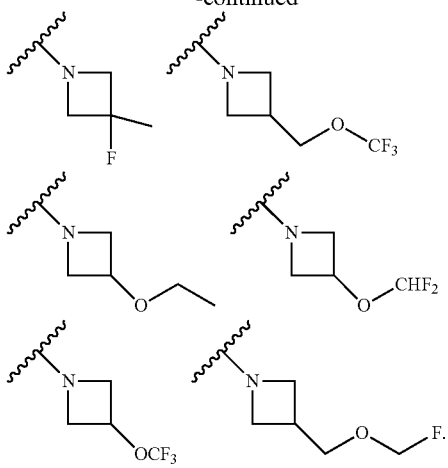

In one embodiment of Formula IV, $R^6$ and $R^7$ together with the nitrogen atom to which they are attached form a saturated 4-6 membered monocyclic ring optionally substituted with F. Examples include the structures:

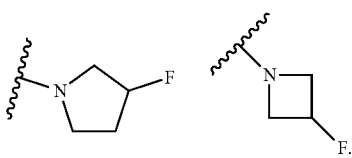 [SMILES: *N1CCC(F)C1 ; *N1CC(F)C1]

In one embodiment of Formula IV, $R^6$ and $R^7$ together with the nitrogen atom to which they are attached form a 6-7 membered fused bicyclic ring optionally substituted with 1 or 2 substituents independently selected from F and —CH$_3$. Non-limiting examples include the structures:

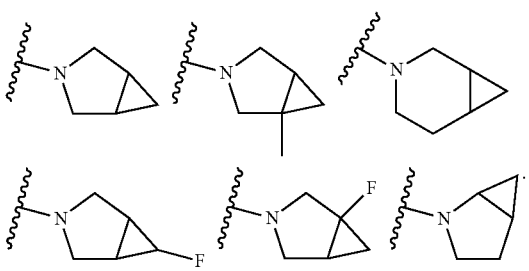

In one embodiment of Formula IV, $R^6$ and $R^7$ together with the nitrogen atom to which they are attached form a 6-7 membered bridged ring. Non-limiting examples include the structures:

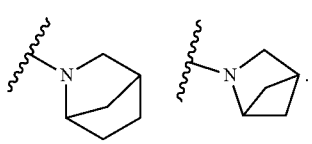

In one embodiment of Formula IV, $R^6$ and $R^7$ together with the nitrogen atom to which they are attached form a 6-8-membered spirocyclic ring. A non-limiting example includes the structure:

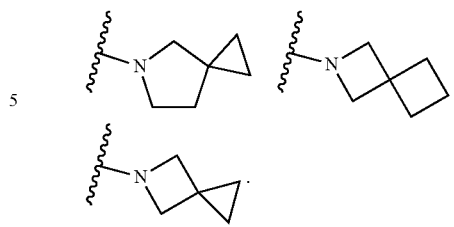

Any of the aforementioned embodiments of Formula IV may be combined with each other.

In one embodiment, provided herein is a compound of Formula V

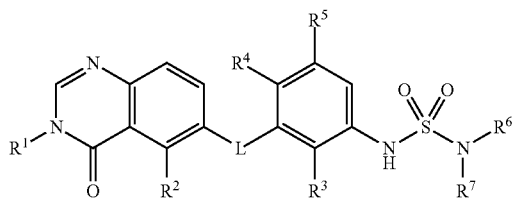

or a pharmaceutically acceptable salt thereof, wherein:
L is NH;
$R^1$ is C1-C6 alkyl;
$R^2$ is F or Cl;
$R^3$ is Cl;
$R^4$ is F;
$R^5$ is H;
$R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, and (iii) a 6-7 membered bridged ring.

In one embodiment of Formula V, $R^6$ and $R^7$ together with the nitrogen atom to which they are attached form a saturated 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN.

In one embodiment of Formula V, $R^6$ and $R^7$ together with the nitrogen atom to which they are attached form a saturated 4-6 membered monocyclic ring, wherein said ring is optionally substituted with 1 or 2 substituents independently selected from F.

In one embodiment of Formula V, $R^6$ and $R^7$ together with the nitrogen atom to which they are attached form a saturated 6-7 membered bridged ring.

In one embodiment of Formula V, $R^1$ is methyl.
In one embodiment of Formula V, $R^3$ is F.
In one embodiment of Formula V, $R^3$ is Cl.
In one embodiment of Formula V, $R^1$ is methyl, $R^3$ is F, and $R^6$ and $R^7$ together with the nitrogen atom to which they are attached form a saturated 4-6 membered monocyclic ring, wherein said ring is optionally substituted with 1 or 2 substituents independently selected from F. In one embodiment, said ring is substituted with one F.

In one embodiment of Formula V, $R^1$ is methyl, $R^3$ is chloro, and $R^6$ and $R^7$ together with the nitrogen atom to which they are attached form a saturated 6-7 membered bridged ring.

The compounds of Formula I, Formula I-A, Formula II, Formula III, Formula IV and Formula V, Formula IV and Formula V include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I, Formula I-A, Formula II, Formula III, Formula IV or Formula V and/or for separating enantiomers of compounds of Formula I, Formula I-A, Formula II, Formula III, Formula IV or Formula V.

The term "pharmaceutically acceptable salt" refers to a conventional acid addition or base addition salt which preserves the biological efficacy and properties of the compounds of formula (I) and which can be formed with suitable non-toxic organic or inorganic acids or organic or inorganic bases. Examples of acid addition salts include salts derived from inorganic acids, such as, but not limited to, hydrochloric acid, hydrobromic acid, hydroiodic acid, sulfuric acid, sulphamic acid, phosphoric acid, nitric acid and perchloric acid and derived from various organic acids, such as, but not limited to, acetic acid, propionic acid, benzoic acid, glycolic acid, phenylacetic acid, salicylic acid, malonic acid, maleic acid, oleic acid, pamoic acid, palmitic acid, benzenesulfonic acid, toluenesulfonic acid, methanesulfonic acid, oxalic acid, tartaric acid, succinic acid, citric acid, malic acid, lactic acid, glutamic acid, fumaric acid and the like. Examples of base addition salts are salts derived from ammonium-, potassium-, sodium- and quaternary ammonium hydroxides such as tetramethylammonium hydroxide. These salts often exhibit more favorable solubility properties than the compounds used for their preparation and are therefore more suitable for use in the preparation of various pharmaceutical formulations.

It will further be appreciated that the compounds of Formula I, Formula I-A, Formula II, Formula III, Formula IV or Formula V or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

The term "solvate" refers to non-covalent stoichiometric or nonstoichiometric combinations of solvent and solute. The term "hydrate" refers to non-covalent stoichiometric or nonstoichiometric combinations of water and solute. For example, compounds of Formula I, Formula I-A, Formula II, Formula III, Formula IV or Formula V or a pharmaceutically acceptable salt or polymorph thereof, can exist in unsolvated as well as solvated forms with pharmaceutically acceptable solvents such as anisole, dichloromethane, toluene, 1,4-dioxane, water, and the like.

Compounds provided herein may contain one or more centers of asymmetry and may therefore be prepared and isolated in a mixture of isomers such as a racemic mixture, or in an enantiomerically pure form. The present invention includes all the individual stereoisomers and geometric isomers of the compounds of the invention and mixtures thereof. Individual enantiomers can be obtained by chiral separation or using the relevant enantiomer in the synthesis. Bonds to a carbon atom of the compounds of the invention may be depicted herein using a solid line (———), a straight thick bar (▬), a straight dashed bar (⦀⦀⦀), a solid wedge (◢◣) or a dashed wedge (⦙⦙⦙⦙). The use of a solid line to depict bonds to asymmetric carbon atoms is meant to indicate that all possible stereoisomers (e.g., specific enantiomers, racemic mixtures, etc.) at that carbon atom are included. The use of either a straight thick bar or straight dashed bar is meant to indicate relative stereochemistry. The use of either a solid wedge or dashed wedge is meant to indicate absolute stereochemistry. For compounds disclosed in the Examples comprising one or more stereocenters, if specific stereochemistry is not shown, the compound is intended to include a mixture of stereoisomers. As used herein, the term "stereocenter" refers to an atom with three or more different attachments, wherein interchanging of two of these attachments leads to another stereoisomer. Examples include, but are not limited to, an $sp^3$ (tetrahedral) carbon atom bearing four different attachments.

The compounds of Formula I, Formula I-A, Formula II, and Formula III may exist in various geometric isomeric forms. In addition, certain compounds of Formula I, Formula I-A, Formula II, Formula III, Formula IV or Formula V may contain one or more asymmetric centers, thus exist in stereoisomeric and diastereomeric forms. The term "stereoisomer" denotes a compound that possesses identical molecular connectivity and bond multiplicity, but which differs in the arrangement of its atoms in space. All of these compounds, such as cis isomers, trans isomers, diastereomeric mixtures, racemates, non-racemic mixtures of enantiomers, substantially pure and pure enantiomers are within the scope of the invention. In one embodiment, the substantially pure enantiomers contain up to 5 wt % of the corresponding opposite enantiomer. In one embodiment, the substantially pure enantiomers contain up to 2 wt % of the corresponding opposite enantiomer. In one embodiment, the substantially pure enantiomers contain up to 1 wt %, of the corresponding opposite enantiomer.

Optical isomers can be prepared by resolving the racemic mixtures by known methods, for example, by using an optically active acid or base to form diastereoisomeric salts or by forming covalent diastereomers. Suitable acids include, for example, tartaric acid, diacetyltartaric acid, dibenzoyltartaric acid, ditoluoyltartaric acid and camphorsulfonic acid. Diastereoisomeric mixtures can be separated into individual diastereomers based on their physical and/or chemical differences, by methods known to those skilled in the art, such as chromatography or fractional crystallization. Subsequently, the optically active bases or acids are liberated from the separated diastereoisomeric salts. Various methods of separating optical isomers include chiral chromatography (e.g., chiral HPLC columns) optionally used by derivatization with the aim to maximize the separation of enantiomers. Appropriate chiral HPLC columns are Diacel columns, such as CHIRALPAK or CHIRALCEL columns, which can be routinely chosen as desired. Where applicable, enzymatic separator carried out by derivatization may also be used. The optically active compounds of Formula I, Formula I-A, Formula II, Formula III, Formula IV or Formula V can also be prepared using optically active starting materials using chiral synthesis without racemization reaction conditions.

Also included are acid addition salts or base addition salts, wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluent affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diastereomeric excess (de).

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form nontoxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, g hydroxy butyrate, iodide, isobutyrate, isothionate, lactate, lactobionate, laurate, malate, maleate, malonate, mandelate, mesylate, metaphosphate, methane sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds useful that are acidic in nature may be capable of forming base salts with various pharmacologically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form nontoxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form nontoxic base salts with such compounds. Such nontoxic base salts include, but are not limited to, those derived from such pharmacologically acceptable cations such as alkali metal cations (e.g., potassium and sodium) and alkaline earth metal cations (e.g., calcium and magnesium), ammonium or water soluble amine addition salts such as N-methylglucamine (meglumine), and the lower alkanolammonium and other base salts of pharmaceutically acceptable organic amines.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley VCH, 2002). Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost nonionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, d6-acetone, d6-DMSO.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Prodrugs as Novel Delivery Systems, Vol. 14, *ACS Symposium Series* (T Higuchi and W Stella); 'Bioreversible Carriers in Drug Design', Pergamon Press, 1987 (ed. E B Roche, American Pharmaceutical Association), and Guarino, V. R; Stella, V. J.: Biotech Pharm. Aspects 2007 5 (Pt2) 133-187, the disclosures of which are incorporated herein by reference in their entireties.

In one embodiment, a compound of Formula I, Formula I-A, Formula II, Formula III, Formula IV or Formula V is a compound selected from Examples 1-164 or a pharmaceutically acceptable salt thereof. In one embodiment, a compound of any one of Examples 1-164 may be in the free base form. In one embodiment, a compound of any one of Examples 1-164 may be in the acid salt form. In one embodiment, certain compounds of Examples 1-164 are isolated as trifluoroacetate salts.

Compounds provided herein may also contain unnatural proportions of atomic isotopes at one or more of the atoms that constitute such compounds. That is, an atom, in particular when mentioned in relation to a compound according to Formula I, Formula I-A, Formula II, Formula III, Formula IV and Formula V, comprise all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}$, $^{16}O$, $^{17}O$, $^{18}O$ or mixtures thereof; and when fluoro is mentioned, it is understood to refer to $^{18}F$, $^{19}F$ or mixtures thereof. As noted above, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention. Certain isotopically labeled compounds of the invention, for example those into which radioactive isotopes such as $^3H$ and $^{14}C$ are incorporated, are useful in drug and/or substrate tissue distribution assays. Tritiated, i.e., $^3H$, and carbon 14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the invention may generally be prepared by carrying out the procedures disclosed in the Schemes and/or in the Examples and Preparations below, by substituting an isotopically labeled reagent for a non-isotopically labeled reagent.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, *ACS Symposium Series* (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with (C1-C8)alkyl;

(ii) where the compound contains an alcohol functionality (—OH), an ether thereof, for example, replacement of the hydrogen with (C1-C6)alkanoyloxymethyl, or with a phosphate ether group; and (iii) where the compound contains a primary or secondary amino functionality (—NH2 or —NHR where $R^1H$), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug.

For illustrative purposes, Schemes 1-10 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions.

In addition, many of the compounds prepared by the methods described below can be further modified in light of this disclosure using conventional chemistry well known to those skilled in the art.

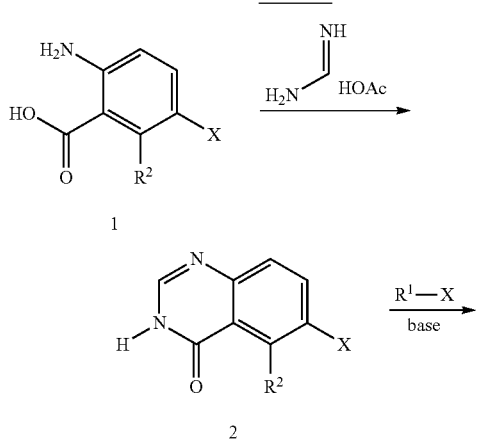

Scheme 1

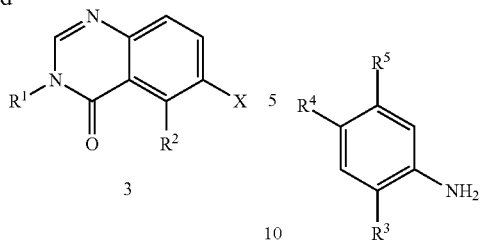

3

Scheme 1 describes the synthesis of intermediate 3 wherein X is halogen, which is useful for preparing compounds of Formula I wherein $R^1$ and $R^2$ are as defined for Formula I. Compound 1 may be cyclized with formamidine acetate in an organic solvent, such as EtOH, at elevated temperature to provide compound 2. Compound 2 may be alkylated with a reagent having the formula $R^1 X$ wherein $R^1$ is as defined for Formula I and X is halogen, in the presence of a base such as $Cs_2CO_3$, in a solvent, such as DMF to provide compound 3.

Scheme 2

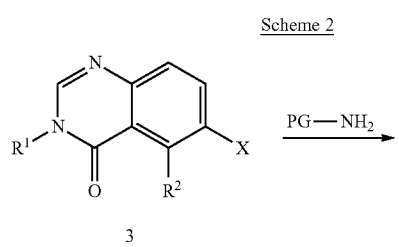

Scheme 2 describes the synthesis of intermediate 5, which is useful for preparing compounds of Formula I wherein $R^1$ and $R^2$ are as defined for Formula I and L is NH. Compound 3 (prepared e.g., according to Scheme 1) may be coupled with a reagent having the formula $(PG)NH_2$ wherein PG is an amine protecting group (such as p-methoxybenzyl (PMB) or tert-butoxycarbonyl (Boc)) in the presence of a catalyst, such as a palladium catalyst (e.g., $Pd_2(dba)_3$) and a ligand (e.g., Xantphos) to provide compound 4. Compound 4 may be deprotected under standard conditions, for example using TFA, to provide compound 5.

Scheme 3

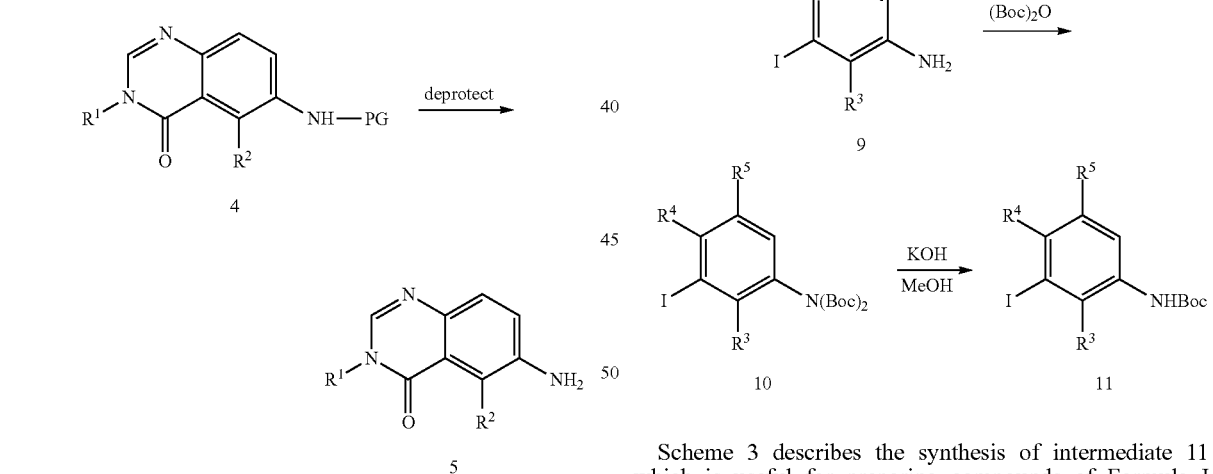

Scheme 3 describes the synthesis of intermediate 11 which is useful for preparing compounds of Formula I wherein $R^3$, $R^4$ and $R^5$ are defined for Formula I. Compound 6 (wherein $R^3$, $R^4$ and $R^5$ are as defined for Formula I) may be reacted with 1,2-bis(chlorodimethylsilyl)ethane in the presence of a strong base, such as n-butyllithium, in a suitable solvent, such as THF, at low temperatures, e.g., −78° C., to form the 1-aza-2,5-disilacyclopentane compound 7. Compound 7 may be reacted with iodine, in the presence of, for example, n-butyllithium or a comparable agent in a suitable solvent, such as THF, to provide compound 8. Compound 8 may be deprotected by reaction with an acid, such as HCl, in a suitable solvent, to provide compound 9. Compound 9 maybe reacted with di-tert-butyl dicarbonate $((Boc)_2O)$ in the presence of a catalyst, such as 4-dimethylaminopyridine (DMAP), in a suitable solvent, such as THF, to provide compound 10. Compound 10 may be deprotected in the presence of a base, such as K$_2$CO$_3$, in a suitable solvent, such as MeOH, to provide compound 11.

and R$^7$ are as defined for Formula I. Amine 14 may be coupled with sulfuryl dichloride 15 in the presence of a base, such as TEA, in a suitable solvent, such as DCM, to provide compound 16.

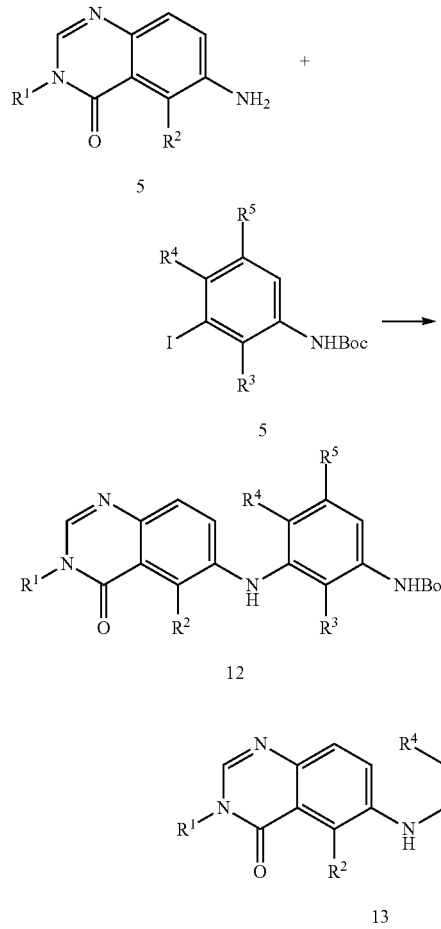

Scheme 4

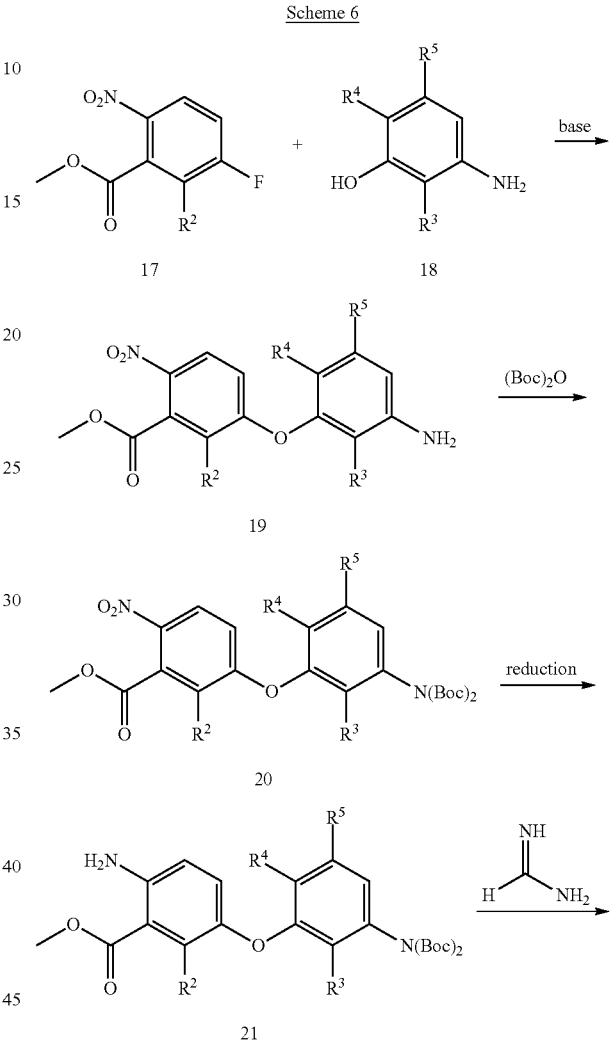

Scheme 6

Scheme 4 describes the synthesis of compound 13, which is an intermediate useful for preparing compounds of Formula I wherein R$^1$, R$^2$, R$^3$, R$^4$ and R$^5$ are as defined for Formula I and L is NH. Compound 5 (prepared e.g., according to Scheme 2) may be coupled with compound 11 (prepared, e.g., according to Scheme 3) in the presence of a catalyst (e.g., a palladium catalyst, e.g., Pd$_2$(dba)$_3$) and a ligand (e.g., Xantphos) followed by deprotection under standard conditions (e.g. with TFA), to provide compound 13.

Scheme 5

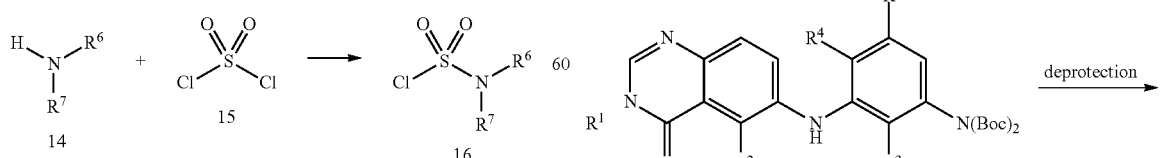

Scheme 5 describes the synthesis of compound 16, which is useful for preparing compounds of Formula I wherein R$^6$ -continued

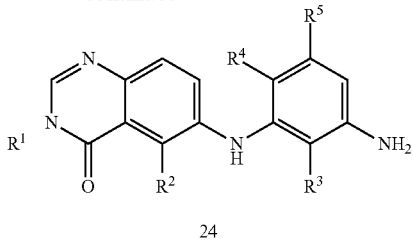

24

Scheme 6 describes the synthesis of a compound of Formula 24, which is useful for preparing compounds of Formula I wherein $R^1$, $R^2$, $R^3$, $R^4$ and $R^5$ are as defined for Formula I and L is O. Compound 17 (wherein $R^2$ is as defined for Formula I) may be coupled with compound 18, wherein $R^3$, $R^4$ and $R^5$ are as defined for Formula I, in a suitable solvent, such as DMSO, in the presence of a base, such as $Cs_2CO_3$, at elevated temperature to provide compound 19. Compound 19 maybe reacted with $(Boc)_2O$ in the presence of a catalyst, such as DMAP, in a suitable solvent, such as THF, to provide compound 20. The nitro group of compound 20 may be reduced under standard nitro reduction conditions, such as treatment with Fe and $NH_4Cl$ to provide compound 21. Compound 21 may be cyclized with formamidine acetate in an organic solvent, such as EtOH, at elevated temperature to provide compound 22. Compound 22 may be alkylated with a reagent having the formula $R^1 X$ wherein $R^1$ is as defined for Formula I and X is halogen, in the presence of a base such as $Cs_2CO_3$, in a solvent, such as DMF to provide compound 23. Compound 23 may be deprotected under standard conditions (e.g. with TFA), to provide compound 24.

Scheme 7

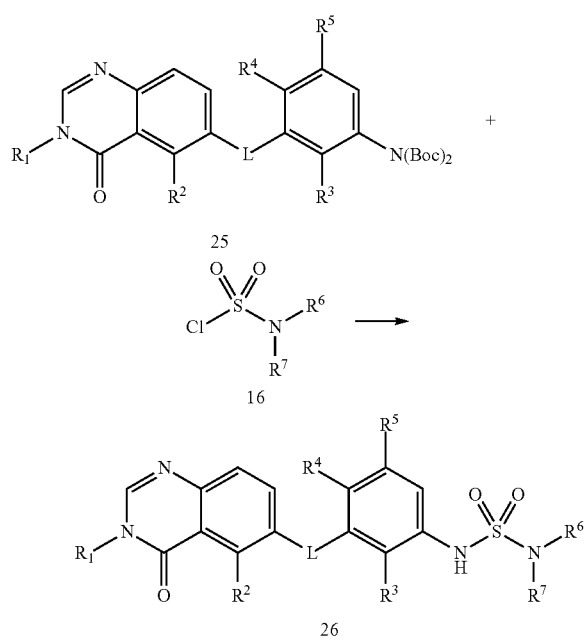

Scheme 7 describes the synthesis of a compound of Formula 26, which is a compound of Formula I wherein $R^1$, $R^2$, $R^3$, $R^4$, $R^5$, $R^6$ and $R^7$ are as defined for Formula I and L is NH (e.g., prepared according to Scheme 4) or O (e.g., prepared according to Scheme 6). Compound 25 may be coupled with compound 16 in the presence of a suitable base, such as pyridine, or in the presence of calcium triflimide in an organic solvent, such as toluene, at elevated temperatures, to provide compound 26.

Scheme 8

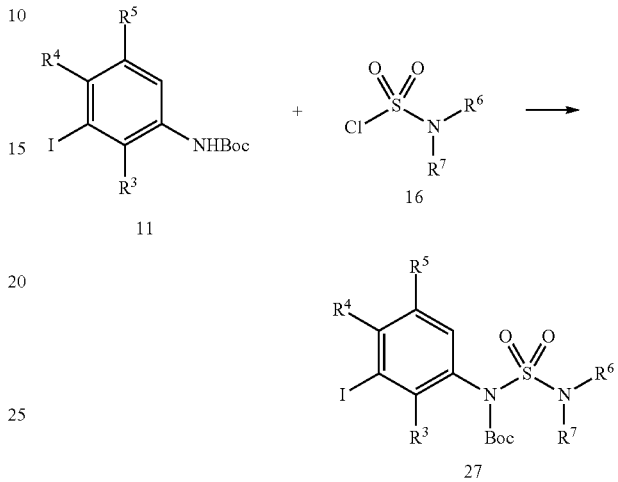

Scheme 8 describes the synthesis of compound 27, which is useful for preparing compounds of Formula I wherein $R^3$, $R^4$, $R^5$, $R^6$ and $R^7$ are as defined for Formula I. Amine 11, wherein $R^3$, $R^4$, $R^5$, $R^6$ and $R^7$ are as defined for Formula I, may be coupled with sulfamide chloride 16 wherein $R^6$ and $R^7$ are as defined for Formula I in the presence of a base, such as NaH, in a suitable solvent, such as THF, to provide compound 27.

Scheme 9

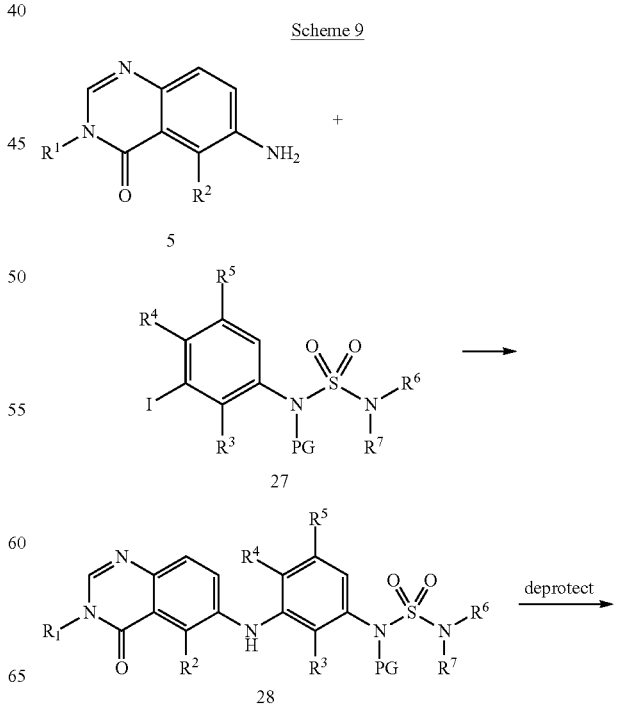

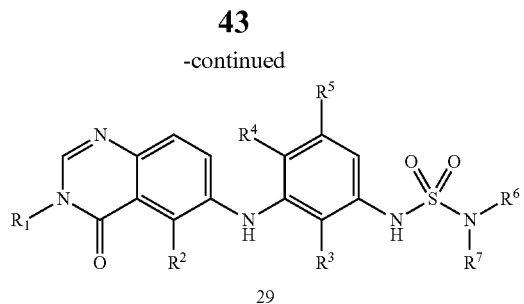

29

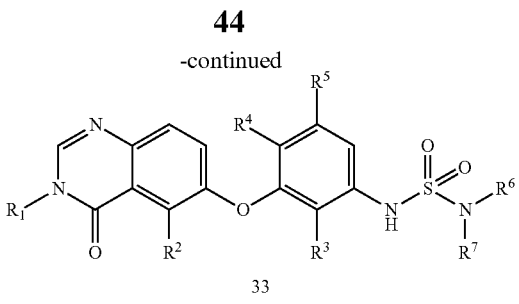

33

Scheme 9 describes the synthesis of a compound of Formula 29, which is a compound of Formula I wherein $R^1$, $R^2$, $R^3$, $R^4$, $R^5$, $R^6$ and $R^7$ are as defined for Formula I. Compound 5 (prepared e.g., according to Scheme 2), wherein $R^1$ and $R^2$ are as defined for Formula I, may be coupled with compound 27 (prepared, e.g., according to Scheme 8), wherein $R^3$, $R^4$, $R^5$, $R^6$ and $R^7$ are as defined for Formula I and PG is an amine protecting group (such as p-methoxybenzyl (PMB) or tert-butoxycarbonyl (Boc)), in the presence of a catalyst (e.g., a palladium catalyst, e.g., $Pd_2(dba)_3$) and a ligand (e.g., Xantphos) followed by deprotection under standard conditions (e.g. with TFA), to provide compound 29.

Scheme 10 describes the synthesis of compound 33, which is a compound of Formula I wherein $R^1$, $R^2$, $R^3$, $R^4$ and $R^5$ are as defined for Formula I and L is O. The amine group of compound 24 (wherein $R^1$, $R^2$, $R^3$, $R^4$ and $R^5$ are as defined for Formula I) may be di-protected with a suitable amine protecting group (e.g., p-methoxybenzyl (PMB) or tert-butoxycarbonyl (Boc)) by reacting with a suitable reagent (e.g., by reacting with $(Boc)_2O$ in the presence of a catalyst, such as DMAP, in a suitable solvent, such as THF), to provide compound 30 wherein PG is an amine protecting group (e.g., p-methoxybenzyl (PMB) or tert-butoxycarbonyl (Boc). Compound 30 may be deprotected under suitable conditions (e.g., in the presence of $K_2CO_3$ in an organic solvent, such as MeOH, at elevated temperature) to provide the mono-protected compound 31. Compound 31 may be coupled with sulfamoyl chloride 16 in the presence of a base, such as NaH, in a suitable solvent, such as THF, to provide compound 32. Compound 32 may be deprotected under standard conditions (e.g. with TFA), to provide compound 33.

The processes shown in Schemes 1-10 are useful for preparing compounds of Formulas II, III and IV as well as preparing intermediates useful for preparing compounds of Formulas II, III and IV.

In one embodiment, provided herein is a process for preparing of a compound of Formula I or a pharmaceutically acceptable salt thereof which comprises:

(a) for a compound of Formula I wherein L, $R^1$, $R^2$, $R^3$, $R^4$, $R^5$, $R^6$ and $R^7$ are as defined for Formula I, coupling a compound having the formula (25)

Scheme 10

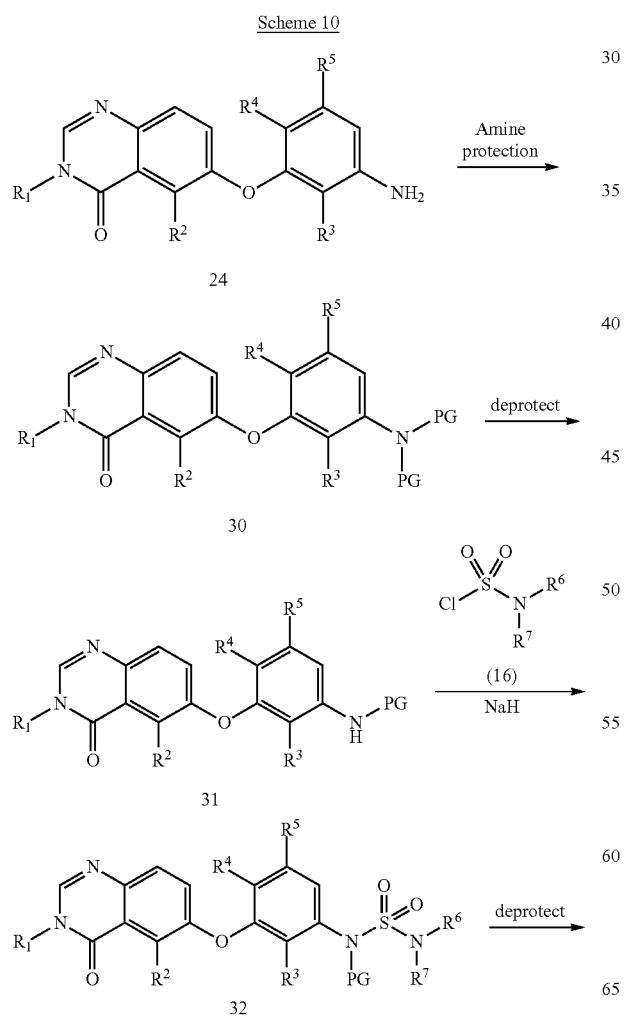

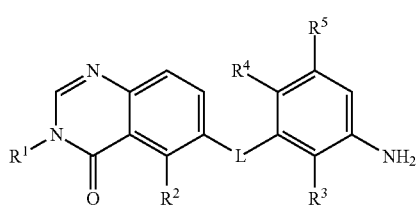

25 wherein L, $R^1$, $R^2$, $R^3$, $R^4$ and $R^5$ are as defined for Formula I, with a compound having the formula (16)

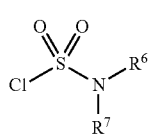

16 wherein $R^6$ and $R^7$ are as defined for Formula I, in the presence of a suitable base; or (b) for a compound of Formula I wherein $R^1$, $R^2$, $R^3$, $R^4$ and $R^5$ are as defined for Formula I and L is NH, reacting a compound of formula (5)

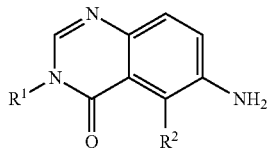

5 wherein $R^1$ and $R^2$ are as defined for Formula I, with a compound having the formula (27)

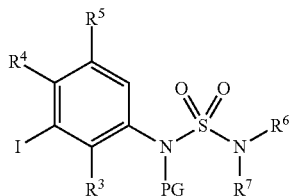

27 wherein $R^3$, $R^4$, $R^5$, $R^6$, and $R^7$ are as defined for Formula I and PG is an amine protecting group, in the presence of a palladium catalyst and a ligand, followed by removal of the amine protecting group; or (c) for a compound of Formula I wherein $R^1$, $R^2$, $R^3$, $R^4$ and $R^5$ are as defined for Formula I and L is O, reacting a compound having the formula (31)

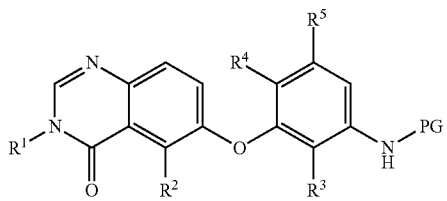

31 wherein $R^1$, $R^2$, $R^3$, $R^4$ and $R^5$ are as defined for Formula I and PG is an amine protecting group, with a reagent having the formula

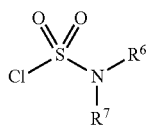

in the presence of a base, followed by removal of the amine protecting group; and optionally forming a pharmaceutically acceptable salt thereof.

Compounds of formulas 3, 5, 12, 13, 19, 20, 21, 22, 23, 24, 25, 28, 21 and 32 are synthetic intermediates useful for the preparation of compounds of Formula I, and are a further aspect of this invention.

The term "amine protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amine protecting groups are t-butyloxycarbonyl ("Boc"), 2-trimethylsilylethoxymethyl (SEM), and p-methoxybenzyl (PMB). Further examples of these groups, and other protecting groups, are found in T. W. Greene, et al., *Greene's Protective Groups in Organic Synthesis*. New York: Wiley Interscience, 2014.

Compounds of Formula I, Formula I-A, Formula II, Formula III, Formula IV and Formula V or a pharmaceutically acceptable salt thereof are useful for treating diseases and disorders which can be treated with a BRAF kinase inhibitor, such as BRAF-associated diseases and disorders, e.g., proliferative disorders such as cancers, including solid tumors. The ability of test compounds to act as BRAF inhibitors may be demonstrated by the enzyme assay described in Example A1, the cell assay described in Example A2, the cellular assay described in Example A3, and the proliferation assay described in Example A4. $IC_{50}$ values are shown in Tables A1 and A2.

In some embodiments, certain compounds of Formula I, Formula I-A, Formula II, Formula III, Formula IV and Formula V, or a pharmaceutically acceptable salt thereof, exhibit surprising brain and/or CNS penetrance. Such compounds are capable of crossing the BBB and inhibiting a BRAF kinase in the brain and/or other CNS structures. In some embodiments, the compounds provided herein are capable of crossing the BBB in a therapeutically effective amount. For example, treatment of a subject with cancer (e.g., a BRAF-associated cancer such as a BRAF-associated CNS cancer) can include administration (e.g., oral administration) of a compound of Formula I, Formula I-A, Formula II, Formula III, Formula IV, or Formula V, or a pharmaceutically acceptable salt thereof to the subject. Accordingly, in some embodiments, compounds provided herein are useful for treating a CNS cancer.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. However, "treat" or "treatment" can also include therapeutic measures (e.g., inhibition of BRAF kinase in a BRAF-associated tumor) that temporarily worsen the appearance and/or symptoms of the subject. As used herein, the terms "treating" and "treating" when referring, e.g., to the treatment of a cancer, are not intended to be absolute terms. For example, "treatment of cancer" and "treating cancer", as used in a clinical setting, is intended to include obtaining beneficial or desired clinical results and can include an improvement in the condition of a subject having cancer. Beneficial or desired clinical results include, but are not limited to, one or more of the following: reducing the proliferation of (or destroying) neoplastic or cancerous cells, inhibiting metastasis of neoplastic cells, a decrease in metastasis in a subject, shrinking or decreasing the size of a tumor, change in the growth rate of one or more tumor(s) in a subject, an increase in the period of remission for a subject (e.g., as compared to the one or more metric(s) in a subject having a similar cancer receiving no treatment or a different treatment, or as compared to the one or more metric(s) in the same subject prior to treatment), decreasing symptoms resulting from a disease, increasing the quality of life of those suffering from a disease (e.g., assessed using FACT-G or EORTC-QLQC30), decreasing the dose of other medications required to treat a disease, delaying the progression of a disease, and/or prolonging survival of subjects having a disease. "Treatment" can also mean prolonging survival as compared to expected survival if not receiving treatment, for example, an increase in overall survival (OS) compared to a subject not receiving treatment as described herein, and/or an increase in progression-free survival (PFS) compared to a subject not receiving treatment as described herein.

As used herein, the term "subject" refers to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented. In some embodiments, the subject has been identified or diagnosed as having a tumor with a BRAF mutation (a BRAF-associated tumor) (e.g., as determined using a regulatory agency-approved, e.g., FDA-approved, assay or kit). In some embodiments, the subject has a tumor that is positive for a BRAF mutation (e.g., as determined using a regulatory agency-approved assay or kit). The subject can be a subject whose tumors have a BRAF mutation (e.g., where the tumor is identified as such using a regulatory agency-approved, e.g., FDA-approved, kit or assay). In some embodiments, the subject is suspected of having a BRAF-associated tumor. In some embodiments, the subject has a clinical record indicating that the subject has a tumor that has a BRAF mutation (and optionally the clinical record indicates that the subject should be treated with any of the compositions provided herein). In some embodiments, the subject is a human. In some embodiments, the human subject is a pediatric subject.

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E, *Nelson Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I, Formula I-A, Formula II, Formula III, Formula IV, or Formula V, or a pharmaceutically acceptable salt thereof are useful for preventing diseases and disorders as defined herein. The term "preventing" as used herein means the prevention of the onset, recurrence or spread, in whole or in part, of the disease or condition as described herein.

The term "BRAF-associated" with respect to a disease or disorder as used herein refers to diseases or disorders associated with or having one or more BRAF mutations and/or BRAF fusions. Non-limiting examples of a BRAF-associated disease or disorder include, for example, BRAF-associated tumors.

The phrase "BRAF mutation" refers to a genetic mutation (e.g., a chromosomal translocation that results in one or more mutations in a BRAF gene that results in the expression of a BRAF protein with one or more point mutations as compared to a wild type BRAF protein), or an alternative spliced version of a BRAF mRNA that results in a BRAF protein having a deletion of at least one amino acid in the BRAF protein as compared to the wild-type BRAF protein (i.e., a splice variant). Non-limiting examples of BRAF mutations include Class I BRAF mutations (e.g., BRAF V600 mutations, e.g., BRAF V600E and BRAF V600K), Class II BRAF mutations (e.g., BRAF non-V600 mutations and BRAF splice variants) and BRAF Class III mutations.

The term "Class I BRAF mutations" refers to BRAF V600 mutations which signal as Ras-independent active monomers. Examples include BRAF V600E and BRAF V600K mutations.

The term "Class II BRAF mutations" includes (i) BRAF non-V600 mutations which function as RAS-independent activated dimers of BRAF and/or CRAF and (ii) BRAF splice variants which are dependent on dimerization for activity in a RAS-independent fashion.

Examples of BRAF non-V600 (Class II) mutations include G469A, G469R, G469V, K601E, K601N, K601T, L597Q and L597V. In one embodiment, the BRAF non-V600 mutation is G469A.

The term "BRAF splice variant" refers to aberrantly spliced BRAF V600E isoforms. BRAF splice variants are BRAF V600E resistance mutations that lack exons encoding part of the RAS-binding domain and exhibit enhanced dimerization in cells with low levels of RAS activation (Poulikakos et al., *Nature,* 480(7377):387-390. Examples of BRAF V600E splice variants include those lacking exons 4-8 (also known as p61BRAF(V600E)), exons 4-10, exons 2-8 or exons 2-10. In one embodiment, the resistance mutation is p61BRAF(V600E).

The term "resistance mutation" refers to a mutation in a BRAF V600E mutation that results after exposure of the BRAF V600E mutant to a BRAF inhibitor, either alone or in combination with another anticancer agent such as a MEK inhibitor. Tumors having resistance mutations become less sensitive to (e.g., resistant to treatment with) BRAF inhibitor. In one embodiment, the resistance mutation results after exposure to vemurafenib.

The term "Class III BRAF mutations" refers to BRAF non-V600 mutations which function as RAS-dependent activated dimers of BRAF and/or CRAF. Non-limiting examples of BRAF Class III mutations include G466A, G466E, G466R, G466V, D594A, D594E, D594G, D594H, G594N, D287H, V549L, S467A, S467E, S467L, G469E, N581S, N581I, F595L, G596A, G596C, G596D, G596R, and K483M.

The term "BRAF fusion" refers to a BRAF gene translocation that results in the expression of a fusion protein. In one embodiment, a BRAF-associated tumor or BRAF-associated cancer has one or more BRAF fusions that lead to constitutive kinase activation and transformation, including but not limited to KIAA11549-BRAF, MKRN1-BRAF, TRIM24-BRAF, AGAP3-BRAF, ZC3HAV1-BRAF, AKAP9-BRAF, CCDC6-BRAF, AGK-BRAF, EPS15-BRAF, NUP214-BRAF, ARMC10-BRAF, BTF3L4-BRAF, GHR-BRAF, ZC3HAV1-BRAF, ZNF767-BRAF, CCDC91-BRAF, DYNC112-BRAF, ZKSCAN1-BRAF, GTF21-BRAF, MZT1-BRAF, RAD18-BRAF, CUX1-BRAF, SLC12A7-BRAF, MYRIP-BRAF, SND1-BRAF, NUB1-BRAF, KLHL7-BRAF, TANK-BRAF, RBMS3-BRAF, STRN3-BRAF, STK35-BRAF, ETFA-BRAF, SVOPL-BRAF, JHDM1D-BRAF, or BCAP29-BRAF.

The term "BRAF-associated tumor" or "BRAF-associated cancer" as used herein refers to tumors or cancers associated with or having a BRAF mutation and includes tumors having a Class I BRAF V600 mutation, e.g., a BRAF V600E or V600K, mutation, and tumors having a Class II BRAF mutation. BRAF-associated tumors include both benign BRAF-associated tumors and malignant BRAF-associated tumors (i.e., BRAF-associated cancers).

The term "tumor" as used herein refers to an abnormal growth of tissue that arises from uncontrolled usually rapid cellular proliferation. The tumor may be a benign tumor (non-cancerous) or a malignant tumor (i.e., cancer). The tumor may be a solid tumor or a liquid tumor (i.e., a hematologic tumor, also known as blood cancer).

The term "wild type" describes a nucleic acid (e.g., a BRAF gene or a BRAF mRNA) that is typically found in a subject that does not have a disease or disorder related to the reference nucleic acid or protein.

The term "wild type BRAF" describes a BRAF nucleic acid (e.g., a BRAF gene or a BRAF mRNA) or a BRAF protein that is found in a subject that does not have a BRAF-associated disease, e.g., a BRAF-associated cancer (and optionally also does not have an increased risk of developing a BRAF-associated disease and/or is not suspected of having a BRAF-associated disease), or is found in a cell or tissue from a subject that does not have a BRAF-associated disease, e.g., a BRAF-associated cancer (and optionally also does not have an increased risk of developing a BRAF-associated disease and/or is not suspected of having a BRAF-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating a BRAF-associated tumor in a subject in need of such treatment, the method comprising administering to the subject a therapeutically effective amount of a compound of Formula I, Formula I-A, Formula II, Formula III, Formula IV or Formula V, or a pharmaceutically acceptable salt thereof, or a pharmaceutical composition thereof. For example, provided herein are methods for treating a BRAF-associated tumor in a subject in need of such treatment, the method comprising a) detecting a BRAF mutation in a sample from the subject; and b) administering a therapeutically effective amount of a compound of Formula I, Formula I-A, Formula II, Formula III, Formula IV or Formula V, or a pharmaceutically acceptable salt thereof. In some embodiments, the BRAF mutation is a Class I mutation. In some embodiments, the Class I BRAF mutation is BRAFV600E. In some embodiments, the BRAF mutation is a Class II mutation. In some embodiments, the Class II mutation is a non-V600 mutation. In some embodiments, the non-V600 mutation is G469A. In some embodiments, the Class II mutation is a BRAF V600E splice variant. In some embodiments, the BRAF V600E splice variant is p61BRAF(V600E).

In some embodiments of any of the methods of use described herein, the BRAF-associated tumor is a solid tumor. In some embodiments, the tumor is intracranial. In some embodiments, the tumor is extracranial. In some embodiments of any of the methods of uses described herein, the BRAF-associated tumor is a malignant BRAF-associated tumor (i.e., a BRAF-associated cancer). In some embodiments of any of the methods of use described herein, the cancer is melanoma, colon cancer, colorectal cancer, lung cancer (e.g., small cell lung cancer or non-small cell lung cancer), thyroid cancer (e.g., papillary thyroid cancer, medullary thyroid cancer, differentiated thyroid cancer, recurrent thyroid cancer, or refractory differentiated thyroid cancer), breast cancer, bladder cancer, ovarian cancer (ovary carcinoma), cancer of the CNS (including gliomas and LMDs), bone cancer, cancer of the anus, anal canal, or anorectum, angiosarcoma, adenoid cystic carcinoma, appendiceal cancer, cancer of the eye, bile duct cancer (cholangiocarcinoma), cervical cancer, ductal carcinoma in situ, endometrial cancer, gallbladder, hepatobiliary cancer, hepato-pancreato-biliary carcinoma, head and neck squamous cell carcinoma, oral cancer, oral cavity cancer, leukemia, lip cancer, oropharyngeal cancer, cancer of the nose, nasal cavity or middle ear, cancer of the vulva, esophageal cancer, esophagogastric cancer, cervical cancer, gastrointestinal carcinoid tumor, gastrointestinal neuroendocrine cancer, hypopharynx cancer, kidney cancer, larynx cancer, liver cancer, nasopharynx cancer, non-Hodgkin's lymphoma, peripheral nervous system cancers (e.g., neuroblastoma), neuroendocrine cancer, pancreatic cancer, peritoneum, plasma cell neoplasm, omentum, and mesentery cancer, pharynx cancer, prostate cancer, renal cancer (e.g., renal cell carcinoma (RCC)), small bowel cancer, small intestine cancer, soft tissue sarcoma, stomach cancer, testicular cancer, uterine cancer, ureter cancer, or urinary bladder cancer.

In one embodiment, the BRAF-associated cancer is a CNS cancer, melanoma, colorectal cancer, thyroid cancer, non-small cell lung cancer, ovarian cancer, renal cell carcinoma, or a primary brain tumor.

In some embodiments, the BRAF-associated cancer is an extracranial cancer selected from melanoma, colorectal cancer, thyroid cancer, non-small cell lung cancer, ovarian cancer, and neuroblastoma. In some embodiments, the BRAF-associated cancer is melanoma. In some embodiments, the BRAF-associated cancer is colorectal cancer. In some embodiments, the BRAF-associated cancer is thyroid cancer. In some embodiments, the BRAF-associated cancer is non-small cell lung cancer. In some embodiments, the BRAF-associated cancer is ovarian cancer. In some embodiments, the BRAF-associated cancer is neuroblastoma.

In some embodiments, the BRAF-associated cancer is an intracranial cancer (brain cancer). In some embodiment, the BRAF-associated cancer is a CNS cancer.

In some embodiments, the BRAF-associated cancer is a cancer having a BRAF Class I mutation. In some embodiments, the BRAF-associated cancer is a cancer having a BRAF V600E or BRAF V600K mutation. In some embodiments, the BRAF-associated cancer having a BRAF V600E or BRAF V600K mutation is selected from melanoma, colorectal cancer, thyroid cancer, non-small cell lung cancer, ovarian cancer, renal cell carcinoma, and metastatic cancers thereof, and primary brain tumors. In some embodiments, the BRAF-associated cancer having a BRAF V600E or BRAF V600K mutation is a CNS tumor. In some embodiments, the CNS tumor is a malignant tumor (a CNS cancer). In some embodiments, the malignant tumor is a metastatic CNS cancer. In some embodiments, the metastatic CNS cancer is selected from metastatic melanoma, metastatic colorectal cancer, metastatic non-small cell lung cancer, metastatic thyroid cancer, and metastatic ovarian cancer. In some embodiments, the CNS tumor is intracranial LMD or extracranial LMD.

In some embodiments, the BRAF-associated cancer is a cancer having a BRAF Class II mutation. In one embodiment, the cancer having a BRAF Class II mutation is selected from lung cancer (e.g., non-small cell lung cancer), melanoma, colorectal cancer, breast cancer, pancreatic cancer, thyroid cancer, prostate cancer, adenoid cystic carcinoma, appendiceal cancer, small intestine cancer, gastrointestinal neuroendocrine cancer, head and neck squamous cell carcinoma, angiosarcoma, bladder cancer, plasma cell neoplasm, hepatobiliary cancer, hepato-pancreato-biliary carcinoma, ovarian cancer, endometrial cancer, neuroendocrine cancer, cholangiocarcinoma, esophagogastric cancer, soft tissue sarcoma, leukemia, non-Hodgkin's lymphoma, and CNS cancers (e.g., gliomas). In one embodiment, the cancer has a BRAF G469A mutation.

In some embodiments, the BRAF-associated cancer is a cancer having a BRAF Class III mutation, In one embodiment, the cancer having a BRAF class III mutation is selected from melanoma, small bowel cancer, colorectal cancer, non-small cell lung cancer, endometrial cancer, cervical cancer, leukemia, bladder cancer, non-Hodgkin's lymphoma, glioma, ovarian cancer, prostate cancer, hepatobiliary cancer, esophagogastric cancer, soft tissue sarcoma, and breast cancer. In one embodiment, the cancer has a BRAF G466V or BRAF D594G mutation. In one embodiment, the cancer has a BRAF G466V mutation. In one embodiment, the cancer has a BRAF D594G mutation.

In one embodiment, the BRAF-associated tumor has a BRAF-fusion protein, wherein the tumor is breast carcinoma (e.g., breast invasive ductal carcinoma) colorectal carcinoma (e.g., colon adenocarcinoma), esophageal carcinoma (e.g., esophagus adenocarcinoma), glioma (e.g., brain desmoplastic infantile ganglioglioma, brain pilocytic astrocytoma, brain pleomorphic xanthoastrocytoma, spinal cord low-grade glioma (NOS), anaplastic oligodendroglioma, anaplastic ganglioglioma), head & neck carcinoma (e.g., head and neck neuroendocrine carcinoma), lung carcinoma (e.g., lung adenocarcinoma, lung non-small-cell lung cancer (NOS)), melanoma (e.g., cutaneous melanoma Spitzoid, mucosal melanoma non-Spitzoid, cutaneous melanoma Spitzoid, unknown primary melanoma, cutaneous melanoma non-Spitzoid), pancreatic carcinoma (e.g., adenocarcinoma, pancreas acinar cell carcinoma), prostatic carcinoma (e.g., prostate acinar adenocarcinoma), sarcoma (malignant solid fibrous tumor), thyroid carcinoma (thyroid papillary carcinoma), unknown primary carcinoma (e.g., unknown primary, adenocarcinoma), pleura mesothelioma, rectum adenocarcinoma, uterus endometrial carcinoma (e.g., uterus endometrial adenocarcinoma (NOS)) or ovary serous carcinoma.

In one embodiment, the BRAF-associated cancer is selected from the cancers having the BRAF-fusion proteins described in Table 1 (J. S. Ross, et al., *Int. J. Cancer:* 138, 881-890 (2016)).

TABLE 1

Exemplary BRAF Fusion Partners and Cancers

| Tumor group | histology | tumor type | fusion |
|---|---|---|---|
| breast carcinoma | | | BCAP29-BRAF |
| breast carcinoma | breast carcinoma | metastatic | KIAA11549-BRAF |
| colorectal carcinoma | colon adenocarcinoma | primary | MKRN1-BRAF |
| colorectal carcinoma | colon adenocarcinoma | metastatic | TRIM24-BRAF |
| colorectal carcinoma | colon adenocarcinoma | primary | AGAP3-BRAF |
| esophageal carcinoma | esophagus adenocarcinoma | primary | ZC3HAV1-BRAF |
| glioma | brain desmoplastic infantile ganglioglioma | primary | KIAA11549-BRAF |
| glioma | brain pilocytic astrocytoma | primary | KIAA11549-BRAF |
| glioma | brain pleomorphic xanthoastrocytoma | primary | KIAA11549-BRAF |
| glioma | spinal cord low-grade glioma (NOS) | primary | KIAA11549-BRAF |
| glioma | brain pilocytic astrocytoma | primary | AKAP9-BRAF |
| glioma | brain pleomorphic xanthoastrocytoma | primary | CCDC6-BRAF |
| glioma | brain pleomorphic xanthoastrocytoma | primary | AGK-BRAF |
| glioma | not pilocytic; anaplastic oligodendroglioma | primary | AGK-BRAF |
| glioma | not pilocytic; anaplastic ganglioglioma | primary | KIAA11549-BRAF |
| head & neck carcinoma | head and neck neuroendocrine carcinoma | primary | MKRN1-BRAF |
| lung carcinoma | lung adenocarcinoma | metastatic | EPS15-BRAF |
| lung carcinoma | lung non-small cell lung cancer (NOS) | primary | NUP214-BRAF |
| lung carcinoma | lung adenocarcinoma | primary | ARMC10-BRAF |
| lung carcinoma | lung adenocarcinoma | primary | BTF3L4-BRAF |
| lung carcinoma | lung adenocarcinoma | primary | AGK-BRAF |
| lung carcinoma | lung adenocarcinoma | metastatic | GHR-BRAF |
| lung carcinoma | lung adenocarcinoma | primary | ZC3HAV1-BRAF |
| lung carcinoma | lung non-small cell lung cancer (NOS) | primary | TRIM224-BRAF |
| melanoma | cutaneous melanoma Spitzoid | primary | TRIM24-BRAF |

TABLE 1-continued

Exemplary BRAF Fusion Partners and Cancers

| Tumor group | histology | tumor type | fusion |
|---|---|---|---|
| melanoma | mucosal melanoma non-Spitzoid | metastatic | ZNF767-BRAF |
| melanoma | cutaneious melanoma non-Spitzoid | metastatic | CCDC91-BRAF |
| melanoma | cutaneous melanoma Spitzoid | primary | DYNC1I2-BRAF |
| melanoma | cutaneous melanoma Spitzoid | metastatic | AKAP9-BRAF |
| melanoma | cutaneous melanoma Spitzoid | metastatic | ZKSCAN1-BRAF |
| melanoma | unknown primary melanoma | metastatic | GTF2I-BRAF |
| melanoma | cutaneous melanoma non-Spitzoid | metastatic | AGAP3-BRAF |
| melanoma | cutaneous melanoma Spitzoid | metastatic | AGK-BRAF |
| melanoma | cutaneous melanoma Spitzoid | metastatic | MZT1-BRAF |
| melanoma | cutaneious melanoma non-Spitzoid | primary | RAD18-BRAF |
| melanoma | cutaneous melanoma Spitzoid | metastatic | CUX1-BRAF |
| melanoma | cutaneous melanoma Spitzoid | metastatic | SLC12A7-BRAF |
| pancreatic carcinoma | pancreas ductal adenocarcinoma | primary | MYRIP-BRAF |
| pancreatic carcinoma | pancreas acinar cell carcinoma | metastatic | SND1-BRAF |
| prostatic carcinoma | prostate acinar adenocarcinoma | metastatic | NUB1-BRAF |
| sarcoma | malignant solid fibrous tumor | primary | KIAA1549-BRAF |
| thyroid carcinoma | thyroid papillary carcinoma | primary | KLHL7-BRAF |
| thyroid carcinoma | thyroid papillary carcinoma | primary | TANK-BRAF |
| thyroid carcinoma | thyroid papillary carcinoma | metastatic | RBMS3-BRAF |
| unknown primary carcinoma | unknown primary, adenocarcinoma | metastatic | STRN3-BRAF |
| unknown primary carcinoma | unknown primary, carcinoma (NOS) | metastatic | SND1-BRAF |
| pleura mesothelioma | pleura mesothelioma | primary | STK35-BRAF |
| rectum adenocarcinoma | rectum adenocarcinoma | metastatic | ETFA-BRAF |
| uterus endometrial carcinoma | uterus endometrial adenocarcinoma (NOS) | metastatic | SVOPL-BRAF |
| ovary serous carcinoma | ovary serous carcinoma | metastatic | JHDM1D-BRAF |

The term "metastasis" is an art known term that refers to the spread of cancer cells from the place where they first formed (the primary site) to one or more other sites in a subject (one or more secondary sites). In metastasis, cancer cells break away from the original (primary) tumor, travel through the blood or lymph system, and form a new tumor (a metastatic tumor) in other organs or tissues of the body. The new, metastatic tumor includes the same or similar cancer cells as the primary tumor. At the secondary site, the tumor cell may proliferate and begin the growth or colonization of a secondary tumor at this distant site.

The term "metastatic cancer" (also known as "secondary cancer") as used herein refers to a type of cancer that originates in one tissue type, but then spreads to one or more tissues outside of the (primary) cancer's origin. Metastatic brain cancer refers to cancer in the brain, i.e., cancer which originated in a tissue other than the brain and has metastasized to the brain.

In one embodiment, the BRAF-associated tumor is a malignant BRAF-associated CNS tumor (i.e., a BRAF-associated CNS cancer). The term "CNS cancer" or "cancer of the CNS" or as used interchangeably herein refers to a cancer (i.e., a malignant tumor) of the CNS, including cancers of the brain (also known as intracranial tumors), cancers of the spinal cord, and cancers of the meninges surrounding the brain and spinal cord. The term "BRAF-associated CNS cancer" refers to CNS cancer associated with or having a BRAF mutation. Cancers of the CNS include metastatic brain cancers and malignant primary brain tumors.

In one embodiment, the BRAF-associated CNS cancer is a BRAF-associated metastatic brain cancer. The BRAF-associated metastatic brain cancer may be the result of any cancer described herein, wherein the subject has developed at least one brain metastasis. In one embodiment, the BRAF-associated metastatic brain cancer is metastatic melanoma, metastatic colorectal cancer, or metastatic non-small cell lung cancer. In one embodiment, the BRAF-associated metastatic brain cancer is metastatic melanoma. In one embodiment, the BRAF-associated metastatic brain cancer is metastatic colorectal cancer. In one embodiment, the BRAF-associated metastatic brain cancer is metastatic non-small cell lung cancer. In one embodiment, the BRAF-associated metastatic brain cancer is metastatic ovarian cancer. In one embodiment, the metastatic brain cancer is metastatic thyroid cancer. In one embodiment, the BRAF-associated metastatic brain cancer is kidney cancer. In one embodiment, the cancer is BRAF-associated metastatic cancer with at least one brain metastasis (i.e., a metastatic brain cancer). In one embodiment, the cancer is BRAF-associated metastatic melanoma with at least one brain metastasis. In one embodiment, the cancer is BRAF-associated metastatic colorectal cancer with at least one brain metastasis. In one embodiment, the cancer is BRAF-associated metastatic non-small cell lung cancer with at least one brain metastasis. In one embodiment, the cancer is BRAF-associated metastatic ovarian cancer with at least one brain metastasis. In one embodiment, the cancer is BRAF-associated metastatic thyroid cancer with at least one brain metastasis. In one embodiment, the cancer is BRAF-associated neuroblastoma with at least one brain metastasis.

Leptomeningeal metastases (leptomeningeal disease (LMD)) represent a subset of CNS metastases that grow in the lining of the brain or spine and/or in the cerebrospinal fluid (CSF), or leptomeningeal carcinomatosis. In mammals, the meninges are the dura mater, the arachnoid mater, and the pia mater. CSF is located in the subarachnoid space between the arachnoid mater and the pia mater. The arachnoid and pia mater together are sometimes called the leptomeninges. When LMD occurs in the leptomeninges and/or CSF surrounding the spinal cord, it may be referred to as "extracranial LMD". When LMD occurs in the leptomeninges and/or CSF of the brain, it may be referred to as "intracranial LMD". Since LMD cancer cells can be suspended in the CSF, they can quickly spread throughout the CNS. As a result, LMD has a poor prognosis, with survival typically measured in months. In one embodiment, the metastatic cancer is BRAF-associated LMD. In one embodiment, the metastatic cancer is intracranial BRAF-associated LMD. In one embodiment, the metastatic cancer is extracranial BRAF-associated LMD. BRAF-associated cancers with the highest incidences of leptomeningeal metastases are lung cancer and melanoma. In one embodiment the BRAF-associated LMD is LMD derived from melanoma metastases (i.e., the LMD is metastatic melanoma). In one embodiment the BRAF-associated LMD is LMD derived from colorectal cancer metastases (i.e., the LMD is metastatic colorectal cancer). In one embodiment the BRAF-associated LMD is LMD derived from non-small cell lung cancer metastases (i.e., the LMD is metastatic non-small cell lung cancer).

In one embodiment, the cancer is a BRAF-associated cancer having a high risk of metastasis. In one embodiment, the BRAF-associated cancer having a high risk of metastasis is a cancer having a BRAF V600E or a BRAF V600K mutation. In one embodiment, the BRAF-associated cancer having a high risk of metastasis is melanoma, colorectal cancer, thyroid cancer, non-small cell lung cancer, ovarian cancer or neuroblastoma. In one embodiment, the BRAF-associated cancer having a high risk of metastasis is melanoma, colorectal cancer, thyroid cancer, non-small cell lung cancer, ovarian cancer or neuroblastoma, each of which has a BRAF V600E or BRAF V600K mutation. In one embodiment, the BRAF-associated cancer having a high risk of metastasis is melanoma. In one embodiment, the BRAF-associated cancer having a high risk of metastasis is melanoma having a BRAF V600E mutation or a BRAF V600K mutation. In one embodiment, the BRAF-associated cancer having a high risk of metastasis is colorectal cancer. In one embodiment, the BRAF-associated cancer having a high risk of metastasis is colorectal cancer having a BRAF V600E mutation or a BRAF V600K mutation. In one embodiment, the BRAF-associated cancer having a high risk of metastasis is thyroid cancer. In one embodiment, the BRAF-associated cancer having a high risk of metastasis is thyroid cancer having a BRAF V600E mutation or a BRAF V600K mutation. In one embodiment, the BRAF-associated cancer having a high risk of metastasis is non-small cell lung cancer. In one embodiment, the BRAF-associated cancer having a high risk of metastasis is non-small cell lung cancer having a BRAF V600E mutation or a BRAF V600K mutation. In one embodiment, the BRAF-associated cancer having a high risk of metastasis is ovarian cancer. In one embodiment, the BRAF-associated cancer having a high risk of metastasis is ovarian cancer having a BRAF V600E mutation or a BRAF V600K mutation. In one embodiment, the BRAF-associated cancer having a high risk of metastasis is neuroblastoma. In one embodiment, the BRAF-associated cancer having a high risk of metastasis is neuroblastoma having a BRAF V600E mutation or a BRAF V600K mutation.

In one embodiment, the cancer is a BRAF-associated cancer having a Class II mutation. In one embodiment, the Class II mutation is a non-V600 mutation. In one embodiment, the non-V600 mutation is G469A, G469R, G469V, K601E, K601N, K601T, L597Q or L597V. In one embodiment, the non-V600 mutation is G469A. In one embodiment, the Class II mutation is a BRAF splice variant. In one embodiment, the BRAF splice variant lacks exons 4-8 (also known as p61BRAF(V600E)), exons 4-10, exons 2-8 or exons 2-10. In one embodiment, the BRAF splice variant is p61BRAF(V600E). Non-limiting examples of BRAF-associated cancers having Class II mutations include lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, bladder carcinoma, plasma cell neoplasm, hepato-pancreato-biliary carcinoma, ovarian cancer, neuroendocrine cancer, cholangiocarcinoma and CNS tumors.

In one embodiment, the BRAF-associated cancer is a BRAF-associated CNS tumor. In one embodiment, the BRAF-associated CNS tumor is a BRAF-associated primary brain tumor. In one embodiment, the primary brain tumor is a malignant primary brain tumor. In one embodiment, the primary brain tumor is a benign primary brain tumor. In one embodiment, the primary brain tumor has Class I mutation. In one embodiment the primary brain tumor has a BRAF V600 mutation. In one embodiment the primary brain tumor has a BRAF V600E or BRAF V600K mutation. In one embodiment, the primary brain tumor has a Class II mutation. In one embodiment, the primary brain tumor has a Class II mutation selected from G469A, G469R, G469V, K601E, K601N, K601T, L597Q and L597V. In one embodiment, the primary brain tumor has a G469A mutation. Primary brain tumors are tumors that start in the brain or spine and are known collectively as gliomas. The term "glioma" is used to describe tumors that originate in glial cells present in the CNS. According to the WHO classification of brain tumors, gliomas are graded by the cell activity and aggressiveness on a scale including Grade I (benign CNS tumors) and Grades II to IV (malignant CNS tumors):

Grade I glioma (Pilocytic astrocytoma): typically occurs in children in the cerebellum or brainstem, and occasionally in the cerebral hemispheres, and are slow growing. Grade I can occur in adults. Although they are benign (WHO grade 1), the difficulty in curing this disease makes their growth malignant in behavior with high morbidity rates (Rostami, *Acta Neurochir* (Wien). 2017; 159(11): 2217-2221).

Grade II glioma (Low-grade gliomas): includes astrocytoma, oligodendroglioma, and mixed oligoastrocytma. Grade II gliomas typically occur in young adults (20s-50s) and are most often found in the cerebral hemispheres. Due to the infiltrative nature of these tumors, recurrences may occur. Some grade II gliomas recur and evolve into more aggressive tumors (grade III or IV).

Grade III glioma (Malignant glioma): includes anaplastic astrocytoma, anaplastic oligodendroglioma, and anaplastic mixed oligoastrocytoma. Grade III tumors are aggressive, high-grade cancers and invade nearby brain tissue with tentacle-like projections, making complete surgical removal more difficult.

Grade IV gliomas: includes Glioblastoma multiforme (GBM) and gliosarcoma; (GBM) is a malignant glioma. GBM is the most aggressive and most common primary brain tumor. Glioblastoma multiforme usually spreads quickly and invades other parts of the brain, with tentacle-like projections, making complete surgical removal more difficult. Gliosarcoma is a malignant cancer and is defined as a glioblastoma consisting of gliomatous and sarcomatous components.

In one embodiment, the BRAF-associated primary brain tumor is a glioma. In some embodiments, the BRAF-associated primary brain tumor is a glioma having a Class I mutation. In some embodiments, the BRAF-associated primary brain tumor is a glioma having a Class II mutation.

Benign primary brain tumors can cause severe pain, permanent brain damage and death, and in some cases, become malignant. Non-limiting examples of benign primary brain tumors include Grade I gliomas, papillary craniopharyngiomas, meningioma (including rhabdoid meningioma), atypical teratoid/rhabdoid tumors, and dysembryoplastic neuroepithelial tumor (DNT), pilocytic astrocytoma, oligodendroglioma, mixed oligoastrocytma, anaplastic astrocytoma, anaplastic oligodendroglioma, anaplastic mixed oligoastrocytoma, diffuse astrocytoma, ependymoma, a pleomorphic xanthoastrocytoma (PXA), a ganglioglioma, a gliosarcoma, or an anaplastic ganglioglioma. In one embodiment, the BRAF-associated tumor is a benign primary brain tumor.

In one embodiment, the BRAF-associate cancer is a peripheral nervous system cancer. In one embodiment, the peripheral nervous system cancer is neuroblastoma. In one embodiment, the cancer is a BRAF-associated cancer.

Certain compounds of Formula I, Formula I-A, Formula II, Formula III, Formula IV or Formula V or pharmaceutically acceptable salts thereof, were found to exhibit good brain and/or CNS penetrance and/or exhibit low efflux. Such compounds are capable of crossing the BBB and may be useful in inhibiting a BRAF kinase in the brain and/or other CNS structures.

Accordingly, certain compounds of Formula I, Formula I-A, Formula II, Formula III, Formula IV, or Formula V, or a pharmaceutically acceptable salt thereof described herein may also be used to treat BRAF-associated tumors of the CNS. For example, treatment of a subject with a BRAF-associated CNS tumor can include administration (e.g., oral administration) of a compound of Formula I, Formula I-A, Formula II, Formula III, Formula IV, or Formula V, or a pharmaceutically acceptable salt thereof to the subject. In some embodiments, the BRAF-associated CNS cancer has a BRAF V600 mutation. In some embodiments, the BRAF-associated CNS cancer has a BRAF V600E and/or V600K mutation. In some embodiments, the BRAF-associated CNS cancer has a BRAF V600E mutation. In some embodiments, the BRAF-associated CNS cancer has a BRAF V600K mutation. In some embodiments, the subject has previously been treated with one or more other anticancer therapies, e.g., an anticancer agent, surgery and/or radiotherapy, e.g., as described hereinbelow. In some embodiments, the subject is treated with a compound of Formula I, Formula I-A, Formula II, Formula III, Formula IV, or Formula V, or a pharmaceutically acceptable salt thereof in combination with one or more other anticancer therapies, e.g., an anticancer agent, surgery and/or radiotherapy, e.g., as described hereinbelow. In some embodiments, the subject is treated with one or more anticancer therapies e.g., an anticancer agent, surgery and/or radiotherapy after administration of a compound of Formula I, Formula I-A, Formula II, Formula III, Formula IV, or Formula V, or a pharmaceutically acceptable salt thereof, e.g., as described hereinbelow.

In some embodiments of any of the methods described herein, the tumor is a BRAF-associated CNS tumor and the method includes administering a compound of Formula I, Formula I-A, Formula II, Formula III, Formula IV, or Formula V, or a pharmaceutically acceptable salt thereof. In some embodiments, the BRAF-associated tumor is a CNS tumor. In some embodiments, the BRAF-associated CNS tumor is a malignant CNS tumor (CNS cancer). In some embodiments, the malignant CNS tumor is a metastatic CNS cancer. In some embodiments, the metastatic CNS cancer is metastatic melanoma. In some embodiments, the metastatic CNS cancer is colorectal cancer. In some embodiments, the metastatic CNS cancer is metastatic non-small cell lung cancer. In some embodiments, the metastatic CNS cancer is metastatic thyroid cancer. In some embodiments, the metastatic CNS cancer is metastatic ovarian cancer. In some embodiments, the BRAF-associated CNS tumor is LMD. In some embodiments, the LMD is intracranial. In some embodiments, the LMD is extracranial. In some embodiments, the LMD is metastatic melanoma. In some embodiments, the LMD is metastatic colorectal cancer. In some embodiments, the LMD is metastatic non-small cell lung cancer. In some embodiments, the BRAF-associated CNS cancer is a primary brain tumor. In some embodiments, the primary brain tumor is a Grade 2 glioma. In some embodiments, the primary brain tumor is a Grade 3 glioma. In some embodiments, the primary brain tumor is a Grade 4 glioma. In some embodiments, the BRAF-associated CNS tumor is a benign tumor. In some embodiments, the benign CNS tumor is a papillary craniopharyngioma, a meningioma (including rhabdoid meningioma), an atypical teratoid/rhabdoid tumor, or a dysembryoplastic neuroepithelial tumor (DNT). In some embodiments, the compound is selected from a compound of Examples 1-164 or a pharmaceutically acceptable salt thereof.

The ability to determine whether a compound may be suitable for treating a CNS cancer may be determined, for example, by identifying if the compound is a substrate of an efflux transporter and/or measuring the cell permeability and/or measuring the free brain-to-free plasma ratio, as described herein.

In some embodiments, compounds of Formula I, Formula I-A, Formula II, Formula III, Formula IV or Formula V, or pharmaceutically acceptable salts thereof, exhibit high cell permeability. Methods for determining the permeability of a compound can be determined according to the assay described in Example B, and permeability coefficients for compounds of Formula I, Formula I-A, Formula II, Formula III, Formula IV or Formula V are provided in Table B1.

Certain compounds of Formula I, Formula I-A, Formula II, Formula III, Formula IV or Formula V, or a pharmaceutically acceptable salt thereof, exhibit low efflux. In vitro methods of evaluating whether compounds are substrates for the efflux transporters P-glycoprotein (P-gp or Multi-drug Resistance 1 (MDR1) protein) and Breast cancer resistance protein (BCRP) are described in Example B, and efflux ratios of compounds of Formula I, Formula I-A, Formula II, Formula III, Formula IV or Formula V are provided in Table B2. In one embodiment, compounds of Formula I, Formula I-A, Formula II, Formula III, Formula IV, or Formula V, or a pharmaceutically acceptable salt thereof, have an efflux ratio of ≤3.5 when tested in cells that express P-gp. In one embodiment, compounds of Formula I, Formula I-A, Formula II, Formula III, Formula IV or Formula V or a pharmaceutically acceptable salt thereof have an efflux ratio of ≤3.5 when tested in cells that express P-gp and an efflux ratio of ≤5.5 when tested in cells that express BCRP.

In some embodiments, certain compounds of Formula I, Formula I-A, Formula II, Formula III, Formula IV, or Formula V, or a pharmaceutically acceptable salt thereof, exhibit medium-to-high brain (unbound)/plasma (unbound) ratios (i.e., medium-to-high free brain/plasma ratios). The ability of a compound of to penetrate the BBB of a subject (e.g., a human) can be determined in a suitable animal model (e.g., a rodent, such as a mouse). For example, the ability of certain compounds of Formula I, Formula I-A, Formula II, Formula III, Formula IV or Formula V to penetrate the BBB in mice was determined by evaluating the unbound brain-to-unbound plasma concentration (free B/P) ratio in mice e.g. as described in Example C, and the free brain-to-free plasma ratios are provided in Table C. Free brain-to-free plasma ratios equal to or greater than 0.3 are evidence of a significant degree of free CNS penetration.

Accordingly, in some embodiments, the methods of the present invention include methods for treating a BRAF-associated CNS cancer in a subject in need thereof. In one embodiment, the method includes administration of a compound of Formula I, Formula I-A, Formula II, Formula III, Formula IV, or Formula V, or a pharmaceutically acceptable salt thereof, such that at least a portion of the compound of Formula I, Formula I-A, Formula II, Formula III, Formula IV or Formula V penetrates the BBB, as demonstrated in a suitable animal model. In some embodiments, the brain/plasma ratio of total drug is at least approximately 0.3 after administration (e.g. oral or intravenous administration) to a subject. It is to be noted that the percentage of a compound that penetrates the BBB is calculated based upon the area under the concentration-time curve for a given time period ($AUC_{0-4}$) in the brain versus the plasma. Accordingly, the percentages represent a ratio of concentrations. That is, if ($AUC_{0-24h}$) for a compound is 30 ng/mL in the brain and 70 ng/mL in the plasma, then the percentage of the compound that penetrates the BBB is 30% (30 ng/mL in the brain divided by the total concentration of (30 ng/mL+70 ng/mL)) (i.e., a brain-to-plasma ratio of 0.30). In some embodiments, the percentages are calculated based upon the area under the concentration-time curve for the time period from t=0 (time of dosing) to the last quantifiable concentration point, i.e., ($AUC_{0-last}$).

Mutations in the BRAF gene have been identified in malignant melanomas, papillary thyroid carcinomas, colorectal carcinomas, non-small cell lung carcinoma (NSCLC), and ovarian carcinomas and metastatic tumors thereof, and in primary brain tumors (Davies et al., 2002). For example, BRAF mutations have been observed in numerous metastatic CNS tumors, including melanoma brain metastases (Flaherty K T, et al., *Nat Rev Cancer* (2012) 12(5):349-61), brain metastases of colorectal cancers and brain metastases of non-small cell lung cancer (Berghoff, A S, Preusser M., *Curr Opin Neurol* (2014) 27(6):689-696), papillary thyroid cancer (Kim, W W et al., *J Otolaryngol Head Neck Surg.* 2018; 47: 4), and ovarian cancer (Grisham R N., et al., *Cancer.* 2013; 119:548-554).

BRAF mutations have also been observed in malignant primary brain tumors, including Grade IV gliomas, e.g., glioblastomas and gliosarcomas, anaplastic astrocytomas (high-grade tumors) and WHO grade III anaplastic gangliogliomas (Berghoff, A S, Preusser M., *Curr Opin Neurol* (2014) 27(6):689-696); Schindler et al. (*Acta Neuropathol* 121(3):397-405, 2011); Behling et al. (*Diagn Pathol* 11(1): 55, 2016)), in pediatric and adult populations.

BRAF mutations have also been observed in benign primary brain tumors, for example in WHO Grade II astrocytomas, WHO grade II pleomorphic xanthoastrocytomas (PXAs), pleomorphic xanthoastrocytomas with anaplasia, Pilocytic astrocytoma (PA), papillary craniopharyngiomas, gangliogliomas, astroblastomas, pilocytic astrocytomas, atypical teratoid/rhabdoid tumors, rhabdoid meningiomas (Berghoff, A S, Preusser M., *Curr Opin Neurol* (2014) 27(6):689-696; Schindler et al. (*Acta Neuropathol* 121(3): 397-405, 2011); Behling et al. (*Diagn Pathol* 11(1):55, 2016); (Behling et al., *Diagn Pathol* 11(1):55, 2016; Brastianos et al., *Nat Genet* 46(2):161-165, 2014; Dougherty et al., *Neuro Oncol* 12(7):621-630, 2010; Lehman et al., *Neuro Oncol* 19(1):31-42, 2017; Mordechai et al., *Pediatr Hematol Oncol* 32(3):207-211, 2015; Myung et al., *Transl Oncol* 5(6):430-436, 2012; Schindler et al., *Acta Neuropathol* 121(3):397-405, 2011)), in pediatric and adult populations.

BRAF mutations have also been detected in relapsed neuroblastomas (Eleveld, T F, et al., *Nat Genet* 47(8):864-871, 2015). Neuroblastoma is a pediatric tumor of the peripheral nervous system. The majority of neuroblastoma subjects have tumors that initially respond to chemotherapy, but a large proportion of subjects will experience therapy-resistant relapses.

Accordingly, also provided herein is a method for treating a subject diagnosed with or identified as having a BRAF-associated tumor, e.g., any of the exemplary BRAF-associated tumors disclosed herein, comprising administering to the subject a therapeutically effective amount of a compound of Formula I, Formula I-A, Formula II, Formula III, Formula IV, or Formula V, or a pharmaceutically acceptable salt thereof, or a pharmaceutical composition thereof as defined herein. In some embodiments, the subject that has been identified or diagnosed as having a BRAF-associated tumor through the use of a regulatory agency-approved, e.g., FDA-approved test or assay for identifying BRAF mutation in a subject or a biopsy sample from the subject or by performing any of the non-limiting examples of assays described herein. In some embodiments, the test or assay is provided as a kit. In one embodiment, the BRAF-associated tumor can be a cancer that has one or more Class I BRAF mutations (e.g., V600E and/or V600K). In one embodiment, the BRAF-associated tumor can be a cancer that has one or more Class II mutations (e.g., G469A). In some embodiments, a compound of Formula I, Formula I-A, Formula II, Formula III, Formula IV or Formula V is a compound selected from Examples 1-164 or a pharmaceutically acceptable salt thereof. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF associated tumor is a benign CNS tumor. In some embodiments, the cancer is selected from lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors. In some embodiments, the compound is selected from a compound of Examples 1-164 or a pharmaceutically acceptable salt thereof. In some embodiments, the subject is an adult subject. In some embodiments, the subject is a pediatric subject.

Also provided are methods for treating a tumor in a subject in need thereof, comprising: (a) detecting a BRAF-associated tumor in the subject; and (b) administering to the subject a therapeutically effective amount of a compound of Formula I, Formula I-A, Formula II, Formula III, Formula IV or Formula V, or a pharmaceutically acceptable salt thereof or a pharmaceutical composition thereof. In some embodiments of these methods, the tumor is a benign BRAF-associated tumor. In some embodiments of these methods, the tumor is a malignant BRAF-associated tumor. In some embodiments of these methods, the tumor is a malignant BRAF-associated tumor (e.g., any of the malignant BRAF-associated tumors described herein), and the method further include administering to the subject one or more additional anticancer therapies, e.g., surgery (e.g., at least partial resection of the tumor) and/or radiotherapy and/or an anticancer agent. In some embodiments of these methods, the tumor is a benign BRAF-associated tumor, e.g., a benign BRAF-associated CNS tumor, and the method further includes administering to the subject one or more additional anticancer therapies, e.g., surgery (e.g., at least partial resection of the tumor) and/or radiotherapy and/or an anticancer agent. In some embodiments, the subject is determined to have a BRAF-associated tumor through the use of a regulatory agency-approved, e.g., FDA-approved test or assay for identifying a BRAF mutation in a subject or a biopsy sample from the subject (e.g., a tissue or liquid biopsy) or by performing any of the non-limiting examples of assays described herein. In some embodiments, the test or assay is provided as a kit. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF associated tumor is a benign CNS tumor. In some embodiments, the cancer is selected from lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors. In some embodiments, the compound is selected from a compound of Examples 1-164 or a pharmaceutically acceptable salt thereof. In some embodiments, the subject is an adult subject. In some embodiments, the subject is a pediatric subject.

Also provided are methods of treating a subject having BRAF-associated tumor that include performing an assay on a sample obtained from the subject to determine that the subject has a tumor having a BRAF mutation, and administering a therapeutically effective amount of a compound of Formula I, Formula I-A, Formula II, Formula III, Formula IV or Formula V, or a pharmaceutically acceptable salt thereof or a pharmaceutical composition thereof to the subject determined to have a BRAF mutation. In some embodiments of these methods, the BRAF-associated tumor is a malignant BRAF-associated tumor (i.e., a BRAF-associated cancer), and the method further includes administering to the subject one or more other anticancer therapies, e.g., surgery (e.g., at least partial resection of a tumor) and/or radiotherapy and/or treatment with an anticancer agent. In some embodiments of these methods, the subject was previously treated with another anticancer treatment, e.g., surgery (e.g., at least partial resection of a tumor) and/or radiotherapy and/or treatment with an anticancer agent. In some embodiments, the subject is a subject suspected of having a BRAF-associated tumor, a subject presenting with one or more symptoms of a BRAF-associated tumor, or a subject having an elevated risk of developing a BRAF-associated tumor. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the biopsy is a tissue biopsy. In some embodiments, the cancer is a CNS cancer and the biopsy is a liquid biopsy (e.g., CSF). In some embodiment, the cancer is a CNS cancer and the biopsy is a tissue biopsy (e.g., a tumor sample obtained during traditional surgery or a stereotactic needle biopsy, e.g., a stereotactic need biopsy guided by CT or MRI scanning). Additional, non-limiting assays that may be used in these methods are described herein. Additional assays are also known in the art. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF-associated tumor is a benign CNS tumor. In some embodiments, the cancer is selected from lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors. In some embodiments, the subject is an adult subject. In some embodiments, the subject is a pediatric subject.

Also provided is a compound of Formula I, Formula I-A, Formula II, Formula III, Formula IV or Formula V, or a pharmaceutically acceptable salt thereof for use in treating a BRAF-associated tumor in a subject identified or diagnosed as having a BRAF-associated tumor through a step of performing an assay (e.g., an in vitro assay) on a sample obtained from the subject to determine that the subject has a BRAF mutation, where the presence of a BRAF mutation identifies that the subject has a BRAF-associated tumor. Also provided is the use of a compound of Formula I, Formula I-A, Formula II, Formula III, Formula IV or Formula V, or a pharmaceutically acceptable salt thereof for the manufacture of a medicament for treating a BRAF-associated tumor in a subject identified or diagnosed as having a BRAF-associated tumor through a step of performing an assay on a sample obtained from the subject to determine whether the subject has a BRAF mutation identifies that the subject has a BRAF-associated tumor. Some embodiments of any of the methods or uses described herein further include recording in the subject's clinical record (e.g., a computer readable medium) that the subject is determined to have a BRAF mutation through the performance of the assay, should be administered a compound of Formula I, Formula I-A, Formula II, Formula III, Formula IV or Formula V, or a pharmaceutically acceptable salt thereof or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF-associated tumor is a benign CNS tumor. In some embodiments, the cancer is selected from lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors. In some embodiments, the subject is an adult subject. In some embodiments, the subject is a pediatric subject.

Also provided is a compound of Formula I, Formula I-A, Formula II, Formula III, Formula IV or Formula V, or a pharmaceutically acceptable salt thereof, for use in the treatment of a BRAF-associated tumor in a subject in need thereof or a subject identified or diagnosed as having a BRAF-associated tumor. Also provided is the use of a compound of Formula I, Formula I-A, Formula II, Formula III, Formula IV or Formula V, or a pharmaceutically acceptable salt thereof for the manufacture of a medicament for treating a BRAF-associated tumor in a subject identified or diagnosed as having a BRAF-associated tumor. In some embodiments, a subject is identified or diagnosed as having a BRAF-associated tumor using a regulatory agency-approved, e.g., FDA-approved, kit for identifying a BRAF mutation in a subject or a biopsy sample from the subject. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF associated tumor is a benign CNS tumor. In some embodiments, the cancer is selected from lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors. In some embodiments, the subject is an adult subject. In some embodiments, the subject is a pediatric subject.

In some embodiments of any of the methods or uses described herein, an assay used to determine whether the subject has a BRAF mutation using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting a BRAF mutation. In some embodiments, the sample is a biological sample or a biopsy sample (e.g., a paraffin-embedded biopsy sample) from the subject. In some embodiments, the subject is a subject suspected of having a BRAF-associated tumor, a subject having one or more symptoms of a BRAF-associated tumor, and/or a subject that has an increased risk of developing a BRAF-associated tumor).

In some embodiments, the biopsy is a tumor biopsy (e.g., a tumor sample obtained during traditional surgery or a stereotactic needle biopsy, e.g., a stereotactic need biopsy guided by CT or MRI scanning). Tissue biopsy methods can be used to detect total tumor burden and/or the BRAF mutation.

In some embodiments, the BRAF mutation can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.,* 3(3):36, 2016. Liquid biopsy methods can be used to detect total tumor burden and/or the BRAF mutation. Liquid biopsies can be performed on biological samples obtained relatively easily from a subject (e.g., via a simple blood draw) and are generally less invasive than traditional methods used to detect tumor burden and/or BRAF mutation. In some embodiments, liquid biopsies can be used to detect the presence of a BRAF mutation at an earlier stage than traditional methods. In some embodiments, the biological sample to be used in a liquid biopsy can include, CSF, blood, plasma, urine, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify a BRAF mutation.

In some embodiments, a BRAF mutation identified using a liquid biopsy is also present in a cancer cell that is present in the subject (e.g., in a tumor). In some embodiments, any of the types of BRAF mutations can be detected using a liquid biopsy. In some embodiments, a genetic mutation identified via a liquid biopsy can be used to identify the subject as a candidate for a particular treatment. For example, detection of a BRAF mutation in the subject can indicate that the subject will be responsive to a treatment that includes administration of a compound of Formula I, Formula I-A, Formula II, Formula III, Formula IV or Formula V, or a pharmaceutically acceptable salt thereof.

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., magnetic resonance imaging (MRI) scans, computed tomography (CT), multidetector CT (MDCT), positron emission tomography (PET), X-ray, ultrasound, or bone scan.

The term "tumor size" or "size of the tumor" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., MRI scans, bone scan, ultrasound, or CT.

Liquid biopsies can be performed at multiple times during a course of diagnosis, a course of monitoring, and/or a course of treatment to determine one or more clinically relevant parameters including, without limitation, progression of the disease or efficacy of a treatment, after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable). In some embodiments, a treatment to be administered to a subject can include a compound of Formula I, Formula I-A, Formula II, Formula III, Formula IV or Formula V, or a pharmaceutically acceptable salt thereof.

In one embodiment, a compound of Formula I, Formula I-A, Formula II, Formula III, Formula IV or Formula V, or a pharmaceutically acceptable salt thereof, may be used alone or in combination with one or more different forms of treatment to treat a subject with a malignant tumor. For example, a compound of Formula I, Formula I-A, Formula II, Formula III, Formula IV or Formula V, or a pharmaceutically acceptable salt thereof may also be used in combination with one or more additional anticancer therapies, for example surgery, radiotherapy, and/or an anticancer agent that works by the same or by a different mechanism of action. In one embodiment, treatment of a subject having a BRAF-associated malignant tumor with a compound of Formula I, Formula I-A, Formula II, Formula III, Formula IV or Formula V, or a pharmaceutically acceptable salt thereof in combination with one or more additional therapies, e.g., surgery, radiotherapy, and/or an anticancer agent, can have increased therapeutic efficacy as compared to treatment of the same subject or a similar subject with a compound of Formula I, Formula I-A, Formula II, Formula III, Formula IV or Formula V or a pharmaceutically acceptable salt as a monotherapy.

Accordingly, in one embodiment, provided herein are methods of treating a subject having a BRAF-associated tumor (e.g., any of the BRAF-associated tumors described herein) that include: administering to the subject (i) a therapeutically effective amount of a compound of Formula I, Formula I-A, Formula II, Formula III, Formula IV, or Formula V, or a pharmaceutically acceptable salt thereof as a monotherapy, or (ii) a therapeutically effective amount of a compound of Formula I, Formula I-A, Formula II, Formula III, Formula IV or Formula V, or a pharmaceutically acceptable salt thereof in combination with one or more additional anticancer therapies. In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a second anticancer therapy during said period of time. In one embodiment, the second anticancer therapy is a second anticancer agent.

Also provided herein is a compound of Formula I, Formula I-A, Formula II, Formula III, Formula IV, or Formula V, or a pharmaceutically acceptable salt thereof, for use in combination with an additional anticancer therapy. Also provide herein is an additional anticancer therapy for use in combination with a compound of Formula I, Formula I-A, Formula II, Formula III, Formula IV, or Formula V, or a pharmaceutically acceptable salt thereof.

Also provided herein is a compound of Formula I, Formula I-A, Formula II, Formula III, Formula IV, or Formula V, or a pharmaceutically acceptable salt thereof, for use in treating a BRAF-associated tumor by co-administration with an additional anticancer therapy. Also provide herein is an additional anticancer therapy for use in treating a BRAF-associated tumor by co-administration with a compound of Formula I, Formula I-A, Formula II, Formula III, Formula IV, or Formula V, or a pharmaceutically acceptable salt thereof.

In some embodiments, the subject is administered one or more anticancer therapies other than a compound of Formula I, Formula I-A, Formula II, Formula III, Formula IV or Formula V, or a pharmaceutically acceptable salt thereof, prior to administration of a compound of Formula I, Formula I-A, Formula II, Formula III, Formula IV or Formula V, or a pharmaceutically acceptable salt thereof. In some embodiments, the one or more anticancer therapies is selected from surgery and/or radiotherapy, and/or an anticancer agent that works by the same or by a different mechanism of action. For example, in some embodiments, a subject in need thereof may undergo at least partial resection of the tumor prior to administration of a compound of Formula I, Formula I-A, Formula II, Formula III, Formula IV or Formula V, or a pharmaceutically acceptable salt thereof. In some embodiments, the treatment by at least partial resection of the tumor reduces the size of the tumor (e.g., the tumor burden) occurs prior to administration of one or more doses of a compound of Formula I, Formula I-A, Formula II, Formula III, Formula IV or Formula V, or a pharmaceutically acceptable salt thereof. In some embodiments, a subject in need thereof may undergo radiotherapy prior to administration of a compound of Formula I, Formula I-A, Formula II, Formula III, Formula IV or Formula V, or a pharmaceutically acceptable salt thereof. In some embodiments, a subject in need thereof may undergo treatment with one or more anticancer agents other than a compound of Formula I, Formula I-A, Formula II, Formula III, Formula IV or Formula V, or a pharmaceutically acceptable salt thereof prior to administration of a compound of Formula I, Formula I-A, Formula II, Formula III, Formula IV or Formula V, or a pharmaceutically acceptable salt thereof. In some embodiments, a subject has a cancer that is resistant or intolerant to the previous therapy.

Accordingly, in some embodiments provided herein are methods of treating a subject having a BRAF-associated tumor, comprising (i) administering one or more anticancer therapies to said subject during a period of time, and (ii) after (i), administering (a) a compound of Formula I, Formula I-A, Formula II, Formula III, Formula IV or Formula V, or a pharmaceutically acceptable salt thereof, as monotherapy or (b) a compound of Formula I, Formula I-A, Formula II, Formula III, Formula IV or Formula V, or a pharmaceutically acceptable salt thereof, in combination with one or more additional anticancer therapies.

In some embodiments, a compound of Formula I, Formula I-A, Formula II, Formula III, Formula IV or Formula V, or a pharmaceutically acceptable salt thereof, can be administered prior to administration of one or more anticancer therapies (for example surgery, radiotherapy, and/or an anticancer agent that works by the same or by a different mechanism of action) to treat a subject with the tumor. For example, in some embodiments, a subject in need thereof may undergo at least partial resection of the tumor after administration of a compound of Formula I, Formula I-A, Formula II, Formula III, Formula IV or Formula V, or a pharmaceutically acceptable salt thereof. In some embodiments, a subject in need thereof may undergo radiotherapy after to administration of a compound of Formula I, Formula I-A, Formula II, Formula III, Formula IV or Formula V, or a pharmaceutically acceptable salt thereof. In some embodiments, a subject in need thereof may undergo treatment with a compound of Formula I, Formula I-A, Formula II, Formula III, Formula IV or Formula V, or a pharmaceutically acceptable salt thereof, prior to administration of a compound one or more anticancer agents other than a compound of Formula I, Formula I-A, Formula II, Formula III, Formula IV or Formula V, or a pharmaceutically acceptable salt thereof. In one embodiment, the compound of Formula I is a compound selected from Examples 1-164 or a pharmaceutically acceptable salt thereof.

Accordingly, in some embodiments provided herein are methods of treating a subject having a BRAF-associated tumor, comprising (i) administration of Formula I, Formula I-A, Formula II, Formula III, Formula IV or Formula V, or a pharmaceutically acceptable salt thereof, during a period of time, and (ii) subsequent to said period of time, administration of one or more anticancer therapies. For example, a subject in need thereof can be administered one or more doses of a compound of Formula I, Formula I-A, Formula II, Formula III, Formula IV or Formula V, or a pharmaceutically acceptable salt thereof for a period of time and then undergo at least partial resection of the tumor. In some embodiments, the treatment with one or more doses of a compound of Formula I, Formula I-A, Formula II, Formula III, Formula IV or Formula V, or a pharmaceutically acceptable salt thereof reduces the size of the tumor (e.g., the tumor burden) prior to the at least partial resection of the tumor. In one embodiment, the compound of Formula I is a compound selected from Examples 1-164 or a pharmaceutically acceptable salt thereof.

In some embodiments of any of the above described methods, the additional anticancer therapy is surgery, radiotherapy, and/or an anticancer agent that works by the same or by a different mechanism of action.

Non-limiting examples of additional anticancer agents that can be used in combination with a compound of Formula I, II or III or a pharmaceutically acceptable salt thereof according to any of the above-described methods include but are not limited to, MEK inhibitors, BRAF inhibitors (e.g., BRAF inhibitors other than a compound of Formula I, Formula I-A, Formula II, Formula III, Formula IV or Formula V), EGFR inhibitors, inhibitors of HER2 and/or HER3, Axl inhibitors, PI3K inhibitors, and SOS1 inhibitors), signal transduction pathway inhibitors, checkpoint inhibitors, modulators of the apoptosis pathway, cytotoxic chemotherapeutics, angiogenesis-targeted therapies, and immune-targeted agents including immunotherapy.

In one embodiment, the anticancer agent that can be used in combination with a compound of Formula I, Formula I-A, Formula II, Formula III, Formula IV, or Formula V, or a pharmaceutically acceptable salt thereof according to any of the above-described methods is a targeted therapeutic agent. A "targeted therapeutic agent" as used herein includes, refers to a molecule that blocks the growth of cancer cells by interfering with specific targeted molecules needed for carcinogenesis and tumor growth, rather than by simply interfering with all rapidly dividing cells (e.g., with traditional cytotoxic chemotherapy), and includes but is not limited to, receptor tyrosine kinase-targeted therapeutic agents, signal transduction pathway inhibitors (for example, Ras-Raf-MEK-ERK pathway inhibitors, PI3K-Akt-mTOR-S6K pathway inhibitors ("PI3K inhibitors")), and modulators of the apoptosis pathway.

In some embodiments, the anticancer agent that can be used in combination with a compound of Formula I, Formula I-A, Formula II, Formula III, Formula IV, or Formula V, or a pharmaceutically acceptable salt thereof according to any of the above-described methods is a MEK inhibitor. In one embodiment, the MEK inhibitor is binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (Cl-1040), 3-[2(R), 3-dihydroxypropyl]-6-fluoro-5-(2-fluoro-4-iodophenylamino)-8-methylpyrido[2,3-d]pyrimidine-4,7(3H,8H)- dione (TAK-733), or a pharmaceutically acceptable salt thereof. Additional examples of MEK inhibitors include the compounds disclosed in WO 03/077914, WO 2005/023759, WO 2005/051301, U.S. Pat. Nos. 7,517,994, 7,732,616, WO 2005/051906, WO 2005/051302, WO 2005/051300, and WO 2007/044084. In some embodiments, the MEK inhibitor is binimetinib, or a pharmaceutically acceptable salt thereof.

In some embodiments, the anticancer agent that can be used in combination with a compound of Formula I, Formula I-A, Formula II, Formula III, Formula IV, or Formula V, or a pharmaceutically acceptable salt thereof according to any of the above-described methods is another BRAF inhibitor other than a compound of Formula I, Formula I-A, Formula II, Formula III, Formula IV or Formula V. Non-limiting examples of other BRAF inhibitors include encorafenib, dabrafenib, vemurafenib, N-[3-(5-chloro-1H-pyrrolo[2,3-b]pyridin-3-ylcarbonyl)-2,4-difluorophenyl] propane-1-sulfonamide (PLX4720), (3R)-N-(3-[[5-(2-cyclopropylpyrimidin-5-yl)-1H-pyrrolo[2,3-b]pyridin-3-yl] carbonyl]-2,4-difluorophenyl)-3-fluoropyrrolidine-1-sulfonamide (PLX8394), and pharmaceutically acceptable salts thereof, and the compounds disclosed in International Application No. PCT/IB2020/055992, published Dec. 30, 2020 as PCT Publication No. WO 2020/261156 A1, including, for example, a compound selected from:

N-(3-((3,5-dimethyl-4-oxo-3,4-dihydroquinazolin-6-yl) amino)-2,4-difluorophenyl)propane-1-sulfonamide;
N-(2-chloro-3-((3,5-dimethyl-4-oxo-3,4-dihydroquinazolin-6-yl)amino)phenyl)-3-fluoropropane-1-sulfonamide;
N-(2-chloro-3-((3,5-dimethyl-4-oxo-3,4-dihydroquinazolin-6-yl)amino)-4,5-difluorophenyl)propane-1-sulfonamide;
N-(2-chloro-3-((3,5-dimethyl-4-oxo-3,4-dihydroquinazolin-6-yl)amino)-4-fluorophenyl)propane-1-sulfonamide;
N-(2-chloro-3-((3,5-dimethyl-4-oxo-3,4-dihydroquinazolin-6-yl)amino)-4-fluorophenyl)-3-fluoropropane-1-sulfonamide;
N-(2-chloro-4-fluoro-3-((5-methyl-3-(methyl-d3)-4-oxo-3,4-dihydroquinazolin-6-yl)amino)-phenyl)-3-fluoropropane-1-sulfonamide;
N-{2-chloro-3-[(3,5-dimethyl-4-oxo-3,4-dihydroquinazolin-6-yl)oxy]-4-fluorophenyl}propane-1-sulfonamide;
N-(3-chloro-4-((3,5-dimethyl-4-oxo-3,4-dihydroquinazolin-6-yl)oxy)-5-fluoropyridin-2-yl)propane-1-sulfonamide; and
N-{2-chloro-3-[(3,5-dimethyl-4-oxo-3,4-dihydroquinazolin-6-yl)oxy]-4-fluorophenyl}-3-fluoropropane-1-sulfonamide;
or a pharmaceutically acceptable salt thereof. In one embodiment, the BRAF inhibitor is encorafenib or a pharmaceutically acceptable salt thereof. In one embodiment, the BRAF inhibitor is N-(2-chloro-3-((3,5-dimethyl-4-oxo-3,4-dihydroquinazolin-6-yl)amino)-4-fluorophenyl)-3-fluoropropane-1-sulfonamide or a pharmaceutically acceptable salt thereof. Additional examples of BRAF inhibitors are known in the art.

In some embodiments, the anticancer agent that can be used in combination with a compound of Formula I, Formula I-A, Formula II, Formula III, Formula IV, or Formula V, or a pharmaceutically acceptable salt thereof according to any of the above-described methods is an EGFR inhibitor. Non-limiting examples of EGFR inhibitors include cetuximab (Erbitux®), panitumumab (Vectibix®), osimertinib (merelectinib, Tagrisso®), erlotinib (Tarceva®), gefitinib (Iressa®), necitumumab (Portrazza™), neratinib (Nerlynx®), lapatinib (Tykerb®), vandetanib (Caprelsa®), brigatinib (Alunbrig®) and inhibitors of EGFR disclosed in PCT Publication Nos. WO 2019/071351 and WO 2017/117680, which are both incorporated herein by reference in their entirety. Additional examples of EGFR inhibitors are known in the art. In one embodiment, the EGFR inhibitor is cetuximab.

In some embodiments, the anticancer agent that can be used in combination with a compound of Formula I, Formula I-A, Formula II, Formula III, Formula IV, or Formula V, or a pharmaceutically acceptable salt thereof according to any of the above-described methods is a HER2 and/or HER3 inhibitor. Non-limiting examples of HER2 and/or HER3 inhibitors include lapatinib, canertinib, (E)-2-methoxy-N-(3-(4-(3-methyl-4-(6-methylpyridin-3-yloxy)phenylamino) quinazolin-6-yl)allyl)acetamide (CP-724714), sapitinib, 7-[[4-[(3-ethynylphenyl)amino]-7-methoxy-6-quinazolinyl] oxy]-N-hydroxy-heptanamide (CUDC-101), mubritinib, 6-[4-[(4-ethylpiperazin-1-yl)methyl]phenyl]-N-[(1R)-1-phenylethyl]-7H-pyrrolo[2,3-d]pyrimidin-4-amine (AEE788), irbinitinib (tucatinib), poziotinib, N-[4-[1-[4-(4-acetyl-1-piperazinyl)cyclohexyl]-4-amino-3-pyrazolo[3,4-d]pyrimidinyl]-2-methoxyphenyl]-1-methyl-2-indolecarboxamide (KIN001-111), 7-cyclopentyl-5-(4-phenoxyphenyl)-7H-pyrrolo[2,3-d]pyrimidin-4-ylamine (KIN001-051), 6,7-dimethoxy-N-(4-phenoxyphenyl)quinazolin-4-amine (KIN001-30), dasatinib, and bosutinib.

In some embodiments, the anticancer agent that can be used in combination with a compound of Formula I, Formula I-A, Formula II, Formula III, Formula IV, or Formula V, or a pharmaceutically acceptable salt thereof according to any of the above-described methods is an Axl inhibitor. Non-limiting examples of Axl inhibitors include bemcentinib, YW327.6S2 (monoclonal antibody), GL21.T (decoy receptor), 2-(5-chloro-2-(4-((4-methylpiperazin-1-yl) methyl)phenylamino)pyrimidin-4-ylamino)-N,N-dimethylbenzenesulfonamide (TP-0903), 3-[2-[[3-fluoro-4-(4-methyl-1-piperazinyl)phenyl]amino]-5-methyl-7Hpyrrolo [2,3-d]pyrimidin-4-yl]-benzeneacetonitrile (SGI-7079), gilteritinib, bosutinib, cabozantinib, sunitinib, foretinib, amuvatinib, glesatinib, N-(4-((2-amino-3-chloropyridin-4-yl)oxy)-3-fluorophenyl)-4-ethoxy-1-(4-fluorophenyl)-2-oxo-1,2-dihydropyridine-3-carboxamide (BMS777607), merestinib, (Z)-3-((3-((4-(morpholinomethyl)-1H-pyrrol-2-yl)methylene)-2-oxoindolin-5-yl)methyl)thiazolidine-2,4-dione (S49076), and (R)-N-(3-fluoro-4-((3-((1-hydroxypropan-2-yl)amino)-1H-pyrazolo[3,4-b]pyridin-4-yl)oxy) phenyl)-3-(4-fluorophenyl)-1-isopropyl-2,4-dioxo-1,2,3,4-tetrahydropyrimidine-5-carboxamide.

In some embodiments, the anticancer agent that can be used in combination with a compound of Formula I, Formula I-A, Formula II, Formula III, Formula IV, or Formula V, or a pharmaceutically acceptable salt thereof to any of the above-described methods is a SOS1 inhibitor. Non-limiting examples of SOS1 inhibitors include those disclosed in PCT Publication No. WO 2018/115380, which is incorporated herein by reference in its entirety.

In some embodiments, the anticancer agent that can be used in combination with a compound of Formula I, Formula I-A, Formula II, Formula III, Formula IV, or Formula V, or a pharmaceutically acceptable salt thereof to any of the above-described methods is a PI3K inhibitor. Non-limiting examples include buparlisib (BKM120), alpelisib (BYL719), samotolisib (LY3023414), 8-[(1R)-1-[(3,5-difluorophenyl)amino]ethyl]-N,N-dimethyl-2-(morpholin-4-yl)-4-oxo-4H-chromene-6-carboxamide (AZD8186), tenalisib (RP6530), voxtalisib hydrochloride (SAR-245409), gedatolisib (PF-05212384), panulisib (P-7170), taselisib (GDC-0032), trans-2-amino-8-[4-(2-hydroxyethoxy)cyclohexyl]-6-(6-methoxypyridin-3-yl)-4-methylpyrido[2,3-d]pyrimidin-7(8H)-one (PF-04691502), duvelisib (ABBV-954), N2-[4-oxo-4-[4-(4-oxo-8-phenyl-4H-1-benzopyran-2-yl)morpholin-4-ium-4-ylmethoxy]butyryl]-L-arginyl-glycyl-L-aspartyl-L-serine acetate (SF-1126), pictilisib (GDC-0941), 2-methyl-1-[2-methyl-3-(trifluoromethyl)benzyl]-6-(morpholin-4-yl)-1H-benzimidazole-4-carboxylic acid (GSK2636771), idelalisib (GS-1101), umbralisib tosylate (TGR-1202), pictilisib (GDC-0941), copanlisib hydrochloride (BAY 84-1236), dactolisib (BEZ-235), 1-(4-[5-[5-amino-6-(5-tert-butyl-1,3,4-oxadiazol-2-yl)pyrazin-2-yl]-1-ethyl-1H-1,2,4-triazol-3-yl]piperidin-1-yl)-3-hydroxypropan-1-one (AZD-8835), 5-[6,6-dimethyl-4-(morpholin-4-yl)-8,9-dihydro-6H-[1,4]oxazino[4,3-e]purin-2-yl]pyrimidin-2-amine (GDC-0084) everolimus, rapamycin, perifosine, sirolimus, and temsirolimus.

In some embodiments, the anticancer agent that can be used in combination with a compound of Formula I, Formula I-A, Formula II, Formula III, Formula IV, or Formula V, or a pharmaceutically acceptable salt thereof to any of the above-described methods is an immunotherapy. The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy that can be used in combination with a compound of Formula I, Formula I-A, Formula II, Formula III, Formula IV, or Formula V, or a pharmaceutically acceptable salt thereof to any of the above-described methods is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab, amatuximab, blinatumomab (AMG103; Blincyto®) or midostaurin (Rydapt).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is an antibody-drug conjugate. In some embodiments, the antibody-drug conjugate is gemtuzumab ozogamicin (Mylotarg™) inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine.

In some embodiments, the immunotherapy that can be used in combination with a compound of Formula I, Formula I-A, Formula II, Formula III, Formula IV, or Formula V, or a pharmaceutically acceptable salt thereof to any of the above-described methods includes a toxin. In some embodiments, the immunotherapy is denileukin diftitox (Ontak®).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™). In some embodiments, the PD-1 inhibitor is RN888 (sasanlimab).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is mRNA-based immunotherapy. In some embodiments, the mRNA-based immunotherapy is CV9104 (see, e.g., Rausch et al. (2014) *Human Vaccine Immunother* 10(11): 3146-52; and Kubler et al. (2015) *J. Immunother Cancer* 3:26).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is an oncolytic virus therapy. In some embodiments, the oncolytic virus therapy is talimogene alherparepvec (T-VEC; Imlygic®).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is a cancer vaccine. In some embodiments, the cancer vaccine is a human papillomavirus (HPV) vaccine. In some embodiments, the HPV vaccine is Gardasil®, Gardasil® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxlD®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy that can be used in combination with a compound of Formula I, Formula I-A, Formula II, Formula III, Formula IV, or Formula V, or a pharmaceutically acceptable salt thereof to any of the above-described methods is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) *Nature* 547: 217-221; Sahin et al. (2017) *Nature* 547: 222-226).

In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) *Oncolmmunology* 5(2): e1069940). In some embodiments, the immunotherapy that can be used in combination with a compound of Formula I, Formula I-A, Formula II, Formula III, Formula IV, or Formula V, or a pharmaceutically acceptable salt thereof to any of the above-described methods is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) *Drugs* 71(1): 101-108). In some embodiments, the cellular immunotherapy includes cells that express a chimeric antigen receptor (CAR). In some embodiments, the cellular immunotherapy is a CAR-T cell therapy.

In some embodiments, the CAR-T cell therapy is tisagenlecleucel (Kymriah™) In some embodiments, the anticancer agent that can be used in combination with a compound of Formula I, I-A, II, III, IV or V or a pharmaceutically acceptable salt thereof to any of the above-described methods is a cytotoxic chemotherapeutic. Non-limiting examples of cytotoxic chemotherapeutics include arsenic trioxide, bleomycin, cabazitaxel, capecitabine, carboplatin, cisplatin, cyclophosphamide, cytarabine, dacarbazine, daunorubicin, docetaxel, doxorubicin, etoposide, 5-fluorouracil, folinic acid, gemcitabine, irinotecan, lomustine, methotrexate, mitomycin C, oxaliplatin, paclitaxel, pemetrexed, temozolomide, and vincristine, and combinations thereof, e.g., Nordic FLOX (fluorouracil, folinic acid and oxaliplatin), FOLFOXIRI (oxaliplatin, irinotecan and fluorouracil), FOLFIRI (folinic acid, fluorouracil and irinotecan) or CAPEOX (capecitabine and oxaliplatin).

In some embodiments, the anticancer agent that can be used in combination with a compound of Formula I, Formula I-A, Formula II, Formula III, Formula IV, or Formula V, or a pharmaceutically acceptable salt thereof according to any of the above-described methods is an angiogenesis-targeted therapy. Non-limiting examples of angiogenesis-targeted therapies include aflibercept and bevacizumab.

In some embodiments, the anticancer agent that can be used in combination with a compound of Formula I, Formula I-A, Formula II, Formula III, Formula IV, or Formula V, or a pharmaceutically acceptable salt thereof according to any of the above-described methods includes modulators of the apoptosis pathway (e.g. obataclax).

In some embodiments, the anticancer therapy that can be used in combination with a compound of Formula I, Formula I-A, Formula II, Formula III, Formula IV, or Formula V, or a pharmaceutically acceptable salt thereof to any of the above-described methods is radiotherapy. Non-limiting examples of radiotherapy include external radiation beam therapy (e.g., external beam therapy using kilovoltage X-rays or megavoltage X-rays) or internal radiotherapy. Internal radiotherapy (also called brachytherapy) can include the use of, e.g., low-dose internal radiotherapy or high-dose internal radiotherapy. Low-dose internal radiotherapy includes, e.g., inserting small radioactive pellets (also called seeds) into or proximal to a cancer tissue in the subject. High-dose internal radiotherapy includes, e.g., inserting a thin tube (e.g., a catheter) or an implant into or proximal to a cancer tissue in the subject, and delivering a high dose of radiation to the thin tube or implant using a radiation machine. Methods for performing radiotherapy on a subject having a cancer are known in the art. In embodiments wherein the tumor is a CNS tumor, the radiotherapy may include whole brain radiotherapy (WBRT) or stereotactic radiosurgery (SRS) such as Cyberknife®, XKnife®, Gamma Knife®, or ExacTrac®.

In some embodiments, the anticancer therapy that can be used in combination with a compound of Formula I, Formula I-A, Formula II, Formula III, Formula IV, or Formula V, or a pharmaceutically acceptable salt thereof to any of the above-described methods is surgery. Non-limiting examples of surgery include, e.g., open surgery or minimally invasive surgery. Surgery can include, e.g., at least a partial resection of the tumor, removing an entire tumor, debulking of a tumor, or removing a tumor that is causing pain or pressure in the subject. Methods for performing open surgery and minimally invasive surgery on a subject having a cancer are known in the art.

In some embodiments, the additional therapy includes any one of the above listed therapies or anticancer agents which are standards of care in cancers wherein the cancer has a BRAF mutation.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a MEK inhibitor (e.g., any of the MEK inhibitors disclosed herein) during said period of time. In one embodiment, the MEK inhibitor is binimetinib, or a pharmaceutically acceptable salt thereof. In one embodiment, the compound of Formula I is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a BRAF inhibitor (e.g., any of the BRAF inhibitors disclosed herein, including a second compound of Formula I, Formula I-A, Formula II, Formula III, Formula IV, or Formula V, or a pharmaceutically acceptable salt thereof) during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered an EGFR inhibitor (e.g., any of the EGFR inhibitors disclosed herein) during said period of time. In one embodiment, the compound is a compound selected from Examples 1-164 or a pharmaceutically acceptable salt thereof. In one embodiment, the tumor is lung cancer.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered an inhibitor of HER2 and/or HER3 during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered an Axl inhibitor (e.g., any of the Axl inhibitors disclosed herein) during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a SOS1 inhibitor (e.g., any of the SOS1 inhibitors disclosed herein) during said period of time. In one embodiment, the compound I is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a signal transduction inhibitor (e.g., any of the signal transduction inhibitors disclosed herein) during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a checkpoint inhibitor (e.g., any of the checkpoint inhibitors disclosed herein) during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a modulator of the apoptosis pathway (e.g., any of the modulators of the apoptosis pathway disclosed herein) during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered a cytotoxic chemotherapeutic (e.g., any of the cytotoxic chemotherapeutics disclosed herein) during said period of time. In one embodiment, the compound is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered an angiogenesis-targeted therapy (e.g., any of the angiogenesis-targeted therapies disclosed herein) during said period of time. In one embodiment, the compound of Formula I is a compound selected from Examples 1-164 or a pharmaceutically acceptable salt thereof.

In one embodiment, provided herein is a method of treating a subject having a BRAF-associated tumor (e.g., any of the BRAF-associated tumors described herein) comprising administering a therapeutically effective amount of a compound of Formula I, Formula I-A, Formula II, Formula III, Formula IV or Formula V, or a pharmaceutically acceptable salt thereof for a period of time, wherein the subject is administered an immune-targeted agent (e.g., any of the immune-targeted agents disclosed herein) during said period of time. In one embodiment, the compound of Formula I is a compound selected from Examples 1-164 or a pharmaceutically acceptable salt thereof.

Also provided herein is a pharmaceutical combination for treating a BRAF-associated tumor in a subject in need thereof, which comprises (a) a compound of Formula I, Formula I-A, Formula II, Formula III, Formula IV or Formula V, or a pharmaceutically acceptable salt thereof, and (b) at least one additional anticancer agent (e.g., any of the exemplary additional anticancer agents described herein or known in the art), wherein the compound of Formula I, Formula I-A, Formula II, Formula III, Formula IV or Formula V, or a pharmaceutically acceptable salt thereof, and the at least one additional anticancer agent are formulated separately for simultaneous, separate or sequential use for the treatment of the tumor, wherein the amounts of the compound of Formula I, Formula I-A, Formula II, Formula III, Formula IV or Formula V, or pharmaceutically acceptable salt thereof, and of the additional anticancer agent are together effective in treating the tumor; (ii) the use of such a combination for the preparation of a medicament for the treatment of the tumor; and (iii) a commercial package or product comprising such a combination as a combined preparation for simultaneous, separate or sequential use; and to a method of treatment of a tumor in a subject in need thereof.

The term "pharmaceutical combination", as used herein, refers to a non-fixed combination of the active ingredients. The term "non-fixed combination" means that a compound of Formula I, Formula I-A, Formula II, Formula III, Formula IV or Formula V, or a pharmaceutically acceptable salt thereof, and at least one additional anticancer agent are formulated as separate compositions or dosages such that they may be administered to a subject in need thereof simultaneously, concurrently or sequentially with variable intervening time limits, wherein such administration provides effective levels of the two or more compounds in the body of the subject. These also apply to cocktail therapies, e.g. the administration of three or more active ingredients Accordingly, also provided herein is a method of treating a BRAF-associated tumor, comprising administering to a subject in need thereof a pharmaceutical combination for treating said tumor which comprises (a) a compound of Formula I, Formula I-A, Formula II, Formula III, Formula IV or Formula V, or a pharmaceutically acceptable salt thereof, and (b) an additional anticancer agent for simultaneous, separate or sequential use for the treatment of the tumor, wherein the amounts of the compound of Formula I, Formula I-A, Formula II, Formula III, Formula IV or Formula V, or a pharmaceutically acceptable salt thereof, and the additional anticancer agent are together effective in treating the tumor. In one embodiment, the BRAF-associated tumor is a malignant tumor, and the additional anticancer agent is an anticancer agent, e.g., any of the anticancer agents described herein. In some embodiments, the compound of Formula I, Formula I-A, Formula II, Formula III, Formula IV or Formula V, or pharmaceutically acceptable salt thereof, and the additional anticancer agent are administered simultaneously as separate dosages. In some embodiments, the compound of Formula I, Formula I-A, Formula II, Formula III, Formula IV or Formula V, or pharmaceutically acceptable salt thereof, and the additional anticancer agent are administered as separate dosages sequentially in any order, e.g. in daily or intermittent dosages, in jointly therapeutically effective amounts. The additional anticancer agents may be administered with one or more doses of the compound of Formula I, Formula I-A, Formula II, Formula III, Formula IV or Formula V, or a pharmaceutically acceptable salt thereof, or pharmaceutical composition thereof, as part of the same or separate dosage forms, via the same or different routes of administration, and/or on the same or different administration schedules according to standard pharmaceutical practice known to one skilled in the art. In some embodiments, the BRAF-associated tumor is a malignant BRAF-associated tumor (i.e., a BRAF-associated cancer). In some embodiments, the BRAF-associated cancer is a BRAF-associated CNS cancer. In some embodiments, the BRAF-associated CNS cancer is a BRAF-associated metastatic cancer. In some embodiments, the BRAF-associated metastatic cancer is metastatic melanoma. In some embodiments, the BRAF-associated metastatic cancer is metastatic colorectal cancer. In some embodiments, the BRAF-associated metastatic cancer is metastatic non-small cell lung cancer. In some embodiments, the BRAF-associated metastatic cancer is metastatic thyroid cancer. In some embodiments, the BRAF-associated metastatic cancer is metastatic ovarian cancer. In some embodiments, the BRAF-associated metastatic cancer is intracranial LMD or extracranial LMD. In some embodiments, the BRAF-associated CNS cancer is a primary brain tumor. In some embodiments, the BRAF-associated tumor is a benign CNS tumor. In some embodiments, the cancer is selected from lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors.

In some embodiments of any of the methods described herein, a subject has a BRAF-associated tumor (e.g., a benign, malignant, or metastatic tumor), wherein the subject has been treated with prior therapy or standard therapy (e.g., treatment with one or more anticancer agents other than a compound of Formula I, Formula I-A, Formula II, Formula III, Formula IV, or Formula V, or a pharmaceutically acceptable salt thereof and/or radiotherapy and/or surgery) wherein said BRAF-associated tumor has become resistant or intolerant to said prior therapy. In some embodiments, a subject has a BRAF-associated tumor (e.g., a locally advanced or metastatic tumor) that has no standard therapy. In one embodiment, method comprises administering a compound of Formula I selected from Examples 1-164, or a pharmaceutically acceptable salt thereof.

Accordingly, in one embodiment provided herein is a method of treating a subject having a BRAF-associated tumor, wherein the subject was previously treated with one or more anticancer therapies (e.g., an anticancer agent, radiotherapy and/or surgery), the method comprising administering to the subject a therapeutically effective amount of a compound of Formula I, Formula I-A, Formula II, Formula III, Formula IV, or Formula V, or a pharmaceutically acceptable salt thereof. In one embodiment, the BRAF-associated tumor has become resistant to said prior therapy. In one embodiment, the cancer is a BRAF-associated cancer having a Class II mutation. In one embodiment, the Class II mutation is a non-V600 mutation. In one embodiment, the non-V600 mutation is G469A, G469R, G469V, K601E, K601N, K601T, L597Q or L597V. In one embodiment, the non-V600 mutation is G469A. In one embodiment, the Class II mutation is a BRAF splice variant. In one embodiment, the BRAF splice variant lacks exons 4-8 (also known as p61BRAF(V600E)), exons 4-10, exons 2-8 or exons 2-10. In one embodiment, the BRAF splice variant is p61BRAF (V600E). Non-limiting examples of BRAF-associated cancers having Class II mutations include lung cancer (e.g., non-small cell lung cancer and small cell lung cancer), melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, and CNS tumors.

In some embodiments, a subject having a BRAF-associated cancer was previously treated with a BRAF inhibitor (i.e., a BRAF inhibitor other than a compound of Formula I, Formula I-A, Formula II, Formula III, Formula IV or Formula V, or a pharmaceutically acceptable salt thereof), alone or in combination with another anticancer agent, prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof. In one embodiment, the subject was previously treated with a BRAF inhibitor selected from encorafenib, dabrafenib and vemurafenib, or a pharmaceutically acceptable salt thereof. In one embodiment, the BRAF-associate cancer that was treated with the prior BRAF inhibitor was a BRAF V600 mutant cancer (e.g., a BRAF V600E or BRAF V600K mutant cancer). In one embodiment, the BRAF-associated cancer became resistant to said prior treatment. In one embodiment, the BRAF-associated cancer expressed a BRAF V600 resistance mutation during or after said prior treatment. In one embodiment, the subject developed brain metastasis during said prior treatment.

In some embodiments, a subject having a BRAF-associated metastatic melanoma has received treatment with a BRAF inhibitor (i.e., a BRAF inhibitor other than a compound of Formula I, Formula I-A, Formula II, Formula III, Formula IV or Formula V, or a pharmaceutically acceptable salt thereof) prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof. In one embodiment, the subject was previously treated with a BRAF inhibitor selected from encorafenib, dabrafenib and vemurafenib, or a pharmaceutically acceptable salt thereof. In one embodiment, the melanoma became resistant to said prior treatment. In one embodiment, the melanoma expressed a BRAF V600E resistance mutation during or after said prior treatment. In one embodiment, the subject developed brain metastasis during said prior treatment.

In some embodiments, a subject having a BRAF-associated metastatic melanoma has received treatment with a BRAF inhibitor (e.g., other than a compound of Formula I, Formula I-A, Formula II, Formula III, Formula IV or Formula V, or a pharmaceutically acceptable salt thereof) and a MEK inhibitor prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, and a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof. In one embodiment, the subject was previously treated with a BRAF inhibitor selected from encorafenib, dabrafenib and vemurafenib, or a pharmaceutically acceptable salt thereof, and a MEK inhibitor selected from binimetinib, trametinib, and cobimetinib, or a pharmaceutically acceptable salt thereof. In one embodiment, the subject was previously treated with encorafenib, or a pharmaceutically acceptable salt thereof, and binimetinib, or a pharmaceutically acceptable salt thereof. In one embodiment, the subject was previously treated with dabrafenib, or a pharmaceutically acceptable salt thereof, and trametinib, or a pharmaceutically acceptable salt thereof. In one embodiment, the subject was previously treated with vemurafenib, or a pharmaceutically acceptable salt thereof and cobimetinib, or a pharmaceutically acceptable salt thereof. In one embodiment, the melanoma became resistant to said prior treatment. In one embodiment, the melanoma expressed a BRAF V600E resistance mutation during or after said prior treatment. In one embodiment, the subject developed brain metastasis during said prior treatment.

In some embodiments, a subject having a BRAF-associated metastatic melanoma has received treatment with one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV, or Formula V, or a pharmaceutically acceptable salt thereof. In one embodiment, the subject was previously treated with one or more checkpoint inhibitors independently selected from ipilimumab, nivolumab, pembrolizumab and avelumab. In one embodiment, the melanoma became resistant to said prior treatment. In one embodiment, the subject developed brain metastasis during said prior treatment.

In some embodiments, a subject having a BRAF-associated metastatic melanoma has received treatment with one or more inhibitors of PI3K prior to treatment with a compound of Formula I, Formula I-A, Formula II, Formula III, Formula IV, or Formula V, or a pharmaceutically acceptable salt thereof. In one embodiment, the subject was previously treated with one or more PI3K inhibitors selected from buparlisib (BKM120), alpelisib (BYL719), samotolisib (LY3023414), 8-[(1R)-1-[(3,5-difluorophenyl)amino]ethyl]-N,N-dimethyl-2-(morpholin-4-yl)-4-oxo-4H-chromene-6-carboxamide (AZD8186), tenalisib (RP6530), voxtalisib hydrochloride (SAR-245409), gedatolisib (PF-05212384), panulisib (P-7170), taselisib (GDC-0032), trans-2-amino-8-[4-(2-hydroxyethoxy)cyclohexyl]-6-(6-methoxypyridin-3-yl)-4-methylpyrido[2,3-d]pyrimidin-7(8H)-one (PF-04691502), duvelisib (ABBV-954), N2-[4-oxo-4-[4-(4-oxo-8-phenyl-4H-1-benzopyran-2-yl) morpholin-4-ium-4-ylmethoxy]butyryl]-L-arginyl-glycyl-L-aspartyl-L-serine acetate (SF-1126), pictilisib (GDC-0941), 2-methyl-1-[2-methyl-3-(trifluoromethyl)benzyl]-6-(morpholin-4-yl)-1H-benzimidazole-4-carboxylic acid (GSK2636771), idelalisib (GS-1101), umbralisib tosylate (TGR-1202), pictilisib (GDC-0941), copanlisib hydrochloride (BAY 84-1236), dactolisib (BEZ-235), 1-(4-[5-[5-Amino-6-(5-tert-butyl-1,3,4-oxadiazol-2-yl)pysrazin-2-yl]-1-ethyl-1H-1,2,4-triazol-3-yl]piperidin-1-yl)-3-hydroxypropan-1-one (AZD-8835), 5-[6,6-Dimethyl-4-(morpholin-4-yl)-8,9-dihydro-6H-[1,4]oxazino[4,3-e]purin-2-yl]pyrimidin-2-amine (GDC-0084) everolimus, rapamycin, perifosine, sirolimus, and temsirolimus. In one embodiment, the subject was previously treated with buparlisib or alpelisib, alone or in combination. In one embodiment, the melanoma became resistant to said prior treatment. In one embodiment, the subject developed brain metastasis during said prior treatment. In one embodiment, the subject developed brain metastasis during said prior treatment.

In some embodiments, a subject having a BRAF-associated metastatic melanoma has received treatment with a BRAF inhibitor other than a compound of Formula I, Formula I-A, Formula II, Formula III, Formula IV or Formula V, or a pharmaceutically acceptable salt thereof, and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof and one or more checkpoint inhibitors independently selected from ipilimumab, nivolumab and pembrolizumab. In one embodiment, the melanoma became resistant to said prior treatment. In one embodiment, the subject developed brain metastasis during said prior treatment.

In some embodiments, a subject having a BRAF-associated metastatic melanoma has received treatment with a BRAF inhibitor (e.g., other than a compound of Formula I, Formula I-A, Formula II, Formula III, Formula IV or Formula V, or a pharmaceutically acceptable salt thereof), a MEK inhibitor, and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and one or checkpoint inhibitors (e.g., any of the checkpoint inhibitors disclosed herein, e.g., a CTLA-4 inhibitor, a PD-1 inhibitor, and/or a PD-L1 inhibitor). In one embodiment, the subject was previously treated with a BRAF inhibitor selected from encorafenib, dabrafenib and vemurafenib, or a pharmaceutically acceptable salt thereof, a MEK inhibitor selected from binimetinib, trametinib and cobimetinib, and one or more checkpoint inhibitors independently selected from ipilimumab, nivolumab, pembrolizumab and avelumab. In one embodiment, the melanoma became resistant to said prior treatment. In one embodiment, the subject developed brain metastasis during said prior treatment.

In some embodiments, a subject having a BRAF-associated metastatic melanoma has received treatment with one or more alkylating agent prior to treatment with a compound of Formula I, Formula I-A, Formula II, Formula III, Formula IV, or Formula V, or a pharmaceutically acceptable salt thereof. In one embodiment, the subject was previously treated with one or more alkylating agents selected from temozolomide, fotemustine, lomustine and carmustine. In one embodiment, the subject was previously treated with temozolomide. In one embodiment, the melanoma became resistant to said prior treatment. In one embodiment, the subject developed brain metastasis during said prior treatment.

In some embodiments, a subject having a BRAF-associated metastatic colorectal cancer has received treatment with a BRAF inhibitor other than a compound of Formula I, Formula I-A, Formula II, Formula III, Formula IV, or Formula V, or a pharmaceutically acceptable salt thereof, a MEK inhibitor and an EGFR inhibitor prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and an EGFR inhibitor selected from cetuximab, panitumumab, osimertinib, erlotinib, gefitinib, necitumumab, neratinib, lapatinib, vandetanib and brigatinib. In one embodiment, the subject was previously treated with a BRAF inhibitor selected from encorafenib, dabrafenib and vemurafenib, or a pharmaceutically acceptable salt thereof, a MEK inhibitor selected from binimetinib, trametinib and cobimetinib, or a pharmaceutically acceptable salt thereof, and an EGFR inhibitor selected from cetuximab and panitumumab. In one embodiment, the subject was previously treated with encorafenib, or a pharmaceutically acceptable salt thereof, binimetinib, or a pharmaceutically acceptable salt thereof, and cetuximab. In one embodiment, the subject was previously treated with dabrafenib, or a pharmaceutically acceptable salt thereof, trametinib, or a pharmaceutically acceptable salt thereof, and panitumumab. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with an EGFR inhibitor prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib and a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof. In some embodiments, a subject having a BRAF-associated metastatic colorectal cancer has received treatment with cetuximab or panitumumab prior to treatment with a compound of Formula I, Formula I-A, Formula II, Formula III, Formula IV, or Formula V, or a pharmaceutically acceptable salt thereof. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with an EGFR inhibitor and one or more cytotoxic chemotherapy agents prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer has received treatment with an EGFR inhibitor selected from cetuximab, panitumumab, osimertinib, erlotinib, gefitinib, necitumumab, neratinib, lapatinib, vandetanib and brigatinib and one or more cytotoxic chemotherapeutic agents. In some embodiments, a subject having a BRAF-associated metastatic colorectal cancer (e.g., a BRAF mutant metastatic colorectal cancer) has received treatment with an EGFR inhibitor selected from cetuximab or panitumumab and one or more cytotoxic chemotherapeutic agents such as Nordic FLOX (fluorouracil, folinic acid and oxaliplatin) prior to treatment with a compound of Formula I, Formula I-A, Formula II, Formula III, Formula IV, or Formula V, or a pharmaceutically acceptable salt thereof. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with an EGFR inhibitor and a BRAF inhibitor prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer has received treatment with an EGFR inhibitor selected from cetuximab, panitumumab, osimertinib, erlotinib, gefitinib, necitumumab, neratinib, lapatinib, vandetanib and brigatinib and a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof. In one embodiment, the subject was previously treated with an EGFR inhibitor selected from cetuximab and panitumumab and a BRAF inhibitor selected from encorafenib, dabrafenib and vemurafenib, or a pharmaceutically acceptable salt thereof. In one embodiment, the subject was previously treated with encorafenib, or a pharmaceutically acceptable salt thereof and cetuximab. In one embodiment, the subject was previously treated with vemurafenib, or a pharmaceutically acceptable salt thereof and panitumumab. In one embodiment, the subject was previously treated with dabrafenib, or a pharmaceutically acceptable salt thereof and panitumumab. In one embodiment, the colorectal cancer became resistant to said prior treatment. In one embodiment, the subject developed brain metastasis during said prior treatment.

In some embodiments, a subject having metastatic colorectal cancer has received treatment with a MEK inhibitor and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV, or Formula V, or a pharmaceutically acceptable salt thereof. In one embodiment, the subject was previously treated with a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (Cl-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and one or checkpoint inhibitors (e.g., any of the checkpoint inhibitors disclosed herein, e.g., a CTLA-4 inhibitor, a PD-1 inhibitor, and/or a PD-L1 inhibitor). In one embodiment, the subject was previously treated with a MEK inhibitor selected from binimetinib, trametinib and cobimetinib, and one or more checkpoint inhibitors independently selected from ipilimumab, nivolumab, pembrolizumab and avelumab. In one embodiment, the subject was previously treated with the MEK inhibitor which is binimetinib and the checkpoint inhibitors nivolumab and ipilimumab. In one embodiment, the subject was previously treated with the MEK inhibitor binimetinib and the checkpoint inhibitor pembrolizumab. In one embodiment, the subject was previously treated with the MEK inhibitor binimetinib and the checkpoint inhibitor avelumab. In one embodiment, the subject was previously treated with the MEK inhibitor trametinib and the checkpoint inhibitors nivolumab and ipilimumab. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with Formula I, Formula I-A, Formula II, Formula III, Formula IV, or Formula V, or a pharmaceutically acceptable salt thereof. In one embodiment, the subject was previously treated with one or more checkpoint inhibitors independently selected from ipilimumab, nivolumab, pembrolizumab and avelumab. In one embodiment, the subject was previously treated with nivolumab. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with one or more cytotoxic chemotherapeutic agents prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer (e.g., a BRAF mutant metastatic colorectal cancer) has received treatment with oxaliplatin, irinotecan, FOLFOXIRI (oxaliplatin, irinotecan and fluorouracil), FOLFIRI (folinic acid, fluorouracil and irinotecan) or CAPEOX (capecitabine and oxaliplatin) prior to treatment with a compound of Formula I, Formula I-A, Formula II, Formula III, Formula IV, or Formula V, or a pharmaceutically acceptable salt thereof. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with an antibody therapy and one or more cytotoxic chemotherapeutic agents prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer (e.g., a BRAF mutant metastatic colorectal cancer) has received treatment with an antibody therapy which is bevacizumab and one or more cytotoxic chemotherapeutic agents. In some embodiments, a subject having a BRAF-associated metastatic colorectal cancer (e.g., a BRAF mutant metastatic colorectal cancer) has received treatment with bevacizumab and irinotecan, bevacizumab and FOLFOXIRI (oxaliplatin, irinotecan and fluorouracil), or bevacizumab and FOLFIRI (folinic acid, fluorouracil and irinotecan) prior to treatment with a compound of Formula I, Formula I-A, Formula II, Formula III, Formula IV, or Formula V, or a pharmaceutically acceptable salt thereof. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with an EGFR inhibitor, a BRAF inhibitor other than a compound of Formula I, Formula I-A, Formula II, Formula III, Formula IV or Formula V, and one or more cytotoxic chemotherapeutic agents prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer (has received treatment with an EGFR inhibitor selected from cetuximab, panitumumab, osimertinib, erlotinib, gefitinib, necitumumab, neratinib, lapatinib, vandetanib and brigatinib, a BRAF inhibitor selected from a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, and one or more cytotoxic chemotherapeutic agents. In some embodiments, a subject having a BRAF-associated metastatic colorectal cancer has received treatment with an EGFR inhibitor selected from cetuximab, and panitumumab, a BRAF inhibitor which is vemurafenib, or a pharmaceutically acceptable salt thereof, and a cytotoxic chemotherapeutic agent which is irinotecan. In one embodiment, the colorectal cancer became resistant to said prior treatment. In one embodiment, the subject developed brain metastasis during said prior treatment.

In some embodiments, a subject having a BRAF-associated metastatic colorectal cancer (e.g., a BRAF mutant metastatic colorectal cancer) has received treatment with an EGFR inhibitor and one or more cytotoxic chemotherapeutic agents prior to treatment with a compound of Formula I, Formula I-A, Formula II, Formula III, Formula IV, or Formula V, or a pharmaceutically acceptable salt thereof. In some embodiments, a subject having a BRAF-associated metastatic colorectal cancer (e.g., a BRAF mutant metastatic colorectal cancer) has received treatment with an EGFR inhibitor selected from cetuximab, panitumumab, osimertinib, erlotinib, gefitinib, necitumumab, neratinib, lapatinib, vandetanib and brigatinib, and one or more cytotoxic chemotherapeutic agents. In some embodiments, a subject having a BRAF-associated metastatic colorectal cancer (e.g., a BRAF mutant metastatic colorectal cancer) has received treatment with an EGFR inhibitor selected from cetuximab, and panitumumab, and a cytotoxic chemotherapeutic agent which is irinotecan or FOLFIRI (folinic acid, fluorouracil and irinotecan). In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with surgery prior to treatment with a compound of Formula I, Formula I-A, Formula II, Formula III, Formula IV, or Formula V, or a pharmaceutically acceptable salt thereof. In one embodiment, the subject became refractory to said prior treatment. In one embodiment, the subject developed brain metastasis during said prior treatment.

In some embodiments, a subject having a BRAF-associated metastatic colorectal cancer has received treatment with surgery followed by treatment with a BRAF inhibitor other than a compound of Formula I, Formula I-A, Formula II, Formula III, Formula IV or Formula V, or a pharmaceutically acceptable salt thereof, a MEK inhibitor and an EGFR inhibitor prior to treatment with a compound of Formula I, Formula I-A, Formula II, Formula III, Formula IV, or Formula V, or a pharmaceutically acceptable salt thereof. In one embodiment, the subject was previously treated with surgery and previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and an EGFR inhibitor selected from cetuximab, panitumumab, osimertinib, erlotinib, gefitinib, necitumumab, neratinib, lapatinib, vandetanib and brigatinib. In one embodiment, the subject was previously treated with surgery and previously treated with a BRAF inhibitor selected from encorafenib, dabrafenib and vemurafenib, a MEK inhibitor selected from binimetinib, trametinib and cobimetinib, or a pharmaceutically acceptable salt thereof, and an EGFR inhibitor selected from cetuximab and panitumumab. In one embodiment, the colorectal cancer became resistant to said prior treatment. In one embodiment, the subject developed brain metastasis during said prior treatment.

In some embodiments, a subject having a BRAF-associated metastatic colorectal cancer has received treatment with radiotherapy (e.g., whole brain radiotherapy or stereotactic radiosurgery) prior to treatment with a compound of Formula I, Formula I-A, Formula II, Formula III, Formula IV, or Formula V, or a pharmaceutically acceptable salt thereof. In one embodiment, the subject became resistant to said prior treatment. In one embodiment, the subject developed brain metastasis during said prior treatment.

In some embodiments, a subject having a BRAF-associated metastatic colorectal cancer has received treatment with radiotherapy (e.g., whole brain radiotherapy or stereotactic radiosurgery) followed by treatment with a BRAF inhibitor, a MEK inhibitor and an EGFR inhibitor prior to treatment with a compound of Formula I, Formula I-A, Formula II, Formula III, Formula IV, or Formula V, or a pharmaceutically acceptable salt thereof. In one embodiment, the subject was previously treated with radiotherapy and previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and an EGFR inhibitor selected from cetuximab, panitumumab, osimertinib, erlotinib, gefitinib, necitumumab, neratinib, lapatinib, vandetanib and brigatinib. In one embodiment, the subject was previously treated with surgery and previously treated with a BRAF inhibitor selected from encorafenib, dabrafenib and vemurafenib, or a pharmaceutically acceptable salt thereof, a MEK inhibitor selected from binimetinib, trametinib and cobimetinib, or a pharmaceutically acceptable salt thereof, and an EGFR inhibitor selected from cetuximab and panitumumab. In one embodiment, the colorectal cancer became resistant to said prior treatment. In one embodiment, the subject developed brain metastasis during said prior treatment.

In some embodiments, a subject having a BRAF-associated metastatic non-small cell lung cancer (e.g., a BRAF mutant metastatic non-small cell lung cancer) has received treatment with one or more EGFR inhibitors prior to treatment with a compound of Formula I, Formula I-A, Formula II, Formula III, Formula IV, or Formula V, or a pharmaceutically acceptable salt thereof. In one embodiment, the subject was previously treated with one or more EGFR inhibitors independently selected from cetuximab, panitumumab, osimertinib, erlotinib, gefitinib, necitumumab, neratinib, lapatinib, vandetanib and brigatinib. In one embodiment, the subject was previously treated with erlotinib. In one embodiment, the subject was previously treated with gefitinib. In one embodiment, the subject was previously treated with erlotinib and gefitinib. In one embodiment, the non-small cell lung cancer became resistant to said prior treatment. In one embodiment, the subject developed brain metastasis during said prior treatment.

In some embodiments, a subject having a BRAF-associated metastatic non-small cell lung cancer has received treatment with a BRAF inhibitor other that a compound of Formula I, Formula I-A, Formula II, Formula III, Formula IV, or Formula V, or a pharmaceutically acceptable salt thereof, prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and an EGFR inhibitor selected from cetuximab, panitumumab, osimertinib, erlotinib, gefitinib, necitumumab, neratinib, lapatinib, vandetanib and brigatinib. In one embodiment, the subject was previously treated with a BRAF inhibitor selected from vemurafenib, dabrafenib and encorafenib, or a pharmaceutically acceptable salt thereof and an EGFR inhibitor selected from cetuximab and panitumumab prior to treatment with a compound of Formula I, Formula I-A, Formula II, Formula III, Formula IV, or Formula V, or a pharmaceutically acceptable salt thereof. In one embodiment, the non-small cell lung cancer became resistant to said prior treatment. In one embodiment, the subject developed brain metastasis during said prior treatment.

In some embodiments, a subject having a BRAF-associated metastatic thyroid cancer (e.g., a BRAF mutant metastatic thyroid cancer) has received treatment with a BRAF inhibitor (i.e., a BRAF inhibitor other than a compound of Formula I, Formula I-A, Formula II, Formula III, Formula IV, or Formula V, or a pharmaceutically acceptable salt thereof) prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and an EGFR inhibitor selected from cetuximab, panitumumab, osimertinib, erlotinib, gefitinib, necitumumab, neratinib, lapatinib, vandetanib and brigatinib. In one embodiment, the subject was previously treated with a BRAF inhibitor selected from vemurafenib, dabrafenib and encorafenib prior to treatment with a compound of Formula I, Formula I-A, Formula II, Formula III, Formula IV, or Formula V, or a pharmaceutically acceptable salt thereof. In one embodiment, the thyroid cancer became resistant to said prior treatment. In one embodiment, the subject developed brain metastasis during said prior treatment.

In one embodiment, the subject has a BRAF-associated LMD and was previously treated with a BRAF inhibitor (i.e., a BRAF inhibitor other than a compound of Formula I, Formula I-A, Formula II, Formula III, Formula IV or Formula V, or a pharmaceutically acceptable salt thereof) and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, and one or more checkpoint inhibitors independently selected from ipilimumab, nivolumab, pembrolizumab and avelumab. In one embodiment, the LMD became resistant to said prior treatment.

In one embodiment, the subject has a BRAF-associated LMD and was previously treated with a BRAF inhibitor (i.e., a BRAF inhibitor other than a compound of Formula I, Formula I-A, Formula II, Formula III, Formula IV or Formula V, or a pharmaceutically acceptable salt thereof), a MEK inhibitor, and one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof, a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), or a pharmaceutically acceptable salt thereof, and a checkpoint inhibitor (e.g., any of the checkpoint inhibitors disclosed herein, e.g., a CTLA-4 inhibitor, a PD-1 inhibitor, and/or a PD-L1 inhibitor). In one embodiment, the subject was previously treated with a BRAF inhibitor selected from encorafenib, dabrafenib and vemurafenib, or a pharmaceutically acceptable salt thereof, a MEK inhibitor selected from binimetinib, trametinib and cobimetinib, or a pharmaceutically acceptable salt thereof, and one or more checkpoint inhibitors independently selected from ipilimumab, nivolumab, pembrolizumab and avelumab. In one embodiment, the LMD became resistant to said prior treatment.

In one embodiment, the subject has a BRAF-associated LMD and was previously treated with one or more checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, Formula I-A, Formula II, Formula III, Formula IV, or Formula V, or a pharmaceutically acceptable salt thereof. In one embodiment, the subject was previously treated with one or more checkpoint inhibitors independently selected from ipilimumab, nivolumab, pembrolizumab, avelumab and RN888. In one embodiment, the LMD became resistant to said prior treatment.

In one embodiment, the subject has a BRAF-associated glioma and was previously treated with surgery prior to treatment with a compound of Formula I, Formula I-A, Formula II, Formula III, Formula IV, or Formula V, or a pharmaceutically acceptable salt thereof. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with radiotherapy (e.g., whole brain radiotherapy or stereotactic radiosurgery) prior to treatment with a compound of Formula I, Formula I-A, Formula II, Formula III, Formula IV, or Formula V, or a pharmaceutically acceptable salt thereof. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with one or more cytotoxic chemotherapy agents prior to treatment with a compound of Formula I, Formula I-A, Formula II, Formula III, Formula IV, or Formula V, or a pharmaceutically acceptable salt thereof. In one embodiment, the subject was previously treated with one or more cytotoxic chemotherapy agents independently selected from cisplatin, pemetrexed, vinorelbine and paclitaxel. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with an ornithine decarboxylase inhibitor prior to treatment with a compound of Formula I, Formula I-A, Formula II, Formula III, Formula IV, or Formula V, or a pharmaceutically acceptable salt thereof. In one embodiment, the subject previously received treatment with an ornithine decarboxylase inhibitor which is eflornithine (as the racemate, or D or L enantiomer). In one embodiment, the glioma became resistant to said prior treatment. In one embodiment, the glioma is a Grade 2, Grade 3 or Grade 4 glioma.

In one embodiment, the subject has a BRAF-associated glioma and was previously treated with an alkylating agent prior to treatment with a compound of Formula I, Formula I-A, Formula II, Formula III, Formula IV, or Formula V, or a pharmaceutically acceptable salt thereof. In one embodiment, the subject previously received treatment with an alkylating agent selected from temozolomide, lomustine, and carmustine. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with an alkylating agent and an ornithine decarboxylase inhibitor prior to treatment with a compound of Formula I, Formula I-A, Formula II, Formula III, Formula IV, or Formula V, or a pharmaceutically acceptable salt thereof. In one embodiment, the subject previously received treatment with an alkylating agent selected from temozolomide, lomustine, and carmustine, and an ornithine decarboxylase inhibitor which is eflornithine (as the racemate, or D or L enantiomer). In one embodiment, the glioma became resistant to said prior treatment. In one embodiment, the glioma is a Grade 2, Grade 3 or Grade 4 glioma.

In one embodiment, the subject has a BRAF-associated glioma and was previously treated with radiotherapy (e.g., whole brain radiotherapy or stereotactic radiosurgery) and an alkylating agent prior to treatment with a compound of Formula I, Formula I-A, Formula II, Formula III, Formula IV or Formula V, or a pharmaceutically acceptable salt thereof. In one embodiment, the subject previously received treatment with radiotherapy (e.g., whole brain radiotherapy or stereotactic radiosurgery) and an alkylating agent selected from temozolomide, lomustine, and carmustine. In one embodiment, the subject became resistant to said prior treatment. In one embodiment, the glioma is a Grade 2, Grade 3 or Grade 4 glioma.

In one embodiment, the subject has a BRAF-associated glioma and was previously treated with an antibody therapy prior to treatment with a compound of Formula I, Formula I-A, Formula II, Formula III, Formula IV, or Formula V, or a pharmaceutically acceptable salt thereof. In one embodiment, the subject previously received treatment with an antibody therapy which is bevacizumab. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with surgery and radiotherapy prior to treatment with a compound of Formula I, Formula I-A, Formula II, Formula III, Formula IV, or Formula V, or a pharmaceutically acceptable salt thereof. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with surgery, radiotherapy and an alkylating agent prior to treatment with a compound of Formula I, Formula I-A, Formula II, Formula III, Formula IV or Formula V, or a pharmaceutically acceptable salt thereof. In one embodiment, the subject was previously treated with surgery, radiotherapy (e.g., whole brain radiotherapy or stereotactic radiosurgery) and an alkylating agent selected from temozolomide, lomustine, and carmustine. In one embodiment, the glioma became resistant to said prior treatment. In one embodiment, the glioma is a Grade 2, Grade 3 or Grade 4 glioma.

In one embodiment, the subject has a BRAF-associated glioma and was previously treated with a BRAF inhibitor (i.e., a BRAF inhibitor other than a compound of Formula I, Formula I-A, Formula II, Formula III, Formula IV or Formula V, or a pharmaceutically acceptable salt thereof) prior to treatment with compound of Formula I, Formula I-A, Formula II, Formula III, Formula IV or Formula V, or a pharmaceutically acceptable salt thereof. In one embodiment, the subject previously received treatment with a BRAF inhibitor selected from N-[3-(5-chloro-1H-pyrrolo[2,3-b]pyridin-3-ylcarbonyl)-2,4-difluorophenyl]propane-1-sulfonamide (PLX4720), vemurafenib, dabrafenib, encorafenib and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the glioma became resistant to said prior treatment. In one embodiment, the glioma is a Grade 2, Grade 3 or Grade 4 glioma.

In one embodiment, the subject has a BRAF-associated glioma and was previously treated with a BRAF inhibitor (i.e., a BRAF inhibitor other than a compound of Formula I, Formula I-A, Formula II, Formula III, Formula IV or Formula V, or a pharmaceutically acceptable salt thereof) and a MEK inhibitor prior to treatment with compound of Formula I, Formula I-A, Formula II, Formula III, Formula IV or Formula V, or a pharmaceutically acceptable salt thereof. In one embodiment, the subject previously received treatment with a BRAF inhibitor selected from N-[3-(5-chloro-1H-pyrrolo[2,3-b]pyridin-3-ylcarbonyl)-2,4-difluorophenyl]propane-1-sulfonamide (PLX4720), vemurafenib, dabrafenib, encorafenib and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394) and a MEK inhibitor selected from binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide (Cl-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733). In one embodiment, the subject was previously treated with a BRAF inhibitor selected from encorafenib, dabrafenib and vemurafenib, or a pharmaceutically acceptable salt thereof, and a MEK inhibitor selected from binimetinib, trametinib, and cobimetinib, or a pharmaceutically acceptable salt thereof. In one embodiment, the glioma became resistant to said prior treatment. In one embodiment, the glioma is a Grade 2, Grade 3 or Grade 4 glioma.

In one embodiment, the subject has a BRAF-associated brainstem ganglioglioma and was previously treated with a BRAF inhibitor (i.e., a BRAF inhibitor other than a compound of Formula I, Formula I-A, Formula II, Formula III, Formula IV or Formula V, or a pharmaceutically acceptable salt thereof) prior to treatment with a compound of Formula I, Formula I-A, Formula II, Formula III, Formula IV, or Formula V, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)-N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), or a pharmaceutically acceptable salt thereof. In one embodiment, the subject was previously treated with a BRAF inhibitor selected from encorafenib, dabrafenib and vemurafenib, or a pharmaceutically acceptable salt thereof. In one embodiment, the ganglioglioma became resistant to said prior treatment.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis.

Accordingly, also provided herein are methods for treating, inhibiting, preventing, aiding in the prevention, or decreasing the symptoms of metastasis of a BRAF-associated cancer in a subject in need thereof, the method comprising administering to the subject a therapeutically effective amount of a compound of Formula I, Formula I-A, Formula II, Formula III, Formula IV or Formula V, or a pharmaceutically acceptable salt thereof, or a pharmaceutical composition thereof. In some embodiments, the compound of Formula I, Formula I-A, Formula II, Formula III, Formula IV or Formula V, or a pharmaceutically acceptable salt thereof, is used in combination with another anticancer treatment, e.g., surgery (e.g., at least partial resection of a tumor) and/or radiotherapy and/or treatment with an anticancer agent. In one embodiment, the cancer is metastatic cancer with brain metastasis and the method comprises administering a compound of Formula I, Formula I-A, Formula II, Formula III, Formula IV or Formula V, or a pharmaceutically acceptable salt thereof. In one embodiment, the cancer is metastatic melanoma with brain metastasis. In one embodiment, the cancer is metastatic colorectal cancer with brain metastasis. In one embodiment, the cancer is metastatic non-small cell lung cancer with brain metastasis. In one embodiment, the cancer is metastatic ovarian cancer with brain metastasis. In one embodiment, the cancer is metastatic thyroid cancer with brain metastasis. In one embodiment, the cancer is neuroblastoma with brain metastasis, and the method comprises administering a compound of Formula I, Formula I-A, Formula II, Formula III, Formula IV or Formula V, or a pharmaceutically acceptable salt thereof. In one embodiment, the subject was previously treated with another anticancer treatment, e.g., surgery (e.g., at least partial resection of a tumor) and/or radiotherapy and/or treatment with an anticancer agent. In one embodiment, the subject became resistant to said previous treatment. In one embodiment, the subject is treated with a compound of Formula I, Formula I-A, Formula II, Formula III, Formula IV, or Formula V, or a pharmaceutically acceptable salt thereof, in combination with another anticancer treatment, e.g., surgery (e.g., at least partial resection of a tumor) and/or radiotherapy and/or treatment with an anticancer agent.

Also provided herein are methods for inhibiting metastasis in a subject in need thereof, the method comprising administering to the subject a therapeutically effective amount of a compound of Formula I, Formula I-A, Formula II, Formula III, Formula IV or Formula V, or a pharmaceutically acceptable salt thereof, or a pharmaceutical composition thereof. In some embodiments, the compound of Formula I, Formula I-A, Formula II, Formula III, Formula IV or Formula V, or a pharmaceutically acceptable salt thereof, is used in combination with another anticancer treatment, e.g., surgery (e.g., at least partial resection of a tumor) and/or radiotherapy and/or treatment with an anticancer agent. In one embodiment, the cancer is metastatic cancer with brain metastasis. In one embodiment, the cancer is metastatic melanoma with brain metastasis. In one embodiment, the cancer is metastatic colorectal cancer with brain metastasis. In one embodiment, the cancer is metastatic non-small cell lung cancer with brain metastasis. In one embodiment, the cancer is metastatic ovarian cancer with brain metastasis. In one embodiment, the cancer is metastatic thyroid cancer with brain metastasis. In one embodiment, the cancer is neuroblastoma with brain metastasis. In one embodiment, the subject was previously treated with another anticancer treatment, e.g., surgery (e.g., at least partial resection of a tumor) and/or radiotherapy and/or treatment with an anticancer agent. In one embodiment, the subject became resistant to said previous treatment. In one embodiment, the subject is treated with a compound of Formula I, Formula I-A, Formula II, Formula III, Formula IV, or Formula V, or a pharmaceutically acceptable salt thereof, in combination with another anticancer treatment, e.g., surgery (e.g., at least partial resection of a tumor) and/or radiotherapy and/or treatment with an anticancer agent. In one embodiment, the additional anticancer therapy is an anticancer agent. In one embodiment, the additional anticancer agent selected from MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents. In one embodiment, the additional anticancer agent is a MEK inhibitor. In one embodiment, the MEK inhibitor is binimetinib, trametinib, cobimetinib, or a pharmaceutically acceptable salt thereof. In one embodiment, the MEK inhibitor is binimetinib, or a pharmaceutically acceptable salt thereof.

As used herein, the term "treating metastasis" means reducing the size, progression, and/or further spread of one or more metastases.

Also provide herein are methods of inhibiting metastasis in a subject in need thereof, the method comprising administering to the subject a therapeutically effective amount of a compound of Formula I, Formula I-A, Formula II, Formula III, Formula IV or Formula V, or a pharmaceutically acceptable salt thereof or a pharmaceutical composition thereof. In some embodiments, the compound of Formula I, Formula I-A, Formula II, Formula III, Formula IV or Formula V, or a pharmaceutically acceptable salt thereof, is used in combination with another anticancer treatment, e.g., surgery (e.g., at least partial resection of a tumor) and/or radiotherapy and/or treatment with an anticancer agent. In one embodiment, the cancer is metastatic cancer with brain metastasis. In one embodiment, the cancer is metastatic melanoma with brain metastasis. In one embodiment, the cancer is metastatic colorectal cancer with brain metastasis. In one embodiment, the cancer is metastatic non-small cell lung cancer with brain metastasis. In one embodiment, the cancer is metastatic ovarian cancer with brain metastasis. In one embodiment, the cancer is metastatic thyroid cancer with brain metastasis. In one embodiment, the cancer is neuroblastoma with brain metastasis. In one embodiment, the subject was previously treated with another anticancer treatment, e.g., surgery (e.g., at least partial resection of a tumor) and/or radiotherapy and/or treatment with an anticancer agent. In one embodiment, the subject became resistant to said previous treatment. In one embodiment, the subject is treated with a compound of Formula I, Formula I-A, Formula II, Formula III, Formula IV, or Formula V, or a pharmaceutically acceptable salt thereof, in combination with another anticancer treatment, e.g., surgery (e.g., at least partial resection of a tumor) and/or radiotherapy and/or treatment with an anticancer agent. In one embodiment, the anticancer therapy is an anticancer agent. In one embodiment, the anticancer agent selected from MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents. In one embodiment, the anticancer agent is a MEK inhibitor. In one embodiment, the MEK inhibitor is binimetinib, trametinib, cobimetinib, or a pharmaceutically acceptable salt thereof. In one embodiment, the MEK inhibitor is binimetinib, or a pharmaceutically acceptable salt thereof.

As used herein, the term "inhibiting metastasis" means reducing the occurrence (or reoccurrence) of one or more metastases, preventing the occurrence (or reoccurrence) of one or more metastases, or reducing the spread of one or more metastases.

Also provided are methods of decreasing the risk of developing one or more metastases or one or more additional metastases in a subject having a BRAF-associated cancer that include: selecting, identifying, or diagnosing a subject as having a BRAF-associated cancer, and administering a therapeutically effective amount of a compound of Formula I, Formula I-A, Formula II, Formula III, Formula IV or Formula V, or a pharmaceutically acceptable salt thereof, to the subject selected, identified, or diagnosed as having a BRAF-associated cancer. Also provided are methods of decreasing the risk of developing one or more metastases or one or more additional metastases in a subject having a BRAF-associated cancer that includes administering a therapeutically effective amount of a compound of Formula I, Formula I-A, Formula II, Formula III, Formula IV or Formula V, or a pharmaceutically acceptable salt thereof, to a subject having a BRAF-associated cancer. The decrease in the risk of developing one or more metastases or one or more additional metastases in a subject having a BRAF-associated cancer can be compared to the risk of developing one or more metastases or one or more additional metastases in the subject prior to treatment, or as compared to a subject or a population of subjects having a similar or the same BRAF-associated cancer that has received no treatment or a different treatment.

The phrase "risk of developing one or more metastases" means the risk that a subject or subject having a primary tumor will develop an additional tumor (e.g., a solid tumor) at a site distant from a primary tumor in a subject or subject over a set period of time, where the additional tumor includes the same or similar cancer cells as the primary tumor. Methods for reducing the risk of developing one or more metastases in a subject or subject having a cancer are described herein.

The phrase "risk of developing additional metastases" means the risk that a subject or subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Also provided herein is a method of treating a BRAF-associated tumor, metastasis of a BRAF-associated tumor, or a combination thereof, in a subject in need thereof, the method comprising administering a compound of Formula I, Formula I-A, Formula II, Formula III, Formula IV, or Formula V, or a pharmaceutically acceptable salt thereof, to the subject. In one embodiment, the subject has at least one metastasis or is at risk of developing at least one metastasis. In one embodiment, the subject has at least one metastasis. In one embodiment, the subject is at risk of developing at least one metastasis. In one embodiment, the subject is at risk of developing at least one metastasis, wherein said subject has a cancer selected from melanoma, colorectal cancer, thyroid cancer, non-small cell lung cancer, or ovarian cancer. In one embodiment, the cancer is a cancer having a BRAF Class I mutation (e.g., a BRAF V600 mutant cancer, e.g., a cancer having a BRAF V600E and/or BRAF V600K mutation). In one embodiment, the cancer is a cancer having a BRAF Class II mutation (e.g., a G469A mutation or a BRAF V600E splice variant). In one embodiment, the subject was previously treated with another anticancer treatment, e.g., surgery (e.g., at least partial resection of a tumor) and/or radiotherapy and/or treatment with an anticancer agent. In one embodiment, the subject became resistant to said previous treatment. In one embodiment, the subject is treated with a compound of Formula I, Formula I-A, Formula II, Formula III, Formula IV, or Formula V, or a pharmaceutically acceptable salt thereof, in combination with another anticancer treatment, e.g., surgery (e.g., at least partial resection of a tumor) and/or radiotherapy and/or treatment with an anticancer agent. In one embodiment, the anticancer therapy is an anticancer agent selected from MEK inhibitors, BRAF inhibitors, EGFR inhibitors, SOS1 inhibitors, inhibitors of HER2 and/or HER3, Axl inhibitors, PI3K inhibitors, signal transduction pathway inhibitors, checkpoint inhibitors, modulators of the apoptosis pathway, cytotoxic chemotherapeutics, angiogenesis-targeted therapies, and immune-targeted agents. In one embodiment, the anticancer agent is a MEK inhibitor. In one embodiment, the MEK inhibitor is binimetinib, trametinib, cobimetinib, or a pharmaceutically acceptable salt thereof. In one embodiment, the MEK inhibitor is binimetinib, or a pharmaceutically acceptable salt thereof.

In some embodiments, a subject is administered one or more agents to ameliorate side effects of treatment (e.g., one or more of corticosteroids, serotonin antagonists, dopamine antagonists, NK-1 inhibitors, cannabinoids, anti-anxiety drugs (e.g., lorazepam or diazepam), antibiotics, anti-fungal agents, colony-stimulating factor, iron supplements, Procrit, epoetin alfa, darbepoetin alfa, anti-emetics, diuretics, NSAIDs, analgesics, methotrexate, anti-diuretics, probiotics, blood pressure medications, anti-nausea agents, laxatives, etc.).

In one embodiment, the BRAF-associated tumor is a benign tumor, and a compound of Formula I, Formula I-A, Formula II, Formula III, Formula IV or Formula V, or a pharmaceutically acceptable salt thereof, may be used alone or in combination with one or more different forms of treatment to treat a subject with a benign tumor.

In some embodiments, a subject has a CNS tumor and is administered one or more agents to ameliorate one or more symptoms associated with a CNS tumor, including, but not limited to, seizures, nausea, headaches, blurred vision, loss of vision, loss of balance, changes in fine motor skills, and drowsiness. Examples of such agents to ameliorate one or more symptoms associated with a CNS tumor include corticosteroids, anti-seizure medications (e.g., cannabidiol, gabapentin or pregabalin), pain medications (e.g., NSAIDS, acetaminophen) and anti-nausea agents.

Also provided is a method for inhibiting BRAF kinase activity in a mammalian cell, comprising contacting the cell with an effective amount of a compound of Formula I, Formula I-A, Formula II, Formula III, Formula IV, or Formula V, or a pharmaceutically acceptable salt thereof. In some embodiments, the contacting is in vitro. In some embodiments, the contacting is in vivo. In some embodiments, the contacting is in vivo, wherein the method comprises administering a therapeutically effective amount of a compound of Formula I, Formula I-A, Formula II, Formula III, Formula IV or Formula V, or a pharmaceutically acceptable salt thereof to a subject having a cell having BRAF kinase activity. In some embodiments, the cell is a cancer cell. In some embodiments, the cancer cell is any cancer as described herein. In some embodiments, the cancer cell is a BRAF-associated cancer cell. In some embodiments, the cell is a brain cell (e.g., a neural cell or a glial cell).

As used herein, the term "contacting" refers to the bringing together of indicated moieties in an in vitro system or an in vivo system. For example, "contacting" a BRAF kinase with a compound provided herein includes contacting a cell containing a BRAF kinase with the compound provided herein, as well as, for example, introducing a compound provided herein into a sample containing a cellular or purified preparation containing the BRAF kinase.

Also provided herein is a method of inhibiting cell proliferation, in vitro or in vivo, the method comprising contacting a cell with a therapeutically effective amount of a compound of Formula I, Formula I-A, Formula II, Formula III, Formula IV or Formula V, or a pharmaceutically acceptable salt thereof, or a pharmaceutical composition thereof as defined herein.

As used herein, a "therapeutically effective amount" of a compound, pharmaceutical composition thereof, or pharmaceutical combination thereof, is an amount sufficient to achieve any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include providing a therapeutic effect can include reducing the size of a tumor, inhibiting (e.g., slowing, to some extent, preferably stopping) tumor progression, inhibiting (e.g., slowing, to some extent, preferably stopping) tumor growth, inhibiting (e.g., slowing, to some extent, preferably stopping) tumor invasiveness, and/or inhibiting (e.g., slowing, to some extent, preferably stopping) tumor metastasis. The skilled person understands that tumor progression in human subjects can be determined by a variety of methods. For example, the size of a tumor close to the skin can be measured by establishing the width and depth of the tumor with calipers, and then calculating the tumor volume. Less accessible tumors, such as lung and CNS cancers can be measured by observation of the images obtained from Magnetic Resonance Imaging (MRI) scanning. CNS tumors, such as brain tumors, can be measured by a combination of MRI scanning and by monitoring neurological performance. Growth of a brain tumor is typically associated with decreasing neurological performance. Providing a therapeutic effect also includes prolonging survival of a subject or subject beyond that expected in the absence of treatment and/or relieving to some extent (or preferably eliminating) one or more signs or symptoms associated with cancer. In one embodiment, treatment of a subject or subject with a compound or combination according to an invention prolongs survival beyond that expected in the absence of treatment by 1 or months, e.g., by 3 or more months, e.g., by 6 or more months, e.g., by 1 or more years, e.g., by 2 or more years, e.g., by 3 or more years, e.g., by 5 or more years, e.g., by 10 or more years. Providing a therapeutic effect also includes reducing the number of cancer cells. Providing a therapeutic effect also includes eliminating cancer cells. Providing a therapeutic effect also includes tumor mass reduction. Providing a therapeutic effect also includes causing a cancer to go into remission. A therapeutically effective amount can be administered in one or more administrations. For purposes of this invention, dosage therapeutically effective amount of a compound, or pharmaceutical composition thereof is an amount sufficient to accomplish prophylactic or therapeutic treatment either directly or indirectly. As is understood in the clinical context, dosage therapeutically effective amount of a compound or pharmaceutical composition thereof may be achieved in conjunction with another therapy. Thus, a "therapeutically effective amount" may be considered in the context of administering one or more therapies (e.g., one or more anticancer agents), and a single agent may be considered to be given in a therapeutically effective amount if, in conjunction with one or more other agents, a desirable result may be or is achieved. In reference to the treatment of cancer, a therapeutically effective amount may also refer to that amount which has the effect of (1) reducing the size of the tumor, (2) inhibiting (that is, slowing to some extent, preferably stopping) tumor metastasis emergence, (3) inhibiting to some extent (that is, slowing to some extent, preferably stopping) tumor growth or tumor invasiveness, and/or (4) relieving to some extent (or, preferably, eliminating) one or more signs or symptoms associated with the cancer. Therapeutic or pharmacological effectiveness of the doses and administration regimens may also be characterized as the ability to induce, enhance, maintain or prolong disease control and/or overall survival in subjects with these specific tumors, which may be measured as prolongation of the time before disease progression.

In one embodiment, a subject treated according to any of the methods disclosed herein may be assessed according to one or more standard response assessment criteria known in the art, including RECIST (Response Evaluation Criteria in Solid Tumors, e.g., RECIST version 1.0, RECIST version 1.1, and modified RECIST 1.1 (mRECIST 1.1)), RANO-BM (Response Assessment in Neuro-Oncology Brain Metastases), Macdonald, RANO-LMD, and NANO (Neurologic Assessment in Neuro-Oncology). In one embodiment of any of said criteria, the tumor is assessed by an imaging study (e.g., MRI, CT, MDCT or PET). In one embodiment the treatment response is assessed in accordance with RECIST version 1.1, wherein: complete response (CR) is defined as the complete disappearance of all tumor lesions; partial response (PR) is defined as a reduction in the sum of tumor measurements by at least 30%; progressive disease (PD) is defined as at least 20% increase in the sum of tumor measurements (wherein the development of new lesions or substantial progression of non-target lesions is also was defined as PD) wherein an increase of at least 5 mm from baseline is evaluated as PD; and stable disease (SD) is defined as neither sufficient shrinkage to qualify for PR nor sufficient increase to qualify for PD, taking as reference the smallest sum diameters while on treatment. In one embodiment, assessments include intracranial response (assessed as per modified RECIST using gadolinium enhanced MRI), extracranial response, global response rate, disease control rate (DCR), duration of response (DOR), progression free survival (PFS), and overall survival (OS).

In one embodiment, the subject has a CNS tumor and has at least one measurable intracranial tumor. In one embodiment, the at least one measurable intracranial tumor is measured by MRI CT scanning.

A "measurable" tumor (tumor lesion) means a tumor that can be accurately measured in at least one dimension (longest diameter in the plane of measurement is not recorded) with a minimum size of: 10 mm by CT scan (CT scan slice thickness no greater than 5 mm); 10 mm caliper measurement by clinical exam; 20 mm by chest X-ray.

When employed as pharmaceuticals, a compound of Formula I, Formula I-A, Formula II, Formula III, Formula IV or Formula V, or a pharmaceutically acceptable salt thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders.

Conventional pharmaceutical carriers, aqueous, powder or oily bases, thickeners and the like may be necessary or desirable.

Also provided herein are pharmaceutical compositions which contain, as the active ingredient, a compound of Formula I, Formula I-A, Formula II, Formula III, Formula IV or Formula V, or a pharmaceutically acceptable salt thereof, in combination with one or more pharmaceutically acceptable carriers (excipients). For example, a pharmaceutical composition prepared using a compound of Formula I, Formula I-A, Formula II, Formula III, Formula IV, or Formula V, or a pharmaceutically acceptable salt thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I, Formula I-A, Formula II, Formula III, Formula IV or Formula V, or a pharmaceutically acceptable salt thereof with a pharmaceutically acceptable carrier. Pharmaceutical compositions containing a compound of Formula I, Formula I-A, Formula II, Formula III, Formula IV or Formula V, or a pharmaceutically acceptable salt thereof as the active ingredient can be prepared by intimately mixing the compound of Formula I, Formula I-A, Formula II, Formula III, Formula IV or Formula V, or a pharmaceutically acceptable salt thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In preparing the compositions in oral dosage form, any of the usual pharmaceutical media can be employed. Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver a therapeutically effective amount as described herein.

The compositions comprising a compound of Formula I, Formula I-A, Formula II, Formula III, Formula IV or Formula V, or a pharmaceutically acceptable salt thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other subjects, each unit containing a predetermined quantity of active material (i.e., a compound of Formula I, Formula I-A, Formula II, Formula III, Formula IV, or Formula V, or a pharmaceutically acceptable salt thereof) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain about 10 mg, about 20 mg, about 80 mg, or about 160 mg of the active ingredient.

The daily dosage of the compound of Formula I, Formula I-A, Formula II, Formula III, Formula IV, or Formula V, or a pharmaceutically acceptable salt thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the subject to be treated. A therapeutically effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula I, Formula I-A, Formula II, Formula III, Formula IV, or Formula V, or a pharmaceutically acceptable salt thereof can be administered on a regimen of 1 to 4 times per day or in a single daily dose.

The active compound may be effective over a wide dosage range and is generally administered in a therapeutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily (QD) or twice-daily (BID) administration. In some embodiments, such administration can be on an intermittent dosing schedule.

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, can be completed according to methods well known in the clinical and medical arts.

Provided herein are pharmaceutical kits useful, for example, in the treatment of BRAF-associated diseases or disorders, such as cancer, which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Also provided herein are the following embodiments:

Embodiment 1. A compound of Formula I

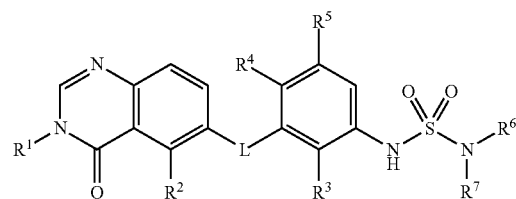

I or a pharmaceutically acceptable salt thereof, wherein:

L is NH or O;

$R^1$ is C1-C6 alkyl, C1-C6 deuteroalkyl, C1-C6 fluoroalkyl, C3-C6 cycloalkyl, (C3-C6 cycloalkyl)$CH_2$—, (C1-C6 alkoxy)C1-C6 alkyl-, $Ar^1$, $Ar^1CH_2$—, $hetAr^1$ or $hetCyc^1$;

$Ar^1$ is phenyl which is optionally substituted with 1, 2, 3, 4 or 5 substituents independently selected from halogen and C1-C3 alkyl;

$hetAr^1$ is a 5-6 membered heteroaryl ring having 1 or 2 ring nitrogen atoms and which is optionally substituted with 1, 2 or 3 substituents independently selected from halogen and C1-C3 alkyl;

$hetCyc^1$ is a 4-6 membered saturated monocyclic heterocyclic ring having a ring oxygen atom;

$R^2$ is —$CH_3$, —$CH_2CH_3$, —CH=$CH_2$, F, Cl, Br or CN;

$R^3$ is F or Cl;

$R^4$ is H or F;

$R^5$ is H, F or Cl;

$R^6$ is C1-C6 alkyl, and $R^7$ is C1-C6 alkyl, $hetCyc^2$ or C3-C6 cycloalkyl, or $R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —$OCH_3$, —$OCHF_2$, —$OCD_3$, —$CH_3$, —$CH_2CH_3$, —$CH_2OCH_3$, —$CH_2OCH_2F$, —$CH_2OCHF_2$, —$CH_2OCF_3$, —$OCF_3$, —$OCH_2CH_3$, and CN, (ii) a 6-7 membered fused bicyclic ring optionally substituted with 1 or 2 substituents independently selected from F and —$CH_3$, (iii) a 6-7 membered bridged ring, and (iv) a 6-8-membered spirocyclic ring; and $hetCyc^2$ is a 5-6 membered saturated monocyclic heterocyclic ring having 1 or 2 ring heteroatoms independently selected from N and O;

provided that the compound is not:

N-(2-chloro-3-((3,5-dimethyl-4-oxo-3,4-dihydroquinazolin-6-yl)amino)-4-fluorophenyl)pyrrolidine-1-sulfonamide, (R)-N-(2-chloro-3-((3,5-dimethyl-4-oxo-3,4-dihydroquinazolin-6-yl)amino)-4-fluorophenyl)-3-fluoropyrrolidine-1-sulfonamide, or N-(2-chloro-3-((3,5-dimethyl-4-oxo-3,4-dihydroquinazolin-6-yl)amino)-4-fluorophenyl)-N-ethyl-N-methylamino-1-sulfonamide.

Embodiment 2. A compound of Formula II

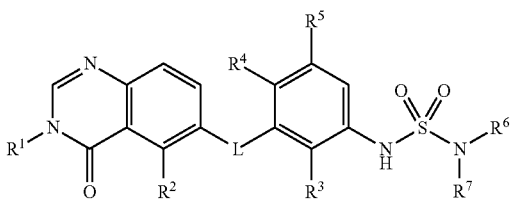

or a pharmaceutically acceptable salt thereof, wherein:
L is NH or O;
R$^1$ is C1-C6 alkyl or C1-C6 fluoroalkyl;
R$^2$ is —CH$_3$, —CH$_2$CH$_3$, —CH=CH$_2$, F, Cl, Br or CN;
R$^3$ is F or Cl;
R$^4$ is H or F;
R$^5$ is H, F or Cl;
R$^6$ is C1-C6 alkyl, and
R$^7$ is C1-C6 alkyl, hetCyc$^2$ or C3-C6 cycloalkyl,
or R$^6$ and R$^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and
hetCyc$^2$ is a 5-6 membered saturated monocyclic heterocyclic ring having 1 or 2 ring heteroatoms independently selected from N and O;
provided that the compound is not:
N-(2-chloro-3-((3,5-dimethyl-4-oxo-3,4-dihydroquinazolin-6-yl)amino)-4-fluorophenyl)pyrrolidine-1-sulfonamide,
(R)-N-(2-chloro-3-((3,5-dimethyl-4-oxo-3,4-dihydroquinazolin-6-yl)amino)-4-fluorophenyl)-3-fluoropyrrolidine-1-sulfonamide, or
N-(2-chloro-3-((3,5-dimethyl-4-oxo-3,4-dihydroquinazolin-6-yl)amino)-4-fluorophenyl)-N-ethyl-N-methylamino-1-sulfonamide.

Embodiment 3. A compound of Formula III

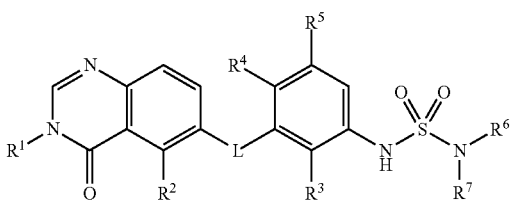

or a pharmaceutically acceptable salt thereof, wherein:
L is NH or O;
R$^1$ is C1-C6 alkyl, C1-C6 deuteroalkyl, C1-C6 fluoroalkyl, C3-C6 cycloalkyl, (C3-C6 cycloalkyl)CH$_2$—, (C1-C6 alkoxy)C1-C6 alkyl-, Ar$^1$, Ar$^1$CH$_2$—, hetAr$^1$ or hetCyc$^1$;

Ar$^1$ is phenyl which is optionally substituted with 1, 2, 3, 4 or 5 substituents independently selected from halogen and C1-C3 alkyl;
hetAr$^1$ is a 5-6 membered heteroaryl ring having 1 or 2 ring nitrogen atoms and which is optionally substituted with 1, 2 or 3 substituents independently selected from halogen and C1-C3 alkyl;
hetCyc$^1$ is a 4-6 membered saturated monocyclic heterocyclic ring having a ring oxygen atom;
R$^2$ is —CH$_2$CH$_3$, —CH=CH$_2$, F, Cl, Br or CN;
R$^3$ is F or Cl;
R$^4$ is H or F;
R$^5$ is H, F or Cl;
R$^6$ is C1-C6 alkyl, and
R$^7$ is C1-C6 alkyl, hetCyc$^2$ or C3-C6 cycloalkyl,
or R$^6$ and R$^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and
hetCyc$^2$ is a 5-6 membered saturated monocyclic heterocyclic ring having 1 or 2 ring heteroatoms independently selected from N and O.

Embodiment 4. A compound of Formula IV

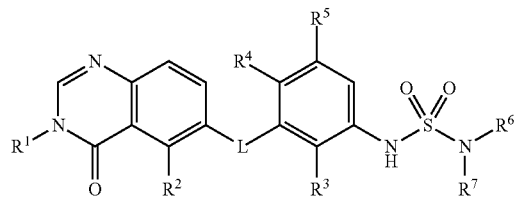

or a pharmaceutically acceptable salt thereof, wherein:
L is NH or O;
R$^1$ is C1-C6 alkyl, C1-C6 deuteroalkyl, C1-C6 fluoroalkyl, C3-C6 cycloalkyl, (C3-C6 cycloalkyl)CH$_2$—, (C1-C6 alkoxy)C1-C6 alkyl-, Ar$^1$, Ar$^1$CH$_2$—, hetAr$^1$ or hetCyc$^1$;
Ar$^1$ is phenyl which is optionally substituted with 1, 2, 3, 4 or 5 substituents independently selected from halogen and C1-C3 alkyl;
hetAr$^1$ is a 5-6 membered heteroaryl ring having 1 or 2 ring nitrogen atoms and which is optionally substituted with 1, 2 or 3 substituents independently selected from halogen and C1-C3 alkyl;
hetCyc$^1$ is a 4-6 membered saturated monocyclic heterocyclic ring having a ring oxygen atom;
R$^2$ is —CH$_3$, —CH$_2$CH$_3$, —CH=CH$_2$, F, Cl, Br or CN;
R$^3$ is F or Cl;
R$^4$ is H or F;
R$^5$ is H, F or Cl;
R$^6$ is C1-C6 alkyl, and
R$^7$ is C1-C6 alkyl, hetCyc$^2$ or C3-C6 cycloalkyl,
or R$^6$ and R$^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring; and hetCyc$^2$ is a 5-6 membered saturated monocyclic heterocyclic ring having 1 or 2 ring heteroatoms independently selected from N and O;

wherein when R$^1$ is methyl, L is NH, R$^3$ is Cl, R$^4$ is F, R$^5$ is H, and R$^6$ is methyl and R$^7$ is ethyl, or R$^6$ and R$^7$ together with the nitrogen atom to which they are attached form a pyrrolidinyl or 3-fluoropyrrolidinyl, then R$^2$ is —CH$_2$CH$_3$, —CH=CH$_2$, F, Cl, Br or CN.

Embodiment 5. The compound according to any one of Embodiments 1-4 or a pharmaceutically acceptable salt thereof, wherein R$^1$ is C1-C6 alkyl.

Embodiment 6. The compound according to Embodiment 5 or a pharmaceutically acceptable salt thereof, wherein R$^1$ is methyl.

Embodiment 7. The compound according to any one of Embodiments 1-4 or a pharmaceutically acceptable salt thereof, wherein R$^1$ is C1-C6 fluoroalkyl.

Embodiment 8. The compound according to Embodiment 7 or a pharmaceutically acceptable salt thereof, wherein R$^1$ is fluoromethyl.

Embodiment 9. The compound according to any one of Embodiments 1-8 or a pharmaceutically acceptable salt thereof, wherein R$^2$ is F or Cl.

Embodiment 10. The compound according to any one of Embodiments 1-9 or a pharmaceutically acceptable salt thereof, wherein:
R$^6$ is C1-C6 alkyl, and
R$^7$ is C1-C6 alkyl, hetCyc$^2$ or C3-C6 cycloalkyl.

Embodiment 11. The compound according to any one of Embodiments 1-9 or a pharmaceutically acceptable salt thereof, wherein R$^6$ and R$^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, (ii) a 6-7 membered fused bicyclic ring optionally substituted with 1 or 2 substituents independently selected from F and —CH$_3$, (iii) a 6-7 membered bridged ring, and (iv) a 6-8-membered spirocyclic ring.

Embodiment 12. The compound according to Embodiment 11 or a pharmaceutically acceptable salt thereof, wherein R$^6$ and R$^7$ together with the nitrogen atom to which they are attached form a saturated 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN.

Embodiment 13. The compound according to Embodiment 11 or a pharmaceutically acceptable salt thereof, wherein R$^6$ and R$^7$ together with the nitrogen atom to which they are attached form a saturated 4-6 membered monocyclic ring optionally substituted with F.

Embodiment 14. The compound according to any one of Embodiments 1-13 or a pharmaceutically acceptable salt thereof, wherein L is O.

Embodiment 15. The compound according to any one of Embodiments 1-13 or a pharmaceutically acceptable salt thereof, wherein L is NH.

Embodiment 16. The compound according to Embodiment 1, selected from:

(R)-N-(2-chloro-3-((3,5-dimethyl-4-oxo-3,4-dihydroquinazolin-6-yl)amino)-4-fluorophenyl)-3-methoxypyrrolidine-1-sulfonamide;

N-(2-chloro-3-((3,5-dimethyl-4-oxo-3,4-dihydroquinazolin-6-yl)amino)-4-fluorophenyl)-(N-ethyl-N-methyl)-sulfamide;

N-(2-chloro-3-((5-chloro-3-methyl-4-oxo-3,4-dihydroquinazolin-6-yl)amino)-4-fluorophenyl)-(N,N-dimethyl)-sulfamide;

N-(2-chloro-4-fluoro-3-((5-fluoro-3-methyl-4-oxo-3,4-dihydroquinazolin-6-yl)amino)phenyl)-(N-ethyl-N-methyl)-sulfamide;

(R)-N-(2-chloro-4-fluoro-3-((5-fluoro-3-methyl-4-oxo-3,4-dihydroquinazolin-6-yl)amino)phenyl)-3-methoxypyrrolidine-1-sulfonamide;

(R)-N-(2-chloro-4-fluoro-3-((5-chloro-3-methyl-4-oxo-3,4-dihydroquinazolin-6-yl)amino)phenyl)-3-methoxypyrrolidine-1-sulfonamide;

N-(2-chloro-4-fluoro-3-((5-fluoro-3-methyl-4-oxo-3,4-dihydroquinazolin-6-yl)amino)phenyl)pyrrolidine-1-sulfonamide;

(R)-N-(3-((5-bromo-3-methyl-4-oxo-3,4-dihydroquinazolin-6-yl)amino)-2-chloro-4-fluorophenyl)-3-methoxypyrrolidine-1-sulfonamide;

N-(2-chloro-3-((5-chloro-3-methyl-4-oxo-3,4-dihydroquinazolin-6-yl)amino)-4-fluorophenyl)-2-azabicyclo[2.1.1]hexane-2-sulfonamide;

(R)-N-(2-chloro-3-((3,5-dimethyl-4-oxo-3,4-dihydroquinazolin-6-yl)oxy)-4-fluorophenyl)-3-methoxypyrrolidine-1-sulfonamide;

N-(3-((5-bromo-3-methyl-4-oxo-3,4-dihydroquinazolin-6-yl)amino)-2-chloro-4-fluorophenyl)pyrrolidine-1-sulfonamide;

N-(2-chloro-3-((5-chloro-3-methyl-4-oxo-3,4-dihydroquinazolin-6-yl)amino)-4-fluorophenyl)pyrrolidine-1-sulfonamide;

N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide;

(R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide;

cis-N-(2-chloro-4-fluoro-3-((5-fluoro-3-methyl-4-oxo-3,4-dihydroquinazolin-6-yl)amino)phenyl)-3-fluoro-4-methoxypyrrolidine-1-sulfonamide;

cis-N-(3-((5-bromo-3-methyl-4-oxo-3,4-dihydroquinazolin-6-yl)amino)-2-chloro-4-fluorophenyl)-3-fluoro-4-methoxypyrrolidine-1-sulfonamide;

N-(2-chloro-3-((5-chloro-3-methyl-4-oxo-3,4-dihydroquinazolin-6-yl)amino)-4-fluorophenyl)-3-azabicyclo[3.1.0]hexane-3-sulfonamide;

cis-N-(2-chloro-3-((5-chloro-3-methyl-4-oxo-3,4-dihydroquinazolin-6-yl)amino)-4-fluorophenyl)-3-fluoro-4-methoxypyrrolidine-1-sulfonamide;

(R)-N-(2-chloro-3-((5-chloro-3-methyl-4-oxo-3,4-dihydroquinazolin-6-yl)amino)-4-fluorophenyl)-3-fluoropyrrolidine-1-sulfonamide;

(R)-N-(2-chloro-4-fluoro-3-((5-fluoro-3-methyl-4-oxo-3,4-dihydroquinazolin-6-yl)oxy)phenyl)-3-fluoropyrrolidine-1-sulfonamide;

cis-N-(2-chloro-4-fluoro-3-((5-fluoro-3-methyl-4-oxo-3,4-dihydroquinazolin-6-yl)amino)phenyl)-3,4-difluoropyrrolidine-1-sulfonamide;

cis-N-(2-chloro-3-((5-chloro-3-methyl-4-oxo-3,4-dihydroquinazolin-6-yl)amino)-4-fluorophenyl)-3,4-difluoropyrrolidine-1-sulfonamide;

N-(2-chloro-4-fluoro-3-((5-fluoro-3-methyl-4-oxo-3,4-dihydroquinazolin-6-yl)amino)phenyl)-3,3-difluoropyrrolidine-1-sulfonamide;

(R)-N-(3-((5-bromo-3-methyl-4-oxo-3,4-dihydroquinazolin-6-yl)amino)-2-chloro-4-fluorophenyl)-3-fluoropyrrolidine-1-sulfonamide;

N-(2-chloro-3-((5-chloro-3-methyl-4-oxo-3,4-dihydroquinazolin-6-yl)amino)-4-fluorophenyl)-3,3-difluoropyrrolidine-1-sulfonamide;

(R)-N-(2-chloro-4-fluoro-3-((5-fluoro-3-methyl-4-oxo-3,4-dihydroquinazolin-6-yl)amino)phenyl)-3-(difluoromethoxy)pyrrolidine-1-sulfonamide;

(S)-N-(2-chloro-4-fluoro-3-((5-fluoro-3-methyl-4-oxo-3,4-dihydroquinazolin-6-yl)amino)phenyl)-3-fluoropyrrolidine-1-sulfonamide;

(S)-N-(2-chloro-3-((5-chloro-3-methyl-4-oxo-3,4-dihydroquinazolin-6-yl)amino)-4-fluorophenyl)-3-fluoropyrrolidine-1-sulfonamide;

(R)-N-(2-chloro-3-((5-chloro-3-methyl-4-oxo-3,4-dihydroquinazolin-6-yl)amino)-4-fluorophenyl)-3-(difluoromethoxy)pyrrolidine-1-sulfonamide;

N-(2-chloro-4-fluoro-3-((5-fluoro-3-methyl-4-oxo-3,4-dihydroquinazolin-6-yl)amino)phenyl)-3-azabicyclo[3.1.0]hexane-3-sulfonamide;

N-(2-chloro-3-((5-chloro-3-methyl-4-oxo-3,4-dihydroquinazolin-6-yl)amino)-4,5-difluorophenyl)pyrrolidine-1-sulfonamide;

(R)-N-(2-chloro-3-((5-chloro-3-methyl-4-oxo-3,4-dihydroquinazolin-6-yl)amino)-4,5-difluorophenyl)-3-methoxypyrrolidine-1-sulfonamide;

(R)-N-(2-chloro-3-((5-chloro-3-methyl-4-oxo-3,4-dihydroquinazolin-6-yl)amino)-4,5-difluorophenyl)-3-fluoropyrrolidine-1-sulfonamide;

(R)-N-(3-((5-chloro-3-methyl-4-oxo-3,4-dihydroquinazolin-6-yl)amino)-2,4,5-trifluorophenyl)-3-methoxypyrrolidine-1-sulfonamide;

(R)-N-(2-chloro-3-((3,5-dimethyl-4-oxo-3,4-dihydroquinazolin-6-yl)amino)-4,5-difluorophenyl)-3-fluoropyrrolidine-1-sulfonamide;

(R)-N-(3-((5-chloro-3-methyl-4-oxo-3,4-dihydroquinazolin-6-yl)amino)-2,4,5-trifluorophenyl)-3-fluoropyrrolidine-1-sulfonamide;

(R)-N-(2-chloro-3-((5-chloro-3-methyl-4-oxo-3,4-dihydroquinazolin-6-yl)oxy)-4-fluorophenyl)-3-methoxypyrrolidine-1-sulfonamide;

(R)-N-(2-chloro-3-((5-chloro-3-methyl-4-oxo-3,4-dihydroquinazolin-6-yl)oxy)-4-fluorophenyl)-3-fluoropyrrolidine-1-sulfonamide;

N-(2-chloro-3-((5-chloro-3-methyl-4-oxo-3,4-dihydroquinazolin-6-yl)oxy)-4-fluorophenyl)pyrrolidine-1-sulfonamide;

N-(2-chloro-4,5-difluoro-3-((5-fluoro-3-methyl-4-oxo-3,4-dihydroquinazolin-6-yl)amino)phenyl)pyrrolidine-1-sulfonamide;

N-(2-chloro-4,5-difluoro-3-((5-fluoro-3-methyl-4-oxo-3,4-dihydroquinazolin-6-yl)amino)phenyl)-2-azabicyclo[2.1.1]hexane-2-sulfonamide;

N-(2-chloro-4-fluoro-3-((5-fluoro-3-(fluoromethyl)-4-oxo-3,4-dihydroquinazolin-6-yl)amino)phenyl)pyrrolidine-1-sulfonamide;

N-(3-((5-chloro-3-methyl-4-oxo-3,4-dihydroquinazolin-6-yl)amino)-2,4,5-trifluorophenyl)pyrrolidine-1-sulfonamide;

N-(2-chloro-4-fluoro-3-((5-fluoro-3-methyl-4-oxo-3,4-dihydroquinazolin-6-yl)oxy)phenyl)pyrrolidine-1-sulfonamide;

N-(2-chloro-4,5-difluoro-3-((5-fluoro-3-methyl-4-oxo-3,4-dihydroquinazolin-6-yl)phenyl)-(N-ethyl-N-methyl)-sulfamide;

(R)-N-(2-chloro-4,5-difluoro-3-((5-fluoro-3-methyl-4-oxo-3,4-dihydroquinazolin-6-yl)amino)phenyl)-3-fluoropyrrolidine-1-sulfonamide;

(R)-N-(2-chloro-4,5-difluoro-3-((5-fluoro-3-methyl-4-oxo-3,4-dihydroquinazolin-6-yl)amino)phenyl)-3-methoxypyrrolidine-1-sulfonamide;

(R)-N-(2-chloro-4-fluoro-3-((5-fluoro-3-methyl-4-oxo-3,4-dihydroquinazolin-6-yl)oxy)phenyl)-3-methoxypyrrolidine-1-sulfonamide;

N-(2-chloro-4-fluoro-3-((5-fluoro-3-methyl-4-oxo-3,4-dihydroquinazolin-6-yl)oxy)phenyl)-2-azabicyclo[2.1.1]hexane-2-sulfonamide;

N-(2-chloro-3-((5-cyano-3-methyl-4-oxo-3,4-dihydroquinazolin-6-yl)amino)-4-fluorophenyl)pyrrolidine-1-sulfonamide;

N-(2-chloro-4-fluoro-3-((3-methyl-4-oxo-5-vinyl-3,4-dihydroquinazolin-6-yl)amino)phenyl)pyrrolidine-1-sulfonamide;

N-(2-chloro-3-((5-ethyl-3-methyl-4-oxo-3,4-dihydroquinazolin-6-yl)amino)-4-fluorophenyl)pyrrolidine-1-sulfonamide;

(R)-N-(2-chloro-3-((5-chloro-3-methyl-4-oxo-3,4-dihydroquinazolin-6-yl)amino)-4-fluorophenyl)-3-(methoxy-d3)pyrrolidine-1-sulfonamide;

(R)-N-(2-chloro-4-fluoro-3-((5-fluoro-3-methyl-4-oxo-3,4-dihydroquinazolin-6-yl)amino)phenyl)-3-(methoxy-d3)pyrrolidine-1-sulfonamide;

(R)-N-(2-chloro-3-((3,5-dimethyl-4-oxo-3,4-dihydroquinazolin-6-yl)amino)-4-fluorophenyl)-3-(methoxy-d3)pyrrolidine-1-sulfonamide;

(R)-N-(5-((5-chloro-3-methyl-4-oxo-3,4-dihydroquinazolin-6-yl)amino)-2-fluorophenyl)-3-fluoropyrrolidine-1-sulfonamide;

(R)-N-(2-chloro-3-((3,5-dimethyl-4-oxo-3,4-dihydroquinazolin-6-yl)oxy)-4-fluorophenyl)-3-(difluoromethoxy)pyrrolidine-1-sulfonamide;

(R)-N-(5-chloro-2-fluoro-3-((5-fluoro-3-methyl-4-oxo-3,4-dihydroquinazolin-6-yl)amino)phenyl)-3-fluoropyrrolidine-1-sulfonamide;

cis-N-(2-chloro-3-((5-chloro-3-methyl-4-oxo-3,4-dihydroquinazolin-6-yl)oxy)-4-fluorophenyl)-3,4-difluoropyrrolidine-1-sulfonamide;

(R)-N-(2-chloro-3-((5-chloro-3-methyl-4-oxo-3,4-dihydroquinazolin-6-yl)oxy)-4-fluorophenyl)-3-(difluoromethoxy)pyrrolidine-1-sulfonamide;

N-(2-chloro-3-((5-chloro-3-methyl-4-oxo-3,4-dihydroquinazolin-6-yl)oxy)-4-fluorophenyl)-3,3-difluoropyrrolidine-1-sulfonamide;

(R)-N-(2-chloro-4-fluoro-3-((5-fluoro-3-methyl-4-oxo-3,4-dihydroquinazolin-6-yl)amino)phenyl)-3-ethylpyrrolidine-1-sulfonamide;

N-(2-chloro-4-fluoro-3-((5-fluoro-3-methyl-4-oxo-3,4-dihydroquinazolin-6-yl)oxy)phenyl)-3,3-difluoropyrrolidine-1-sulfonamide;

cis-N-(2-chloro-4-fluoro-3-((5-fluoro-3-methyl-4-oxo-3,4-dihydroquinazolin-6-yl)oxy)phenyl)-3,4-difluoropyrrolidine-1-sulfonamide;
N-(2-chloro-4-fluoro-3-((5-fluoro-3-methyl-4-oxo-3,4-dihydroquinazolin-6-yl)oxy)phenyl)-3-azabicyclo[3.1.0]hexane-3-sulfonamide;
(R)-N-(2-chloro-4-fluoro-3-((5-fluoro-3-methyl-4-oxo-3,4-dihydroquinazolin-6-yl)oxy)phenyl)-3-(difluoromethoxy)pyrrolidine-1-sulfonamide;
N-(2-chloro-3-((5-chloro-3-methyl-4-oxo-3,4-dihydroquinazolin-6-yl)oxy)-4-fluorophenyl)-2-azabicyclo[2.1.1]hexane-2-sulfonamide;
6-(2-Chloro-3-{[ethyl(methyl)sulfamoyl]amino}-6-fluorophenoxy)-3,5-dimethyl-3,4 dihydroquinazolin-4-one
N-(2-chloro-3-((3,5-dimethyl-4-oxo-3,4-dihydroquinazolin-6-yl)oxy)-4-fluorophenyl)pyrrolidine-1-sulfonamide;
(R)-N-(2-chloro-3-((3,5-dimethyl-4-oxo-3,4-dihydroquinazolin-6-yl)oxy)-4-fluorophenyl)-3-fluoropyrrolidine-1-sulfonamide;
N-(2-chloro-3-((3,5-dimethyl-4-oxo-3,4-dihydroquinazolin-6-yl)amino)-4-fluorophenyl)-(N, N-dimethyl)-sulfamide;
N-(2-chloro-3-((3,5-dimethyl-4-oxo-3,4-dihydroquinazolin-6-yl)amino)-4-fluorophenyl)-(N-methyl-N-(tetrahydrofuran-3-yl))-sulfamide;
N-(2-chloro-3-((3,5-dimethyl-4-oxo-3,4-dihydroquinazolin-6-yl)amino)-4-fluorophenyl)-(N-cyclopropyl-N-methyl)-sulfamide;
N-(2-chloro-3-((3,5-dimethyl-4-oxo-3,4-dihydroquinazolin-6-yl)amino)-4-fluorophenyl)-(N-cyclobutyl-N-methyl)-sulfamide;
N-(2-chloro-3-((3,5-dimethyl-4-oxo-3,4-dihydroquinazolin-6-yl)amino)-4-fluorophenyl)-4-methoxypiperidine-1-sulfonamide;
N-(2-chloro-3-((3,5-dimethyl-4-oxo-3,4-dihydroquinazolin-6-yl)amino)-4-fluorophenyl)-3-(trifluoromethyl)pyrrolidine-1-sulfonamide;
N-(2-chloro-3-((3,5-dimethyl-4-oxo-3,4-dihydroquinazolin-6-yl)amino)-4-fluorophenyl)-4-hydroxypiperidine-1-sulfonamide;
(trans)-N-(2-chloro-3-((3,5-dimethyl-4-oxo-3,4-dihydroquinazolin-6-yl)amino)-4-fluorophenyl)-3-fluoro-4-methoxypyrrolidine-1-sulfonamide;
N-(2-chloro-3-((3,5-dimethyl-4-oxo-3,4-dihydroquinazolin-6-yl)amino)-4-fluorophenyl)morpholine-4-sulfonamide;
N-(2-chloro-3-((3,5-dimethyl-4-oxo-3,4-dihydroquinazolin-6-yl)amino)-4-fluorophenyl)-(N-isopropyl-N-methyl)-sulfamide;
N-(2-chloro-3-((3,5-dimethyl-4-oxo-3,4-dihydroquinazolin-6-yl)amino)-4-fluorophenyl)-2-azabicyclo[2.2.1]heptane-2-sulfonamide;
N-(2-chloro-3-((3,5-dimethyl-4-oxo-3,4-dihydroquinazolin-6-yl)amino)-4-fluorophenyl)-5-azaspiro[2.4]heptane-5-sulfonamide;
N-(2-chloro-4-fluoro-3-((5-fluoro-3-methyl-4-oxo-3,4-dihydroquinazolin-6-yl)amino)phenyl)-(N,N-dimethyl)-sulfamide;
N-(2-chloro-3-((3,5-dimethyl-4-oxo-3,4-dihydroquinazolin-6-yl)amino)-4-fluorophenyl)piperidine-1-sulfonamide;
(trans)-N-(2-chloro-3-((3,5-dimethyl-4-oxo-3,4-dihydroquinazolin-6-yl)amino)-4-fluorophenyl)-3,4-difluoropyrrolidine-1-sulfonamide;
(S)-N-(2-chloro-3-((3,5-dimethyl-4-oxo-3,4-dihydroquinazolin-6-yl)amino)-4-fluorophenyl)-3-fluoropyrrolidine-1-sulfonamide;
N-(2-chloro-3-((3,5-dimethyl-4-oxo-3,4-dihydroquinazolin-6-yl)amino)-4-fluorophenyl)-2-azabicyclo[2.1.1]hexane-2-sulfonamide;
N-(2-chloro-3-((3,5-dimethyl-4-oxo-3,4-dihydroquinazolin-6-yl)amino)-4-fluorophenyl)-(N-isopropyl-N-methyl)-sulfamide;
N-(2-chloro-3-((3,5-dimethyl-4-oxo-3,4-dihydroquinazolin-6-yl)amino)-4-fluorophenyl)-(N-isopropyl-N-methyl)-sulfamide;
(cis)-N-(2-chloro-3-((3,5-dimethyl-4-oxo-3,4-dihydroquinazolin-6-yl)amino)-4-fluorophenyl)-3,4-difluoropyrrolidine-1-sulfonamide;
N-(2-chloro-3-((3,5-dimethyl-4-oxo-3,4-dihydroquinazolin-6-yl)amino)-4-fluorophenyl)-(N-isopropyl-N-methyl)-sulfamide;
N-(2-chloro-3-((3,5-dimethyl-4-oxo-3,4-dihydroquinazolin-6-yl)amino)-4-fluorophenyl)-3-azabicyclo[3.1.0]hexane-3-sulfonamide;
N-(2-chloro-3-((3,5-dimethyl-4-oxo-3,4-dihydroquinazolin-6-yl)amino)-4-fluorophenyl)-3,3-difluoropyrrolidine-1-sulfonamide;
N-(2-chloro-3-((5-chloro-3-methyl-4-oxo-3,4-dihydroquinazolin-6-yl)amino)-4-fluorophenyl)-3-ethylpyrrolidine-1-sulfonamide;
cis-N-(2-chloro-3-((3,5-dimethyl-4-oxo-3,4-dihydroquinazolin-6-yl)amino)-4,5-difluorophenyl)-3,4-difluoropyrrolidine-1-sulfonamide;
N-(2-chloro-3-((3,5-dimethyl-4-oxo-3,4-dihydroquinazolin-6-yl)amino)-4,5-difluorophenyl)pyrrolidine-1-sulfonamide;
N-(2-chloro-3-((3,5-dimethyl-4-oxo-3,4-dihydroquinazolin-6-yl)amino)-4,5-difluorophenyl)-(N-ethyl-N-methyl)-sulfamide;
N-(2-chloro-3-((3,5-dimethyl-4-oxo-3,4-dihydroquinazolin-6-yl)amino)-4,5-difluorophenyl)-(N,N-dimethyl)-sulfamide;
(R)-N-(2-chloro-3-((3,5-dimethyl-4-oxo-3,4-dihydroquinazolin-6-yl)amino)-4,5-difluorophenyl)-3-methoxypyrrolidine-1-sulfonamide;
cis-N-(2-chloro-3-((3,5-dimethyl-4-oxo-3,4-dihydroquinazolin-6-yl)amino)-4,5-difluorophenyl)-3-fluoro-4-methoxypyrrolidine-1-sulfonamide;
N-(2-chloro-3-((3,5-dimethyl-4-oxo-3,4-dihydroquinazolin-6-yl)amino)-4,5-difluorophenyl)-2-azabicyclo[2.1.1]hexane-2-sulfonamide;
N-(2-chloro-3-((3,5-dimethyl-4-oxo-3,4-dihydroquinazolin-6-yl)amino)-4,5-difluorophenyl)-3-azabicyclo[3.1.0]hexane-3-sulfonamide;
(R)-N-(5-chloro-3-((3,5-dimethyl-4-oxo-3,4-dihydroquinazolin-6-yl)amino)-2-fluorophenyl)-3-fluoropyrrolidine-1-sulfonamide;
N-(5-chloro-3-((3,5-dimethyl-4-oxo-3,4-dihydroquinazolin-6-yl)amino)-2-fluorophenyl)pyrrolidine-1-sulfonamide;
(R)-N-(5-chloro-3-((3,5-dimethyl-4-oxo-3,4-dihydroquinazolin-6-yl)amino)-2-fluorophenyl)-3-methoxypyrrolidine-1-sulfonamide;
(R)-N-(2-chloro-3-((5-chloro-3-methyl-4-oxo-3,4-dihydroquinazolin-6-yl)amino)-4-fluorophenyl)-3-ethylpyrrolidine-1-sulfonamide;
(S)-N-(2-chloro-3-((5-chloro-3-methyl-4-oxo-3,4-dihydroquinazolin-6-yl)oxy)-4-fluorophenyl)-3-fluoropyrrolidine-1-sulfonamide;
N-(2-chloro-3-((5-chloro-3-methyl-4-oxo-3,4-dihydroquinazolin-6-yl)oxy)-4-fluorophenyl)-3-azabicyclo[3.1.0]hexane-3-sulfonamide;
N-(2-chloro-3-((5-chloro-3-methyl-4-oxo-3,4-dihydroquinazolin-6-yl)oxy)-4-fluorophenyl)-(N-ethyl-N-methyl)-sulfamide;

N-(2-chloro-3-((5-chloro-3-methyl-4-oxo-3,4-dihydroquinazolin-6-yl)oxy)-4-fluorophenyl)-(N,N-dimethyl)-sulfamide;

N-(2-chloro-4-fluoro-3-((5-fluoro-3-methyl-4-oxo-3,4-dihydroquinazolin-6-yl)oxy)phenyl)-(N,N-dimethyl)-sulfamide;

N-(2-chloro-4-fluoro-3-((5-fluoro-3-methyl-4-oxo-3,4-dihydroquinazolin-6-yl)oxy)phenyl)-(N-ethyl-N-methyl)-sulfamide;

N-(3-((3,5-dimethyl-4-oxo-3,4-dihydroquinazolin-6-yl)amino)-2,4-difluorophenyl)pyrrolidine-1-sulfonamide;

(R)-N-(3-((3,5-dimethyl-4-oxo-3,4-dihydroquinazolin-6-yl)amino)-2,4-difluorophenyl)-3-fluoropyrrolidine-1-sulfonamide;

N-(2-chloro-3-((3,5-dimethyl-4-oxo-3,4-dihydroquinazolin-6-yl)oxy)-4-fluorophenyl)-3-(methoxymethyl)azetidine-1-sulfonamide;

N-(2-chloro-3-((3,5-dimethyl-4-oxo-3,4-dihydroquinazolin-6-yl)oxy)-4-fluorophenyl)-3-fluoroazetidine-1-sulfonamide;

N-(2-chloro-3-((3,5-dimethyl-4-oxo-3,4-dihydroquinazolin-6-yl)oxy)-4-fluorophenyl)-3-methoxyazetidine-1-sulfonamide;

N-(2-chloro-3-((5-chloro-3-methyl-4-oxo-3,4-dihydroquinazolin-6-yl)oxy)-4-fluorophenyl)-3-(methoxymethyl)azetidine-1-sulfonamide;

N-(2-chloro-3-((5-chloro-3-methyl-4-oxo-3,4-dihydroquinazolin-6-yl)oxy)-4-fluorophenyl)-3-methoxyazetidine-1-sulfonamide;

N-(2-chloro-3-((5-chloro-3-methyl-4-oxo-3,4-dihydroquinazolin-6-yl)oxy)-4-fluorophenyl)-3-fluoroazetidine-1-sulfonamide;

N-(2-chloro-4-fluoro-3-((5-fluoro-3-methyl-4-oxo-3,4-dihydroquinazolin-6-yl)oxy)phenyl)-3-(methoxymethyl)azetidine-1-sulfonamide;

N-(2-chloro-4-fluoro-3-((5-fluoro-3-methyl-4-oxo-3,4-dihydroquinazolin-6-yl)oxy)phenyl)-3-fluoroazetidine-1-sulfonamide;

N-(2-chloro-4-fluoro-3-((5-fluoro-3-methyl-4-oxo-3,4-dihydroquinazolin-6-yl)oxy)phenyl)-3-methoxyazetidine-1-sulfonamide;

N-(2-chloro-3-((3,5-dimethyl-4-oxo-3,4-dihydroquinazolin-6-yl)amino)-4-fluorophenyl)azetidine-1-sulfonamide;

N-(2-chloro-3-((3,5-dimethyl-4-oxo-3,4-dihydroquinazolin-6-yl)amino)-4-fluorophenyl)-3-fluoroazetidine-1-sulfonamide;

N-(2-chloro-3-((5-chloro-3-methyl-4-oxo-3,4-dihydroquinazolin-6-yl)amino)-4-fluorophenyl)-3-fluoroazetidine-1-sulfonamide;

N-(2-chloro-4-fluoro-3-((5-fluoro-3-methyl-4-oxo-3,4-dihydroquinazolin-6-yl)amino)phenyl)-3-fluoroazetidine-1-sulfonamide;

N-(2-chloro-3-((3,5-dimethyl-4-oxo-3,4-dihydroquinazolin-6-yl)amino)-4-fluorophenyl)-3-methoxyazetidine-1-sulfonamide;

N-(2-chloro-3-((5-chloro-3-methyl-4-oxo-3,4-dihydroquinazolin-6-yl)amino)-4-fluorophenyl)-3-methoxyazetidine-1-sulfonamide;

N-(2-chloro-4-fluoro-3-((5-fluoro-3-methyl-4-oxo-3,4-dihydroquinazolin-6-yl)amino)phenyl)-3-methoxyazetidine-1-sulfonamide;

N-(2-chloro-3-((3,5-dimethyl-4-oxo-3,4-dihydroquinazolin-6-yl)amino)-4-fluorophenyl)-3-(methoxymethyl)azetidine-1-sulfonamide;

N-(2-chloro-3-((5-chloro-3-methyl-4-oxo-3,4-dihydroquinazolin-6-yl)amino)-4-fluorophenyl)-3-(methoxymethyl)azetidine-1-sulfonamide;

N-(2-chloro-4-fluoro-3-((5-fluoro-3-methyl-4-oxo-3,4-dihydroquinazolin-6-yl)amino)phenyl)-3-(methoxymethyl)azetidine-1-sulfonamide;

N-(2-chloro-3-((3,5-dimethyl-4-oxo-3,4-dihydroquinazolin-6-yl)amino)-4-fluorophenyl)-3,3-difluoroazetidine-1-sulfonamide;

N-(2-chloro-3-((5-chloro-3-methyl-4-oxo-3,4-dihydroquinazolin-6-yl)amino)-4-fluorophenyl)-3,3-difluoroazetidine-1-sulfonamide;

N-(2-chloro-4-fluoro-3-((5-fluoro-3-methyl-4-oxo-3,4-dihydroquinazolin-6-yl)amino)phenyl)-3,3-difluoroazetidine-1-sulfonamide;

N-(2-chloro-3-((3,5-dimethyl-4-oxo-3,4-dihydroquinazolin-6-yl)amino)-4-fluorophenyl)-3-((difluoromethoxy)methyl)azetidine-1-sulfonamide;

N-(2-chloro-3-((5-chloro-3-methyl-4-oxo-3,4-dihydroquinazolin-6-yl)amino)-4-fluorophenyl)-3-((difluoromethoxy)methyl)azetidine-1-sulfonamide;

N-(2-chloro-4-fluoro-3-((5-fluoro-3-methyl-4-oxo-3,4-dihydroquinazolin-6-yl)amino)phenyl)-3-((difluoromethoxy)methyl)azetidine-1-sulfonamide;

N-(2-chloro-3-((3,5-dimethyl-4-oxo-3,4-dihydroquinazolin-6-yl)amino)-4-fluorophenyl)-3-(methoxymethyl)-3-methylazetidine-1-sulfonamide;

N-(2-chloro-3-((5-chloro-3-methyl-4-oxo-3,4-dihydroquinazolin-6-yl)amino)-4-fluorophenyl)-3-ethoxyazetidine-1-sulfonamide;

N-(2-chloro-4-fluoro-3-((5-fluoro-3-methyl-4-oxo-3,4-dihydroquinazolin-6-yl)amino)phenyl)-3-ethoxyazetidine-1-sulfonamide;

N-(2-chloro-3-((5-chloro-3-methyl-4-oxo-3,4-dihydroquinazolin-6-yl)amino)-4-fluorophenyl)-3-(difluoromethoxy)azetidine-1-sulfonamide;

N-(2-chloro-4-fluoro-3-((5-fluoro-3-methyl-4-oxo-3,4-dihydroquinazolin-6-yl)amino)phenyl)-3-(difluoromethoxy)azetidine-1-sulfonamide;

N-(2-chloro-3-((3,5-dimethyl-4-oxo-3,4-dihydroquinazolin-6-yl)amino)-4-fluorophenyl)-3-fluoro-3-(methoxymethyl)azetidine-1-sulfonamide;

N-(2-chloro-3-((3,5-dimethyl-4-oxo-3,4-dihydroquinazolin-6-yl)amino)-4-fluorophenyl)-3-cyanoazetidine-1-sulfonamide;

N-(2-chloro-3-((3,5-dimethyl-4-oxo-3,4-dihydroquinazolin-6-yl)amino)-4-fluorophenyl)-3-methylazetidine-1-sulfonamide;

N-(2-chloro-3-((3,5-dimethyl-4-oxo-3,4-dihydroquinazolin-6-yl)amino)-4-fluorophenyl)-6-fluoro-3-azabicyclo[3.1.0]hexane-3-sulfonamide;

N-(2-chloro-3-((3,5-dimethyl-4-oxo-3,4-dihydroquinazolin-6-yl)amino)-4-fluorophenyl)-1-fluoro-3-azabicyclo[3.1.0]hexane-3-sulfonamide;

N-(2-chloro-3-((3,5-dimethyl-4-oxo-3,4-dihydroquinazolin-6-yl)amino)-5-fluorophenyl)pyrrolidine-1-sulfonamide;

(R)-N-(2-chloro-3-((3,5-dimethyl-4-oxo-3,4-dihydroquinazolin-6-yl)amino)-5-fluorophenyl)-3-fluoropyrrolidine-1-sulfonamide;

(R)-N-(2-chloro-3-((3,5-dimethyl-4-oxo-3,4-dihydroquinazolin-6-yl)amino)-5-fluorophenyl)-3-methoxypyrrolidine-1-sulfonamide;

N-(2-chloro-3-((3,5-dimethyl-4-oxo-3,4-dihydroquinazolin-6-yl)amino)-4-fluorophenyl)-2-azabicyclo[3.1.0]hexane-2-sulfonamide;

N-(3-((3,5-dimethyl-4-oxo-3,4-dihydroquinazolin-6-yl)amino)-2,5-difluorophenyl)pyrrolidine-1-sulfonamide;

N-(2-chloro-3-((3,5-dimethyl-4-oxo-3,4-dihydroquinazolin-6-yl)amino)-4-fluorophenyl)-3-fluoro-3-methylazetidine-1-sulfonamide;

N-(2-chloro-3-((3,5-dimethyl-4-oxo-3,4-dihydroquinazolin-6-yl)amino)-4-fluorophenyl)-3-((trifluoromethoxy)methyl)azetidine-1-sulfonamide;
N-(2-chloro-3-((3,5-dimethyl-4-oxo-3,4-dihydroquinazolin-6-yl)amino)-4-fluorophenyl)-2-azaspiro[3.3]heptane-2-sulfonamide;
N-(2-chloro-3-((5-chloro-3-methyl-4-oxo-3,4-dihydroquinazolin-6-yl)amino)-4-fluorophenyl)-2-azaspiro[3.3]heptane-2-sulfonamide;
N-(2-chloro-4-fluoro-3-((5-fluoro-3-methyl-4-oxo-3,4-dihydroquinazolin-6-yl)amino)phenyl)-2-azaspiro[3.3]heptane-2-sulfonamide;
N-(2-chloro-3-((3,5-dimethyl-4-oxo-3,4-dihydroquinazolin-6-yl)amino)-4-fluorophenyl)-3-ethoxyazetidine-1-sulfonamide;
N-(2-chloro-3-((3,5-dimethyl-4-oxo-3,4-dihydroquinazolin-6-yl)amino)-4-fluorophenyl)-3-(difluoromethoxy)azetidine-1-sulfonamide;
N-(2-chloro-3-((3,5-dimethyl-4-oxo-3,4-dihydroquinazolin-6-yl)amino)-4-fluorophenyl)-3-(trifluoromethoxy)azetidine-1-sulfonamide;
N-(2-chloro-3-((3,5-dimethyl-4-oxo-3,4-dihydroquinazolin-6-yl)amino)-4-fluorophenyl)-5-azaspiro[2.3]hexane-5-sulfonamide;
N-(2-chloro-3-((3,5-dimethyl-4-oxo-3,4-dihydroquinazolin-6-yl)amino)-4-fluorophenyl)-3-((fluoromethoxy)methyl)azetidine-1-sulfonamide;
or a pharmaceutically acceptable salt thereof.

Embodiment 17. A compound of Formula V

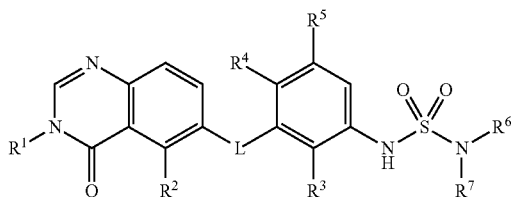

or a pharmaceutically acceptable salt thereof, wherein:
L is NH;
$R^1$ is C1-C6 alkyl;
$R^2$ is F or Cl;
$R^3$ is Cl;
$R^4$ is F;
$R^5$ is H;
$R^6$ and $R^7$ together with the nitrogen atom to which they are attached form a saturated ring system selected from (i) a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN, and (iii) a 6-7 membered bridged ring.

Embodiment 18. A compound according to Embodiment 17, wherein $R^6$ and $R^7$ together with the nitrogen atom to which they are attached form a 4-6 membered monocyclic ring optionally having a second ring heteroatom which is O, wherein said ring is optionally substituted with 1 or 2 substituents independently selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN.

Embodiment 19. A compound according to Embodiment 18, wherein $R^6$ and $R^7$ together with the nitrogen atom to which they are attached form a 4-6 membered monocyclic ring, wherein said ring is substituted a substituent selected from F, —OH, —OCH$_3$, —OCHF$_2$, —OCD$_3$, —CH$_3$, —CH$_2$CH$_3$, —CH$_2$OCH$_3$, —CH$_2$OCH$_2$F, —CH$_2$OCHF$_2$, —CH$_2$OCF$_3$, —OCF$_3$, —OCH$_2$CH$_3$, and CN.

Embodiment 20. A compound according to Embodiment 19, wherein $R^6$ and $R^7$ together with the nitrogen atom to which they are attached form a saturated 4-6 membered monocyclic ring substituted with F.

Embodiment 21. A compound which is selected from:
N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide having the structure:

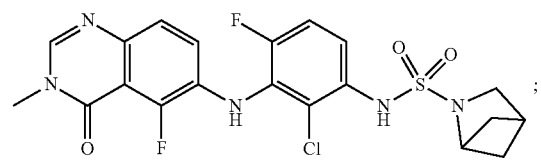 [SMILES: Cn1cnc2ccc(Nc3c(F)ccc(NS(=O)(=O)N4CC5CC4C5)c3Cl)c(F)c2c1=O]

(R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide and crystalline form (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide having the structure

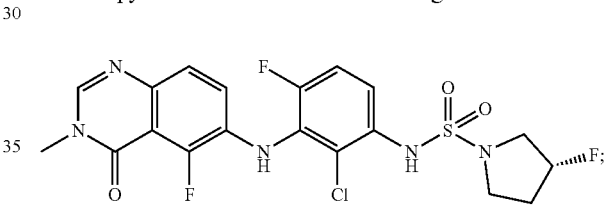

and
N-(2-chloro-3-((5-chloro-3-methyl-4-oxo-3,4-dihydroquinazolin-6-yl)amino)-4-fluorophenyl)-3-fluoroazetidine-1-sulfonamide having the structure:

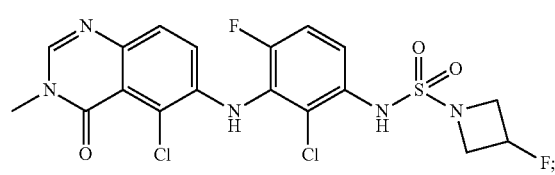 [SMILES: Cn1cnc2ccc(Nc3c(F)ccc(NS(=O)(=O)N4CC(F)C4)c3Cl)c(Cl)c2c1=O]

or a pharmaceutically acceptable salt thereof.

Embodiment 22. A compound which is N-(2-chloro-3-((5-chloro-3-methyl-4-oxo-3,4-dihydroquinazolin-6-yl)amino)-4-fluorophenyl)-3-fluoroazetidine-1-sulfonamide having the structure:

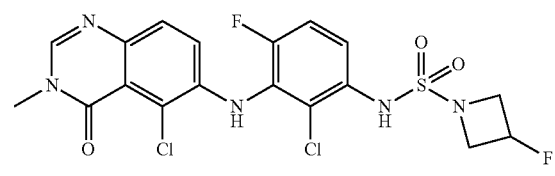 [SMILES: Cn1cnc2ccc(Nc3c(F)ccc(NS(=O)(=O)N4CC(F)C4)c3Cl)c(Cl)c2c1=O]

or a pharmaceutically acceptable salt thereof.

Embodiment 23. A compound which is N-(2-chloro-3-((5-chloro-3-methyl-4-oxo-3,4-dihydroquinazolin-6-yl)amino)-4-fluorophenyl)-3-fluoroazetidine-1-sulfonamide having the structure:

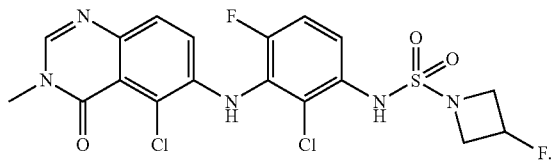 [SMILES: Cn1cnc2ccc(Nc3c(F)ccc(NS(=O)(=O)N4CC(F)C4)c3Cl)c(Cl)c2c1=O]

Embodiment 24. A pharmaceutical composition, comprising a compound according to any one of Embodiments 1-23 or pharmaceutically acceptable salt thereof and one or more pharmaceutically acceptable carriers.

Embodiment 25. A process for preparing a compound according to Embodiment 1, or a pharmaceutically acceptable salt thereof, comprising:

(a) for a compound of Embodiment 1 wherein L, $R^1$, $R^2$, $R^3$, $R^4$, $R^5$, $R^6$ and $R^7$ are as defined in Embodiment 1, coupling a compound having the formula (25)

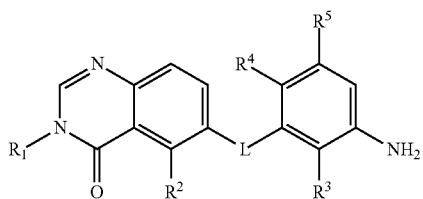

wherein L, $R^1$, $R^2$, $R^3$, $R^4$ and $R^5$ are as defined in Embodiment 1, with a compound having the formula (16)

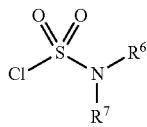

wherein $R^6$ and $R^7$ are as defined in Embodiment 1, in the presence of a suitable base; or (b) for a compound of Embodiment 1 wherein $R^1$, $R^2$, $R^3$, $R^4$ and $R^5$ are as defined in Embodiment 1 and L is NH, reacting a compound of formula (5)

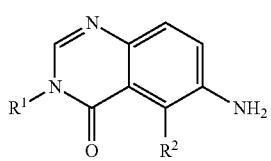

wherein $R^1$ and $R^2$ are as defined in Embodiment 1, with a compound having the formula (27)

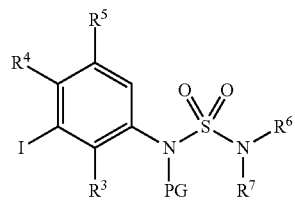

wherein $R^3$, $R^4$, $R^5$, $R^6$, and $R^7$ are as defined in Embodiment 1 and PG is an amine protecting group, in the presence of a palladium catalyst and a ligand, followed by removal of the amine protecting group; or (c) for a compound of Formula I wherein $R^1$, $R^2$, $R^3$, $R^4$ and $R^5$ are as defined in Embodiment 1 and L is O, reacting a compound having the formula (31)

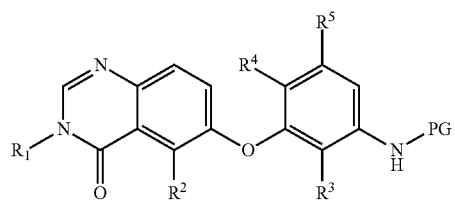

wherein $R^1$, $R^2$, $R^3$, $R^4$ and $R^5$ are as defined in Embodiment 1 and PG is an amine protecting group, with a reagent having the formula

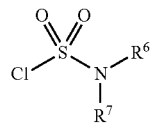

in the presence of a base, followed by removal of the amine protecting group; and optionally forming a pharmaceutically acceptable salt thereof.

Embodiment 26. A method of treating a BRAF-associated tumor in a subject in need thereof, comprising administering to the subject a therapeutically effective amount of a compound according to any one of Embodiments 1-23 or a pharmaceutically acceptable salt thereof.

Embodiment 27. The method according to Embodiment 26, wherein said BRAF-associated tumor has a BRAF Class II mutation.

Embodiment 28. The method according to Embodiment 27, wherein said BRAF Class II mutation is a BRAF non-V600 mutation.

Embodiment 29. The method according to Embodiment 28, wherein said BRAF non-V600 mutation is BRAF G469A or G469R.

Embodiment 30. The method according to Embodiment 29, wherein said BRAF Class II mutation is a BRAF V600E splice variant.

Embodiment 31. The method according to Embodiment 30, wherein said BRAF V600E splice variant is p61BRAF (V600E).

Embodiment 32. The method according to any one of Embodiments 26-31, wherein said BRAF-associated tumor is a cancer is selected from lung cancer, melanoma, colorectal cancer, breast cancer, pancreatic cancer, thyroid cancer, prostate cancer, adenoid cystic carcinoma, appendiceal cancer, small intestine cancer, gastrointestinal neuroendocrine cancer, head and neck squamous cell carcinoma, angiosarcoma, bladder cancer, plasma cell neoplasm, hepatobiliary cancer, hepato-pancreato-biliary carcinoma, ovary cancer, neuroendocrine cancer, cholangiocarcinoma, esophagogastric cancer, soft tissue sarcoma, leukemia, non-Hodgkin's lymphoma, and CNS cancers.

Embodiment 33. The method according to any one of Embodiments 26-31, wherein said tumor is a metastatic cancer.

Embodiment 34. The method according to Embodiment 33, wherein said cancer is a metastatic CNS cancer.

Embodiment 35. The method according to any one of Embodiments 26-31, wherein said BRAF-associated tumor is a primary tumor.

Embodiment 36. The method according to Embodiment 35, wherein said primary brain tumor is a malignant tumor.

Embodiment 37. The method according to Embodiment 35, wherein said primary brain tumor is a Grade 2 glioma, a Grade 3 glioma, or a Grade 4 glioma.

Embodiment 38. The method according to Embodiment 26, wherein said BRAF-associated tumor has a BRAF Class I mutation.

Embodiment 38. The method according to Embodiment 38, wherein said BRAF Class I mutation is BRAF V600E or BRAF V600K.

Embodiment 40. The method according to Embodiment 38 or 39, wherein said BRAF-associated tumor is selected from melanoma, colorectal cancer, thyroid cancer, non-small cell lung cancer, ovarian cancer, renal cell carcinoma, and metastatic cancers thereof, and primary brain tumors.

Embodiment 41. The method according to Embodiment 38 or 39, wherein said BRAF-associated tumor is a CNS tumor.

Embodiment 42. The method according to Embodiment 41, wherein said CNS tumor is a malignant tumor.

Embodiment 43. The method according to Embodiment 42 wherein said malignant tumor is a metastatic CNS cancer.

Embodiment 44. The method according to Embodiment 43, wherein said metastatic CNS cancer is selected from metastatic melanoma, metastatic colorectal cancer, metastatic non-small cell lung cancer, metastatic thyroid cancer, and metastatic ovarian cancer.

Embodiment 45. The method according to Embodiment 41, wherein said CNS tumor is intracranial LMD or extracranial LMD.

Embodiment 46. The method according to Embodiment 41, wherein said CNS tumor is a primary brain tumor.

Embodiment 47. The method according to Embodiment 46, wherein said primary brain tumor is a malignant tumor.

Embodiment 48. The method according to Embodiment 47, wherein said primary brain tumor is a Grade 2 glioma, a Grade 3 glioma, or a Grade 4 glioma.

Embodiment 49. The method according to Embodiment 26, wherein said BRAF-associated tumor has a BRAF Class III mutation.

Embodiment 50. The method according to Embodiment 29, wherein said BRAF-associated tumor is a cancer selected from melanoma, small bowel cancer, colorectal cancer, non-small cell lung cancer, endometrial cancer, cervical cancer, leukemia, bladder cancer, non-Hodgkin's lymphoma, glioma, ovarian cancer, prostate cancer, hepatobiliary cancer, esophagogastric cancer, soft tissue sarcoma, and breast cancer.

Embodiment 51. The method according to Embodiment 49 or 50, wherein the cancer has a BRAF G466V or BRAF D594G mutation.

Embodiment 52. The method according to any one of Embodiments 26-51, wherein said subject is naïve to treatment.

Embodiment 53. The method according to any one of Embodiments 26-52, wherein the method further comprises administering an additional anticancer therapy.

Embodiment 54. The method of Embodiment 53, wherein the additional anticancer therapy is selected from one or more of surgery, radiotherapy and an anticancer agent.

Embodiment 55. The method of Embodiment 54, wherein the additional anticancer therapy is an anticancer agent.

Embodiment 56. The method of Embodiment 55, wherein the additional anticancer agent is selected from MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents.

Embodiment 57. The method of Embodiment 56, wherein the additional anticancer agent is a MEK inhibitor.

Embodiment 58. The method of Embodiment 57, wherein the MEK inhibitor is binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide, 3-[2(R),3-dihydroxypropyl]-6-fluoro-5-(2-fluoro-4-iodophenylamino)-8-methylpyrido[2,3-d]pyrimidine-4,7(3H,8H)-dione, or a pharmaceutically acceptable salt thereof.

Embodiment 59. The method of Embodiment 58, wherein the MEK inhibitor is binimetinib, or a pharmaceutically acceptable salt thereof.

Embodiment 60. The method of Embodiment 56, wherein the additional anticancer agent is an EGFR inhibitor.

Embodiment 61. The method of Embodiment 60, wherein the EGFR inhibitor is cetuximab.

Embodiment 62. A method of treating a subject having a BRAF-associated metastatic cancer, wherein the subject was previously treated with an anticancer therapy, the method comprising administering to the subject a therapeutically effective amount of a compound according to any one of Embodiments 1-23.

Embodiment 63. The method according to Embodiment 62, wherein said BRAF-associated cancer has a Class II BRAF mutation.

Embodiment 64. The method according to Embodiment 63, wherein said Class II mutation is a non-V600 mutation.

Embodiment 65. The method according to Embodiment 62, wherein said BRAF-associated cancer has a Class I BRAF mutation.

Embodiment 66. The method according to Embodiment 65, wherein said BRAF-associated cancer has a BRAF V600E or V600K mutation.

Embodiment 67. The method according to any one of Embodiments 62-66, wherein said subject was previously treated with an anticancer therapy which is one or more anticancer agents independently selected from MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents.

Embodiment 68. The method according to Embodiment 67, wherein the subject was previously treated with a BRAF inhibitor.

Embodiment 69. The method according to Embodiment 67, wherein the subject was previously treated with a combination of a BRAF inhibitor and a MEK inhibitor.

Embodiment 70. The method according to Embodiment 67, wherein the subject was previously treated with one or more checkpoint inhibitors.

Embodiment 71. The method according to Embodiment 67, wherein the subject was previously treated with one or more inhibitors of PI3K.

Embodiment 72. The method of Embodiment 67, wherein the subject was previously treated with a combination of a BRAF inhibitor and a checkpoint inhibitor.

Embodiment 73. The method of Embodiment 67, wherein the subject was previously treated with a combination of a BRAF inhibitor, a MEK inhibitor and a checkpoint inhibitor.

Embodiment 74. The method of Embodiment 67, wherein the subject was previously treated with one or more alkylating agents.

Embodiment 75. The method of Embodiment 67, wherein the subject was previously treated with a combination of a BRAF inhibitor, a MEK inhibitor and an EGFR inhibitor.

Embodiment 76. The method of Embodiment 67, wherein the subject was previously treated with an EGFR inhibitor.

Embodiment 77. The method of Embodiment 67, wherein the subject was previously treated with a combination of an EGFR inhibitor and one or more cytotoxic chemotherapy agents.

Embodiment 78. The method of Embodiment 67, wherein the subject was previously treated with a combination of an EGFR inhibitor and a BRAF inhibitor.

Embodiment 79. The method of Embodiment 67, wherein the subject was previously treated with a combination of a MEK inhibitor and one or more checkpoint inhibitors.

Embodiment 80. The method of Embodiment 67, wherein the subject was previously treated with one or more cytotoxic chemotherapeutic agents.

Embodiment 81. The method of Embodiment 67, wherein the subject was previously treated with a combination of an antibody therapy and one or more cytotoxic chemotherapeutic agents.

Embodiment 82. The method of Embodiment 67, wherein the subject was previously treated with a combination of an EGFR inhibitor, a BRAF inhibitor and one or more cytotoxic chemotherapeutic agents.

Embodiment 83. The method of Embodiment 67, wherein the subject was previously treated with an EGFR inhibitor and one or more cytotoxic chemotherapeutic agents.

Embodiment 84. The method according to any one of Embodiments 67, 68, 69, 72, 73, 75, and 82, wherein the BRAF inhibitor is encorafenib, dabrafenib, vemurafenib, or a pharmaceutically acceptable salt thereof.

Embodiment 85. The method according to any one of Embodiments 67, 69, 73, 75, and 79, wherein the MEK inhibitor is binimetinib, trametinib, cobimetinib, or a pharmaceutically acceptable salt thereof.

Embodiment 86. The method according to any one of Embodiments 67, 70, 72, 73, and 79, wherein the checkpoint inhibitor is ipilimumab, nivolumab, or pembrolizumab.

Embodiment 87. The method according to Embodiment 67 or 71, wherein the one or more inhibitors of PI3K is selected from buparlisib and alpelisib.

Embodiment 88. The method according to Embodiment 67 or 74, wherein the alkylating agent is selected from temozolomide, fotemustine, lomustine and carmustine.

Embodiment 89. The method according to any one of Embodiments 67, 75, 76, 77, 78, 82 and 83, wherein the EGFR inhibitor is selected from cetuximab, panitumumab, osimertinib, erlotinib, gefitinib, necitumumab, neratinib, lapatinib, vandetanib and brigatinib.

Embodiment 90. The method according to any one of Embodiments 67, 77, 80, 81, 82 and 83, wherein the one or more cytotoxic chemotherapy agents is selected from Nordic FLOX (fluorouracil, folinic acid and oxaliplatin), oxaliplatin, bevacizumab, irinotecan, FOLFOXIRI (oxaliplatin, irinotecan and fluorouracil), FOLFIRI (folinic acid, fluorouracil and irinotecan) or CAPEOX (capecitabine and oxaliplatin).

Embodiment 91. The method according to any one of Embodiments 67-90, wherein the subject is resistant to said previous treatment.

Embodiment 92. The method according to any one of Embodiments 62-91, wherein the subject developed brain metastasis during said previous treatment.

Embodiment 93. The method according to any one of Embodiments 62-92, wherein the method further comprises administering an additional anticancer therapy.

Embodiment 94. The method according to Embodiment 93, wherein the additional anticancer therapy is selected from one or more of surgery, radiotherapy and an anticancer agent.

Embodiment 95. The method according to Embodiment 94, wherein the additional anticancer therapy is an anticancer agent.

Embodiment 96. The method according to Embodiment 95, wherein the additional anticancer agent is selected from MEK inhibitors, BRAF inhibitors, EGFR inhibitors, inhibitors of HER2 and/or HER3, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents.

Embodiment 97. The method according to Embodiment 96, wherein the additional anticancer agent is a MEK inhibitor.

Embodiment 98. The method according to Embodiment 97, wherein the MEK inhibitor is binimetinib, trametinib, cobimetinib, selumetinib, pimasertib, refametinib, mirdametinib, 2-(2-chloro-4-iodophenylamino)-N-(cyclopropylmethoxy)-3,4-difluorobenzamide, 3-[2(R),3-dihydroxypropyl]-6-fluoro-5-(2-fluoro-4-iodophenylamino)-8-methylpyrido[2,3-d]pyrimidine-4,7(3H,8H)-dione, or a pharmaceutically acceptable salt thereof.

Embodiment 99. The method according to Embodiment 95, wherein the MEK inhibitor is binimetinib, or a pharmaceutically acceptable salt thereof.

Embodiment 100. The method according to Embodiment 99, wherein the additional anticancer agent is an EGFR inhibitor.

Embodiment 101. The method according to Embodiment 100, wherein the EGFR inhibitor is cetuximab.

Embodiment 102. A method of treating a BRAF-associated glioma, wherein the subject was previously treated with another anticancer therapy, the method comprising administering a therapeutically effective amount of a compound according to any one of Embodiments 1-23.

Embodiment 103. The method according to Embodiment 102, wherein the subject was previously treated with one or more cytotoxic chemotherapy agents.

Embodiment 104. The method according to Embodiment 103, wherein the one or more cytotoxic chemotherapy agents is selected from cisplatin, pemetrexed, vinorelbine and paclitaxel.

Embodiment 105. The method according to Embodiment 102, wherein the subject was previously treated with an alkylating agent.

Embodiment 106. The method according to Embodiment 102, wherein the subject was previously treated with an ornithine decarboxylase inhibitor.

Embodiment 107. The method according to Embodiment 102, wherein the subject was previously treated with a combination of an alkylating agent and an ornithine decarboxylase inhibitor.

Embodiment 108. The method according to Embodiment 105 or 107, wherein the alkylating agent is selected from temozolomide, lomustine, and carmustine.

Embodiment 109. The method according to Embodiment 106 or 107, wherein the ornithine decarboxylase inhibitor is racemic eflornithine, D-eflornithine or L-eflornithine.

Embodiment 110. The method according to Embodiment 102, wherein the subject was previously treated with a BRAF inhibitor.

Embodiment 111. The method according to Embodiment 102, wherein the subject was previously treated with a combination of a BRAF inhibitor and a MEK inhibitor.

Embodiment 112. The method according to Embodiment 110 or 111, wherein the BRAF inhibitor is encorafenib, dabrafenib, vemurafenib, or a pharmaceutically acceptable salt thereof.

Embodiment 113. The method according to Embodiment 111, wherein the MEK inhibitor is binimetinib, trametinib, cobimetinib, or a pharmaceutically acceptable salt thereof.

Embodiment 114. The method according to any one of Embodiments 102-113, wherein the anticancer therapy included surgery.

Embodiment 115. The method according to any one of Embodiments 102-114, wherein the anticancer therapy included radiotherapy.

EXAMPLES

The following examples illustrate the invention.

Biological Examples

Example A1

BRAF V600E Enzyme Assay

A competitive displacement assay was configured for B-Raf that monitors the amount of a fluorescently-tagged "tracer" bound to B-Raf via TR-FRET from an anti-tag Eu-labeled antibody also bound to B-Raf. For full-length FLAG-tagged B-Raf(V600E), the assay mixtures consisted of 25 mM K$^+$HEPES, pH 7.4, 10 mM MgCl$_2$, 0.01% Triton X-100, 1 mM DTT, 2% DMSO (from compound), 50 nM Tracer 1710 (ThermoFisher, PR9176A), 0.5 nM Eu anti-FLAG (M2)-cryptate Ab (Cisbio, 61FG2KLB) and 5 nM full-length, N-terminally FLAG-tagged B-Raf(V600E) (Origene Technologies, TP700031. Compounds were typically diluted in DMSO across an 11-point dosing range created using a 3-fold serial dilution protocol at a top dose of 10 µM. The assay was run in 384-well, polystyrene, low-volume, non-treated, white microtiter plates (Costar 4512) in a final volume of 12 µL. Low control wells included 1 µM of a potent B-Raf inhibitor as a control. The assays were incubated at ambient temperature (typically 22° C.) for 60 min and then read on a PerkinElmer EnVision microplate reader using standard TRF settings ($\lambda_{Ex}$=320 nm, $\lambda_{Em}$=615 & 665 nm). The ratioed counts (665 nm/615 nm) were converted to percent of control (POC) using the following equation:

$$POC = \frac{\text{Sample} - \overline{X}_{min}}{\overline{X}_{max} - \overline{X}_{min}} \times 100$$

where:
$\overline{X}_{max}$ Average Uninhibited Controls
$\overline{X}_{min}$ Average Background A 4-parameter logistic model was the fit to the POC data for each compound. From that fit, the IC$_{50}$ was estimated and is defined as the concentration of compound at which the best-fit curve crosses 50 POC. Averaged IC$_{50}$ values of compounds disclosed herein when tested in this assay are provided in Table A.

Example A2

Cellular Phospho-ERK Inhibition Assays in A375 and H1755 Cells

A375 and H1755 cells were obtained from the American Type Culture Collection (ATCC, Rockville, MD). A375 cells were maintained in DMEM growth medium containing 10% FBS. H1755 cells were maintained in RPMI growth medium containing 10% FBS.

Cells were harvested according to standard protocols, counted and plated onto flat-bottom, 96-well tissue culture plates (Costar #3599) at 2.5×10$^4$ cells/well for A375 cells and 1.5×10$^4$ cells/well for H1755 cells in 100 µL/well of growth medium containing 10% FBS. After an overnight incubation at 37° C. with 5% CO$_2$ cells were treated for 2 hours at 37° C., 5% CO$_2$ with compounds prepared as a 9-point, 1:3.33 fold dilution series with final compound concentrations ranging from 66 pM-10 µM and a constant DMSO concentration of 0.25%. Control wells contained either 0.25% DMSO alone (uninhibited control) or 10 µM binimetinib (complete inhibition control). The levels of phosphorylated ERK are determined using an In Cell Western protocol: following compound incubation, growth medium was discarded, and cells were fixed with 0.4% formaldehyde in PBS for 20 minutes at room temperature. Cells were permeabilized with 100% methanol for 10 minutes at room temperature. Plates were washed with PBS containing 0.05% Tween-20 and blocked for 1 hour at room temperature with LI-COR Blocking Buffer (LI-COR Biosciences; Cat #927-40000). Plates were then incubated for 2 hours at room temperature with 50 µL of a 1:400 dilution of anti-phospho-ERK1/2 (Thr202/Tyr204) (Cell Signaling; Cat #9101) and a 1:1000 dilution of anti-GAPDH (Millipore; Cat #MAB374) in LI-COR blocking buffer containing 0.05% Tween-20. Plates were washed with PBS containing 0.0$% Tween-20 then incubated at room temperature for 1 hour with 50 µL of a 1:1000 dilution of anti-rabbit AlexaFluor 680 (Life Technologies; Cat #A21109) and a 1:1000 dilution of anti-mouse IRDye 800CW (LI-COR; Cat #926-32210) in LI-COR blocking buffer containing 0.05% Tween-20. Plates were analyzed by reading on an Odyssey CLx infrared scanner. For each well, the phospho-ERK signal was normalized to the GAPDH signal and converted to POC using the following equation:

$$POC = \frac{\text{Sample} - \overline{X}_{min}}{\overline{X}_{max} - \overline{X}_{min}} \times 100$$

Where:
$\overline{X}_{max}$ Average Uninhibited Controls
$\overline{X}_{min}$ Average Complete Inhibition Controls
$IC_{50}$ values were then calculated using a 4-parameter fit in XLfit software and are provided in Table A1.

TABLE A1

| Ex. No. | BRAF V600E enzyme $IC_{50}$ (nM) | A357 cell $IC_{50}$ (nM) | H1755 Cell $IC_{50}$ (nM) |
|---|---|---|---|
| 1 | 60 | 32 | 103 |
| 2 | 36 | 15 | 58 |
| 3 | 30 | 16 | 61 |
| 4 | 32 | 19 | 80 |
| 5 | 14 | 4 | 20 |
| 6 | 13 | 6 | 66 |
| 7 | 12 | 5 | 31 |
| 8 | 10 | 12 | 26 |
| 9 | 7 | 14 | 85 |
| 10 | 8 | 12 | 84 |
| 11 | 7 | 17 | 75 |
| 12 | 7 | 8 | 97 |
| 13 | 6 | 6 | 78 |
| 14 | 5 | 3 | 21 |
| 15 | 6 | 2 | 16 |
| 16 | 6 | 7 | 43 |
| 17 | 4 | 7 | 80 |
| 18 | 4 | 2 | 18 |
| 19 | 4 | 5 | 39 |
| 20 | 3 | 2 | 29 |
| 21 | 3 | 7 | 33 |
| 22 | 3 | 15 | 52 |
| 23 | 3 | 6 | 29 |
| 24 | 2 | 8 | 25 |
| 25 | 2 | 16 | 94 |
| 26 | 6 | 4 | 15 |
| 27 | 5 | 5 | 27 |
| 28 | 4 | 7 | 38 |
| 29 | 3 | 9 | 35 |
| 30 | 2 | 4 | 42 |
| 31 | 1 | 9 | 168 |
| 32 | 2 | 5 | 83 |
| 33 | 1 | 8 | 84 |
| 34 | 4 | 4 | 54 |
| 35 | 2 | 21 | 163 |
| 36 | 1 | 5 | 61 |
| 37 | 4 | 4 | 33 |
| 38 | 2 | 5 | 27 |
| 39 | 3 | 8 | 55 |
| 40 | 2 | 4 | 50 |
| 41 | 3 | 5 | 42 |
| 42 | 2 | 4 | 42 |
| 43 | 1 | 4 | 45 |
| 44 | 2 | 3 | 56 |
| 45 | 4 | 4 | 102 |
| 46 | 1 | 2 | 103 |
| 47 | 2 | 2 | 23 |
| 48 | 3 | 1 | 36 |
| 49 | 2 | 3 | 70 |
| 50 | 2 | 1 | 20 |
| 51 | 77 | 58 | 278 |
| 52 | 141 | 124 | 857 |
| 53 | 7 | 6 | 25 |
| 54 | 17 | 4 | 33 |
| 55 | 45 | 27 | 124 |
| 56 | 1 | 4 | 23 |
| 57 | 3 | 27 | 61 |
| 58 | 3 | 6 | 32 |
| 59 | 1 | 10 | 60 |
| 60 | 2 | 7 | 61 |
| 61 | 2 | 25 | 194 |
| 62 | 13 | 31 | 185 |
| 63 | 1 | 7 | 84 |
| 64 | 2 | 7 | 64 |
| 65 | 2 | 13 | 127 |
| 66 | 4 | 6 | 44 |
| 67 | 2 | 8 | 76 |
| 68 | 21 | 64 | 286 |
| 69 | 7 | 22 | 88 |
| 70 | 8 | 14 | 43 |
| 71 | 301 | 69 | 161 |
| 72 | 299 | 195 | N/A |
| 73 | 234 | 121 | N/A |
| 74 | 203 | 160 | N/A |
| 75 | 191 | 114 | N/A |
| 76 | 183 | 622 | N/A |
| 77 | 177 | 127 | N/A |
| 78 | 114 | 189 | N/A |
| 79 | 111 | 138 | N/A |
| 80 | 103 | 311 | N/A |
| 81 | 75 | 133 | N/A |
| 82 | 69 | 193 | N/A |
| 83 | 67 | 31 | 155 |
| 84 | 53 | 133 | N/A |
| 85 | 52 | 178 | N/A |
| 86 | 42 | 34 | 182 |
| 87 | 33 | 73 | 215 |
| 88 | 27 | 203 | N/A |
| 89 | 14 | 50 | 173 |
| 90 | 9 | 49 | 127 |
| 91 | 9 | 123 | N/A |
| 92 | 8 | 36 | 35 |
| 93 | 3 | 60 | 195 |
| 94 | 20 | 138 | 281 |
| 95 | 2 | 111 | 796 |
| 96 | 3 | 40 | 586 |
| 97 | 10 | 88 | 610 |
| 98 | 20 | 49 | N/A |
| 99 | 5 | 33 | 100 |
| 100 | 6 | 47 | 293 |
| 101 | 3 | 37 | 434 |
| 102 | 1 | 73 | 702 |
| 103 | 5 | 118 | 365 |
| 104 | 5 | 133 | 307 |
| 105 | 15 | 147 | 268 |
| 106 | 12 | 131 | 430 |
| 107 | 1 | 8 | 116 |
| 108 | 1 | 14 | 1592 |
| 109 | 7 | 13 | 272 |
| 110 | 8 | 6 | 48 |
| 111 | 10 | 12 | 80 |
| 112 | 20 | 24 | 105 |
| 113 | 38 | 40 | 358 |
| 114 | 16 | 36 | 174 |
| 115 | 10 | 21 | N/A |
| 116 | 4 | 15 | N/A |
| 117 | 11 | 23 | N/A |
| 118 | 4 | 6 | 41 |
| 119 | 6 | 8 | 51 |
| 120 | 2 | 4 | 69 |
| 121 | 9 | 7 | 18 |
| 122 | 2 | 3 | N/A |
| 123 | 4 | 5 | N/A |
| 124 | 17 | 21 | 10000 |
| 125 | 5 | 18 | 1009 |
| 126 | 3 | 2 | 26 |
| 127 | 2 | 2 | 16 |
| 128 | 16 | 25 | 128 |
| 129 | 12 | 9 | 37 |
| 130 | 11 | 7 | 38 |
| 131 | 16 | 13 | 38 |
| 132 | 13 | 3 | 33 |
| 133 | 5 | 1 | 11 |
| 134 | 7 | 68 | 327 |
| 135 | 3 | 22 | 189 |
| 136 | 6 | 7 | 89 |
| 137 | 8 | 37 | N/A |
| 138 | 3 | 6 | 26 |
| 139 | 4 | 3 | 10 |

TABLE A1-continued

| Ex. No. | BRAF V600E enzyme IC$_{50}$ (nM) | A357 cell IC$_{50}$ (nM) | H1755 Cell IC$_{50}$ (nM) |
|---|---|---|---|
| 140 | 16 | 52 | N/A |
| 141 | 20 | 23 | N/A |
| 142 | 24 | 20 | N/A |
| 143 | 8 | 45 | N/A |
| 144 | 10 | 33 | N/A |
| 145 | 6 | 25 | N/A |
| 146 | 27 | 31 | N/A |
| 147 | 19 | 67 | N/A |
| 148 | 27 | 426 | 854 |
| 149 | 8 | 108 | 337 |
| 150 | 18 | 342 | 548 |
| 151 | 14 | 283 | 538 |
| 152 | 29 | 305 | 329 |
| 153 | 71 | 310 | N/A |
| 154 | 28 | 404 | 879 |
| 155 | 7 | 99 | 1766 |
| 156 | 202 | 872 | N/A |
| 157 | 29 | 886 | N/A |
| 158 | 8 | 156 | N/A |
| 159 | 8 | 90 | N/A |
| 160 | 33 | 87 | N/A |
| 161 | 24 | 245 | N/A |
| 162 | 114 | 1276 | N/A |
| 163 | 8 | 179 | N/A |
| 164 | 113 | 1405 | N/A |

N/A = not available

Example A3

Cellular Phospho-ERK Inhibition Assay

The compounds of Example 13, Example 14 and Example 126 were evaluated in a phospho-ERK assay in two mutant BRAF Class III cell lines: NCI-H1666 (BRAF$^{G466}$V) and WM3629 cells (BRAF$^{D594G}$/NRAS$^{G12D}$). NCI-H1666 cells were obtained from the American Type Culture Collection (ATCC, Rockville, MD) and WM3629 cells were obtained from Rockland Immunochemicals (Limerick, PA). Cells were maintained in RPMI growth medium containing 10% FBS.

Cells were harvested according to standard protocols, counted, and plated onto flat-bottom, 96-well tissue culture plates (Costar #3599) at 2.5×10$^4$ cells/well in 100 μL/well of growth medium containing 10% FBS. After an overnight incubation at 37° C. with 5% CO$_2$ cells were treated for 1 hour at 37° C., 5% CO$_2$ with inhibitors prepared as a 9-point, 1:3.33 fold dilution series with final compound concentrations ranging from 66 pM-10 μM and a constant DMSO concentration of 0.25%. Control wells contained either 0.25% DMSO alone (uninhibited control) or 10 μM binimetinib (complete inhibition control). The levels of phosphorylated ERK were determined using an In Cell Western protocol: following compound incubation, growth medium was discarded, and cells were fixed with 0.4% formaldehyde in PBS for 20 minutes at room temperature. Cells were permeabilized with 100% methanol for 10 minutes at room temperature. Plates were washed with PBS containing 0.05% Tween-20 and blocked for 1 hour at room temperature with LI-COR Blocking Buffer (LI-COR Biosciences; Cat. #927-40000). Plates were then incubated for 2 hours at room temperature with 50 μL of a 1:400 dilution of anti-phospho-ERK1/2 (Thr202/Tyr204) (Cell Signaling; Cat. #9101) and a 1:1000 dilution of anti-GAPDH (Millipore; Cat. #MAB374) in LI-COR blocking buffer containing 0.05% Tween-20. Plates were washed with PBS containing 0.05% Tween-20 then incubated at room temperature for 1 hour with 50 μL of a 1:1000 dilution of anti-rabbit AlexaFluor 680 (Life Technologies; Cat. #A21109) and a 1:1000 dilution of anti-mouse IRDye 800CW (LI-COR; Cat. #926-32210) in LI-COR blocking buffer containing 0.05% Tween-20. Plates were analyzed by reading on an Odyssey CLx infrared scanner. For each well, the phospho-ERK signal was normalized to the GAPDH signal and converted to POC using the following equation:

$$POC = \frac{\text{Sample} - \overline{X}_{min}}{\overline{X}_{max} - \overline{X}_{min}} \times 100$$

Where:

$\overline{X}_{max}$ d Average Uninhibited Controls $\overline{X}_{min}$ Average Complete Inhibition Controls IC$_{50}$ values were then calculated using a 4-parameter fit in XLfit software and are shown in Table A2.

Example A4

Proliferation Assay

The compounds of Example 13, Example 14 and Example 126 were evaluated in a proliferation assay in two mutant BRAF Class III cell lines: NCI-H1666 (BRAF$^{G466}$V) and WM3629 cells (BRAF$^{D594G}$/NRAS$^{G12D}$). NCI-H1666 cells were obtained from the American Type Culture Collection (ATCC, Rockville, MD) and WM3629 cells were obtained from Rockland Immunochemicals (Limerick, PA). Cells were maintained in RPMI growth medium containing 10% FBS.

Cells were harvested according to standard protocols, counted, and plated onto flat-bottom, 96-well tissue culture plates (Costar #3599) at 2000-5000 cells/well in 100 μL/well of growth medium containing 10% FBS. Cells were incubated at 37° C. with 5% CO$_2$ overnight then treated with inhibitors prepared as a 9-point, 1:3.33 fold dilution series with final compound concentrations ranging from 66 pM-10 μM and a constant DMSO concentration of 0.25%. Control wells contained 0.25% DMSO alone. After a 3-5 day incubation at 37° C., 5% CO$_2$, cell viability was determined by adding 100 μL CellTiter-Glo® Reagent (Promega) to each well and incubated for 15 minutes at room temperature. "Day 0" controls were determined by performing CellTiter-Glo© assay on DMSO control wells at the time of compound treatment ("Day 0" control=0 POC). Luminescence was measured on a Cytation 5 plate reader (BioTek) and values were converted to POC using the following equation:

$$POC = \frac{\text{Sample} - \overline{X}_{min}}{\overline{X}_{max} - \overline{X}_{min}} \times 100$$

Where:

$\overline{X}_{max}$ Average DMSO Controls $\overline{X}_{min}$ Average "Day 0" DMSO Controls IC$_{50}$ values were calculated using a 4-parameter fit in XLfit software and are shown in Table A2.

TABLE A2

| | IC$_{50}$ (nM) | | | |
|---|---|---|---|---|
| | NCI-H1666 | | WM3629 | |
| Compound | pERK | Proliferation | pERK | Proliferation |
| Ex. 13 | 15 | 240 | 0.7 | >10000 |
| Ex. 14 | 7.1 | 120 | 0.2 | >10000 |
| Ex. 126 | 15 | 390 | 1.4 | >10000 |

Example B

MDR1 LLC-PK1 and BCRP MDCKII Permeability Assay

Both LLC-PK1 and MDR1 transfected LLC-PK1 cells were cultured and plated according to manufacturer's recommendations with the exception that the passage media contained only 2% fetal bovine serum to extend passage time out to seven days.

BCRP transfected MDCKII cells were cultured and plated according to manufacturer's recommendations. Assay conditions included with and without the BCRP-specific inhibitor, KO143, at a concentration of 0.3 µM to ascertain the contribution of BCRP to the efflux value of the test compound.

Both positive and negative controls were used to assess functionality of P-gp or BCRP efflux in the assays. Stock solutions for assay controls and the test article were prepared in DMSO for final test concentrations of 10 and 1 µM, respectively. Final organic concentration in the assay was 1%. All dosing solutions contained 10 µM lucifer yellow to monitor LLC-PK1 or MDCKII cell monolayer integrity.

For the apical to basolateral determination (A to B), 75 µL of the test article in transport buffer were added to the apical side of the individual transwells and 250 µL of basolateral media, without compound or lucifer yellow, were added to each well. For the basolateral to apical determination (B to A), 250 µL of test article in transport buffer were added to each well and 75 µL transport buffer, without compound or lucifer yellow, were added to each transwell. All tests were performed in triplicate, and each compound was tested for both apical to basolateral and basolateral to apical transport. The plates were incubated for 2 hours on a Lab-Line Instruments Titer Orbital Shaker (VWR, West Chester, PA) at 50 rpm and 37° C. with 5% $CO_2$. All culture plates were removed from the incubator and 50 µL of media were removed from the apical and basolateral portion of each well and added to 150 µL of 1 µM labetalol in 2:1 acetonitrile (acetonitrile): $H_2O$, v/v.

The plates were read using a Molecular Devices (Sunnyvale, CA) Gemini Fluorometer to evaluate the lucifer yellow concentrations at excitation/emission wavelengths of 425/535 nm. These values were accepted when found to be below 2% for apical to basolateral and 5% basolateral to apical flux across the MDR1-transfected LLC-PK1 or BCRP-transfected MDCKII cell monolayers. The plates were sealed and the contents of each well analyzed by LC-MS/MS. The compound concentrations were determined from the ratio of the peak areas of the compound to the internal standard (labetalol) in comparison to the dosing solution.

LC-MS Analysis

The LC-MS/MS system was comprised of an HTS-PAL autosampler (Leap Technologies, Carrboro, NC), an HP1200 HPLC (Agilent, Palo Alto, CA), and a MDS Sciex 4000 Q Trap system (Applied Biosystems, Foster City, CA). Chromatographic separation of the analyte and internal standard was achieved at room temperature using a C18 column (Kinetics*, 50×300 mm, 2.6 µm particle size, Phenomenex, Torrance, CA) in conjunction with gradient conditions using mobile phases A (water containing 1% isopropyl alcohol and 0.1% formic acid) and B (0.1% formic acid in acetonitrile). The total run time, including re-equilibration, for a single injection was 1.2 minutes. Mass spectrometric detection of the analytes was accomplished using the ion spray positive mode. Analyte responses were measured by multiple reaction monitoring (MRM) of transitions unique to each compound (the protonated precursor ion and selected product ions for each test article and m/z 329 to m/z 162 for labetalol, the internal standard).

The permeability coefficient ($P_{app}$) is calculated from the following equation:

$$P_{app} = [((C_d * V * (1 \times 10^6))/(t * 0.12 \text{ cm}^2 * C)]$$

where $C_d$, V, t and $C_0$ are the detected concentration (µM), the volume on the dosing side (mL), the incubation time (s) and the initial dosing concentration (µM), respectively. The calculations for $P_{app}$ were made for each replicate and then averaged. Permeability coefficients for compounds of Formula I are provided in Table B1. In this assay, a compound is defined has having high permeability if the permeability is greater than $8 \times 10^{-6}$ cm/sec, a compound is defined has having medium permeability if the permeability is from $2 \times 10^{-6}$ cm/sec to $8 \times 10^{-6}$ cm/sec, and a compound is defined has having low permeability if the permeability is less than $2 \times 10^{-6}$ cm/sec.

TABLE B1

| Ex. No. | Permeability (*$10^{-6}$ cm/s) |
|---|---|
| 1 | 31 |
| 2 | 31 |
| 3 | 33 |
| 4 | 27 |
| 5 | 27 |
| 6 | 27 |
| 7 | 29 |
| 8 | 23 |
| 9 | 29 |
| 10 | 27 |
| 11 | 28 |
| 12 | 28 |
| 13 | 32 |
| 14 | 28 |
| 15 | 26 |
| 16 | 29 |
| 17 | 24 |
| 18 | 40 |
| 19 | 30 |
| 20 | 37 |
| 21 | 26 |
| 22 | 34 |
| 23 | 24 |
| 24 | 27 |
| 25 | 30 |
| 26 | 31 |
| 27 | 39 |
| 28 | 37 |
| 29 | 28 |
| 30 | 40 |
| 31 | 31 |
| 32 | 32 |
| 33 | 25 |
| 34 | 30 |
| 35 | 31 |
| 36 | 25 |

TABLE B1-continued

| Ex. No. | Permeability (*$10^{-6}$ cm/s) |
|---|---|
| 37 | 29 |
| 38 | 33 |
| 39 | 23 |
| 40 | 29 |
| 41 | 29 |
| 42 | 27 |
| 43 | 32 |
| 44 | 34 |
| 45 | 40 |
| 46 | 30 |
| 47 | 26 |
| 48 | 29 |
| 49 | 30 |
| 50 | 26 |
| 51 | N/A |
| 52 | N/A |
| 53 | 30 |
| 54 | 31 |
| 55 | 33 |
| 56 | N/A |
| 57 | 25 |
| 58 | 27 |
| 59 | 31 |
| 60 | 18 |
| 61 | 29 |
| 62 | 29 |
| 63 | 39 |
| 64 | 34 |
| 65 | 28 |
| 66 | 25 |
| 67 | 24 |
| 68 | 25 |
| 69 | 25 |
| 70 | 25 |
| 71 | 40 |
| 72 | N/A |
| 73 | N/A |
| 74 | N/A |
| 75 | N/A |
| 76 | N/A |
| 77 | N/A |
| 78 | 34 |
| 79 | 28 |
| 80 | N/A |
| 81 | N/A |
| 82 | 13 |
| 83 | 32 |
| 84 | 18 |
| 85 | 26 |
| 86 | 28 |
| 87 | 21 |
| 88 | 25 |
| 89 | 21 |
| 90 | 31 |
| 91 | 17 |
| 92 | 22 |
| 93 | 33 |
| 94 | 22 |
| 95 | 25 |
| 96 | 27 |
| 97 | 30 |
| 98 | 31 |
| 99 | 34 |
| 100 | N/A |
| 101 | N/A |
| 102 | N/A |
| 103 | 25 |
| 104 | 22 |
| 105 | N/A |
| 106 | 22 |
| 107 | 30 |
| 108 | 25 |
| 109 | 34 |
| 110 | 34 |
| 111 | 29 |
| 112 | 28 |
| 113 | 18 |
| 114 | 31 |
| 115 | 28 |
| 116 | 34 |
| 117 | 30 |
| 118 | 34 |
| 119 | 32 |
| 120 | 30 |
| 121 | 35 |
| 122 | 31 |
| 123 | 32 |
| 124 | 43 |
| 125 | 37 |
| 126 | 44 |
| 127 | 34 |
| 128 | 49 |
| 129 | 37 |
| 130 | 30 |
| 131 | 55 |
| 132 | 36 |
| 133 | 33 |
| 134 | 33 |
| 135 | 29 |
| 136 | 24 |
| 137 | 36 |
| 138 | 33 |
| 139 | 32 |
| 140 | 48 |
| 141 | 29 |
| 142 | 21 |
| 143 | 16 |
| 144 | 27 |
| 145 | 29 |
| 146 | 17 |
| 147 | 28 |
| 148 | 22 |
| 149 | 25 |
| 150 | 27 |
| 151 | 28 |
| 152 | 37 |
| 153 | N/A |
| 154 | 26 |
| 155 | 34 |
| 156 | N/A |
| 157 | 23 |
| 158 | 26 |
| 159 | 33 |
| 160 | 38 |
| 161 | 27 |
| 162 | N/A |
| 163 | 23 |
| 164 | N/A |

N/A = not available

An efflux ratio is calculated from the mean apical to basolateral (A-B) $P_{app}$ data and basolateral to apical (B-A) $P_{app}$ data using the following equation:

$$\text{Efflux ratio} = P_{app}(B\text{-}A)/P_{app}(A\text{-}B)$$

Efflux ratios for compounds disclosed herein when tested in this assay are provided in Table B2.

TABLE B2

| Ex. No. | MDR1 | BCRP |
|---|---|---|
| 1 | 1.7 | 1.4 |
| 2 | 1.2 | 1.0 |
| 3 | 1.3 | 1.5 |
| 4 | 1.6 | 2.1 |
| 5 | 3.8 | 3.4 |
| 6 | 1.9 | 1.3 |
| 7 | 1.7 | 2.2 |
| 8 | 2.5 | 1.3 |
| 9 | 1.1 | 1.1 |

TABLE B2-continued

| Ex. No. | MDR1 | BCRP |
|---|---|---|
| 10 | 1.6 | 0.7 |
| 11 | 1.3 | 0.8 |
| 12 | 1.1 | 0.9 |
| 13 | 1.5 | 1.8 |
| 14 | 3.2 | 5.4 |
| 15 | 6.8 | 13.4 |
| 16 | 5.9 | 4.5 |
| 17 | 1.3 | 1.1 |
| 18 | 3.0 | 4.9 |
| 19 | 2.1 | 1.3 |
| 20 | 2.2 | 1.8 |
| 21 | 5.6 | 13.0 |
| 22 | 2.7 | 5.6 |
| 23 | 3.0 | 17.6 |
| 24 | 2.5 | 2.6 |
| 25 | 1.6 | 2.4 |
| 26 | 3.3 | 3.7 |
| 27 | 2.7 | 4.4 |
| 28 | 2.0 | 1.7 |
| 29 | 1.7 | 2.9 |
| 30 | 1.5 | 1.2 |
| 31 | 1.2 | 1.0 |
| 32 | 1.8 | 1.0 |
| 33 | 1.7 | 2.2 |
| 34 | 2.9 | 2.6 |
| 35 | 1.5 | 2.1 |
| 36 | 2.9 | 9.9 |
| 37 | 2.4 | 1.5 |
| 38 | 1.2 | 1.8 |
| 39 | 1.3 | 0.9 |
| 40 | 2.0 | 2.3 |
| 41 | 1.9 | 2.5 |
| 42 | 1.8 | 2.4 |
| 43 | 1.8 | 1.9 |
| 44 | 1.4 | 0.9 |
| 45 | 1.6 | 1.6 |
| 46 | 2.8 | 6.3 |
| 47 | 3.6 | 2.5 |
| 48 | 2.2 | 1.7 |
| 49 | 1.4 | 1.0 |
| 50 | 5.3 | 6.3 |
| 51 | N/A | N/A |
| 52 | N/A | N/A |
| 53 | 2.0 | 1.8 |
| 54 | 3.6 | 3.0 |
| 55 | 1.5 | 1.0 |
| 56 | 2.3 | 2.8 |
| 57 | 0.9 | 0.9 |
| 58 | 5.3 | 7.3 |
| 59 | 4.9 | 12.9 |
| 60 | 3.1 | 1.6 |
| 61 | 2.2 | 3.3 |
| 62 | 1.6 | 1.0 |
| 63 | 1.7 | 3.6 |
| 64 | 4.5 | N/A |
| 65 | 1.3 | 1.0 |
| 66 | 2.2 | 3.1 |
| 67 | 1.4 | 1.0 |
| 68 | 0.7 | 1.0 |
| 69 | 0.8 | 0.9 |
| 70 | 1.8 | 1.0 |
| 71 | 1.2 | 0.9 |
| 72 | N/A | N/A |
| 73 | N/A | N/A |
| 74 | N/A | N/A |
| 75 | N/A | N/A |
| 76 | N/A | N/A |
| 77 | N/A | N/A |
| 78 | 1.5 | 1.0 |
| 79 | 1.3 | 1.0 |
| 80 | N/A | 0.6 |
| 81 | N/A | N/A |
| 82 | 1.2 | 1.0 |
| 83 | 2.2 | 1.9 |
| 84 | 0.8 | 0.8 |
| 85 | 1.7 | 0.9 |
| 86 | 1.9 | 1.6 |
| 87 | 1.0 | 0.6 |
| 88 | 1.2 | 0.6 |
| 89 | 1.3 | 1.0 |
| 90 | 2.3 | 3.5 |
| 91 | 1.5 | 0.8 |
| 92 | 1.2 | 1.9 |
| 93 | 1.4 | 0.8 |
| 94 | 0.9 | 1.7 |
| 95 | 2.7 | 6.8 |
| 96 | 1.2 | 1.1 |
| 97 | 0.9 | 1.8 |
| 98 | 1.1 | 1.1 |
| 99 | 1.7 | 1.4 |
| 100 | N/A | N/A |
| 101 | N/A | N/A |
| 102 | N/A | N/A |
| 103 | 3.2 | 3.5 |
| 104 | 1.2 | 1.3 |
| 105 | N/A | N/A |
| 106 | 1.2 | 0.8 |
| 107 | 2.7 | 1.9 |
| 108 | 1.2 | 0.8 |
| 109 | 1.1 | 0.8 |
| 110 | 1.5 | 1.4 |
| 111 | 1.5 | 1.3 |
| 112 | 1.3 | 1.3 |
| 113 | 1.3 | 1.9 |
| 114 | 2.2 | 5.2 |
| 115 | 1.6 | 1.5 |
| 116 | 2.7 | 2.1 |
| 117 | 1.5 | 1.5 |
| 118 | 3.5 | N/A |
| 119 | 3.8 | N/A |
| 120 | 3.8 | N/A |
| 121 | 1.9 | 6.0 |
| 122 | 2.3 | 7.8 |
| 123 | 2.5 | 5.4 |
| 124 | 1.1 | 1.3 |
| 125 | 1.2 | 1.6 |
| 126 | 2.1 | 4.2 |
| 127 | 3.8 | 5.1 |
| 128 | 1.5 | 1.3 |
| 129 | 1.6 | 5.3 |
| 130 | 2.3 | 7.6 |
| 131 | 2.1 | 1.7 |
| 132 | 2.7 | N/A |
| 133 | 5.7 | N/A |
| 134 | 1.4 | 6.4 |
| 135 | 1.9 | 5.1 |
| 136 | 3.0 | 18.3 |
| 137 | 2.0 | 1.5 |
| 138 | 3.1 | 3.1 |
| 139 | 5.3 | N/A |
| 140 | 1.2 | 0.8 |
| 141 | 1.7 | 2.2 |
| 142 | 3.2 | 2.5 |
| 143 | 2.6 | 3.9 |
| 144 | 5.2 | N/A |
| 145 | 2.6 | 2.4 |
| 146 | 6.9 | N/A |
| 147 | 1.0 | N/A |
| 148 | 2.4 | 1.8 |
| 149 | 1.2 | 3.2 |
| 150 | 1.3 | 1.4 |
| 151 | 1.5 | 1.8 |
| 152 | 1.3 | 1.4 |
| 153 | N/A | N/A |
| 154 | 1.4 | 1.3 |
| 155 | 1.4 | 1.2 |
| 156 | N/A | N/A |
| 157 | 1.2 | 1.2 |
| 158 | 1.5 | 1.1 |
| 159 | 1.8 | 1.1 |
| 160 | 1.3 | 1.3 |
| 161 | 1.9 | 2.6 |

TABLE B2-continued

| Ex. No. | MDR1 | BCRP |
| --- | --- | --- |
| 162 | N/A | N/A |
| 163 | 1.9 | 1.4 |
| 164 | N/A | N/A |

N/A = not available

Example C

PK (Free Brain-to-Free Plasma Ratio) (Mouse)

The ability of representative compounds to penetrate the BBB in mice was determined by evaluating the unbound brain-to-unbound plasma (also referred to as free brain-to-free plasma) concentration ratio in male CD-1 mice.

Brain compound levels were generated from oral mouse PK dosing with typical sampling times of 2, 4, 8, 12 and 24 hours post oral gavage dosing at 10 mg/kg. Brain samples were stored at −20±5° C. prior to analysis. Concentrations of test compound in mouse brain homogenate were determined by liquid chromatography tandem mass spectrometry (LC-MS/MS) following protein precipitation with acetonitrile. A 12-point calibration curve, ranging from 0.5 to 10,000 ng/mL, was prepared in duplicate. A solution of 400 µg/mL of test compound in dimethyl sulfoxide (DMSO) was serially diluted (3-fold) in 100% DMSO, and then 2.5 µL of each standard solution was added to 100 µL of naïve male CD-1 mice brain homogenate. To mimic the extraction in the standard curve, 2.5 µL of DMSO was added to all test samples. Both calibration and test brain homogenate samples were spiked with 10 µL of an IS (1 µg/mL of a structural analog). Brain homogenate was generated by adding 0.75 mL of 4:1 water:MeOH to each brain sample followed by homogenization for 1 minute with bead beater tubes a 6 m/s using an MP Fast Prep-24®. Proteins were precipitated from 100 µL of brain homogenate sample by the addition of 300 µL of acetonitrile. Samples were vortex-mixed for 5 minutes and spun in an Allegra X-12R centrifuge (Beckman Coulter, Fullerton, CA; SX4750A rotor) for 15 min at approximately 1,500×g at 4° C. A 100 µL aliquot of each supernatant was transferred via a 550 µL Personal Pipettor (Apricot Designs, Monrovia, CA) to 96-well plates and diluted 1:1 with HPLC grade water. The resulting plates were sealed with aluminum for LC-MS/MS analysis.

Brain-to-plasma ratios were calculated using the concentration of compound measured in the brain divided by the concentration of compound measured in the plasma. Brain-to-plasma ratios were always generated from a single animal and time point. Free brain-to-free plasma ratios were calculated by multiplying the brain-to-plasma ratio by the in vitro brain homogenate free fraction divided by the in vitro plasma free fraction using the following equation: (B/P)* $(B_{fu}/P_{fu})$. Table C provides the free brain-to-free plasma ratios of compounds disclosed herein.

TABLE C

| Ex. No. | B/P ratio (free) |
| --- | --- |
| 6 | 0.87-1.76 |
| 7 | 0.37-0.61 |
| 9 | 0.36-0.40 |
| 12 | 0.34-0.39 |
| 13 | 0.75-0.93 |
| 14 | 0.13-0.39 |
| 17 | 0.61-0.64 |

TABLE C-continued

| Ex. No. | B/P ratio (free) |
| --- | --- |
| 19 | 0.61-0.83 |
| 20 | 0.40-0.58 |
| 29 | 0.41-0.55 |
| 30 | 0.51-0.64 |
| 37 | 0.66-0.73 |
| 38 | 0.20-0.24 |
| 40 | 0.55-0.72 |
| 41 | 0.35-0.45 |
| 44 | 0.35-0.47 |
| 48 | 0.29-0.33 |
| 70 | 0.17-0.36 |
| 126 | 0.12-0.17 |
| 129 | 0.18-0.22 |
| 130 | 0.12-0.16 |
| 131 | 0.30-0.50 |

Synthetic Examples

Preparation of Synthetic Intermediates

Intermediate P1

6-bromo-5-methylquinazolin-4(3H)-one

6-Amino-3-bromo-2-methylbenzoic acid (10 g, 43 mmol) and formamidine acetate (5.4 g, 52 mmol) were dissolved in ethanol (172 mL) in a 500 mL flask with a reflux condenser. The reaction mixture was heated to 80° C. for 16 hours. The mixture was cooled to ambient temperature and concentrated in vacuo. The residue was diluted with water (300 mL) and stirred vigorously for 60 minutes. The resulting solid was isolated by filtration and the filter cake was washed with water (500 mL). The solids were dried under vacuum to afford 6-bromo-5-methylquinazolin-4(3H)-one (6.9 g, 66%) as a white solid. MS (apci, m/z)=239.0, 241.0 (M+H).

Intermediate P2

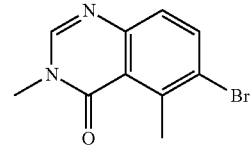

6-bromo-3,5-dimethylquinazolin-4(3H)-one

6-Bromo-5-methylquinazolin-4(3H)-one (Intermediate P1) (11 g, 46.0 mmol), potassium carbonate (14.0 g, 101 mmol) and iodomethane (13.1 g, 92.0 mmol) were dissolved in anhydrous DMF (250 mL). The reaction mixture was stirred at ambient temperature for 2 hours. The entire reaction mixture was poured directly into 900 mL water and the resulting slurry was stirred at ambient temperature for 30 minutes. The solids were collected by filtration and dried overnight under high vacuum to afford 6-bromo-3,5-dimethylquinazolin-4(3H)-one (10.1 g, 87%) as a white solid. MS (apci, m/z)=253.0, 255.0 (M+H).

Intermediate P3

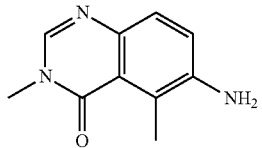

6-Amino-3,5-dimethylquinazolin-4(3H)-one

Step 1: Preparation of 6-((4-methoxybenzyl)amino)-3,5-dimethylquinazolin-4(3H)-one. A solution of (4-methoxyphenyl)methanamine (1.20 mL, 9.18 mmol), 6-bromo-3,5-dimethylquinazolin-4(3H)-one (Intermediate P2) (2.02 g, 7.98 mmol), Pd$_2$(dba)$_3$ (0.365 g, 0.399 mmol), Xantphos (0.693 g, 1.20 mmol), and Cs$_2$CO$_3$ (7.80 g, 23.9 mmol) in toluene (53.2 mL) was placed in a pressure tube and sparged with argon for 10 minutes. The reaction vessel was sealed and heated to 90° C. for 60 hours. Additional Pd$_2$(dba)$_3$ (0.365 g, 0.399 mmol) and Xantphos (0.693 g, 1.20 mmol) were added and the solution was again sparged with argon for 10 minutes, sealed and heated to 90° C. for another 16 hours. The reaction mixture was cooled to ambient temperature, filtered, concentrated, and purified by column chromatography, eluting with 5 to 95% EtOAc/DCM to afford 6-((4-methoxybenzyl)amino)-3,5-dimethylquinazolin-4(3H)-one (2.4 g, 97%). MS (apci, m/z)=310.2 (M+H).

Step 2: Preparation of 6-amino-3,5-dimethylquinazolin-4(3H)-one. A solution of 6-((4-methoxybenzyl)amino)-3,5-dimethylquinazolin-4(3H)-one (2.4 g, 7.76 mmol) was stirred in 50 mL of DCM and 25 mL of TFA for 2 hours. The solution was concentrated, and the residue was dissolved in 100 mL of DCM, 10 mL of MeOH, and stirred vigorously with 4 g of K$_2$CO$_3$ for 30 minutes. The K$_2$CO$_3$ was removed by filtration and the filtrate was concentrated and the residue was purified by column chromatography, eluting with 1 to 10% MeOH/DCM (1% NH$_4$OH) to afford 6-amino-3,5-dimethylquinazolin-4(3H)-one (1.45 g, 99%). $^1$H NMR (400 MHz, CDCl$_3$) δ 8.2 (s, 1H), 7.5 (d, 1H), 7.1 (d, 1H), 4.2 (br-s, 2H), 3.6 (s, 3H), 2.8 (s, 3H); MS (apci, m/z)=190.1 (M+H).

Intermediate P4

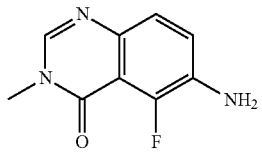

6-Amino-5-fluoro-3-methylquinazolin-4(3H)-one

Step 1: Preparation of 6-bromo-5-fluoroquinazolin-4(3H)-one. 6-Amino-3-bromo-2-fluorobenzoic acid (4.51 g, 19.3 mmol) was dissolved in EtOH (200 mL) and then treated with formamidine acetate (6.02 g, 57.8 mmol) and then heated to 80° C. for 16 hours. The reaction mixture was treated with additional formamidine acetate (3.01 g, 28.9 mmol) and stirred at 80° C. for an additional 4 hrs. The reaction mixture was cooled to ambient temperature and poured into water and then extracted with EtOAc (3×). The combined organic layers were washed with brine (1×) and then dried over Na$_2$SO$_4$, filtered, and concentrated to provide 6-bromo-5-fluoroquinazolin-4(3H)-one (4.28 g, 91%). MS (apci, m/z)=243.0, 245.0 (M+H).

Step 2: Preparation of 6-bromo-5-fluoro-3-methylquinazolin-4(3H)-one 6-Bromo-5-fluoroquinazolin-4(3H)-one (4.28 g, 17.6 mmol) was dissolved in DMF (70 mL) and then treated with iodomethane (1.32 mL, 21.1 mmol) followed by potassium carbonate (3.65 g, 26.4 mmol) and the reaction mixture was allowed to stir at ambient temperature for 1 hr. The reaction mixture was poured into water and extracted with EtOAc (3×). The combined organic layers were washed with water (3×) followed by brine (1×) then dried over Na$_2$SO$_4$, filtered, and concentrated. The resulting residue was purified by silica gel chromatography (DCM/EtOAc) to provide 6-bromo-5-fluoro-3-methylquinazolin-4(3H)-one (3.33 g, 74%). MS (apci, m/z)=257.0, 259.0 (M+H).

Step 3: Preparation of 6-amino-5-fluoro-3-methylquinazolin-4(3H)-one. 6-Bromo-5-fluoro-3-methylquinazolin-4(3H)-one (3.18 g, 12.37 mmol) was dissolved in toluene (125 mL) and treated with tert-butyl carbamate (1.59410 g, 13.61 mmol), tris(dibenzylideneacetone)dipalladium (1.13 g, 1.24 mmol), 4,5-bis(diphenylphosphino)-9,9-dimethylxanthene (1.79 g, 3.09 mmol), and cesium carbonate (12.09 g, 37.11 mmol) and then sparged with argon for several minutes and heated to 110° C. under an argon balloon for 16 hours. The reaction mixture was cooled to ambient temperature and diluted with DCM (1 L) and stirred for 15 minutes filtered through a pad of Celite® and concentrated. The resulting residue was dissolved in 1:1 DCM:TFA (20 mL) and stirred at ambient temperature for 1 hour. The reaction mixture was concentrated and then purified by reverse phase C18 chromatography (water/ACN with 0.1% TFA). The desired fractions were combined and partitioned between 4:1 DCM:IPA and saturated NaHCO$_3$ (1×). The combined organic layers were dried over Na$_2$SO$_4$, filtered, and concentrated to provide 6-amino-5-fluoro-3-methylquinazolin-4(3H)-one (1.57 g, 65.7%). $^1$H NMR (400 MHz, DMSO) δ 8.05 (s, 1H), 7.27-7.22 (m, 2H), 5.51 (br-s, 2H), 3.40 (s, 3H); MS (apci, m/z)=194.1 (M+H).

Intermediate P5

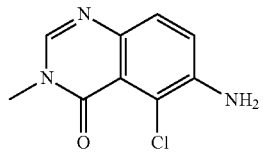

6-Amino-5-chloro-3-methylquinazolin-4(3H)-one

6-Amino-3-methylquinazolin-4(3H)-one (3.00 g, 17.1 mmol) was dissolved in THF (170 mL) and then treated with N-chlorosuccinimide (2.40 g, 18.0 mmol) and heated to 50° C. for 16 hours. The reaction mixture was treated with additional N-chlorosuccinimide (1.14 g, 8.56 mmol) and stirred at 50° C. for an additional 3 hours. The reaction mixture was concentrated, and the resulting residue was diluted with 1.0 M HCl and extracted with DCM (3×). The combined DCM combined organic layers were washed with 1.0 M HCl (2×) and the aqueous layer was neutralized with solid NaHCO₃ to about pH 7-8 and then extracted with 4:1 DCM:IPA (2×). The combined DCM:IPA extracts were dried over Na₂SO₄, filtered, and concentrated to provide 6-amino-5-chloro-3-methylquinazolin-4(3H)-one (2.47 g, 69%). ¹H NMR (400 MHz, DMSO) δ 8.10 (s, 1H), 7.38-7.36 (d, 2H), 7.29-7.26 (d, 2H), 5.81 (br-s, 2H), 3.40 (s, 3H). MS (apci, m/z)=210.1, 212.1 (M+H).

Intermediate P6

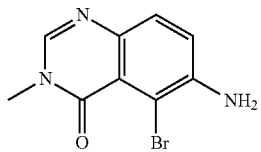

6-Amino-5-bromo-3-methyl-4a,8a-dihydroquinazolin-4(3H)-one

6-Amino-3-methylquinazolin-4(3H)-one (2.00 g, 11.3 mmol) was dissolved in THF (56 mL) and then treated with N-bromosuccinimide (2.11 g, 11.9 mmol) and the mixture was heated to 50° C. for 60 minutes. The reaction mixture was cooled to ambient temperature diluted with ethyl acetate (100 mL) and washed with sodium thiosulfate (saturated aqueous solution, 100 mL, 1×), followed by sodium bicarbonate (saturated aqueous solution, 100 mL, 1×). The combined organic layers were dried over MgSO₄, filtered, and concentrated. The residue was purified by C18 reverse phase silica gel chromatography, eluting with water/acetonitrile to provide 6-Amino-5-bromo-3-methyl-4a,8a-dihydroquinazolin-4(3H)-one (1.01 g, 35%). MS (apci, m/z)=254.0, 256.0 (M+H).

Intermediate P7

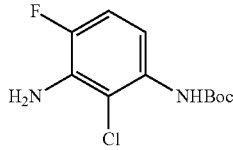

Tert-butyl (3-amino-2-chloro-4-fluorophenyl)carbamate

Step 1: Preparation of methyl 3-((tert-butoxycarbonyl)amino)-2-chloro-6-fluorobenzoate Methyl 3-amino-2-chloro-6-fluorobenzoate (5.06 g, 24.9 mmol) was dissolved in DCM (250 mL) and cooled to 0° C. The reaction mixture was sequentially treated with triethylamine (10.4 mL, 74.6 mmol), 4-(dimethylamino)pyridine (0.304 g, 2.49 mmol) and di-tert-butyl dicarbonate (13.6 g, 62.1 mmol) and allowed to stir at ambient temperature for 16 hours. The reaction mixture was concentrated, and the residue was purified by silica gel chromatography, eluting with hexanes/acetone to provide methyl 3-((tert-butoxycarbonyl)amino)-2-chloro-6-fluorobenzoate (7.55 g, 100%) which was used immediately in the next step as a mixture of mono/bis-Boc products.

Step 2: Preparation of 3-((tert-butoxycarbonyl)amino)-2-chloro-6-fluorobenzoic acid. Methyl 3-((tert-butoxycarbonyl)amino)-2-chloro-6-fluorobenzoate (7.55 g, 24.9 mmol) was dissolved in 1:1 THF/MeOH (120 mL) and then treated with 2.0 M aqueous NaOH (37.3 mL, 74.6 mmol) and allowed to stir at ambient temperature for 16 hours. The reaction mixture was diluted with additional water and extracted with Et₂O (2×250 mL). The Et₂O combined organic layers were combined and washed with 1.0 M NaOH (1×50 mL). The combined aqueous layers were acidified to about pH 4 using 4.0 M HCl and then extracted with 4:1 DCM/IPA (2×250 mL). The combined organic layers were dried over Na₂SO₄, filtered, and concentrated to provide 3-((tert-butoxycarbonyl)amino)-2-chloro-6-fluorobenzoic acid (5.53 g, 77%) which was used directly in the next step without purification.

Step 3: Preparation of tert-butyl (3-amino-2-chloro-4-fluorophenyl)carbamate. 3-((Tert-butoxycarbonyl)amino)-2-chloro-6-fluorobenzoic acid (5.53 g, 19.1 mmol) was dissolved in DMF (100 mL) and treated sequentially with triethylamine (7.98 mL, 57.27 mmol) and diphenylphosphoryl azide (6.17 mL, 28.63 mmol) and stirred at ambient temperature for 1 hour. The reaction mixture was treated with water (20 mL) and heated to 80° C. for 16 hours. The reaction mixture was cooled to ambient temperature and diluted with additional water (50 mL) and then extracted with EtOAc (2×250 mL). The organic extracts were combined and washed with water (3×100 mL) and brine (1×50 mL) then dried over Na₂SO₄, filtered, and concentrated. The residue was purified by silica gel chromatography, eluting with hexanes/acetone and then again with hexanes/MTBE to provide tert-butyl (3-amino-2-chloro-4-fluorophenyl)carbamate (1.05 g, 21%). ¹H NMR (400 MHz, DMSO-d₆) δ 8.41 (s, 1H), 6.99-6.94 (m, 1H), 6.69-6.66 (m, 1H), 5.34 (s, 2H), 1.43 (s, 9H).

Intermediate P8

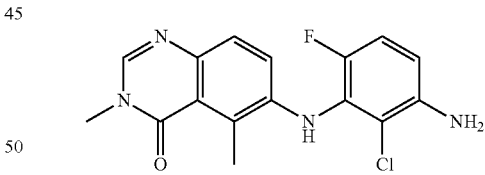

6-((3-Amino-2-chloro-6-fluorophenyl)amino)-3,5-dimethylquinazolin-4(3H)-one

Step 1: Preparation of tert-butyl (2-chloro-3-((3,5-dimethyl-4-oxo-3,4-dihydroquinazolin-6-yl)amino)-4-fluorophenyl)carbamate. Tert-butyl (3-amino-2-chloro-4-fluorophenyl)carbamate (56.7 mg, 0.217 mmol), 6-bromo-3,5-dimethylquinazolin-4(3H)-one (50 mg, 0.198 mmol), cesium carbonate (193 mg, 0.593 mmol), Xantphos (17.1 mg, 0.0296 mmol) and tris(dibenzylideneacetone)dipalladium (0) (9.05 mg, 0.0099) were combined in a vial then degassed under reduced pressure and backfilled with argon gas. Toluene (0.988 mL) was added and the solution was sparged with argon for 5 minutes before the vial was sealed and heated to 100° C. for 16 hours. The reaction mixture was cooled to ambient temperature and was filtered through a pad of Celite® and purified by silica gel chromatography, eluting with DCM/EtOAc to provide tert-butyl (2-chloro-3-((3,5-dimethyl-4-oxo-3,4-dihydroquinazolin-6-yl)amino)-4-fluorophenyl)-carbamate as an off white solid (81 mg, 95%). MS (apci, m/z)=333.1 (M-Boc).

Step 2: Preparation of 6-((3-amino-2-chloro-6-fluorophenyl)amino)-3,5-dimethylquinazolin-4(3H)-one. Tert-butyl (2-chloro-3-((3,5-dimethyl-4-oxo-3,4-dihydroquinazolin-6-yl)amino)-4-fluorophenyl)carbamate (81 mg, 0.187 mmol) was dissolved in DCM (4.7 mL) and treated with trifluoroacetic acid (1.5 mL) and the reaction mixture was allowed to stir at ambient temperature for 1 hour. The reaction mixture was concentrated, and the residue was purified by silica gel chromatography, eluting with DCM/MeOH and 1% NH$_4$OH to obtain 6-((3-amino-2-chloro-6-fluorophenyl)amino)-3,5-dimethylquinazolin-4(3H)-one as a light yellow solid (37 mg, 56%). $^1$H NMR (400 MHz, CDCl$_3$) δ 7.99 (s, 1H), 7.38 (d, 1H), 7.02 (d, 1H), 6.86 (dd, 1H), 6.51 (dd, 1H), 3.50 (s, 3H), 2.90 (s, 3H); MS (apci, m/z)=333.1 (M+H).

Intermediate P9

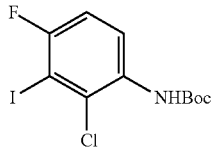

Tert-butyl
(2-chloro-4-fluoro-3-iodophenyl)carbamate

Step 1: Preparation of 2-chloro-4-fluoro-3-iodoaniline. In a 5-L 4-neck flask equipped with 3 addition funnels, an internal temperature probe, and a magnetic stir bar, 2-chloro-4-fluoroaniline (82.03 mL, 687.0 mmol) was dissolved in THF (1.5 L) under a backflow of N$_2$ and cooled to −78° C. The reaction mixture was treated dropwise with butyllithium (2.5 M in hexanes) (299.5 mL, 748.8 mmol) and allowed to stir at −78° C. for 15 minutes after complete addition. The reaction mixture was treated dropwise with a THF solution (500 mL) of 1,2-bis(chlorodimethylsilyl)ethane (155.3 g, 721.4 mmol) and allowed to stir at −78° C. for 30 minutes after complete addition. The reaction mixture was treated dropwise with additional butyllithium (2.5 M in hexanes) (299.5 mL, 748.8 mmol) and then the ice bath was removed after complete addition and the reaction mixture was stirred for 1 hour. The reaction mixture was cooled back to −78° C. and treated dropwise with additional butyllithium (2.5 M in hexanes) (299.5 mL, 748.8 mmol) and stirred at −78° C. for 30 minutes after complete addition. The reaction mixture was treated dropwise with a THF solution (600 mL) of iodine (249.3 g, 982.4 mmol) and the ice bath was removed, and reaction mixture allowed to warm to ambient temperature and stir for 16 hours. The reaction mixture was treated with 1000 mL water followed by hydrochloric acid (4.0 M aqueous solution) (601.1 mL, 2404.5 mmol) and allowed to stir at ambient temperature for 1 hr. The reaction mixture was neutralized to about pH 8 using solid NaHCO$_3$ and then treated with sodium thiosulfate (3.0 M aqueous solution) (801.5 mL, 2404.5 mmol) and allowed to stir at ambient temperature for 30 minutes. The reaction mixture was transferred to an extraction funnel, rinsing the flask with MTBE and water, and then the layers were separated. The organic layer was washed with brine (1×) and dried over Na$_2$SO$_4$, filtered, and concentrated to provide 2-chloro-4-fluoro-3-iodoaniline (186.49 g, 100%). $^1$H NMR (400 MHz, DMSO) δ 6.97-6.93 (m, 1H), 6.81-6.77 (m, 1H), 5.41 (br-s, 2H).

Step 2: Preparation of bis-tert-butyl (2-chloro-4-fluoro-3-iodophenyl)carbamate. In a 3-L 1 neck flask, 2-chloro-4-fluoro-3-iodoaniline (186.49 g, 686.99 mmol) was dissolved in THF (2.0 L) and treated with 4-(dimethylamino)pyridine (8.39 g, 68.7 mmol) followed by addition of di-tert-butyl dicarbonate (314.87 g, 1442.7 mmol) and then stirred at ambient temperature for 1 hour open to air with a Vigreux column. The reaction mixture was concentrated to dryness. The resulting residue was dissolved in DCM (1 L) and diluted with hexanes (1 L) and stirred for 15 minutes, then passed through a small plug of silica eluting with additional 1:1 DCM:Hexanes (2.5 L). The filtrate was concentrated to dryness and the resulting solids were suspended in heptane (500 mL) and stirred at 80° C. for 30 minutes. The mixture was cooled to 0° C. in an ice bath and filtered, rinsed with additional chilled (0° C.) heptane (500 mL), and the light tan solids were collected to provide bis-tert-butyl (2-chloro-4-fluoro-3-iodophenyl)carbamate (145.5 g, 45%). $^1$H NMR (400 MHz, DMSO) δ 7.55-7.51 (m, 1H), 7.32-7.28 (m, 1H), 1.33 (s, 18H).

Step 3: Preparation of tert-butyl (2-chloro-4-fluoro-3-iodophenyl)carbamate. Bis-tert-butyl (2-chloro-4-fluoro-3-iodophenyl)carbamate (331.7 g, 703.2 mmol) was dissolved in MeOH (1.8 L) and treated with potassium carbonate (106.9 g, 773.5 mmol) then heated to 65° C. for 1 hour. The reaction mixture was cooled to ambient temperature and poured into 6.0 L of water and stirred for 30 minutes. The mixture was filtered, rinsed with additional water (1000 mL), and collected the light tan solids to provide tert-butyl (2-chloro-4-fluoro-3-iodophenyl)carbamate (258.0 g, 99%). $^1$H NMR (400 MHz, DMSO) δ 8.82 (s, 1H), 7.53-7.50 (m, 1H), 7.24-7.20 (m, 1H), 1.42 (s, 9H).

Intermediate P10

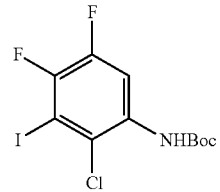 [SMILES: CC(C)(C)OC(=O)Nc1cc(F)c(F)c(I)c1Cl]

Tert-butyl
(2-chloro-4,5-difluoro-3-iodophenyl)carbamate

Step 1: Preparation of 2-chloro-4,5-difluoro-3-iodoaniline. A solution of 2-chloro-4,5-difluoroaniline (26.0 g, 158.97 mmol) was dissolved in THF (1.0 L) under a backflow of N$_2$ and cooled to −78° C. The reaction mixture was treated dropwise with butyllithium (2.5 M in hexanes) (66.768 mL, 166.92 mmol) and allowed to stir at −78° C. for 15 minutes after complete addition. The reaction mixture was treated dropwise with a THF solution (250 mL) of 1,2-bis(chlorodimethylsilyl)ethane (35.932 g, 166.92 mmol) and allowed to stir at −78° C. for 30 minutes after complete addition. The reaction mixture was treated dropwise with additional butyllithium (2.5 M in hexanes) (66.768 mL, 166.92 mmol). The ice bath was removed after complete addition and the reaction mixture was allowed to stir for 1 hour. The reaction mixture was cooled back to −78° C. and treated dropwise with an additional butyllithium (2.5 M in hexanes) (66.768 mL, 166.92 mmol) and allowed to stir at −78° C. for 30 minutes after complete addition. The reaction mixture was treated dropwise with a THE solution (600 mL) of iodine (60.522 g, 238.46 mmol). The ice bath was removed, and reaction mixture allowed to warm to ambient temperature and stir for 16 hours. The reaction mixture was treated with 500 mL water followed by hydrochloric acid (4.0 M aqueous solution) (139.10 mL, 556.40 mmol) and allowed to stir at ambient temperature for 1 hour. The reaction mixture was neutralized to about pH 8 using solid $NaHCO_3$ and then treated with sodium thiosulfate (3.0 M aqueous solution) (185.47 mL, 556.40 mmol) and allowed to stir at ambient temperature for 30 minutes. The layers were separated, and the aqueous layer was extracted with MTBE (1×1000 mL). The combined organic layers were washed with brine (1×500 mL) then dried over $Na_2SO_4$, filtered, and concentrated to provide 2-chloro-4,5-difluoro-3-iodoaniline (46.0 g, 100%). $^1$H NMR (400 MHz, DMSO) δ 6.82-6.77 (m, 1H), 5.68 (br-s, 2H).

Step 2: Preparation of bis-tert-butyl (2-chloro-4,5-difluoro-3-iodophenyl)carbamate. 2-Chloro-4,5-difluoro-3-iodoaniline (46.0 g, 159 mmol) was dissolved in THE (1000 mL) and treated with 4-(dimethylamino)pyridine (1.94 g, 15.9 mmol) followed by di-tert-butyl dicarbonate (72.8 g, 334 mmol) and the reaction mixture was stirred at ambient temperature for 16 hours. The reaction mixture was concentrated to dryness and the resulting residue was dissolved in 1:1 DCM:hexanes (500 mL) and stirred for 15 minutes. The mixture was passed through a plug of silica gel eluting with additional 1:1 DCM:Hexanes (1.5 L). The filtrate was concentrated to dryness to provide bis-tert-butyl (2-chloro-4,5-difluoro-3-iodophenyl)carbamate (77.8 g, 100% yield). $^1$H NMR (400 MHz, DMSO) δ 7.95-7.90 (m, 1H), 1.33 (s, 18H).

Step 3: Preparation of tert-butyl (2-chloro-4,5-difluoro-3-iodophenyl)carbamate. Bis-tert-butyl (2-chloro-4,5-difluoro-3-iodophenyl)carbamate (77.8 g, 159 mmol) was dissolved in MeOH (650 mL) and treated with potassium carbonate (24.2 g, 175 mmol) and the reaction mixture was heated to 65° C. for 1.5 hours. The reaction mixture was cooled to ambient temperature, then poured into water (2 L) and stirred for 15 minutes. The reaction mixture was filtered, rinsed with additional water, and the resulting brown solids were collected. The solids were dried on high vacuum for 16 hours and then suspended in heptane (250 mL) and stirred for 15 minutes. The suspension was filtered, and the solids were rinsed with additional heptane to afford tert-butyl (2-chloro-4,5-difluoro-3-iodophenyl)carbamate (34.9 g, 56.4%). $^1$H NMR (400 MHz, DMSO) δ 8.94 (br-s, 1H), 7.76-7.71 (m, 1H), 1.43 (s, 9H).

Intermediate P11

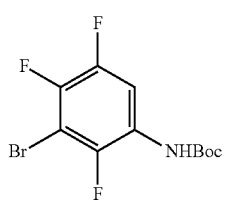

Tert-butyl (3-bromo-2,4,5-trifluorophenyl)carbamate

Step A: Preparation of bis-tert-butyl (2-chloro-4,5-difluoro-3-iodophenyl)carbamate. To a solution of 3-bromo-2,4,5-trifluoroaniline (3.0 g, 13 mmol) in THE (88 mL, 13 mmol) was added DMAP (0.16 g, 1.3 mmol) and di-tert-butyl dicarbonate (6.7 g, 31 mmol) and the solution was stirred at ambient temperature for 16 hours. The reaction mixture was concentrated and purified by silica gel chromatography (50% DCM/hexanes) to give bis-tert-butyl (2-chloro-4,5-difluoro-3-iodophenyl)carbamate, which was used directly in the next step.

Step B: Preparation of tert-butyl (3-bromo-2,4,5-trifluorophenyl)carbamate. To a solution of bis-tert-butyl (2-chloro-4-fluoro-3-iodophenyl)carbamate (5.7 g, 13 mmol) in methanol (67 mL) was added potassium carbonate (2.03 g, 14.7 mmol) and the reaction mixture was heated to 65° C. for 3 hours. The solution was cooled to room temperature and concentrated. The resulting solids were diluted with water, stirred for 15 minutes, and then filtered, rinsed with water, and dried overnight to give tert-butyl (3-bromo-2,4,5-trifluorophenyl)carbamate (4.15 g, 95%). $^1$H NMR (400 MHz, DMSO) δ 9.4 (br-s, 1H), 7.82 (m, 1H), 1.46, (s, 9H).

Intermediate P12

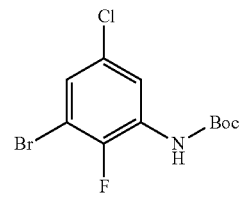

Tert-butyl (3-bromo-5-chloro-2-fluorophenyl)carbamate

3-Bromo-5-chloro-2-fluoroaniline (2.43 g, 10.8 mmol) was dissolved in THF (110 mL) and treated with 4-(dimethylamino)pyridine (0.132 g, 1.08 mmol) followed by di-tert-butyl dicarbonate (4.96 g, 22.7 mmol) and the mixture was stirred at ambient temperature for 16 hours. The reaction mixture was concentrated to dryness and the resulting residue was dissolved in MeOH (100 mL) and treated with potassium carbonate (2.99 g, 21.7 mmol) and heated at 70° C. for 30 minutes. The reaction mixture was cooled to ambient temperature and concentrated. The residue was dissolved in DCM and washed with water (1×), then dried over $Na_2SO_4$, filtered, and concentrated. The resulting residue was purified by silica gel chromatography (Hexanes/EtOAc) to provide tert-butyl (3-bromo-5-chloro-2-fluorophenyl)carbamate (2.92 g, 83%). $^1$H NMR (400 MHz, DMSO) δ 9.45 (br-s, 1H), 7.81-7.79 (m, 1H), 7.54-7.52 (m, 1H), 1.47 (s, 9H).

Intermediate P13

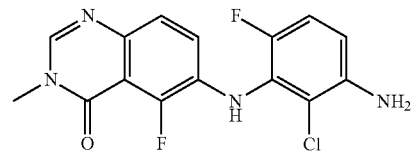 [SMILES: Cn1cnc2ccc(Nc3c(F)ccc(N)c3Cl)c(F)c2c1=O]

6-((3-Amino-2-chloro-6-fluorophenyl)amino)-5-fluoro-3-methylquinazolin-4(3H)-one 6-Amino-5-fluoro-3-methylquinazolin-4(3H)-one (Intermediate P4; 1.50 g, 7.76 mmol) was dissolved in toluene (78 mL) and treated with tert-butyl (2-chloro-4-fluoro-3-iodophenyl)carbamate (Intermediate P9; 3.02 g, 8.15 mmol), tris(dibenzylideneacetone)dipalladium (0) (0.36 g, 0.39 mmol), Xantphos (0.67 g, 1.16 mmol), and cesium carbonate (5.06 g, 15.53 mmol). The reaction mixture was sparged with argon for several minutes and then heated at 110° C. for 24 hours under an argon balloon. The reaction mixture was cooled to ambient temperature and diluted with DCM (1 L) and stirred for 15 minutes then filtered through a pad of Celite® and concentrated. The resulting residue was dissolved in 1:1 DCM:TFA (20 mL) and stirred at ambient temperature for 1 hour. The reaction mixture was concentrated and purified by reverse phase C18 chromatography (water/ACN with 0.1% TFA). The desired fractions were combined and partitioned between 4:1 DCM:IPA and saturated NaHCO$_3$ (1×) and then dried over Na$_2$SO$_4$, filtered, and concentrated to provide 6-((3-amino-2-chloro-6-fluorophenyl)amino)-5-fluoro-3-methylquinazolin-4(3H)-one (1.26 g, 48%). $^1$H NMR (400 MHz, DMSO) δ 8.14 (s, 1H), 7.78 (s, 1H), 7.31-7.29 (d, 1H), 7.05-7.00 (t, 1H), 6.94-6.89 (t, 1H), 6.70-6.67 (m, 1H), 5.28 (br-s, 2H), 3.43 (s, 3H). MS (apci, m/z)=337.1, 339.1 (M+H).

Intermediate P14

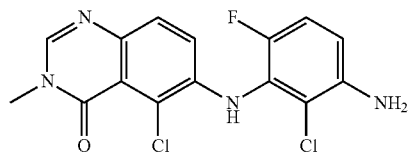

6-((3-Amino-2-chloro-6-fluorophenyl)amino)-5-chloro-3-methylquinazolin-4(3H)-one 6-Amino-5-chloro-3-methylquinazolin-4(3H)-one (2.35 g, 11.2101 mmol) was dissolved in toluene (110 mL) and treated with tert-butyl (2-chloro-4-fluoro-3-iodophenyl)carbamate (4.37 g, 11.77 mmol), tris(dibenzylideneacetone)dipalladium (0) (0.51 g, 0.56 mmol), Xantphos (0.97 g, 1.68 mmol), and cesium carbonate (7.30 g, 22.42 mmol). The reaction mixture was sparged with argon for several minutes and then heated stirred at 110° C. under an argon balloon for 60 hours. The reaction mixture was cooled to ambient temperature and diluted with DCM (1 L) and stirred for 15 minutes then filtered through a pad of Celite® and concentrated. The resulting residue was purified by silica gel chromatography (DCM/Acetone). The isolated product was dissolved in 1:1 DCM:TFA (20 mL) and stirred at ambient temperature for 1 hour. The reaction mixture was concentrated and then purified by reverse phase C18 chromatography (water/ACN with 0.1% TFA). The desired fractions were combined and partitioned between 4:1 DCM:IPA and saturated NaHCO$_3$ (1×) and then dried over Na$_2$SO$_4$, filtered, and concentrated to provide 6-((3-amino-2-chloro-6-fluorophenyl)amino)-5-chloro-3-methylquinazolin-4(3H)-one (2.67 g, 67%). $^1$H NMR (400 MHz, DMSO) δ 8.16 (s, 1H), 7.47 (s, 1H), 7.41-7.39 (d, 1H), 7.08-7.03 (t, 1H), 6.76-6.72 (m, 2H), 5.31 (s, 2H), 3.41 (s, 3H). MS (apci, m/z)=353.0, 355.0 (M+H).

Intermediate P15

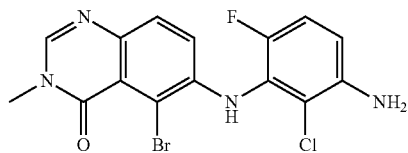 [SMILES: Cn1cnc2ccc(Nc3c(F)ccc(N)c3Cl)c(Br)c2c1=O]

6-((3-Amino-2-chloro-6-fluorophenyl)amino)-5-bromo-3-methylquinazolin-4(3H)-one

6-Amino-5-bromo-3-methylquinazolin-4(3H)-one (800 mg, 3.15 mmol) was dissolved in toluene (32 mL) and treated with tert-butyl (2-chloro-4-fluoro-3-iodophenyl)carbamate (1.23 g, 3.31 mmol), tris(dibenzylideneacetone)dipalladium (0) (144 mg, 0.16 mmol), Xantphos (273 mg, 0.47 mmol), and cesium carbonate (2.05 g, 6.30 mmol). The reaction mixture was sparged with argon for several minutes and then heated and stirred at 110° C. under an argon balloon for 18 hours. The reaction mixture was cooled to ambient temperature and diluted with DCM (100 mL) and stirred for 15 minutes then filtered through a pad of Celite® and concentrated. The resulting residue was purified by reverse-phase chromatography (5-95% ACN/water, 0.1% TFA). The isolated product was dissolved in DCM and washed with saturated aqueous NaHCO$_3$. The combined organic layers were washed with brine, dried with MgSO$_4$, filtered, and concentrated. The resulting residue was dissolved in 1:1 DCM:TFA (20 mL) and stirred at ambient temperature for 1 hour. The reaction mixture was concentrated and washed with saturated aqueous NaHCO$_3$ to provide 6-((3-Amino-2-chloro-6-fluorophenyl)amino)-5-bromo-3-methylquinazolin-4(3H)-one (1.2 g, 96%). MS (apci, m/z)=397.0, 399.0 (M+H).

Intermediate P16

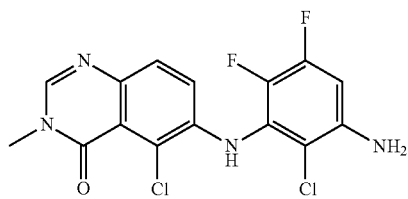 [SMILES: Cn1cnc2ccc(Nc3c(F)c(F)cc(N)c3Cl)c(Cl)c2c1=O]

6-((3-Amino-2-chloro-5,6-difluorophenyl)amino)-5-chloro-3-methylquinazolin-4(3H)-one 6-Amino-5-chloro-3-methylquinazolin-4(3H)-one (1.00 g, 4.77 mmol) was dissolved in toluene (48 mL) and treated with tert-butyl (2-chloro-4,5-difluoro-3-iodophenyl)carbamate (1.95 g, 5.01 mmol), tris(dibenzylideneacetone)dipalladium (0) (218 mg, 0.24 mmol), Xantphos (414 mg, 0.72 mmol), and cesium carbonate (3.89 g, 11.9 mmol). The reaction mixture was sparged with argon for several minutes and stirred at 110° C. under an argon balloon for 18 hours. The reaction mixture was cooled to ambient temperature and diluted with DCM (100 mL) and stirred for 15 minutes then filtered through a pad of Celite® and concentrated. The resulting residue was purified by reverse-phase chromatography (5-95% ACN/water, 0.1% TFA). The isolated product was dissolved in DCM and washed with saturated aqueous NaHCO$_3$. The combined organic layers were washed with brine, dried with MgSO$_4$, filtered, and concentrated. The resulting residue was dissolved in 1:1 DCM:TFA (35 mL) and stirred at ambient temperature for 30 minutes. The reaction mixture was concentrated, dissolved in DCM (75 mL) and washed with saturated aqueous NaHCO$_3$. The DCM organic residue was concentrated and purified by silica gel chromatography (55-90% EtOAc/Hexanes) to give to provide 6-((3-Amino-2-chloro-5,6-difluorophenyl) amino)-5-chloro-3-methylquinazolin-4(3H)-one (390 mg, 22%). MS (apci, m/z)=371.0, 373.1 (M+H).

Intermediate P17

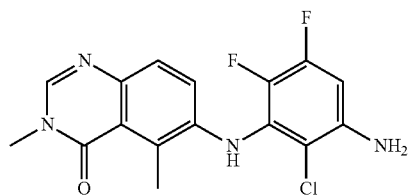

6-((3-Amino-2-chloro-5,6-difluorophenyl)amino)-3, 5-dimethylquinazolin-4(3H)-one 6-Amino-3,5-dimethylquinazolin-4(3H)-one (2.0 g, 11.0 mmol) was dissolved in toluene (106 mL) and treated with tert-butyl (2-chloro-4,5-difluoro-3-iodophenyl)carbamate (4.9 g, 13.0 mmol), tris(dibenzylideneacetone)dipalladium (0) (0.97 g, 1.1 mmol), Xantphos (1.5 g, 2.6 mmol), and cesium carbonate (6.9 g, 21.0 mmol). The reaction mixture was sparged with argon for several minutes and then stirred at 110° C. under an argon balloon for 72 hours. The reaction mixture was cooled to ambient temperature and diluted with DCM (500 mL) and stirred for 15 minutes then filtered through a pad of Celite® and concentrated. The resulting residue was purified by silica gel chromatography (DCM-EtOAc). The resulting residue was dissolved in 1:1 DCM:TFA (22 mL) and stirred at ambient temperature for 1 hour. The reaction mixture was concentrated and treated with 500 mL NaHCO$_3$ and stirred for 30 minutes at ambient temperature. The mixture was extracted with 4:1 DCM:IPA. The organic layer was separated, dried over anhydrous Na$_2$SO$_4$, filtered, and concentrated. The crude product was purified by silica gel chromatography (DCM/Acetone) to give 6-((3-amino-2-chloro-5,6-difluorophenyl)amino)-3,5-dimethylquinazolin-4(3H)-one (1.2 g, 32%) as a tan solid. MS (apci, m/z)=351.0, 353.0 (M+H).

Intermediate P18

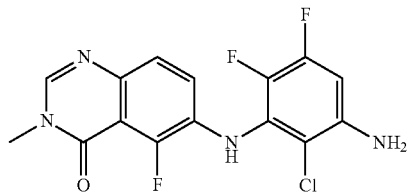 [SMILES: Cc1c(Nc2c(F)c(F)cc(N)c2Cl)ccc2ncn(C)c(=O)c12]

6-((3-Amino-2-chloro-5,6-difluorophenyl)amino)-5-fluoro-3-methylquinazolin-4(3H)-one 6-Amino-5-fluoro-3-methylquinazolin-4(3H)-one (1170 mg, 6.05648 mmol) was dissolved in toluene (61 mL) and treated with tert-butyl (2-chloro-4,5-difluoro-3-iodophenyl) carbamate (2477.37 mg, 6.35931 mmol), tris(dibenzylideneacetone)dipalladium (554.613 mg, 0.605648 mmol), 4,5-bis(diphenylphosphino)-9,9-dimethylxanthene (876.119 mg, 1.51412 mmol), and cesium carbonate (3946.63 mg, 12.1130 mmol). The reaction mixture was sparged with argon for several minutes and heated to 110° C. for 16 hours under an argon balloon. The reaction mixture was cooled to ambient temperature and diluted with DCM and stirred for 15 minutes then filtered through a pad of Celite® and concentrated. The resulting residue was purified by silica gel chromatography (DCM/Acetone) and then the resulting residue was dissolved in 1:1 DCM:TFA (20 mL) and stirred at ambient temperature for 30 minutes. The reaction mixture was concentrated and diluted with 4:1 DCM:IPA and washed with saturated NaHCO$_3$ (1×) then dried over Na$_2$SO$_4$, filtered, and concentrated to provide 6-((3-amino-2-chloro-5, 6-difluorophenyl)amino)-5-fluoro-3-methylquinazolin-4 (3H)-one (1.21 g, 56%). MS (apci, m/z)=355.0, 357.0 (M+H).

Intermediate P19

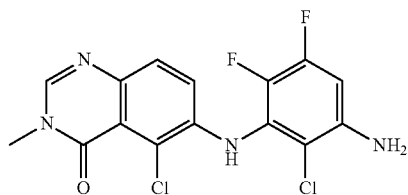 [SMILES: Cn1cnc2ccc(Nc3c(F)c(F)cc(N)c3Cl)c(Cl)c2c1=O]

6-((3-Amino-2,5,6-trifluorophenyl)amino)-5-chloro-3-methylquinazolin-4(3H)-one

Step A: Preparation of tert-butyl (3-((5-chloro-3-methyl-4-oxo-3,4-dihydroquinazolin-6-yl)amino)-2,4,5-trifluorophenyl)carbamate. A solution of 6-amino-5-chloro-3-methylquinazolin-4(3H)-one (200 mg, 0.95 mmol), tert-butyl (3-bromo-2,4,5-trifluorophenyl)carbamate (327 mg, 1.00 mmol), Pd$_2$(dba)$_3$ (43.7 mg, 0.0477 mmol), Xantphos (82.8 mg, 0.143 mmol), and cesium carbonate (777 mg, 2.39 mmol) in toluene (9.5, mL) was sparged with Argon for 5 minutes and then heated to 110° C. under nitrogen for 16 hours. The reaction was cooled to ambient temperature, filtered through Celite®, concentrated, and purified by silica gel chromatography (5-95% DCM/EtOAc) to give tert-butyl (3-((5-chloro-3-methyl-4-oxo-3,4-dihydroquinazolin-6-yl)amino)-2,4,5-trifluorophenyl)carbamate (87 mg, 20.0%). MS (apci, m/z)=455.1 (M+H).

Step B: Preparation of 6-((3-amino-2,5,6-trifluorophenyl)amino)-5-chloro-3-methylquinazolin-4(3H)-one. A solution of tert-butyl (3-((5-chloro-3-methyl-4-oxo-3,4-dihydroquinazolin-6-yl)amino)-2,4,5-trifluorophenyl)carbamate (87 mg, 0.19 mmol) in dichloromethane (960 μL) and TFA (960 μL) was stirred at ambient temperature for 1 hour. The solution was partitioned between dichloromethane and saturated NaHCO₃. The combined organic layers were washed with brine, dried with Na₂SO₄, filtered, concentrated, and purified by silica gel chromatography (5-95% EtOAc/DCM) to give 6-((3-amino-2,5,6-trifluorophenyl)amino)-5-chloro-3-methylquinazolin-4(3H)-one (65 mg, 96%). MS (apci, m/z)=355.1 (M+H).

Intermediate P20

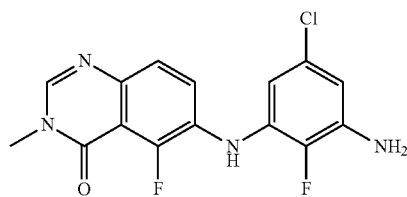 [SMILES: Cn1cnc2ccc(Nc3cc(Cl)cc(N)c3F)c(Cl)c2c1=O]

6-((3-amino-5-chloro-2-fluorophenyl)amino)-5-fluoro-3-methylquinazolin-4(3H)-one Step A: Preparation of tert-butyl (5-chloro-2-fluoro-3-((5-fluoro-3-methyl-4-oxo-3,4-dihydroquinazolin-6-yl)amino)phenyl)carbamate. A solution of 6-amino-5-fluoro-3-methylquinazolin-4(3H)-one (300 mg, 1.6 mmol), tert-butyl (3-bromo-5-chloro-2-fluorophenyl)carbamate (529 mg, 1.63 mmol), Pd₂(dba)₃ (71.1 mg, 0.0776 mmol), Xantphos (135 mg, 0.233 mmol), and cesium carbonate (1265 mg, 3.88 mmol) in toluene (15.5 mL) was sparged with Argon for 5 minutes and then heated to 110° C. under nitrogen for 16 hours. The reaction was cooled to ambient temperature, filtered through Celite®, concentrated, and purified by silica gel chromatography (1-15% MeOH/DCM, 1% NH₄OH) to give tert-butyl (5-chloro-2-fluoro-3-((5-fluoro-3-methyl-4-oxo-3,4-dihydroquinazolin-6-yl)amino)phenyl)carbamate (189 mg, 27.9%). MS (apci, m/z)=437.1 (M+H).

Step B: Preparation of 6-((3-amino-5-chloro-2-fluorophenyl)amino)-5-fluoro-3-methylquinazolin-4(3H)-one. A solution of tert-butyl (5-chloro-2-fluoro-3-((5-fluoro-3-methyl-4-oxo-3,4-dihydroquinazolin-6-yl)amino)phenyl)carbamate (189 mg, 0.433 mmol) in dichloromethane (1082 μL) and TFA (1082 μL) was stirred at ambient temperature for 30 minutes. The solution was concentrated and partitioned between DCM and saturated NaHCO₃. The combined organic layers were washed with brine, dried with Na₂SO₄, filtered, concentrated, and purified by silica gel chromatography (1-15% MeOH/DCM, 1% NH₄OH) to give 6-((3-amino-5-chloro-2-fluorophenyl)amino)-5-fluoro-3-methylquinazolin-4(3H)-one (70 mg, 48.0%). MS (apci, m/z)=337.1 (M+H).

Intermediate P21

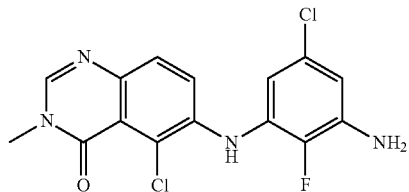

6-((3-amino-5-chloro-2-fluorophenyl)amino)-5-chloro-3-methylquinazolin-4(3H)-one Step A: Preparation of tert-butyl (5-chloro-3-((5-chloro-3-methyl-4-oxo-3,4-dihydroquinazolin-6-yl)amino)-2-fluorophenyl)carbamate. A solution of 6-amino-5-chloro-3-methylquinazolin-4(3H)-one (820 mg, 2.35 mmol), tert-butyl (3-bromo-5-chloro-2-fluorophenyl)carbamate (800 mg, 2.46 mmol), Pd₂(dba)₃ (107 mg, 0.117 mmol), Xantphos (204 mg, 0.352 mmol), and cesium carbonate (1912 mg, 5.87 mmol) in toluene (23.5 mL) was sparged with Argon for 5 minutes and then heated to 110° C. under nitrogen for 16 hours. The reaction was cooled to ambient temperature, filtered through Celite®, concentrated, and purified by silica gel chromatography (5-95% DCM/EtOAc) to give tert-butyl (5-chloro-3-((5-chloro-3-methyl-4-oxo-3,4-dihydroquinazolin-6-yl)amino)-2-fluorophenyl)carbamate (525 mg, 49.3%). MS (apci, m/z)=453.1 (M+H).

Step B: Preparation of 6-((3-amino-5-chloro-2-fluorophenyl)amino)-5-chloro-3-methylquinazolin-4(3H)-one. A solution of tert-butyl (5-chloro-3-((5-chloro-3-methyl-4-oxo-3,4-dihydroquinazolin-6-yl)amino)-2-fluorophenyl)carbamate (525 mg, 1.16 mmol) in dichloromethane (2895 μL) and TFA (2895 μL) was stirred at ambient temperature for 1 hour. The solution was concentrated and partitioned between dichloromethane and saturated NaHCO₃. The combined organic layers were washed with brine, dried with Na₂SO₄, filtered, concentrated, and purified by silica gel chromatography (5-95% EtOAc/DCM) to give 6-((3-amino-5-chloro-2-fluorophenyl)amino)-5-chloro-3-methylquinazolin-4(3H)-one (260 mg, 63.6%). MS (apci, m/z)=353.1 (M+H).

Intermediate P22

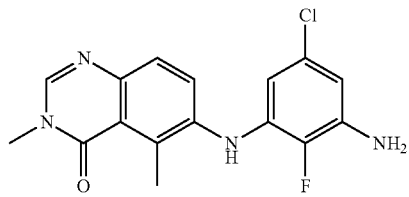 [SMILES: Cc1c(Nc2cc(Cl)cc(N)c2F)ccc2ncn(C)c(=O)c12]

6-((3-amino-5-chloro-2-fluorophenyl)amino)-3,5-dimethylquinazolin-4(3H)-one

6-Amino-3,5-dimethylquinazolin-4(3H)-one (500 mg, 2.64 mmol) was dissolved in toluene (26 mL) and treated with tert-butyl (3-bromo-5-chloro-2-fluorophenyl)carbamate (1.03 g, 3.17 mmol), tris(dibenzylideneacetone)dipalladium (0) (241.98 mg, 0.26 mmol), Xantphos (382.25 mg, 0.66 mmol), and cesium carbonate (1.721 g, 5.28 mmol). The reaction mixture was sparged with argon for several minutes and then heated to 110° C. under an argon balloon for 24 hours. The reaction mixture was cooled to ambient temperature and diluted with DCM (500 mL) and stirred for 15 minutes then filtered through a pad of Celite® and concentrated. The resulting residue was purified by silica gel chromatography (DCM/EtOAc) and then dissolved in 1:1 DCM:TFA (10 mL) and stirred at ambient temperature for 1 hour. The reaction mixture was concentrated and treated with 500 mL NaHCO$_3$ and stirred for 30 minutes at ambient temperature. The mixture was extracted with 4:1 DCM:IPA and the organic layer was separated, dried over anhydrous Na$_2$SO$_4$, filtered, and concentrated to give 6-((3-amino-5-chloro-2-fluorophenyl)amino)-3,5-dimethylquinazolin-4 (3H)-one (0.8 g, 90%) as a yellow solid. MS (apci, m/z) =333.1, 335.1 (M+H).

Intermediate P23

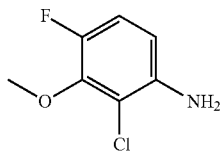

2-Chloro-4-fluoro-3-methoxyaniline

Step 1: Preparation of 2-chloro-4-fluoro-3-methoxybenzaldehyde N,N,N'-trimethylethylenediamine (1.77 mL, 13.6 mmol) was dissolved in THF (50 mL) and cooled to −42° C. under a backflow of nitrogen then treated with n-butyllithium (2.5 M in hexanes, 5.45 mL, 13.6 mmol) and allowed to stir at −42° C. for 30 minutes. The reaction mixture was cooled to −78° C. and treated with a 50 mL THE solution of 4-fluoro-3-methoxybenzaldehyde (2.0 g, 13.0 mmol) and then warmed to −42° C. and stirred for 30 minutes. The reaction mixture was cooled to −78° C. and treated with n-butyllithium (2.5 M in hexanes, 5.45 mL, 13.6 mmol) and then warmed to −42° C. and allowed to stir for 1 hr. The reaction mixture was transferred quickly via cannula to 50 mL THE solution of hexachloroethane (6.14 g, 26.0 mmol) at ambient temperature and allowed to stir at ambient temperature for 2 hours. The reaction mixture was treated with 4.0 M HCl and extracted with Et$_2$O (2×250 mL). The organic phases were combined and washed with 1.0 M NaOH (1×100 mL), 1.0 M HCl (1×100 mL), and brine (1×50 mL) and then dried over Na$_2$SO$_4$, filtered, and concentrated. The residue was purified by reverse phase C18 chromatography (water/acetonitrile with 0.1% TFA) and the fractions containing the desired product were combined and partitioned between 4:1 DCM:IPA and saturated NaHCO$_3$ (1×100 mL), dried over Na$_2$SO$_4$, filtered, and concentrated to afford 2-chloro-4-fluoro-3-methoxybenzaldehyde (1.12 g, 46%). $^1$H NMR (400 MHz, DMSO-d6) δ 10.26 (s, 1H), 7.70-7.67 (m, 1H), 7.52-7.48 (t, 1H), 3.94 (s, 3H).

Step 2: Preparation of 2-chloro-4-fluoro-3-methoxybenzoic acid. 2-Chloro-4-fluoro-3-methoxybenzaldehyde (1.07 g, 5.67 mmol) was dissolved in acetonitrile (57 mL) and treated with an aqueous 1.0 M dibasic sodium phosphate solution (8.51 mL, 8.51 mmol) and then cooled to 0° C. The reaction mixture was treated with an aqueous 35% wt hydrogen peroxide solution (0.732 mL, 8.51 mmol) followed by dropwise addition of an aqueous 1.0 M sodium chlorite solution (8.51 mL, 8.51 mmol) and then allowed to warm to ambient temperature and stirred for 16 hours. The reaction mixture was treated with a 3.0 M sodium thiosulfate solution and diluted with 1.0 M NaOH, then washed with Et$_2$O (2×250 mL). The aqueous layer was acidified to about pH 2 using 4.0 M HCl and extracted with 4:1 DCM:IPA (2×250 mL). The organic extracts were combined and dried over Na$_2$SO$_4$, filtered, and concentrated to provide 2-chloro-4-fluoro-3-methoxybenzoic acid (1.16 g, 99%). $^1$H NMR (400 MHz, DMSO-d6) δ 13.45 (br-s, 1H), 7.59-7.56 (m, 1H), 7.40-7.36 (t, 1H), 3.89 (s, 3H).

Step 3: Preparation of 2-chloro-4-fluoro-3-methoxyaniline. 2-Chloro-4-fluoro-3-methoxybenzoic acid (1.16 g, 5.670 mmol) was dissolved in DMF (57 mL) and treated with triethylamine (2.37 mL, 17.01 mmol) followed by diphenylphosphoryl azide (1.83 mL, 8.51 mmol) and allowed to stir at ambient temperature for 1 hour. The reaction mixture was treated with 10 mL water and heated to 80° C. for 16 hours. The reaction mixture was cooled to ambient temperature, diluted with water, and extracted with EtOAc (2×250 mL). The organic phases were combined and washed with water (3×100 mL) and brine (1×50 mL), dried over Na$_2$SO$_4$, filtered, and concentrated. The residue was purified by silica gel chromatography (Hexanes/EtOAc) to provide 2-chloro-4-fluoro-3-methoxyaniline (640.9 mg, 64%). 1H NMR (400 MHz, DMSO-d6) δ 6.98-6.94 (t, 1H), 6.52-6.49 (m, 1H), 5.24 (br-s, 2H), 3.82 (s, 3H).

Intermediate P24

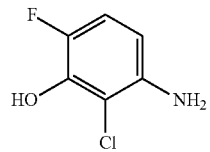

3-Amino-2-chloro-6-fluorophenol

To a solution of 2-chloro-4-fluoro-3-methoxyaniline (400 mg, 2.2 mmol) in DCM (10 mL) was added BBr$_3$ (4.5 mL, 1.0 M in DCM, 4.5 mmol) at 0° C., and the reaction mixture was stirred at ambient temperature for 16 hours. The reaction mixture was quenched with methanol (3 mL) and then poured into cold water (75 mL) and extracted with ethyl acetate (100 mL×2). The organic layers were washed with water (2×50 mL) and brine (50 mL), dried over anhydrous sodium sulfate, filtered and evaporated under reduced pressure. The crude product was purified by silica gel column chromatography (10% ethyl acetate in hexanes) to provide 3-amino-2-chloro-6-fluorophenol as off white solid (220 mg, 60%). $^1$H NMR (400 MHz, DMSO-d$_6$) δ 9.87 (br-s, 1H), 6.83 (dd, 1H), 6.22-60.18 (m, 1H), 5.03 (br-s, 2H). MS (m/z)=159.8 (M−H).

151

Intermediate P25

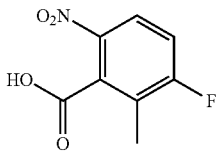

3-Fluoro-2-methyl-6-nitrobenzoic acid

To an ice-cold solution of 3-fluoro-2-methylbenzoic acid (5 g, 32.4 mmol) in concentrated H₂SO₄ (50 mL) was added concentrated HNO₃ (3.5 mL) slowly and the reaction mixture was stirred at ambient temperature for 6 hours. The reaction mixture was poured into ice cold water and the solids were collected by filtration, washed with water (2×50 mL) and dried under reduced pressure to provide 3-fluoro-2-methyl-6-nitrobenzoic acid as off white solid (3.0 g, 47%). $^1$H NMR (400 MHz, MeOD) δ 8.11-8.07 (m, 1H), 7.34 (t, 1H), 2.32 (s, 3H); MS (m/z)=197.6 (M–H).

Intermediate P26

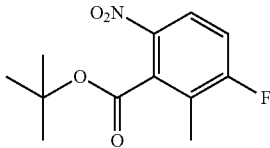 [SMILES: Cc1c(F)ccc([N+](=O)[O-])c1C(=O)OC(C)(C)C]

Tert-butyl 3-fluoro-2-methyl-6-nitrobenzoate

To a stirred solution of 3-fluoro-2-methyl-6-nitrobenzoic acid (800 mg, 4.02 mmol) in a mixture of tert-BuOH and DCM (1:1, 5 mL) was added Boc₂O (1.38 mL, 6.03 mmol) followed by DMAP (147 mg, 1.2 mmol), and the reaction mixture was stirred at ambient temperature for 16 hours under a nitrogen atmosphere. The reaction mixture was concentrated, and the crude residue was quenched with water (150 mL) and extracted with ethyl acetate (2×150 mL). The combined organic layers were washed with water (2×100 mL), brine (100 mL), dried over anhydrous sodium sulfate, filtered, and concentrated under reduced pressure. The crude product was purified by silica gel column chromatography using 15-20% ethyl acetate in hexanes to provide tert-butyl 3-fluoro-2-methyl-6-nitrobenzoate as colorless liquid (600 mg, 60%). $^1$H NMR (400 MHz, CDCl₃) δ 8.10-8.07 (dd, 1H), 7.34 (t, 1H), 2.30 (s, 3H), 1.60 (s, 9H).

Intermediate P27

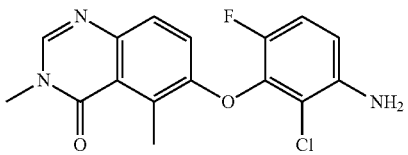 [SMILES: Cc1c(Oc2c(F)ccc(N)c2Cl)ccc2ncn(C)c(=O)c12]

152

6-(3-Amino-2-chloro-6-fluorophenoxy)-3,5-dimethylquinazolin-4(3H)-one

Step 1: Preparation of methyl 3-fluoro-2-methyl-6-nitrobenzoate. Methyl 3-fluoro-2-methylbenzoate (4.17 g, 24.8 mmol) was dissolved in sulfuric acid (24.1 mL, 248 mmol) and the mixture was cooled to 0° C. To this was slowly added nitric acid (1.36 mL, 29.8 mmol) and the mixture was allowed to warm to ambient temperature and stirred for 1 hour. The reaction mixture was poured into 500 mL ice water and stirred for 15 minutes. The mixture was extracted with EtOAc (2×), the combined organic layers were washed with saturated NaHCO₃ (2×), brine (1×), dried over Na₂SO₄, filtered, and concentrated. The crude product was purified by reverse phase chromatography (5->95% water-ACN with 0.1% TFA). The desired fractions were combined and partitioned between 4:1 DCM:IPA and saturated NaHCO₃ (1×). The combined organic layers were dried over Na₂SO₄, filtered, and concentrated to afford methyl 3-fluoro-2-methyl-6-nitrobenzoate (3.80 g, 72%).

Step 2: Preparation of methyl 3-(3-amino-2-chloro-6-fluorophenoxy)-2-methyl-6-nitrobenzoate. To a solution of methyl 3-fluoro-2-methyl-6-nitrobenzoate (686 mg, 3.22 mmol) and 3-amino-2-chloro-6-fluorophenol (572 mg, 3.54 mmol) in DMSO (15 mL) was added potassium carbonate (1112 mg, 8.05 mmol) and the reaction mixture was stirred at ambient temperature for 16 hours. The reaction mixture was diluted with EtOAc and water. The combined organic layers were dried over Na₂SO₄, filtered and concentrated. The crude product was purified by column chromatography, eluting with 10-50% EtOAc in hexanes to give methyl 3-(3-amino-2-chloro-6-fluorophenoxy)-2-methyl-6-nitrobenzoate (950 mg, 83%).

Step 3: Preparation of methyl 3-(3-(bis(tert-butoxycarbonyl)amino)-2-chloro-6-fluorophenoxy)-2-methyl-6-nitrobenzoate. To a solution of methyl 3-(3-amino-2-chloro-6-fluorophenoxy)-2-methyl-6-nitrobenzoate (683.4 mg, 1.927 mmol) in dioxane (17.8 mL) was added TEA (805.6 µL, 5.780 mmol), DMAP (23.54 mg, 0.1927 mmol) and (Boc)₂O (1261 mg, 5.780 mmol) and the reaction mixture was heated to 100° C. for 1 hour. The reaction mixture was cooled to ambient temperature and concentrated. The crude product was purified by silica gel chromatography (5->50% Hexanes-EtOAc) to give 3-(3-(bis(tert-butoxycarbonyl)amino)-2-chloro-6-fluorophenoxy)-2-methyl-6-nitrobenzoate (970 mg, 91%).

Step 4: Preparation of methyl 6-amino-3-(3-(bis(tert-butoxycarbonyl)amino-2-chloro-6-fluorophenoxy)-2-methylbenzoate. To a solution of methyl 3-(3-(bis(tert-butoxycarbonyl)amino)-2-chloro-6-fluorophenoxy)-2-methyl-6-nitrobenzoate (319 mg, 0.575 mmol) in 1:1 THF/saturated aqueous NH₄Cl (10 mL) was added iron powder (321 mg, 5.75 mmol) and the reaction mixture was heated to 65° C. for 16 hours. The reaction mixture was cooled to ambient temperature and diluted with 20% IPA in DCM and water. The solids were removed by filtration and the filtrate was washed with water (1×), brine (1×), dried over Na₂SO₄, filtered, and concentrated to afford 6-amino-3-(3-(bis(tert-butoxycarbonyl)amino-2-chloro-6-fluorophenoxy)-2-methylbenzoate (260 mg). The crude product was used directly in the next step. MS (m/z)=525.2 (M+H).

Step 5: Preparation of tert-butyl (tert-butoxycarbonyl)(2-chloro-4-fluoro-3-((5-methy-4-oxo-3,4-dihydroquinazolin-6-yl)oxy)phenyl)carbamate. A solution of methyl 6-amino-3-(3-(bis(tert-butoxycarbonyl)amino-2-chloro-6-fluorophenoxy)-2-methylbenzoate (260 mg, 0.495 mmol) and formamidine acetate (61.9 mg, 0.594 mmol) in EtOH (4 mL) was heated to 70° C. for 24 hours. The reaction mixture was concentrated and the residue was purified by column chromatography, eluting with 25-100% EtOAc in hexanes to afford tert-butyl (tert-butoxycarbonyl)(2-chloro-4-fluoro-3-((5-methy-4-oxo-3,4-dihydroquinazolin-6-yl)oxy)phenyl) carbamate (0.244 g, 95%). MS (m/z)=520.1 (M+H).

Step 6: Preparation of tert-butyl (tert-butoxycarbonyl)(2-chloro-3-((3,5-dimethy-4-oxo-3,4-dihydroquinazolin-6-yl)oxy)-4-fluorophenyl)carbamate. To a solution of tert-butyl (tert-butoxycarbonyl)(2-chloro-4-fluoro-3-((5-methy-4-oxo-3,4-dihydroquinazolin-6-yl)oxy)phenyl)carbamate (0.244 g, 0.469 mmol) in DMF was added K$_2$CO$_3$ (0.0973 g, 0.704 mmol) followed by MeI (0.0439 mL, 0.704 mmol) and the reaction mixture was stirred at ambient temperature for 16 hours. The reaction mixture was diluted with water and extracted with EtOAc. The combined organic layers were dried over Na$_2$SO$_4$, filtered and concentrated to afford tert-butyl (tert-butoxycarbonyl)(2-chloro-3-((3,5-dimethy-4-oxo-3,4-dihydroquinazolin-6-yl)oxy)-4-fluorophenyl)carbamate. The crude product was used as it is in the next step. MS (m/z)=534.2 (M+H).

Step 7: Preparation of 6-(3-amino-2-chloro-6-fluorophenoxy)-3,5-dimethylquinazolin-4(3H)-one. To a solution of tert-butyl (tert-butoxycarbonyl)(2-chloro-3-((3,5-dimethy-4-oxo-3,4-dihydroquinazolin-6-yl)oxy)-4-fluorophenyl)carbamate (0.251 g, 0.470 mmol) in DCM (4 mL) was added TFA (4 mL) and the reaction mixture was stirred at ambient temperature for 2 hours. The reaction mixture was concentrated, and the residue was purified by column chromatography, eluting with 50-100% EtOAc in hexanes to give 6-(3-amino-2-chloro-6-fluorophenoxy)-3,5-dimethylquinazolin-4(3H)-one (0.144 g, 92%). MS (m/z)=334.1 (M+H).

Intermediate P28

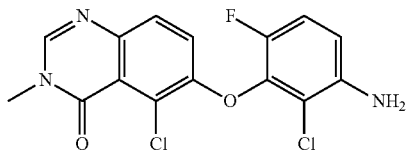 [SMILES: Cn1cnc2ccc(Oc3c(F)ccc(N)c3Cl)c(Cl)c2c1=O]

6-(3-Amino-2-chloro-6-fluorophenoxy)-5-chloro-3-methyl-3, 4-dihydroquinazolin-4-one Step 1: Preparation of methyl 2-chloro-3-fluorobenzoate. To a solution of 2-chloro-3-fluorobenzoic acid (3 g, 17.24 mmol) in methanol (60 mL) was added concentrated H$_2$SO$_4$ (0.5 mL) and the reaction mixture was heated at 60° C. under nitrogen atmosphere for 16 hours. The reaction mixture was cooled to ambient temperature and concentrated under reduced pressure. The reaction mixture was partitioned between ethyl acetate (100 mL) and saturated aqueous NaHCO$_3$ (100 mL). The organic phase was separated and washed with brine (100 mL), dried over anhydrous Na$_2$SO$_4$, filtered and concentrated under reduced pressure to afford methyl 2-chloro-3-fluorobenzoate as a yellow liquid (2.9 g) that was in the next step without further purification $^1$H NMR (400 MHz, DMSO-d$_6$) δ 7.70-7.62 (m, 2H), 7.56-7.48 (m, 1H), 3.88 (s, 3H).

Step 2: Preparation of methyl 2-chloro-3-fluoro-6-nitrobenzoate. To an ice-cold solution of methyl 2-chloro-3-fluorobenzoate (0.531 g, 2.82 mmol) in concentrated H$_2$SO$_4$ (5 mL) was added HNO$_3$ (0.233 mL, 3.52 mmol, 70% w/w). The reaction mixture was removed from the ice-bath and stirred at ambient temperature for 4 hours. The reaction mixture was poured into ice-water (50 mL) and solid Na$_2$CO$_3$ was to adjust the solution to pH 2. The aqueous phase was extracted with DCM (3×25 mL) and the combined organic phases were concentrated to afford a yellow oil that was purified by reverse phase chromatography (5-50% ACN/water with 0.1% TFA). The desired fractions were combined and extracted with DCM (3×25 mL). The organic phases were combined, dried over Na$_2$SO$_4$, filtered and concentrated under reduced pressure to afford methyl 2-chloro-3-fluoro-6-nitrobenzoate (411 mg, 59.4%) as a clear yellow oil. $^1$H NMR (400 MHz, DMSO-d$_6$) δ (8.41-8.36, m, 1H), (7.91-7.84, m, 1H), (3.96, s, 3H).

Step 3: Preparation of methyl 3-(3-amino-2-chloro-6-fluorophenoxy)-2-chloro-6-nitrobenzoate. To a solution of methyl 2-chloro-3-fluoro-6-nitrobenzoate (85 mg, 0.364 mmol) in DMSO (1.8 mL) was added solid K$_2$CO$_3$ (126 mg, 0.910 mmol) and 3-amino-2-chloro-6-fluorophenol (64.7 mg, 0.400 mmol). The reaction mixture was stirred at ambient temperature for 16 hours then partitioned between ethyl acetate (25 mL) and water (15 mL). The organic phase was separated and washed with brine (15 mL), then dried over Na$_2$SO$_4$, filtered and concentrated under reduced pressure to yield a brown solid that was purified by silica gel chromatography (0-50% hexanes/ethyl acetate) to afford methyl 3-(3-amino-2-chloro-6-fluorophenoxy)-2-chloro-6-nitrobenzoate (100 mg, 73.3%) as a yellow solid. $^1$H NMR (400 MHz, CDCl$_3$) δ 8.06 (d, 1H), 7.02 (t, 1H), 6.76-6.68 (m, 2H), 4.09 (bs, 2H), 4.07 (s, 3H).

Step 4: Preparation of methyl 3-(3-(bis(tert-butoxycarbonyl)amino)-2-chloro-6-fluorophenoxy)-2-chloro-6-nitrobenzoate. To a solution of methyl 3-(3-amino-2-chloro-6-fluorophenoxy)-2-chloro-6-nitrobenzoate (100 mg, 0.267 mmol) in 1,4-dioxane (2.6 mL) was added triethylamine (0.112 mL, 0.800 mmol), N,N-dimethylpyridin-4-amine (3.26 mg, 0.0267 mmol) and di-tert-butyl dicarbonate (175 mg, 0.800 mmol). The reaction mixture was heated at 100° C. for 1 hour then cooled to ambient temperature and partitioned between ethyl acetate (25 mL) and water (15 mL). The organic phase was separated and dried over Na$_2$SO$_4$, filtered and concentrated under reduced pressure. The reaction mixture was purified by silica gel chromatography (0-40% hexanes/ethyl acetate) to afford methyl 3-(3-(bis(tert-butoxycarbonyl)amino)-2-chloro-6-fluorophenoxy)-2-chloro-6-nitrobenzoate (128 mg, 84%) as a white solid. $^1$H NMR (400 MHz, CDCl$_3$) δ 8.05 (d, 1H), 7.26-7.22 (m, 2H), 6.63-6.59 (m, 1H), 4.07 (s, 3H), 1.43 (s, 18H).

Step 5: Preparation of methyl 6-amino-3-(3-(bis(tert-butoxycarbonyl)amino)-2-chloro-6-fluorophenoxy)-2-chlorobenzoate. To a solution of methyl 3-(3-(bis(tert-butoxycarbonyl)amino)-2-chloro-6-fluorophenoxy)-2-chloro-6-nitrobenzoate (105 mg, 0.182 mmol) in tetrahydrofuran (2 mL) was added iron powder (102 mg, 1.82 mmol) and saturated aqueous NH$_4$Cl (2 mL). The reaction mixture was heated at 65° C. for 16 hours. The reaction was cooled to ambient temperature and partitioned between ethyl acetate (25 mL) and water (25 mL) then filtered. The organic phase was separated and dried over Na$_2$SO$_4$, filtered and concentrated under reduced pressure to afford methyl 6-amino-3-(3-(bis(tert-butoxycarbonyl)amino)-2-chloro-6-fluorophenoxy)-2-chlorobenzoate as a yellow oil (99 mg) that was used directly in the next step without further purification.

Step 6: Preparation of tert-butyl (tert-butoxycarbonyl)(2-chloro-3-((5-chloro-4-oxo-3,4-dihydroquinazolin-6-yl)oxy)-4-fluorophenyl)carbamate. To a solution of methyl 6-amino-3-(3-(bis(tert-butoxycarbonyl)amino)-2-chloro-6- fluorophenoxy)-2-chlorobenzoate (99 mg, 0.182 mmol) in ethanol (1 mL) was added formamidine acetate (20.0 mg, 0.193 mmol). The reaction mixture was sealed and heated at 100° C. in a microwave reactor for 2 hours. The reaction was cooled to ambient temperature then concentrated to afford a mixture of tert-butyl (tert-butoxycarbonyl)(2-chloro-3-((5-chloro-4-oxo-3,4-dihydroquinazolin-6-yl)oxy)-4-fluorophenyl)carbamate and tert-butyl (2-chloro-3-((5-chloro-4-oxo-3,4-dihydroquinazolin-6-yl)oxy)-4-fluorophenyl)carbamate that was used directly in the next step without further purification. MS (apci, m/z)=540.1 (M+H)

Step 7: Preparation of tert-butyl (tert-butoxycarbonyl)(2-chloro-3-((5-chloro-3-methyl-4-oxo-3,4-dihydroquinazolin-6-yl)oxy)-4-fluorophenyl)carbamate. To a mixture of tert-butyl (tert-butoxycarbonyl)(2-chloro-3-((5-chloro-4-oxo-3,4-dihydroquinazolin-6-yl)oxy)-4-fluorophenyl)carbamate and tert-butyl (2-chloro-3-((5-chloro-4-oxo-3,4-dihydroquinazolin-6-yl)oxy)-4-fluorophenyl)carbamate (99 mg, 0.183 mmol, calculated using molecular mass of tert-butyl (tert-butoxycarbonyl)(2-chloro-3-((5-chloro-4-oxo-3,4-dihydroquinazolin-6-yl)oxy)-4-fluorophenyl)carbamate) in N,N-dimethylformamide (1 mL) was added $K_2CO_3$ (38.0 mg, 0.275 mmol) and iodomethane (12.5 µL, 0.202 mmol). The reaction mixture was stirred at ambient temperature for 16 hours then partitioned between water (10 mL) and ethyl acetate (10 mL). The organic phase was separated and dried over $Na_2SO_4$, filtered and concentrated under reduced pressure to afford a yellow oil that was purified by reverse phase chromatography (5-95% ACN/water with 0.1% TFA) to afford 40 mg of a product mixture containing tert-butyl (tert-butoxycarbonyl)(2-chloro-3-((5-chloro-3-methyl-4-oxo-3,4-dihydroquinazolin-6-yl)oxy)-4-fluorophenyl)carbamate and tert-butyl (2-chloro-3-((5-chloro-3-methyl-4-oxo-3,4-dihydroquinazolin-6-yl)oxy)-4-fluorophenyl)carbamate (40 mg) as a clear oil that was used in the next step without further purification. MS (apci, m/z)=554.1 (M+H).

Step 8: Preparation of 6-(3-amino-2-chloro-6-fluorophenoxy)-5-chloro-3-methylquinazolin-4(3H)-one. A mixture of tert-butyl (tert-butoxycarbonyl)(2-chloro-3-((5-chloro-3-methyl-4-oxo-3,4-dihydroquinazolin-6-yl)oxy)-4-fluorophenyl)carbamate and tert-butyl (2-chloro-3-((5-chloro-3-methyl-4-oxo-3,4-dihydroquinazolin-6-yl)oxy)-4-fluorophenyl)carbamate (40 mg) was dissolved in DCM (1 mL) and trifluoroacetic acid (1 mL). The reaction mixture was stirred at ambient temperature for 1 hour then concentrated to provide a white solid that was purified by reverse phase chromatography (5-95% ACN/water with 0.1% TFA). The desired fractions were diluted with saturated aqueous $NaHCO_3$ (15 mL) and extracted with DCM (3×15 mL). The organic phases were combined and dried over $Na_2SO_4$, filtered and concentrated under reduced pressure to afford 6-(3-amino-2-chloro-6-fluorophenoxy)-5-chloro-3-methylquinazolin-4(3H)-one (29.2 mg, 37% from step 5) as a tan solid. MS (apci, m/z)=354.0 (M+H)

Intermediate P29

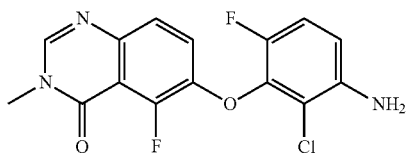

6-(3-Amino-2-chloro-6-fluorophenoxy)-5-fluoro-3-methylquinazolin-4(3H)-one

Step 1: Preparation of methyl 2,3-difluorobenzoate. 2,3-Difluorobenzoic acid (913.1 mg, 5.775 mmol) was dissolved in MeOH (58 mL) then treated with sulfuric acid (140.2 µL, 1.444 mmol) and the mixture was heated to 70° C. for 16 hours. The reaction mixture was cooled to ambient temperature and concentrated. The residue was diluted with DCM and washed with saturated $NaHCO_3$ (1×) then dried over $Na_2SO_4$, filtered, and concentrated to provide methyl 2,3-difluorobenzoate (714.4 mg, 71.9%). $^1$H NMR (400 MHz, DMSO) δ 7.74-7.65 (m, 2H), 7.35-7.29 (m, 1H), 3.85 (s, 3H).

Step 2: Preparation of methyl 2,3-difluoro-6-nitrobenzoate. To a cold (0° C.) solution of methyl 2,3-difluorobenzoate (714.4 mg, 4.150 mmol) in sulfuric acid (4030 µL, 41.50 mmol) was added nitric acid (297.8 µL, 4.565 mmol) dropwise. The reaction mixture was stirred at 0° C. for 15 minutes and then at ambient temperature for 16 hours. The reaction mixture was poured into ice water (100 mL) and stirred for 15 minutes then neutralized to about pH 8 using solid $Na_2CO_3$. The reaction mixture was extracted with EtOAc (2×) and the combined organic layers were washed with water (1×), brine (1×), dried over $Na_2SO_4$, filtered, and concentrated. The resulting residue was purified by silica gel chromatography (Hexanes/Acetone) to provide a 1:1 mixture of methyl 2,3-difluoro-6-nitrobenzoate and methyl 2,3-difluoro-5-nitrobenzoate (665.6 mg, 74%) that was used directly in the next step without purification.

Step 3: Preparation of methyl 3-(3-amino-2-chloro-6-fluorophenoxy)-2-fluoro-6-nitrobenzoate. A mixture of methyl 2,3-difluoro-6-nitrobenzoate and methyl 2,3-difluoro-5-nitrobenzoate (665.6 mg, 3.065 mmol) was dissolved in DMSO (12 mL) and treated with 3-amino-2-chloro-6-fluorophenol (544.8 mg, 3.372 mmol) followed by potassium carbonate (635.5 mg, 4.598 mmol) and the reaction mixture was stirred at ambient temperature for 16 hours. The reaction mixture was poured into water and extracted with EtOAc (2×). The combined organic layers were washed with water (3×), brine (1×), dried over $Na_2SO_4$, filtered, and concentrated to provide a 1:1 mixture of methyl 3-(3-amino-2-chloro-6-fluorophenoxy)-2-fluoro-6-nitrobenzoate and methyl 2-(3-((bis-tert-butoxycarbonyl)amino)-2-chloro-6-fluorophenoxy)-3-fluoro-5-nitrobenzoate (860.9 mg, 78%) that was used directly in the next step without purification.

Step 4: Preparation of methyl 3-(3-((bis-tert-butoxycarbonyl)amino)-2-chloro-6-fluorophenoxy)-2-fluoro-6-nitrobenzoate A 1:1 mixture of methyl 3-(3-amino-2-chloro-6-fluorophenoxy)-2-fluoro-6-nitrobenzoate and methyl 2-(3-((bis-tert-butoxycarbonyl)amino)-2-chloro-6-fluorophenoxy)-3-fluoro-5-nitrobenzoate (860.9 mg, 2.400 mmol) was dissolved in THF (24 mL) and treated with 4-(dimethylamino)pyridine (29.32 mg, 0.2400 mmol), followed by di-tert-butyl dicarbonate (1100 mg, 5.040 mmol) and the reaction mixture was stirred at ambient temperature for 60 hours. The reaction mixture was concentrated and purified by silica gel chromatography (Hexanes/EtOAc) to provide methyl 3-(3-((bis-tert-butoxycarbonyl)amino)-2-chloro-6-fluorophenoxy)-2-fluoro-6-nitrobenzoate (476.9 mg, 36%). $^1$H NMR (400 MHz, DMSO) δ 8.16-8.13 (dd, 1H), 7.63-7.61 (m, 2H), 7.03-6.99 (t, 1H), 3.94 (s, 3H), 1.33 (s, 18H).

Step 5: Preparation of methyl 6-amino-3-(3-((bis-tert-butoxycarbonyl)amino)-2-chloro-6-fluorophenoxy)-2-fluorobenzoate. Methyl 3-(3-((bis-tert-butoxycarbonyl)amino)-2-chloro-6-fluorophenoxy)-2-fluoro-6-nitrobenzoate (461.7 mg, 0.8261 mmol) was dissolved in 1:1 THF:saturated NH₄Cl (16.5 mL, 0.05 M) and then treated with iron (922.6 mg, 16.52 mmol) and the reaction mixture was heated to 65° C. for 16 hours. The reaction mixture was cooled to ambient temperature and diluted with EtOAc. The organic layer was washed with water (1×), brine (1×), dried over Na₂SO₄, filtered, and concentrated to provide a mixture of methyl 6-amino-3-(3-((bis-tert-butoxycarbonyl)amino)-2-chloro-6-fluorophenoxy)-2-fluorobenzoate and methyl 6-amino-3-(3-((tert-butoxycarbonyl)amino)-2-chloro-6-fluorophenoxy)-2-fluorobenzoate (395.1 mg, 90%).

Step 6: Preparation of bis-tert-butyl (2-chloro-4-fluoro-3-((5-fluoro-4-oxo-3,4-dihydroquinazolin-6-yl)oxy)phenyl) carbamate. A mixture of methyl 6-amino-3-(3-((bis-tert-butoxycarbonyl)amino)-2-chloro-6-fluorophenoxy)-2-fluorobenzoate and methyl 6-amino-3-(3-((tert-butoxycarbonyl)amino)-2-chloro-6-fluorophenoxy)-2-fluorobenzoate (395.1 mg, 0.7470 mmol) was dissolved in EtOH (15 mL) and treated with formamidine acetate (388.8 mg, 3.735 mmol) and the reaction mixture was heated to 100° C. for 8 hours in the microwave. The reaction mixture was concentrated and the residue was diluted with EtOAc. The combined organic layers were washed with water (1×), brine (1×), dried over Na₂SO₄, filtered, and concentrated to provide a mixture of bis-tert-butyl (2-chloro-4-fluoro-3-((5-fluoro-4-oxo-3,4-dihydroquinazolin-6-yl)oxy)phenyl)carbamate and tert-butyl (2-chloro-4-fluoro-3-((5-fluoro-4-oxo-3,4-dihydroquinazolin-6-yl)oxy)phenyl)carbamate (342.4 mg, 88%).

Step 7: Preparation of 6-(3-amino-2-chloro-6-fluorophenoxy)-5-fluoro-3-methylquinazolin-4(3H)-one. A mixture of bis-tert-butyl (2-chloro-4-fluoro-3-((5-fluoro-4-oxo-3,4-dihydroquinazolin-6-yl)oxy)phenyl)carbamate and tert-butyl (2-chloro-4-fluoro-3-((5-fluoro-4-oxo-3,4-dihydroquinazolin-6-yl)oxy)phenyl)carbamate (342.4 mg, 0.6535 mmol) was dissolved in DMF (6.5 mL) and treated with potassium carbonate (117.4 mg, 0.8496 mmol) followed by iodomethane (44.75 μL, 0.7189 mmol) and the reaction mixture was stirred at ambient temperature for 1 hour. The reaction mixture was diluted with water and extracted with EtOAc (2×). The combined organic layers were washed with water (3×), brine (1×), dried over Na₂SO₄, filtered, and concentrated. The resulting residue was dissolved in 1:1 DCM:TFA (5.0 mL) and stirred at ambient temperature for 30 minutes. The reaction mixture was concentrated and purified by reverse phase C18 chromatography (water/ACN with 0.1% TFA). The combined desired fractions were then partitioned between 4:1 DCM:IPA and saturated NaHCO₃ (1×). The combined organic layers were dried over Na₂SO₄, filtered, and concentrated to provide 6-(3-amino-2-chloro-6-fluorophenoxy)-5-fluoro-3-methylquinazolin-4(3H)-one (206.1 mg, 93%). MS (apci, m/z)=338.1, 340.1 (M+H).

Intermediate P30

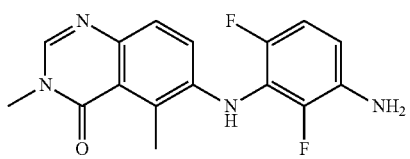

6-((3-amino-2,6-difluorophenyl)amino)-3,5-dimethylquinazolin-4(3H)-one

Step 1: Preparation of di-tert-butyl (3-bromo-2,4-difluorophenyl)dicarbamate 3-Bromo-2,4-difluoroaniline (375 mg, 1.80 mmol) was stirred at ambient temperature with di-tert-butyl dicarbonate (826 mg, 3.79 mmol) and DMAP (44.1 mg, 0.361 mmol) in THF (9.014 mL) for 48 hours. The reaction mixture was diluted with ethyl acetate and washed with saturated aqueous NH₄Cl. The combined organic layers were dried over magnesium sulfate, filtered and concentrated. The product was used directly in the next step without purification.

Step 2: Preparation of tert-butyl (3-bromo-2,4-difluorophenyl)carbamate. Ditert-butyl (3-bromo-2,4-difluorophenyl)dicarbamate (735 mg, 1.80 mmol) was dissolved in MeOH (6.0 mL) and potassium carbonate (113 μL, 1.98 mmol) was added, and the reaction was heated to 65° C. for 1 hour. The reaction mixture was cooled to ambient temperature and was then filtered through a pad of Celite and concentrated. The crude material was purified by normal phase chromatography (0-20% Hexanes/EtOAc) to yield tert-butyl (3-bromo-2,4-difluorophenyl)carbamate as a white solid (447 mg, 81% over 2-steps).

Step 3: Preparation of 6-((3-amino-2,6-difluorophenyl)amino)-3,5-dimethylquinazolin-4(3H)-one. 6-Amino-3,5-dimethylquinazolin-4(3H)-one (50 mg, 0.26 mmol), tert-butyl (3-bromo-2,4-difluorophenyl)carbamate (81 mg, 0.26 mmol), cesium carbonate (172 mg, 0.53 mmol), Pd₂(dba)₃ (24 mg, 0.026 mmol), and Xantphos (38 mg, 0.066 mmol) were dissolved in toluene (2.6 mL) and then heated to 110° C. for 24 hours. The reaction mixture was cooled to ambient temperature, filtered through Celite, concentrated, and then reconstituted in 1:1 DCM/TFA (5 mL). The reaction mixture was stirred at ambient temperature for 15 minutes. The volatiles were removed in vacuo, and the crude product was purified by reverse phase chromatography (0-30% MeCN/H₂O, 0.1% TFA). The resulting product was diluted with DCM, washed with sat. aqueous NaHCO₃, and concentrated to provide 6-((3-amino-2,6-difluorophenyl)amino)-3,5-dimethylquinazolin-4(3H)-one (32 mg, 38%). MS (apci, m/z) =317.1 (M+H).

Intermediate P31

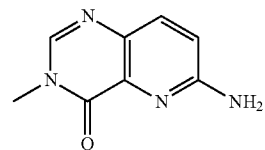

6-amino-3-methylpyrido[3,2-d]pyrimidin-4(3H)-one

Step 1: 6-chloro-3-methylpyrido[3,2-d]pyrimidin-4(3H)-one. To a solution of 6-chloropyrido[3,2-d]pyrimidin-4(3H)-one (100 mg, 0.551 mmol) and iodomethane (44 μL, 0.71 mmol) in N,N-dimethylformamide (1.1 mL) was added potassium carbonate (114 mg, 0.826 mmol) and stirred at room temperature for 16 hours. The reaction mixture was then partitioned between ethyl acetate and water and the organic layer was washed with brine (1×), dried over Na₂SO₄, filtered, and concentrated. The resulting residue was then purified by silica gel chromatography (5-95% EtOAc/DCM) to give 6-chloro-3-methylpyrido[3,2-d]pyrimidin-4(3H)-one (67 mg, 62% yield). MS (apci, m/z)=196.1 (M+H).

Step 2: 6-((4-methoxybenzyl)amino)-3-methylpyrido[3,2-d]pyrimidin-4(3H)-one. A solution of 6-chloro-3-methylpyrido[3,2-d]pyrimidin-4(3H)-one (25 mg, 0.128 mmol), (4-methoxyphenyl)methanamine (33 μL, 0.25 mmol), and Hunig's base (33 μL, 0.19 mmol) in DMSO (426 μL) was heated at 90° C. for 48 hours. The reaction mixture was cooled to ambient temperature and partitioned between DCM and water. The organic layer was washed with brine (1×), dried over Na₂SO₄, filtered, and concentrated. The resulting residue was purified by silica gel chromatography (1-10% MeOH/DCM, 1% NH₄OH) to give impure 6-((4-methoxybenzyl)amino)-3-methylpyrido[3,2-d]pyrimidin-4 (3H)-one (25 mg, 66% yield). MS (apci, m/z)=297.1 (M+H).

Step 3: 6-amino-3-methylpyrido[3,2-d]pyrimidin-4(3H)-one. Impure 6-((4-methoxybenzyl)amino)-3-methylpyrido[3,2-d]pyrimidin-4(3H)-one (25 mg, 0.084 mmol) was stirred in TFA (422 μL) and dichloromethane (422 μL) for 3 hours at ambient temperature. The reaction mixture was then concentrated, dissolved in TFA (422 μL) and then heated in a sealed vial at 60° C. for 3 days. The reaction mixture was then concentrated and dissolved in 1 mL of methanol and 1 mL of DCM and then passed through a bicarbonate base resin. The filtrate was then concentrated and purified by silica gel chromatography (1-15% MeOH/DCM, 1% NH₄OH) to give 6-amino-3-methylpyrido[3,2-d]pyrimidin-4(3H)-one (7.0 mg, 47% yield). MS (apci, m/z)=177.1 (M+H).

Intermediate P32

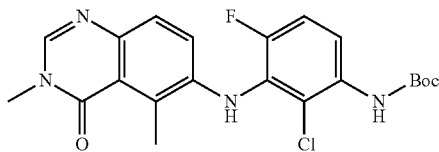 [SMILES: Cc1c(Nc2c(F)ccc(NC(=O)OC(C)(C)C)c2Cl)ccc2ncn(C)c(=O)c12]

tert-butyl (2-chloro-3-((3,5-dimethyl-4-oxo-3,4-dihydroquinazolin-6-yl)oxy)-4-fluorophenyl)carbamate Step 1: Preparation of tert-butyl (tert-butoxycarbonyl)(2-chloro-3-((3,5-dimethyl-4-oxo-3,4-dihydroquinzaolin-6-yl) oxy)-4-fluorophenyl)carbamate. 6-(3-Amino-2-chloro-6-fluorophenoxy)-3,5-dimethylquinazolin-4(3H)-one (1.5 g, 4.5 mmol) was dissolved in THF (22 mL) then treated with di-tert-butyl dicarbonate (2.2 g, 9.9 mmol) and N,N-dimethylpyridin-4-amine (55 mg, 0.45 mmol). The reaction mixture was heated to 45° C. for 12 hours. The reaction mixture was concentrated and purified by silica gel column chromatography (0-20% DCM/EtOAc) to provide tert-butyl (tert-butoxycarbonyl)(2-chloro-3-((3,5-dimethyl-4-oxo-3,4-dihydroquinzaolin-6-yl)oxy)-4-fluorophenyl)carbamate (2 g, 83%) as a white solid. NMR (400 MHz, (CD₃)₂SO) δ 8.28 (s, 1H), 7.55-7.54 (d, 1H), 7.53 (s, 1H), 7.47-7.41 (d, 1H), 6.86-6.78 (d, 1H), 3.46 (s, 3H), 2.92 (s, 3H), 1.36 (s, 18H); MS (apci, m/z)=534.2, 536.2 (M+H).

Step 2: Preparation of tert-butyl (2-chloro-3-((3,5-dimethyl-4-oxo-3,4-dihydroquinazolin-6-yl)oxy)-4-fluorophenyl)carbamate. Tert-butyl (tert-butoxycarbonyl)(2-chloro-3-((3,5-dimethyl-4-oxo-3,4-dihydroquinzaolin-6-yl)oxy)-4-fluorophenyl)carbamate (2 g, 3.7 mmol) was dissolved in MeOH (19 mL) and treated with potassium carbonate (0.62 g, 4.5 mmol) then heated to 60° C. for 12 hours. The reaction mixture was cooled to ambient temperature, poured into water, sonicated, and filtered. The resulting solids were purified by silica gel column chromatography (0-50% DCM/Acetone) to give tert-butyl (2-chloro-3-((3,5-dimethyl-4-oxo-3,4-dihydroquinazolin-6-yl)oxy)-4-fluorophenyl)carbamate (1.5 g, 98%) as a white solid. ¹H NMR (400 MHz, (CD₃)₂SO) δ 8.89 (s, 1H), 8.27 (s, 1H), 7.53-7.40 (m, 3H), 6.97-6.92 (d, 1H), 3.46 (s, 3H), 2.91 (s, 3H), 1.45 (s, 9H); MS (apci, m/z)=434.1, 436.1 (M+H).

Intermediate P33

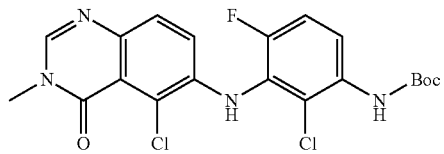 [SMILES: Cn1cnc2ccc(Nc3c(F)ccc(NC(=O)OC(C)(C)C)c3Cl)c(Cl)c2c1=O]

tert-butyl (2-chloro-3-((5-chloro-3-methyl-4-oxo-3,4-dihydroquinazolin-6-yl)ox)-4-fluorophenyl)carbamate Step 1: Preparation of tert-butyl (tert-butoxycarbonyl)(2-chloro-3-((5-chloro-3-methyl-4-oxo-3,4-dihydroquinazolin-6-yl)oxy)-4-fluorophenyl)carbamate. 6-(3-amino-2-chloro-6-fluorophenoxy)-5-chloro-3-methylquinazolin-4(3H)-one (1.5 g, 4.2 mmol) was dissolved in THF (21 mL) and treated with di-tert-butyl dicarbonate (2.0 g, 9.3 mmol) and N,N-dimethylpyridin-4-amine (52 mg, 0.43 mmol) then heated to 45° C. for 12 hours. The reaction mixture was cooled to ambient temperature and concentrated and purified by silica gel column chromatography (0-20% DCM/EtOAc) to give the intermediate tert-butyl (tert-butoxycarbonyl)(2-chloro-3-((5-chloro-3-methyl-4-oxo-3,4-dihydroquinazolin-6-yl) oxy)-4-fluorophenyl)carbamate (2 g, 85%) as a white solid. ¹H NMR (400 MHz, (CD₃)₂SO) δ 8.36 (s, 1H), 7.62-7.54 (m, 3H), 7.02-6.96 (d, 1H), 3.46 (s, 3H), 1.36 (s, 18H); MS (apci, m/z)=554.2, 556.2 (M+H).

Step 2: Preparation of tert-butyl (2-chloro-3-((5-chloro-3-methyl-4-oxo-3,4-dihydroquinazolin-6-yl)oxy)-4-fluorophenyl)carbamate. Tert-butyl (tert-butoxycarbonyl)(2-chloro-3-((5-chloro-3-methyl-4-oxo-3,4-dihydroquinazolin-6-yl)oxy)-4-fluorophenyl)carbamate (2 g, 3.6 mmol) was dissolved in MeOH (18 mL) and treated with potassium carbonate (0.60 g, 4.3 mmol) then heated to 60° C. for 12 hours. The reaction was cooled to ambient temperature, poured into water, sonicated, and filtered and the resulting solids were purified by silica gel column chromatography (0-50% DCM/Acetone) to give tert-butyl (2-chloro-3-((5-chloro-3-methyl-4-oxo-3,4-dihydroquinazolin-6-yl)oxy)-4-fluorophenyl)carbamate (1.6 g, 100%) as a white solid. 1H NMR (400 MHz, (CD₃)₂SO) δ 8.92 (s, 1H), 8.35 (s, 1H), 7.59-7.53 (m, 2H), 7.49-7.43 (t, 1H), 7.15-7.11 (m, 1H), 3.46 (s, 3H), 1.46 (s, 9H); MS (apci, m/z)=454.2, 456.2 (M+H).

Intermediate P34

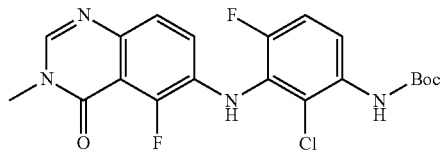

tert-butyl (2-chloro-4-fluoro-3-((5-fluoro-3-methyl-4-oxo-3,4-dihydroquinazolin-6-yl)oxy)phenyl)carbamate Step 1: Preparation of tert-butyl (tert-butoxycarbonyl)(2-chloro-4-3-((5-fluoro-3-methyl-4-oxo-3,4-dihydroquinazolin-6-yl)oxy)phenyl)carbamate. 6-(3-Amino-2-chloro-6-fluorophenoxy)-5-fluoro-3-methylquinazolin-4(3H)-one (1.5 g, 4.4 mmol) was dissolved in THF (22 mL) and treated with di-tert-butyl dicarbonate (2.1 g, 9.8 mmol) and N,N-dimethylpyridin-4-amine (54 mg, 0.44 mmol) then heated to 45° C. for 12 hours. The reaction was concentrated and purified by silica gel column chromatography (0-20% DCM/EtOAc) to tert-butyl (tert-butoxycarbonyl)(2-chloro-4-3-((5-fluoro-3-methyl-4-oxo-3,4-dihydroquinazolin-6-yl)oxy)phenyl)carbamate (1.8 g, 75%) as a white solid. $^1$H NMR (400 MHz, (CD$_3$)$_2$SO) δ 8.34 (s, 1H), 7.57-7.53 (d, 2H), 7.49-7.46 (m, 1H), 7.23-7.17 (t, 1H), 3.45 (s, 3H), 1.35 (s, 18H); MS (apci, m/z)=538.1, 540.1 (M+H).

Step 2: Preparation of tert-butyl (2-chloro-4-fluoro-3-((5-fluoro-3-methyl-4-oxo-3,4-dihydroquinazolin-6-yl)oxy)phenyl)carbamate. Tert-butyl (tert-butoxycarbonyl)(2-chloro-4-3-((5-fluoro-3-methyl-4-oxo-3,4-dihydroquinazolin-6-yl)oxy)phenyl)carbamate (1.8 g, 3.35 mmol) was dissolved in MeOH (16.7 mL) and treated with potassium carbonate (0.55 g, 4.02 mmol) and the reaction was heated to 60° C. for 12 hours. The reaction was cooled to ambient temperature, poured into water, sonicated, and filtered and the resulting solids were purified by silica gel column chromatography (0-50% DCM/Acetone) to give tert-butyl (2-chloro-4-fluoro-3-((5-fluoro-3-methyl-4-oxo-3,4-dihydroquinazolin-6-yl)oxy)phenyl)carbamate (1.16 g, 80%) as a white solid. $^1$H NMR (400 MHz, (CD$_3$)$_2$SO) δ 8.92 (s, 1H), 8.33 (s, 1H), 7.56-7.51 (m 1H), 7.48-7.41 (m, 2H), 7.31-7.25 (t, 1H), 3.46 (s, 3H), 1.45 (s, 9H); MS (apci, m/z)=438.1, 440.1.

Preparation of Synthetic Examples

Example 1

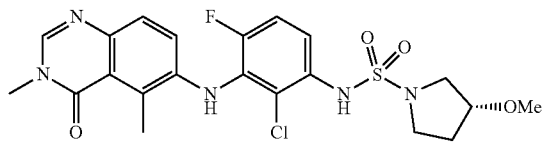 [SMILES: CO[C@@H]1CCN(S(=O)(=O)Nc2ccc(F)c(Nc3ccc4ncn(C)c(=O)c4c3C)c2Cl)C1]

(R)-N-(2-chloro-3-((3,5-dimethyl-4-oxo-3,4-dihydroquinazolin-6-yl)amino)-4-fluorophenyl)-3-methoxypyrrolidine-1-sulfonamide Step 1: Preparation of (R)-3-methoxypyrrolidine-1-sulfonyl chloride. A slurry of (R)-3-methoxypyrrolidine hydrochloride (198 mg, 1.44 mmol) and N,N-diisopropylethylamine (376 µL, 2.16 mmol) was stirred in DCM (6 mL) at ambient temperature until the mixture was fully dissolved. The reaction mixture was cooled to 0° C. and treated with sulfuryl chloride (349 µL, 4.32 mmol). The cold bath was removed after 30 minutes and the mixture was stirred at ambient temperature for 16 hours. The reaction mixture was diluted with additional DCM and washed with 1.0 M HCl (1×). The organic layer was separated, dried over anhydrous Na$_2$SO$_4$, filtered, and concentrated to give crude (R)-3-methoxypyrrolidine-1-sulfonyl chloride (212 mg, 74%), which was used as it is in the next step.

Step 2: Preparation of (R)-N-(2-chloro-3-((3,5-dimethyl-4-oxo-3,4-dihydroquinazolin-6-yl)amino)-4-fluorophenyl)-3-methoxypyrrolidine-1-sulfonamide. A solution of 6-((3-amino-2-chloro-6-fluorophenyl)amino)-3,5-dimethylquinazolin-4(3H)-one (50 mg, 0.15 mmol) and (R)-3-methoxypyrrolidine-1-sulfonyl chloride (212 mg, 1.0 mmol) in pyridine (0.8 mL) was sealed and heated at 65° C. for 16 hours. The reaction mixture was cooled to ambient temperature and concentrated. The crude product was purified by reverse phase chromatography (5-95% ACN/water with 0.1% TFA). The desired fractions were combined and partitioned between 4:1 DCM:IPA and saturated aqueous NaHCO$_3$ (1×). The organic layer was separated, dried over anhydrous Na$_2$SO$_4$, filtered, and concentrated. The material was further purified by silica gel column chromatography (50-100% EtOAc/hexane) to give (R)-N-(2-chloro-3-((3,5-dimethyl-4-oxo-3,4-dihydroquinazolin-6-yl)amino)-4-fluorophenyl)-3-methoxypyrrolidine-1-sulfonamide (40 mg, 54%) as a white solid. $^1$H NMR (400 MHz, CDCl$_3$) δ 7.92 (s, 1H), 7.44-7.39 (m, 2H), 7.08-7.02 (m, 2H), 6.88 (s, 1H), 5.57 (s, 1H), 3.96-3.92 (m, 1H), 3.54 (s, 3H), 3.50-3.41 (m, 4H), 3.25 (s, 3H), 2.96 (s, 3H), 2.09-2.03 (m, 1H), 1.99-1.90 (m, 1H). MS (apci, m/z)=496.1 (M+H).

Example 2

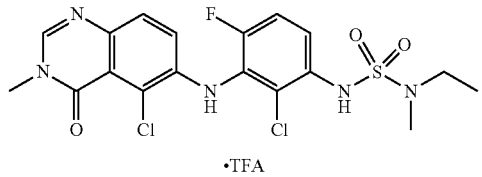 [SMILES: CCN(C)S(=O)(=O)Nc1ccc(F)c(Nc2ccc3ncn(C)c(=O)c3c2Cl)c1Cl]

·TFA

N-(2-chloro-3-((3,5-dimethyl-4-oxo-3,4-dihydroquinazolin-6-yl)amino)-4-fluorophenyl)-(N-ethyl-N-methyl)-sulfamide trifluoroacetate A solution of 6-((3-amino-2-chloro-6-fluorophenyl)amino)-5-chloro-3-methylquinazolin-4(3H)-one (35 mg, 0.10 mmol) and N-ethyl-N-methylsulfamoyl chloride (47 mg, 0.30 mmol) in pyridine (0.50 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, filtered and concentrated, and the residue was purified by reverse phase chromatography (5-95% ACN/water with 0.1% TFA) to provide N-(2-chloro-3-((3,5-dimethyl-4-oxo-3,4-dihydroquinazolin-6-yl)amino)-4-fluorophenyl)-(N-ethyl-N-methyl)-sulfamide trifluoroacetate (22 mg, 48%). $^1$H NMR (400 MHz, CDCl$_3$) δ 8.67 (s, 1H), 7.65 (d, 1H), 7.56-7.52 (m, 1H), 7.17 (t, 1H), 7.01-6.98 (m, 2H), 6.75 (s, 1H), 6.55 (s, 1H), 3.69 (s, 3H), 3.31-3.26 (m, 2H), 2.87 (s, 3H), 1.15 (t, 1H). MS (apci, m/z)=474.1 (M+H).

Example 3

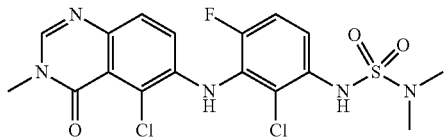

N-(2-chloro-3-((5-chloro-3-methyl-4-oxo-3,4-dihydroquinazolin-6-yl)amino)-4-fluorophenyl)-(N,N-dimethyl)-sulfamide A solution of 6-((3-amino-2-chloro-6-fluorophenyl)amino)-5-chloro-3-methylquinazolin-4(3H)-one (30 mg, 0.08494 mmol) and dimethylsulfamoyl chloride (120 mg, 0.8494 mmol) in pyridine (0.8 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous $Na_2SO_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:APA and saturated aqueous $NaHCO_3$ (1×). The organic layer was separated, dried over anhydrous $Na_2SO_4$, filtered, and concentrated to give N-(2-chloro-3-((5-chloro-3-methyl-4-oxo-3,4-dihydroquinazolin-6-yl)amino)-4-fluorophenyl)-(N,N-dimethyl)-sulfamide (13.6 mg, 35%) as an off-white solid. $^1$H NMR (400 MHz, $(CD_3)_2SO$): δ 9.47 (s, 1H), 8.21 (s, 1H), 7.76 (s, 1H), 7.53-7.33 (m, 3H), 6.78-6.72 (m, 1H), 3.44 (s, 3H), 2.73 (s, 6H); MS (apci, m/z)=460.1, 462.1 (M+H).

Example 4

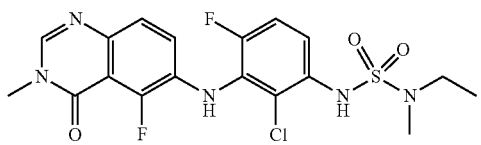 [SMILES: CCN(C)S(=O)(=O)Nc1ccc(F)c(Nc2ccc3ncn(C)c(=O)c3c2F)c1Cl]

N-(2-chloro-4-fluoro-3-((5-fluoro-3-methyl-4-oxo-3,4-dihydroquinazolin-6-yl)amino)phenyl)-(N-ethyl-N-methyl)-sulfamide A solution of 6-((3-amino-2-chloro-6-fluorophenyl)amino)-5-chloro-3-methylquinazolin-4(3H)-one (28 mg, 0.0832 mmol) and ethyl(methyl)sulfamoyl chloride (106 mg, 0.673 mmol) in pyridine (0.8 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous $Na_2SO_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:APA and saturated aqueous $NaHCO_3$ (1×). The organic layer was separated, dried over anhydrous $Na_2SO_4$, filtered, and concentrated to give N-(2-chloro-4-fluoro-3-((5-fluoro-3-methyl-4-oxo-3,4-dihydroquinazolin-6-yl)amino)phenyl)-(N-ethyl-N-methyl)-sulfamide (28 mg, 74%) as an off-white solid. $^1$H NMR (400 MHz, $(CD_3)_2SO$) δ 9.33 (s, 1H), 8.15 (s, 1H), 8.02 (s, 1H), 7.39-7.24 (m, 3H), 7.01-6.93 (t, 1H), 3.41 (s, 3H), 3.13-3.06 (m, 2H), 2.72 (s, 3H), 1.02-0.98 (t, 3H); MS (apci, m/z)=458.1, 460.1 (M+H).

Example 5

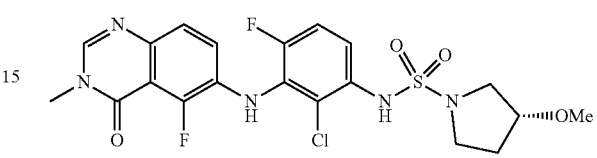

(R)-N-(2-chloro-4-fluoro-3-((5-fluoro-3-methyl-4-oxo-3,4-dihydroquinazolin-6-yl)amino)phenyl)-3-methoxypyrrolidine-1-sulfonamide A solution of 6-((3-amino-2-chloro-6-fluorophenyl)amino)-5-fluoro-3-methylquinazolin-4(3H)-one (70 mg, 0.21 mmol) and (R)-3-methoxypyrrolidine-1-sulfonyl chloride (166 mg, 0.83 mmol) in pyridine (2 mL) was sealed and heated at 65° C. for 16 hours. The reaction mixture was cooled to ambient temperature and concentrated. The crude product was purified by silica gel column chromatography (30-100% EtOAc/hexane) to give (R)-N-(2-chloro-3-((3,5-dimethyl-4-oxo-3,4-dihydroquinazolin-6-yl)amino)-4-fluorophenyl)-(N-isopropyl-N-methyl)-sulfamide (68 mg, 65%). $^1$H NMR (400 MHz, $CDCl_3$) δ 7.89 (s, 1H), 7.54-7.51 (m, 1H), 7.40-7.38 (dd, 1H), 7.14-7.09 (t, 1H), 7.06-6.99 (m, 1H), 6.90 (s, 1H), 5.91 (s, 1H), 3.96-3.93 (m, 1H), 3.57 (s, 3H), 3.52-3.41 (m, 4H), 3.25 (s, 3H), 2.12-2.05 (m, 1H), 2.00-1.91 (m, 1H). MS (apci, m/z)=500.1 (M+H).

Example 6

(R)-N-(2-chloro-4-fluoro-3-((5-chloro-3-methyl-4-oxo-3,4-dihydroquinazolin-6-yl)amino)phenyl)-3-methoxypyrrolidine-1-sulfonamide A solution of 6-((3-amino-2-chloro-6-fluorophenyl)amino)-5-chloro-3-methylquinazolin-4(3H)-one (70 mg, 0.20 mmol) and (R)-3-methoxypyrrolidine-1-sulfonyl chloride (158 mg, 0.79 mmol) in pyridine (2 mL) was sealed and heated at 65° C. for 60 hours. The reaction mixture was cooled to ambient temperature and concentrated. The crude product was purified by silica gel column chromatography (30-100% EtOAc/hexane) to give (R)-N-(2-chloro-4-fluoro-3-((5-chloro-3-methyl-4-oxo-3,4-dihydroquinazolin-6-yl)amino)phenyl)-3-methoxypyrrolidine-1-sulfonamide (59 mg, 58%).

¹H NMR (400 MHz, CDCl₃) δ 7.91 (s, 1H), 7.58-7.54 (m, 1H), 7.50-7.48 (d, 1H), 7.15-7.11 (t, 1H), 6.97-6.94 (m, 1H), 6.91 (s, 1H), 6.44 (s, 1H), 3.96-3.93 (m, 1H), 3.56 (s, 3H), 3.52-3.41 (m, 4H), 3.25 (s, 3H), 2.11-2.05 (m, 1H), 1.99-1.90 (m, 1H). MS (apci, m/z)=516.1 (M+H).

Example 7

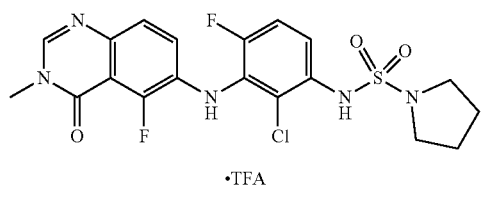 [SMILES: Cn1cnc2ccc(Nc3c(F)ccc(NS(=O)(=O)N4CCCC4)c3Cl)c(F)c2c1=O]

•TFA

N-(2-chloro-4-fluoro-3-((5-fluoro-3-methyl-4-oxo-3,4-dihydroquinazolin-6-yl)amino)phenyl)pyrrolidine-1-sulfonamide trifluoroacetate A solution of 6-((3-amino-2-chloro-6-fluorophenyl)amino)-5-fluoro-3-methylquinazolin-4(3H)-one (150 mg, 0.45 mmol) and pyrrolidine-1-sulfonyl chloride (190 mg, 1.10 mmol) in pyridine (2.2 mL) was sealed and heated at 70° C. for 18 hours. The reaction mixture was cooled to ambient temperature and diluted with DCM (15 mL) and washed with 10% aqueous CuSO₄. The DCM extract was dried over MgSO₄, concentrated and the residue was purified by reverse phase chromatography (5-95% ACN/water with 0.1% TFA) to provide N-(2-chloro-4-fluoro-3-((5-fluoro-3-methyl-4-oxo-3,4-dihydroquinazolin-6-yl)amino)phenyl)pyrrolidine-1-sulfonamide trifluoroacetate (161 mg, 77%). ¹H NMR (400 MHz, CDCl₃) δ 8.32 (s, 1H), 7.56-7.53 (m, 1H), 7.49-7.46 (m, 1H), 7.15 (t, 1H), 7.09-7.03 (m, 1H), 6.75 (s, 1H), 5.98 (s, 1H), 3.64 (s, 3H), 3.37-3.34 (m, 4H), 1.91-1.88 (m, 4H). MS (apci, m/z)=470.1 (M+H).

Example 8

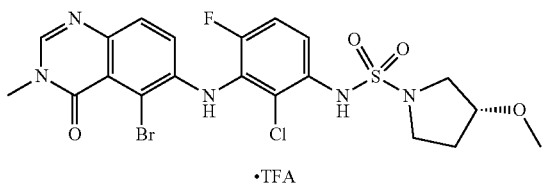

•TFA (R)-N-(3-((5-bromo-3-methyl-4-oxo-3,4-dihydroquinazolin-6-yl)amino)-2-chloro-4-fluorophenyl)-3-methoxypyrrolidine-1-sulfonamide trifluoroacetate A solution of 6-((3-amino-2-chloro-6-fluorophenyl)amino)-5-bromo-3-methylquinazolin-4(3H)-one (35 mg, 0.088 mmol) and (R)-3-methoxypyrrolidine-1-sulfonyl chloride (44 mg, 0.22 mmol) in pyridine (0.44 mL) was sealed and heated at 70° C. for 18 hours. The reaction mixture was cooled to ambient temperature and diluted with DCM (15 mL) and washed with 10% aqueous CuSO₄. The DCM extract was dried over MgSO₄, concentrated and the residue was purified by reverse phase chromatography (5-95% ACN/water with 0.1% TFA) to provide (R)-N-(3-((5-bromo-3-methyl-4-oxo-3,4-dihydroquinazolin-6-yl)amino)-2-chloro-4-fluorophenyl)-3-methoxypyrrolidine-1-sulfonamide trifluoroacetate (20 mg, 40%). ¹H NMR (400 MHz, CDCl₃) δ 8.18 (s, 1H), 7.61-7.57 (m, 1H), 7.15 (t, 1H), 7.00-6.95 (m, 2H), 6.93 (s, 1H), 6.66 (s, 1H), 3.97-3.95 (m, 1H), 3.62 (s, 3H), 3.53-3.43 (m, 2H), 3.27 (s, 3H), 2.07-1.93 (m, 4H). MS (apci, m/z)=560.0, 562.0 (M+H).

Example 9

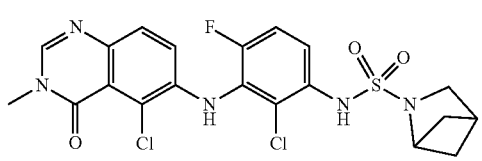

•TFA

N-(2-chloro-3-((5-chloro-3-methyl-4-oxo-3,4-dihydroquinazolin-6-yl)amino)-4-fluorophenyl)-2-azabicyclo[2.1.1]hexane-2-sulfonamide trifluoroacetate A solution of 6-((3-amino-2-chloro-6-fluorophenyl)amino)-5-chloro-3-methylquinazolin-4(3H)-one (30 mg, 0.085 mmol) and 2-azabicyclo[2.1.1]hexane-2-sulfonyl chloride (46 mg, 0.26 mmol) in pyridine (0.43 mL) was sealed and heated at 70° C. for 18 hours. The reaction mixture was cooled to ambient temperature and diluted with DCM (15 mL) and washed with 10% aqueous CuSO₄. The DCM extract was dried over MgSO₄, concentrated and the residue was purified by reverse phase chromatography (5-95% ACN/water with 0.1% TFA) to provide N-(2-chloro-3-((5-chloro-3-methyl-4-oxo-3,4-dihydroquinazolin-6-yl)amino)-4-fluorophenyl)-2-azabicyclo[2.1.1]hexane-2-sulfonamide trifluoroacetate (21 mg, 50%). ¹H NMR (400 MHz, CDCl₃) δ 8.46 (s, 1H), 7.64-7.61 (m, 2H), 7.16 (t, 1H), 7.00-6.97 (m, 1H), 6.82 (s, 1H), 6.51 (s, 1H), 4.27-4.24 (m, 1H), 3.53 (s, 3H), 3.40 (s, 2H), 2.92-2.88 (m, 1H), 1.96-1.94 (m, 2H), 1.55-1.53 (m, 2H). MS (apci, m/z)=498.1 (M+H).

Example 10

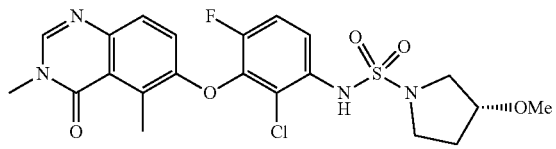 [SMILES: CO[C@@H]1CCN(S(=O)(=O)Nc2ccc(F)c(Oc3ccc4ncn(C)c(=O)c4c3C)c2Cl)C1]

(R)-N-(2-chloro-3-((3,5-dimethyl-4-oxo-3,4-dihydroquinazolin-6-yl)oxy)-4-fluorophenyl)-3-methoxypyrrolidine-1-sulfonamide A solution of 6-(3-amino-2-chloro-6-fluorophenoxy)-3,5-dimethylquinazolin-4(3H)-one (70 mg, 0.21 mmol) and (R)-3-methoxypyrrolidine-1-sulfonyl chloride (167 mg, 0.84 mmol) in pyridine (2 mL) was sealed and heated at 65° C. for 60 hours. The reaction mixture was cooled to ambient temperature and concentrated. The crude product was purified by silica gel column chromatography (30-100% EtOAc/ hexane) to give (R)-N-(2-chloro-3-((3,5-dimethyl-4-oxo-3,4-dihydroquinazolin-6-yl)oxy)-4-fluorophenyl)-3-methoxypyrrolidine-1-sulfonamide (55 mg, 53%). $^1$H NMR (400 MHz, CDCl$_3$) δ 7.94 (s, 1H), 7.58-7.55 (m, 1H), 7.43 (d, 1H), 7.15-7.11 (t, 1H), 6.93-6.91 (m, 2H), 3.96-3.93 (m, 1H), 3.55 (s, 3H), 3.51-3.40 (m, 4H), 3.26 (s, 3H), 3.01 (s, 3H), 2.12-2.05 (m, 1H), 1.99-1.90 (m, 1H). MS (apci, m/z)=497.1 (M+H).

Example 11

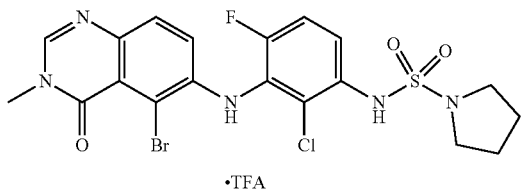 [SMILES: Cn1cnc2ccc(Nc3c(F)ccc(NS(=O)(=O)N4CCCC4)c3Cl)c(Br)c2c1=O]

N-(3-((5-bromo-3-methyl-4-oxo-3,4-dihydroquinazolin-6-yl)amino)-2-chloro-4-fluorophenyl)pyrrolidine-1-sulfonamide trifluoroacetate A solution of 6-((3-amino-2-chloro-6-fluorophenyl)amino)-5-bromo-3-methylquinazolin-4(3H)-one (250 mg, 0.63 mmol) and pyrrolidine-1-sulfonyl chloride (320 mg, 1.89 mmol) in pyridine (3.1 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide N-(3-((5-bromo-3-methyl-4-oxo-3,4-dihydroquinazolin-6-yl)amino)-2-chloro-4-fluorophenyl)pyrrolidine-1-sulfonamide trifluoroacetate (202 mg, 60%). $^1$H NMR (400 MHz, CDCl$_3$) δ 7.98 (s, 1H), 7.58-7.54 (m, 1H), 7.51-7.49 (m, 1H), 7.14 (t, 1H), 6.93-6.90 (m, 1H), 6.64 (s, 1H), 3.57 (s, 3H), 3.36-3.31 (m, 4H), 1.90-1.86 (m, 4H). MS (apci, m/z)=530.0, 532.0 (M+H).

Example 12

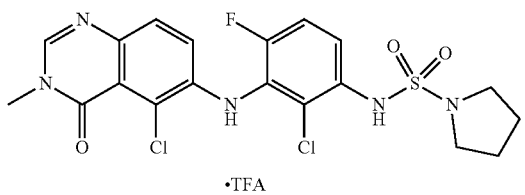 [SMILES: Cn1cnc2ccc(Nc3c(F)ccc(NS(=O)(=O)N4CCCC4)c3Cl)c(Cl)c2c1=O]

N-(2-chloro-3-((5-chloro-3-methyl-4-oxo-3,4-dihydroquinazolin-6-yl)amino)-4-fluorophenyl)pyrrolidine-1-sulfonamide trifluoroacetate A solution of 6-((3-amino-2-chloro-6-fluorophenyl)amino)-5-chloro-3-methylquinazolin-4(3H)-one (150 mg, 0.42 mmol) and pyrrolidine-1-sulfonyl chloride (180 mg, 1.06 mmol) in pyridine (2.1 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide N-(2-chloro-3-((5-chloro-3-methyl-4-oxo-3,4-dihydroquinazolin-6-yl)amino)-4-fluorophenyl)pyrrolidine-1-sulfonamide trifluoroacetate (179 mg, 87%). $^1$H NMR (400 MHz, CDCl$_3$) δ 8.59 (s, 1H), 7.64-7.58 (m, 2H), 7.17 (t, 1H), 7.01-6.97 (m, 1H), 6.77 (s, 1H), 6.54 (s, 1H), 3.68 (s, 1H), 3.38-3.34 (m, 4H), 1.92-1.88 (m, 4H). MS (apci, m/z)=486.1 (M+H).

Example 13

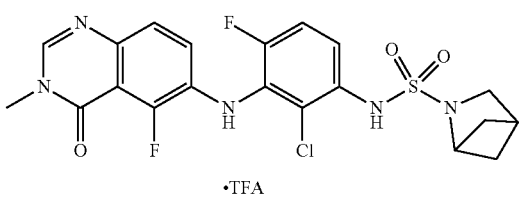 [SMILES: Cn1cnc2ccc(Nc3c(F)ccc(NS(=O)(=O)N4CC5CC4C5)c3Cl)c(F)c2c1=O]

N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide trifluoroacetate A solution of 6-((3-amino-2-chloro-6-fluorophenyl)amino)-5-fluoro-3-methylquinazolin-4(3H)-one (30 mg, 0.089 mmol) and 2-azabicyclo[2.1.1]hexane-2-sulfonyl chloride (49 mg, 0.27 mmol) in pyridine (0.45 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide trifluoroacetate (18 mg, 41%). $^1$H NMR (400 MHz, CDCl$_3$) δ 8.25 (s, 1H), 7.60-7.56 (m, 1H), 7.47-7.56 (m, 1H), 7.14 (t, 1H), 7.08-7.03 (m, 1H), 6.80 (s, 1H), 5.96 (s, 1H), 4.26-4.24 (m, 1H), 3.63 (s, 3H), 3.40 (s, 2H), 2.91-2.88 (m, 1H), 1.96-1.93 (m, 2H), 1.54-1.53 (m, 2H). MS (apci, m/z)=482.1 (M+H).

Example 14

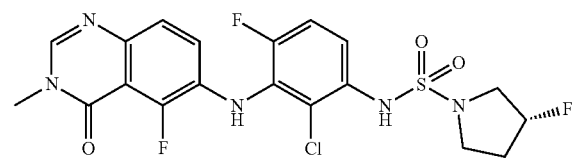 [SMILES: Cn1cnc2ccc(Nc3c(F)ccc(NS(=O)(=O)N4CC[C@@H](F)C4)c3Cl)c(F)c2c1=O]

(R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide and crystalline form (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide Form A Method A for the preparation of (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide.

6-((3-Amino-2-chloro-6-fluorophenyl)amino)-5-fluoro-3-methylquinazolin-4(3H)-one (Intermediate P13; 139.5 mg, 0.4143 mmol) was dissolved in pyridine (4.1 mL) and treated with (3R)-3-fluoropyrrolidine-1-sulfonyl chloride (388.6 mg, 2.071 mmol) and the reaction mixture was heated to 60° C. for 16 hours. The reaction mixture was cooled to ambient temperature and then diluted with EtOAc and washed with 10% citric acid (2×) then brine (1×) then dried over $Na_2SO_4$, filtered, and concentrated. The resulting residue was purified by silica gel chromatography (DCM/Acetone) followed by reverse phase C18 chromatography (water/ACN with 0.1% TFA). The combined desired fractions were then partitioned between 4:1 DCM:IPA and saturated $NaHCO_3$ (1×) then dried over $Na_2SO_4$, filtered, and concentrated. The resulting residue was dissolved in DCM and washed with 1.0 M NaOH (2×) and then the combined aqueous layers were extracted with DCM (1×). The aqueous layer was acidified to about pH 2 using 4.0 M HCl and then extracted with 4:1 DCM:IPA (2×) and then dried over $Na_2SO_4$, filtered, and concentrated to provide (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide (74.8 mg, 37%). $^1$H NMR (400 MHz, $(CD_3)_2SO$) δ 9.54 (s, 1H), 8.18 (s, 1H), 8.07 (s, 1H), 7.42-7.38 (m, 1H), 7.35-7.30 (m, 2H), 7.03-6.99 (t, 1H), 5.39-5.26 (m, 1H), 3.50-3.39 (m, 6H), 3.35-3.28 (m, 1H), 2.15-2.00 (m, 2H). MS (apci, m/z)=488.1, 490.1 (M+H).

Method B for the preparation of (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide.

Step 1: Preparation of tert-butyl (R)-(2-chloro-4-fluoro-3-iodophenyl)((3-fluoropyrrolidin-1-yl)sulfonyl)carbamate. Tert-butyl (2-chloro-4-fluoro-3-iodophenyl)carbamate (Intermediate P9; 20 g, 54 mmol) was dissolved in THF (269 mL) and cooled to 0° C. The reaction mixture was treated with sodium hydride (4.3 g, 108 mmol, 60% wt in mineral oil) portion wise and then the ice bath was removed and the mixture was stirred for 15 minutes. The reaction mixture was treated with (R)-3-fluoropyrrolidine-1-sulfonyl chloride (20 g, 108 mmol) and then heated to 50° C. for 12 hours. The reaction mixture was cooled to ambient temperature and slowly poured into a stirring flask of ice water (500 mL) and then extracted with EtOAc (3×100 mL). The organic extracts were washed with brine (1×50 mL), dried over $Na_2SO_4$, filtered, and concentrated. The residue was purified by silica gel chromatography (50-100% Hexane/DCM). The desired fractions were combined and concentrated and then the resulting solids were sonicated with chilled MeOH, filtered, and rinsed with minimal MeOH to give tert-butyl (R)-(2-chloro-4-fluoro-3-iodophenyl)((3-fluoropyrrolidin-1-yl)sulfonyl)carbamate (21 g, 75%) as a white solid. $^1$H NMR (400 MHz, $CDCl_3$) δ 7.43-7.38 (m, 1H), 7.07-7.03 (m, 1H), 5.39-5.23 (m, 1H), 4.02-3.72 (m, 4H), 2.36-2.03 (m, 2H), 1.39 (s, 9H).

Step 2: Preparation of tert-butyl (R)-(2-chloro-4-fluoro-3-((5-fluoro-3-methyl-4-oxo-3,4-dihydroquinazolin-6-yl)amino)phenyl)((3-fluoropyrrolidin-1-yl)sulfonyl)carbamate. 6-Amino-5-fluoro-3-methylquinazolin-4(3H)-one (15.7 g, 81 mmol), tert-butyl (R)-(2-chloro-4-fluoro-3-iodophenyl)(3-fluoropyrrolidin-1-yl)sulfonyl)carbamate (38.5 g, 73.7 mmol), tri(dibenzylideneacetone)dipalladium (6.74 g, 7.37 mmol), (9,9-dimethyl-9H-xanthene-4,5-diyl)bis(diphenylphosphane) (10.7 g, 18.4 mmol) and cesium carbonate (72.0 g, 221 mmol) were suspended in toluene (491 mL). The reaction mixture was sparged with Argon for 15 minutes and then heated to 100° C. under an Argon balloon for 16 hours. The reaction mixture was cooled to ambient temperature, dissolved in 4:1 DCM:IPA (500 mL) and EtOAc (200 mL) and filtered through a pad of Celite. The Celite was rinsed with additional 4:1 DCM:IPA (2×50 mL) and the filtrate was concentrated to provide crude tert-butyl (R)-(2-chloro-4-fluoro-3-((5-fluoro-3-methyl-4-oxo-3,4-dihydroquinazolin-6-yl)amino)phenyl)((3-fluoropyrrolidin-1-yl)sulfonyl)carbamate (43.3 g, 100%) that was used directly in the next step. MS (apci, m/z)=588.1, 590.1 (M+H).

Step 3: Preparation of (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide. tert-Butyl (R)-(2-chloro-4-fluoro-3-((5-fluoro-3-methyl-4-oxo-3,4-dihydroquinazolin-6-yl)amino)phenyl)((3-fluoropyrrolidin-1-yl)sulfonyl)carbamate (43.3 g, 73.6 mmol) was dissolved in 1:1 DCM:TFA (150 mL) and stirred at ambient temperature for 2 hours. The mixture was concentrated, dissolved in 4:1 DCM:IPA and washed with $NaHCO_3$ (2×100 mL) and brine (1×50 mL). The organics were washed with 1 N NaOH (3×100 mL) and the combined aqueous layers were extracted with DCM (2×50 mL). The NaOH aqueous layer was acidified with 4N HCl to a pH of 1 and extracted with 4:1 DCM:IPA (3×100 mL). The DCM:IPA organics were washed with $NaHCO_3$ (1×100 mL) and brine (1×50 mL), dried over $Na_2SO_4$, filtered, and concentrated. The resulting residue was purified by silica gel chromatography (0-100% DCM/EtOAc) to give (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide (29.7 g, 83%). $^1$H NMR (400 MHz, $CDCl_3$) δ 7.90 (s, 1H), 7.55-7.51 (m, 1H), 7.40-7.38 (m, 1H), 7.15-7.11 (t, 1H), 7.05-7.00 (m, 1H), 6.79 (s, 1H), 5.92 (s, 1H), 5.30-5.15 (m, 1H), 3.69-3.58 (m, 5H), 3.52-3.45 (m, 2H), 2.31-2.21 (m, 1H), 2.13-1.94 (m, 1H). MS (apci, m/z)=488.1, 490.1 (M+H).

Method C. Preparation of crystalline form (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide Form A. (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide, prepared according to Method A or Method B (63.7 g, 131 mmol) was treated with EtOAc (76 mL, 0.83 mg/mL) and the mixture was stirred until dissolved. The reaction mixture was stirred for 1 hour until solidified and then additional EtOAc was added to resume stirring and the mixture was allowed to stir for 12 hours at ambient temperature. The solution was diluted with chilled EtOAc (100 mL), filtered, and rinsed with additional chilled EtOAc (25 mL) to provide (R)-N-(2-chloro-4-fluoro-3-((5-fluoro-3-methyl-4-oxo-3,4-dihydroquinazolin-6-yl)amino)phenyl)-3-fluoropyrrolidine-1-sulfonamide Form A (52.3 g, 82%) as a white solid, which was characterized by Powder X-ray diffraction analysis. Powder X-ray diffraction analysis was conducted using a Rigaku MiniFlex 6G diffractometer equipped with a Cu radiation source. Diffracted radiation was detected by a D/teX Ultra2 detector. The X-ray tube voltage and amperage were set to 40 kV and 15 mA respectively. Data was collected in the MiniFlex goniometer at the Cu wavelength from 3.0 to 45.0° 2-Theta using a step width of 0.01° and a step speed of 3.00°/min. The incident slit box was set to 1.250 and the length-limiting slit was set at 10 mm. The sample was rotated at 10 RPM during collection. Samples were prepared by placing them in a silicon low background sample holder.

Data were collected and analyzed using SmartLab Studio II (version 4.3.147.0) software. The software automatically identified peaks within the PXRD data file was using the second derivative method followed by manual peak selection. In general, peaks with 3% relative intensity were chosen. A typical error associated with the peak position of crystalline material, from PXRD, stated in USP, is up to +/−0.2° 2-Theta (USP-941). FIG. 1 illustrates a PXRD pattern of crystalline pattern of (3R)-N-{2-chloro-4-fluoro-3-[(5-fluoro-3-methyl-4-oxo-3,4-dihydroquinazolin-6-yl)amino]phenyl}-3-fluoropyrrolidine-1-sulfonamide Form A and Table D provides PXRD peaks of crystalline pattern of crystalline form (3R)-N-{2-chloro-4-fluoro-3-[(5-fluoro-3-methyl-4-oxo-3,4-dihydroquinazolin-6-yl)amino]phenyl}-3-fluoropyrrolidine-1-sulfonamide Form A.

TABLE D

| Angle (° 2θ) | Relative intensity (%) |
| --- | --- |
| 5.9 | 36.2 |
| 8.0 | 34.3 |
| 11.3 | 55.7 |
| 12.0 | 100.0 |
| 15.9 | 83.0 |
| 16.7 | 69.4 |
| 17.6 | 60.1 |
| 18.6 | 21.3 |
| 19.3 | 38.0 |
| 19.5 | 13.2 |
| 21.6 | 19.5 |
| 22.5 | 16.2 |
| 23.1 | 64.0 |
| 24.0 | 28.2 |
| 24.9 | 20.6 |
| 25.4 | 27.6 |
| 26.7 | 5.6 |
| 27.3 | 21.5 |
| 27.6 | 31.7 |
| 28.0 | 3.6 |
| 29.0 | 17.2 |
| 29.6 | 25.3 |
| 30.4 | 6.8 |
| 31.5 | 7.6 |
| 32.4 | 14.8 |
| 33.2 | 4.9 |
| 33.7 | 11.4 |
| 34.3 | 22.3 |
| 35.0 | 11.1 |
| 35.5 | 4.0 |
| 36.4 | 3.3 |
| 36.7 | 4.8 |
| 37.6 | 10.2 |
| 38.0 | 6.2 |
| 38.4 | 5.2 |
| 39.0 | 13.8 |
| 40.1 | 4.5 |
| 40.4 | 3.6 |
| 41.8 | 4.4 |
| 44.0 | 3.1 |
| 44.6 | 3.4 |

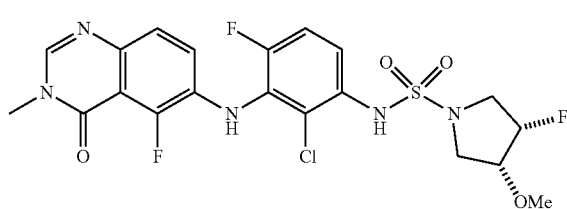 [SMILES: CO[C@@H]1CN(S(=O)(=O)Nc2ccc(F)c(Nc3ccc4ncn(C)c(=O)c4c3F)c2Cl)C[C@@H]1F]

cis-N-(2-chloro-4-fluoro-3-((5-fluoro-3-methyl-4-oxo-3,4-dihydroquinazolin-6-yl)amino)phenyl)-3-fluoro-4-methoxypyrrolidine-1-sulfonamide A solution of 6-((3-amino-2-chloro-6-fluorophenyl)amino)-5-fluoro-3-methylquinazolin-4(3H)-one (30 mg, 0.0891 mmol) and cis-3-fluoro-4-methoxypyrrolidine-1-sulfonyl chloride (97 mg, 0.445 mmol) in pyridine (0.8 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na$_2$SO$_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:IPA and saturated aqueous NaHCO$_3$ (1×). The organic layer was separated, dried over anhydrous Na$_2$SO$_4$, filtered, and concentrated to give cis-N-(2-chloro-4-fluoro-3-((5-fluoro-3-methyl-4-oxo-3,4-dihydroquinazolin-6-yl)amino)phenyl)-3-fluoro-4-methoxypyrrolidine-1-sulfonamide (11.2 mg, 24%) as an off-white solid. $^1$H NMR (400 MHz, CDCl$_3$) δ 7.90 (s, 1H), 7.54-7.46 (m, 1H), 7.43-7.36 (d, 1H), 7.18-7.09 (t, 1H), 7.09-6.99 (m, 1H), 6.76 (s, 1H), 5.92 (s, 1H), 5.23-4.97 (m, 1H), 3.97-3.82 (m, 1H), 3.82-3.74 (m, 1H), 3.70-3.67 (d, 1H), 3.62-3.58 (m, 1H), 3.57 (s, 3H), 3.44 (s, 3H), 3.35-3.26 (m, 1H); MS (apci, m/z)=518.1, 520.1 (M+H).

Example 16

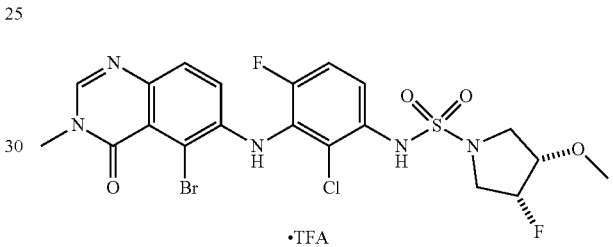

cis-N-(3-((5-bromo-3-methyl-4-oxo-3,4-dihydroquinazolin-6-yl)amino)-2-chloro-4-fluorophenyl)-3-fluoro-4-methoxypyrrolidine-1-sulfonamide trifluoroacetate Step 1: Preparation of cis-3-fluoro-4-methoxypyrrolidine-1-sulfonyl chloride. A slurry of cis-3-fluoro-4-methoxypyrrolidine hydrochloride (0.834 g, 5.36 mmol) and N,N-diisopropylethylamine (1.40 mL, 8.04 mmol) was stirred in DCM (13 mL) at ambient temperature until the mixture was fully dissolved. The reaction mixture was cooled to 0° C. and treated with sulfuryl chloride (1.08 mL, 13.4 mmol). The cold bath was removed after 30 minutes and the mixture was stirred at ambient temperature for 18 hours. The reaction mixture was diluted with additional DCM and washed with 1.0 M HCl (1×). The organic layer was separated, dried over anhydrous MgSO$_4$, filtered, and concentrated to give crude cis-3-fluoro-4-methoxypyrrolidine-1-sulfonyl chloride, which was used as is in the next step.

Step 2: Preparation of cis-N-(3-((5-bromo-3-methyl-4-oxo-3,4-dihydroquinazolin-6-yl)amino)-2-chloro-4-fluorophenyl)-3-fluoro-4-methoxypyrrolidine-1-sulfonamide trifluoroacetate. A solution of 6-((3-amino-2-chloro-6-fluorophenyl)amino)-5-bromo-3-methylquinazolin-4(3H)-one (35 mg, 0.088 mmol) and cis-3-fluoro-4-methoxypyrrolidine-1-sulfonyl chloride (48 mg, 0.22 mmol) in pyridine (0.44 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide cis-N-(3-((5-bromo-3-methyl-4-oxo-3,4-dihydroquinazolin-6-yl)amino)-2-chloro-4-fluorophenyl)-3-fluoro-4-methoxypyrrolidine-1-sulfonamide trifluoroacetate (3.0 mg, 6%). ¹H NMR (400 MHz, CDCl₃) δ 8.17 (s, 1H), 7.59-7.56 (m, 2H), 7.16 (t, 1H), 6.97-6.94 (m, 1H), 6.78 (s, 1H), 6.65 (s, 1H), 5.20-5.04 (m, 1H), 3.96-3.86 (m, 1H), 3.81-3.77 (m, 1H), 3.68-3.67 (m, 1H), 3.61 (s, 3H), 3.45 (m, 3H), 3.32-3.27 (m, 1H), 2.10-2.05 (m, 2H). MS (apci, m/z)=578.0, 580.0 (M+H).

Example 17

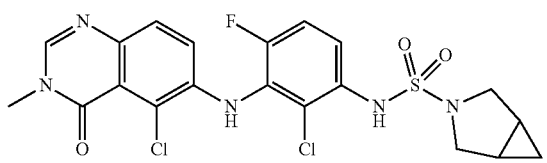 [SMILES: Cn1cnc2ccc(Nc3c(F)ccc(NS(=O)(=O)N4CC5CC5C4)c3Cl)c(Cl)c2c1=O]

N-(2-chloro-3-((5-chloro-3-methyl-4-oxo-3,4-dihydroquinazolin-6-yl)amino)-4-fluorophenyl)-3-azabicyclo[3.1.0]hexane-3-sulfonamide A solution of 6-((3-amino-2-chloro-6-fluorophenyl)amino)-5-chloro-3-methylquinazolin-4(3H)-one (35 mg, 0.099 mmol) and 3-azabicyclo[3.1.0]hexane-3-sulfonyl chloride (72 mg, 0.40 mmol) in pyridine (0.8 mL) was sealed and heated at 65° C. for 60 hours. The reaction mixture was cooled to ambient temperature and concentrated. The crude product was purified by silica gel column chromatography (50-100% EtOAc/hexane) followed by reverse phase chromatography (5-95% ACN/water with 0.1% TFA). The desired fractions were combined and partitioned between 4:1 DCM:IPA and saturated NaHCO₃. The combined organic layers were separated, dried over anhydrous Na₂SO₄, filtered, and concentrated to give N-(2-chloro-3-((5-chloro-3-methyl-4-oxo-3,4-dihydroquinazolin-6-yl)amino)-4-fluorophenyl)-3-azabicyclo[3.1.0]hexane-3-sulfonamide (34 mg, 69%). ¹H NMR (400 MHz, CDCl₃) δ 7.93 (s, 1H), 7.51-7.47 (m, 2H), 7.17-7.12 (t, 1H), 6.96-6.93 (m, 1H), 6.78 (s, 1H), 6.46 (s, 1H), 3.57 (s, 3H), 3.49 (s, 1H), 3.47 (s, 1H), 3.40-3.37 (m, 2H), 1.53-1.50 (m, 2H), 0.64-0.59 (m, 1H), 0.21-0.18 (m, 1H). MS (apci, m/z)=498.1 (M+H).

Example 18

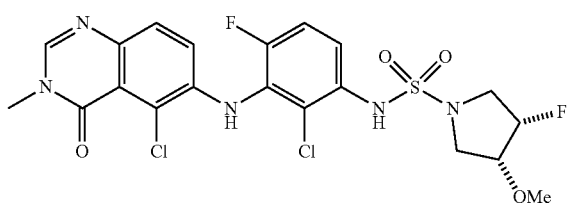 [SMILES: CO[C@@H]1CN(S(=O)(=O)Nc2ccc(F)c(Nc3ccc4ncn(C)c(=O)c4c3Cl)c2Cl)C[C@@H]1F]

cis-N-(2-chloro-3-((5-chloro-3-methyl-4-oxo-3,4-dihydroquinazolin-6-yl)amino)-4-fluorophenyl)-3-fluoro-4-methoxypyrrolidine-1-sulfonamide A solution of 6-((3-amino-2-chloro-6-fluorophenyl)amino)-5-chloro-3-methylquinazolin-4(3H)-one (30 mg, 0.0849 mmol) and cis-3-fluoro-4-methoxypyrrolidine-1-sulfonyl chloride (108 mg, 0.496 mmol) in pyridine (0.8 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na₂SO₄, filtered, and concentrated. The residue was purified by silica gel column chromatography (DCM/EtOAc) to give cis-N-(2-chloro-3-((5-chloro-3-methyl-4-oxo-3,4-dihydroquinazolin-6-yl)amino)-4-fluorophenyl)-3-fluoro-4-methoxypyrrolidine-1-sulfonamide (45.4 mg, 21%) as an off-white solid. ¹H NMR (400 MHz, CDCl₃) δ 7.93 (s, 1H), 7.58-7.53 (m, 1H), 7.53-7.48 (d, 1H), 7.18-7.12 (t, 1H), 6.99-6.92 (m, 1H), 6.78 (s, 1H), 6.45 (s, 1H), 5.20-5.02 (m, 1H), 3.96-3.85 (m, 1H), 3.82-3.76 (m, 1H), 3.71-3.66 (d, 1H), 3.63-3.59 (t, 1H), 3.57 (s, 3H), 3.44 (s, 3H), 3.35-3.25 (m, 1H); MS (apci m/z)=534.1, 536.1 (M+H).

Example 19

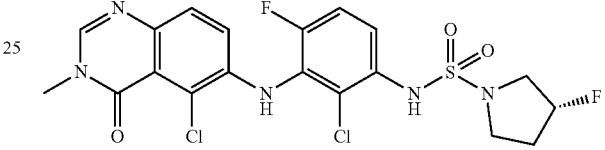

(R)-N-(2-chloro-3-((5-chloro-3-methyl-4-oxo-3,4-dihydroquinazolin-6-yl)amino)-4-fluorophenyl)-3-fluoropyrrolidine-1-sulfonamide 6-((3-Amino-2-chloro-6-fluorophenyl)amino)-5-chloro-3-methylquinazolin-4(3H)-one (152.6 mg, 0.4321 mmol) was dissolved in pyridine (1.8 mL) then treated with (3R)-3-fluoropyrrolidine-1-sulfonyl chloride (121.6 mg, 0.6481 mmol) and heated to 60° C. for 16 hours. The reaction mixture was treated with additional (3R)-3-fluoropyrrolidine-1-sulfonyl chloride (121.6 mg, 0.6481 mmol) and stirred at 60° C. for an additional 3 hours. The reaction mixture was cooled to ambient temperature and diluted with EtOAc and washed with 10% citric acid (2×) and brine (1×) then dried over Na₂SO₄, filtered, and concentrated. The resulting residue was purified by silica gel chromatography (DCM/EtOAc) to provide (R)-N-(2-chloro-3-((5-chloro-3-methyl-4-oxo-3,4-dihydroquinazolin-6-yl)amino)-4-fluorophenyl)-3-fluoropyrrolidine-1-sulfonamide (93.9 mgs, 43%). ¹H NMR (400 MHz, (CD₃)₂SO) δ 9.56 (s, 1H), 8.18 (s, 1H), 7.72 (s, 1H), 7.50-7.46 (m, 1H), 7.41-7.33 (m, 2H), 6.73-6.70 (dd, 1H), 5.36-5.23 (m, 1H), 3.47-3.30 (m, 7H), 2.12-1.97 (m, 2H). MS (apci, m/z)=504.0, 506.0 (M+H).

Example 20

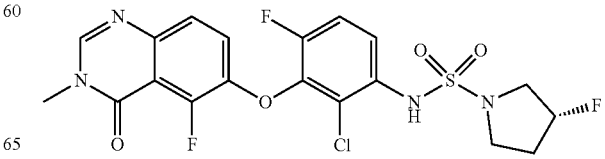

(R)-N-(2-chloro-4-fluoro-3-((5-fluoro-3-methyl-4-oxo-3,4-dihydroquinazolin-6-yl)oxy)phenyl)-3-fluoropyrrolidine-1-sulfonamide To a solution of 6-(3-amino-2-chloro-6-fluorophenoxy)-5-fluoro-3-methylquinazolin-4(3H)-one (30 mg, 0.089 mmol) in pyridine (0.8 mL) was added (R)-3-fluoropyrrolidine-1-sulfonyl chloride (67 mg, 0.36 mmol) and the reaction mixture was sealed and stirred at 65° C. for 48 hours. The reaction mixture was cooled to ambient temperature and concentrated. The crude product was purified by reverse phase chromatography (5-95% ACN/water with 0.1% TFA), followed by silica gel column chromatography (50-100% EtOAc/hexane) to give (R)-N-(2-chloro-4-fluoro-3-((5-fluoro-3-methyl-4-oxo-3,4-dihydroquinazolin-6-yl)oxy)phenyl)-3-fluoropyrrolidine-1-sulfonamide (28 mg, 64%). $^1$H NMR (400 MHz, CDCl$_3$) δ 7.96 (s, 1H), 7.59-7.55 (m, 1H), 7.43-7.40 (dd, 1H), 7.24-7.20 (t, 1H), 7.14-7.09 (t, 1H), 6.80 (s, 1H), 5.29-5.14 (m, 1H), 3.67-3.43 (m, 7H), 2.30-2.20 (m, 1H), 2.11-1.92 (m, 1H). MS (apci, m/z)=489.1 (M+H).

Example 21

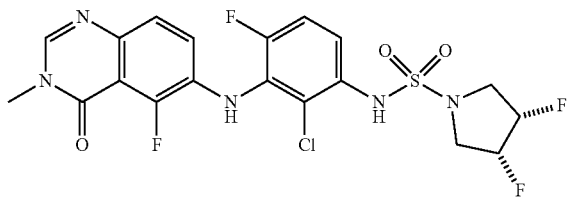 [SMILES: Cn1cnc2ccc(Nc3c(F)ccc(NS(=O)(=O)N4C[C@@H](F)[C@@H](F)C4)c3Cl)c(F)c2c1=O]

cis-N-(2-chloro-4-fluoro-3-((5-fluoro-3-methyl-4-oxo-3,4-dihydroquinazolin-6-yl)amino)phenyl)-3,4-difluoropyrrolidine-1-sulfonamide Step 1: Preparation of cis-3,4-difluoropyrrolidine-1-sulfonyl chloride. A slurry of cis-3,4-difluoropyrrolidine HCl (1.0 g, 6.97 mmol) and N,N-diisopropylethylamine (376 μL, 2.16 mmol) was stirred in DCM (70 mL) at ambient temperature until the mixture was fully dissolved. The reaction mixture was cooled to 0° C. and treated with sulfuryl chloride (1.69 mL, 20.9 mmol). The ice bath was removed after 30 minutes and the mixture was stirred at ambient temperature for 16 hours. The reaction mixture was diluted with additional DCM and washed with 1.0 M HCl (3×). The organic layer was separated, dried over anhydrous Na$_2$SO$_4$, filtered, and concentrated to give crude cis-3,4-difluoropyrrolidine-1-sulfonyl chloride (1.21 g, 85%) which was used directly in the next step.

Step 2: Preparation of cis-N-(2-chloro-4-fluoro-3-((5-fluoro-3-methyl-4-oxo-3,4-dihydroquinazolin-6-yl)amino)phenyl)-3,4-difluoropyrrolidine-1-sulfonamide. A solution of 6-((3-amino-2-chloro-6-fluorophenyl)amino)-5-fluoro-3-methylquinazolin-4(3H)-one (30 mg, 0.0891 mmol) and cis-3,4-difluoropyrrolidine-1-sulfonyl chloride (92 mg, 0.45 mmol) in pyridine (0.8 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na$_2$SO$_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:IPA and saturated aqueous NaHCO$_3$ (1×). The organic layer was separated, dried over anhydrous Na$_2$SO$_4$, filtered, and concentrated to give cis-N-(2-chloro-4-fluoro-3-((5-fluoro-3-methyl-4-oxo-3,4-dihydroquinazolin-6-yl)amino)phenyl)-3,4-difluoropyrrolidine-1-sulfonamide (22 mg, 49%) as an off-white solid. $^1$H NMR (400 MHz, (CD$_3$)$_2$SO) δ 9.70 (s, 1H), 8.18 (s, 1H), 8.05 (s, 1H), 7.40-7.24 (m, 3H), 7.05-6.96 (t, 1H), 5.41-5.15 (m, 2H), 3.70-3.56 (m, 2H), 3.48-3.37 (m, 6H); MS (apci, m/z)=506.1, 508.1 (M+H).

Example 22

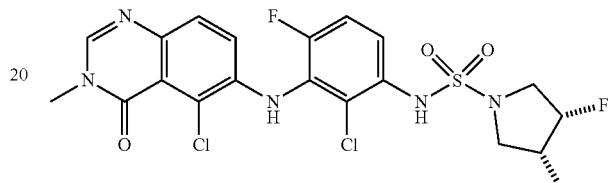

cis-N-(2-chloro-3-((5-chloro-3-methyl-4-oxo-3,4-dihydroquinazolin-6-yl)amino)-4-fluorophenyl)-3,4-difluoropyrrolidine-1-sulfonamide A solution of 6-((3-amino-2-chloro-6-fluorophenyl)amino)-5-chloro-3-methylquinazolin-4(3H)-one (30 mg, 0.085 mmol) and cis-3,4-difluoropyrrolidine-1-sulfonyl chloride (87 mg, 0.42 mmol) in pyridine (0.8 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na$_2$SO$_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:IPA and saturated aqueous NaHCO$_3$ (1×). The organic layer was separated, dried over anhydrous Na$_2$SO$_4$, filtered, and concentrated to give cis-N-(2-chloro-3-((5-chloro-3-methyl-4-oxo-3,4-dihydroquinazolin-6-yl)amino)-4-fluorophenyl)-3,4-difluoropyrrolidine-1-sulfonamide (22 mg, 50%) as an off-white solid. $^1$H NMR (400 MHz, (CD$_3$)$_2$SO) δ 9.73 (s, 1H), 8.18 (s, 1H), 7.73 (s, 1H), 7.49-7.32 (m, 3H), 6.77-6.70 (m, 1H), 5.38-5.16 (m, 2H), 3.68-3.55 (m, 2H), 3.46-3.33 (m, 5H); MS (apci, m/z)=522.0, 524.0 (M+H).

Example 23

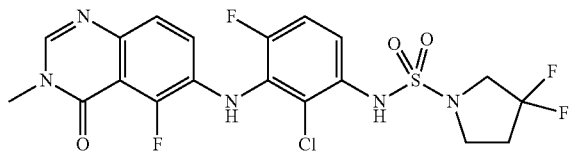 [SMILES: Cn1cnc2ccc(Nc3c(F)ccc(NS(=O)(=O)N4CCC(F)(F)C4)c3Cl)c(F)c2c1=O]

N-(2-chloro-4-fluoro-3-((5-fluoro-3-methyl-4-oxo-3,
4-dihydroquinazolin-6-yl)amino)phenyl)-3,3-difluoropyrrolidine-1-sulfonamide A solution of 6-((3-amino-2-chloro-6-fluorophenyl)amino)-5-fluoro-3-methylquinazolin-4(3H)-one (30 mg, 0.089 mmol) and 3,3-difluoropyrrolidine-1-sulfonyl chloride (55 mg, 0.27 mmol) in pyridine (0.5 mL) was heated at 70° C. for 18 hours. The reaction mixture was cooled to ambient temperature and partitioned between DCM (25 mL) and 10% aqueous $CuSO_4$ (25 mL). The organic phase was separated and dried over $Na_2SO_4$, filtered and concentrated under reduced pressure. The reaction mixture was purified by reverse phase chromatography (5-95% ACN/water with 0.1% TFA). The desired fractions were combined and partitioned between saturated aqueous $NaHCO_3$ (15 mL) and DCM (30 mL). The organic phase was separated, dried over $Na_2SO_4$, filtered and concentrated under reduced pressure to afford N-(2-chloro-4-fluoro-3-((5-fluoro-3-methyl-4-oxo-3,4-dihydroquinazolin-6-yl)amino)phenyl)-3,3-difluoropyrrolidine-1-sulfonamide (8 mg, 18%) as a white solid $^1$H NMR (400 MHz, $CDCl_3$) δ 7.91 (s, 1H), 7.51-7.46 (m, 1H), 7.42-7.38 (m, 1H), 7.15 (t, 1H), 7.00 (m, 1H), 6.75 (s, 1H), 3.71-3.54 (m, 7H), 2.44-2.31 (m, 2H); MS (apci, m/z)=506.1 (M+H).

Example 24

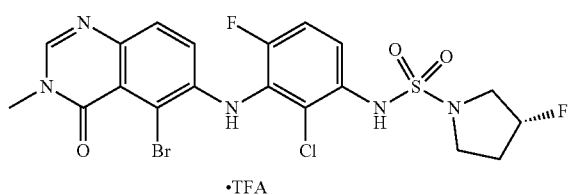 [SMILES: Cn1cnc2ccc(Nc3c(F)ccc(NS(=O)(=O)N4CC[C@@H](F)C4)c3Cl)c(Br)c2c1=O]

·TFA (R)-N-(3-((5-bromo-3-methyl-4-oxo-3,4-dihydroquinazolin-6-yl)amino)-2-chloro-4-fluorophenyl)-3-fluoropyrrolidine-1-sulfonamide trifluoroacetate A solution of 6-((3-amino-2-chloro-6-fluorophenyl)amino)-5-bromo-3-methylquinazolin-4(3H)-one (35 mg, 0.088 mmol) and (R)-3-fluoropyrrolidine-1-sulfonyl chloride (41 mg, 0.22 mmol) in pyridine (0.44 mL) was sealed and heated at 70° C. for 18 hours. The reaction mixture was cooled to ambient temperature and diluted with DCM (15 mL) and washed with 10% aqueous $CuSO_4$. The DCM extract was dried over $MgSO_4$, concentrated and the residue was purified by reverse phase chromatography (5-95% ACN/water with 0.1% TFA) to provide (R)-N-(3-((5-bromo-3-methyl-4-oxo-3,4-dihydroquinazolin-6-yl)amino)-2-chloro-4-fluorophenyl)-3-fluoropyrrolidine-1-sulfonamide trifluoroacetate (3.0 mg, 6%). $^1$H NMR (400 MHz, $CDCl_3$) δ 8.09 (s, 1H), 7.61-7.52 (m, 2H), 7.16 (t, 1H), 6.95-6.92 (m, 1H), 6.78 (s, 1H), 6.63 (s, 1H), 5.30-5.15 (m, 1H), 3.66-3.60 (m, 1H), 3.60 (s, 3H), 3.53-3.45 (m, 1H), 2.35-2.21 (m, 2H), 2.14-2.00 (m, 2H). MS (apci, m/z)=548.0, 550.0 (M+H).

Example 25

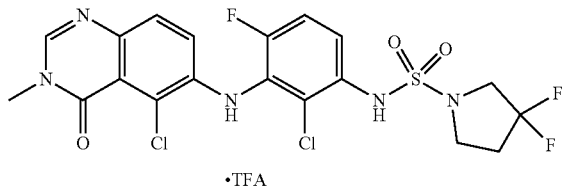 [SMILES: Cn1cnc2ccc(Nc3c(F)ccc(NS(=O)(=O)N4CCC(F)(F)C4)c3Cl)c(Cl)c2c1=O]

·TFA

N-(2-chloro-3-((5-chloro-3-methyl-4-oxo-3,4-dihydroquinazolin-6-yl)amino)-4-fluorophenyl)-3,3-difluoropyrrolidine-1-sulfonamide trifluoroacetate A solution of 6-((3-amino-2-chloro-6-fluorophenyl)amino)-5-chloro-3-methylquinazolin-4(3H)-one (35 mg, 0.099 mmol) and 3,3-difluoropyrrolidine-1-sulfonyl chloride (61 mg, 0.30 mmol) in pyridine (0.50 mL) was sealed and heated at 70° C. for 18 hours. The reaction mixture was cooled to ambient temperature and diluted with DCM (15 mL) and washed with 10% aqueous $CuSO_4$. The DCM extract was dried over $MgSO_4$, concentrated and the residue was purified by reverse phase chromatography (5-95% ACN/water with 0.1% TFA) to provide N-(2-chloro-3-((5-chloro-3-methyl-4-oxo-3,4-dihydroquinazolin-6-yl)amino)-4-fluorophenyl)-3,3-difluoropyrrolidine-1-sulfonamide trifluoroacetate (21 mg, 40%). $^1$H NMR (400 MHz, $CDCl_3$) δ 8.14 (s, 1H), 7.57-7.55 (m, 2H), 7.18 (t, 1H), 6.98-6.95 (m, 1H), 6.77 (s, 1H), 6.49 (s, 1H), 3.67-3.63 (m, 2H), 3.61 (s, 3H), 3.59-3.54 (m, 2H), 2.47-2.33 (m, 2H). MS (apci, m/z)=522.0, 524.0 (M+H).

Example 26

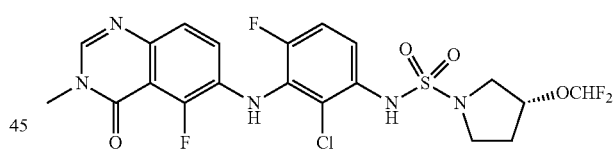

(R)-N-(2-chloro-4-fluoro-3-((5-fluoro-3-methyl-4-oxo-3,4-dihydroquinazolin-6-yl)amino)phenyl)-3-(difluoromethoxy)pyrrolidine-1-sulfonamide Step 1: Preparation of (R)-3-(difluoromethoxy)pyrrolidine-1-sulfonyl chloride. To an ice-cold solution of (R)-3-(difluoromethoxy)pyrrolidine (107 mg, 0.780 mmol) and N-ethyl-N-isopropylpropan-2-amine (204 µL, 1.17 mmol) in DCM (6 mL) was added sulfuryl dichloride (189 µL, 2.34 mmol) and the reaction mixture was stirred at ambient temperature for 18 hours. The reaction mixture was diluted with DCM (20 mL) and washed with aqueous 1M HCl (10 mL). The organic phase was separated and dried over $Na_2SO_4$, filtered and concentrated under reduced pressure to afford (R)-3-(difluoromethoxy)pyrrolidine-1-sulfonyl chloride that was used directly in the next step without further purification. $^1$H NMR (400 MHz, $CDCl_3$) δ 6.47-6.09 (m, 1H), 5.00-4.95 (m, 1H), 3.73-3.58 (m, 4H), 2.30-2.20 (m, 2H).

Step 2: Preparation of (R)-N-(2-chloro-4-fluoro-3-((5-fluoro-3-methyl-4-oxo-3,4-dihydroquinazolin-6-yl)amino)phenyl)-3-(difluoromethoxy)pyrrolidine-1-sulfonamide. A solution of 6-((3-amino-2-chloro-6-fluorophenyl)amino)-5-fluoro-3-methylquinazolin-4(3H)-one (50 mg, 0.149 mmol) and (R)-3-(difluoromethoxy)pyrrolidine-1-sulfonyl chloride (174.9 mg, 0.742 mmol) in pyridine (1 mL) was heated at 70° C. for 18 hours. The reaction mixture was cooled to ambient temperature and partitioned between DCM (25 mL) and 10% aqueous CuSO₄ (25 mL). The organic phase was separated and dried over Na₂SO₄, filtered and concentrated under reduced pressure. The crude material was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO₃ (15 mL) and DCM (30 mL). The organic phase was separated and dried over Na₂SO₄, filtered and concentrated under reduced pressure to afford (R)-N-(2-chloro-4-fluoro-3-((5-fluoro-3-methyl-4-oxo-3,4-dihydroquinazolin-6-yl)amino)phenyl)-3-(difluoromethoxy)pyrrolidine-1-sulfonamide (28.02 mg, 35%) as a white solid. ¹H NMR (400 MHz, CDCl₃) δ 7.99 (s, 1H), 7.55-7.49 (m, 1H), 7.43-7.38 (m, 1H), 7.13 (t, 1H), 7.08-7.01 (m, 1H), 6.77 (s, 1H), 4.87-4.80 (m, 1H), 3.62-3.43 (m, 7H), 2.17-2.08 (m, 2H); MS (apci m/z)=536.1 (M+H).

Example 27

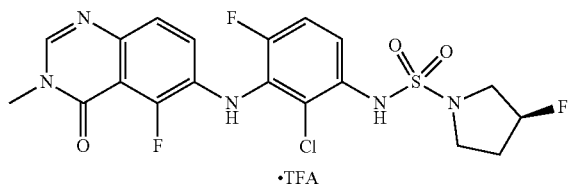 [SMILES: Cn1cnc2ccc(Nc3c(F)ccc(NS(=O)(=O)N4CC[C@H](F)C4)c3Cl)c(F)c2c1=O]

·TFA (S)-N-(2-chloro-4-fluoro-3-((5-fluoro-3-methyl-4-oxo-3,4-dihydroquinazolin-6-yl)amino)phenyl)-3-fluoropyrrolidine-1-sulfonamide trifluoroacetate A solution of 6-((3-amino-2-chloro-6-fluorophenyl)amino)-5-fluoro-3-methylquinazolin-4(3H)-one (30 mg, 0.09 mmol) and (S)-3-fluoropyrrolidine-1-sulfonyl chloride (50 mg, 0.3 mmol) in pyridine (445 μL, 0.0891 mmol) was heated to 70° C. in a sealed vial for 24 hours. The solution was cooled to ambient temperature, concentrated and purified by reverse-phase chromatography (5-95% MeCN/water, 0.1% TFA). The product was lyophilized to give (S)-N-(2-chloro-4-fluoro-3-((5-fluoro-3-methyl-4-oxo-3,4-dihydroquinazolin-6-yl)amino)phenyl)-3-fluoropyrrolidine-1-sulfonamide trifluoroacetate (18.6 mg, 42.8%). ¹H NMR (400 MHz, (CD₃)₂SO) δ 9.54 (s, 1H), 8.21 (s, 1H), 8.09 (s, 1H), 7.42-7.30 (m, 2H), 7.03-6.99 (t, 1H), 5.32 (d, 1H), 3.50-3.30 (m, 7H), 2.16-1.96 (m, 2H); MS (apci m/z)=488.1 (M+H).

Example 28

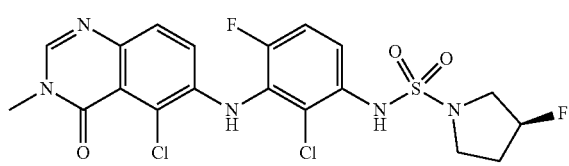 [SMILES: Cn1cnc2ccc(Nc3c(F)ccc(NS(=O)(=O)N4CC[C@H](F)C4)c3Cl)c(Cl)c2c1=O]

(S)-N-(2-chloro-3-((5-chloro-3-methyl-4-oxo-3,4-dihydroquinazolin-6-yl)amino)-4-fluorophenyl)-3-fluoropyrrolidine-1-sulfonamide A solution of 6-((3-amino-2-chloro-6-fluorophenyl)amino)-5-chloro-3-methylquinazolin-4(3H)-one (30 mg, 0.09 mmol) and (S)-3-fluoropyrrolidine-1-sulfonyl chloride (48 mg, 0.25 mmol) in pyridine (425 μL, 0.085 mmol) was heated to 70° C. in a sealed vial for 24 hours. The solution was cooled to ambient temperature, concentrated and purified by silica gel chromatography (1-10% MeOH/DCM, 1% NH₄OH) to give (S)-N-(2-chloro-3-((5-chloro-3-methyl-4-oxo-3,4-dihydroquinazolin-6-yl)amino)-4-fluorophenyl)-3-fluoropyrrolidine-1-sulfonamide (14 mg, 33%). ¹H NMR (400 MHz, CD₃OD) δ 8.44 (s, 1H), 7.67-7.63 (m, 1H), 7.43 (d, 1H), 7.28-7.23 (t, 1H), 6.92-6.89 (m, 1H), 5.31-5.15 (m, 1H), 3.61-3.39 (m, 7H), 2.22-2.00 (m, 2H); MS (apci m/z)=504.1 (M+H).

Example 29

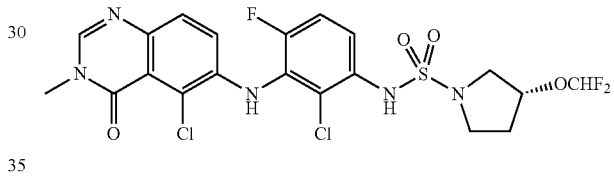

(R)-N-(2-chloro-3-((5-chloro-3-methyl-4-oxo-3,4-dihydroquinazolin-6-yl)amino)-4-fluorophenyl)-3-(difluoromethoxy)pyrrolidine-1-sulfonamide A solution of 6-((3-amino-2-chloro-6-fluorophenyl)amino)-5-chloro-3-methylquinazolin-4(3H)-one (52 mg, 0.1472 mmol) and (R)-3-(difluoromethoxy)pyrrolidine-1-sulfonyl chloride (173.5 mg, 0.7362 mmol) in pyridine (0.800 mL) was heated at 70° C. for 18 hours. The reaction mixture was cooled to ambient temperature and partitioned between DCM (25 mL) and 10% aqueous CuSO₄ (25 mL). The organic phase was separated, dried over Na₂SO₄, filtered and concentrated under reduced pressure. The reaction mixture was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO₃ (15 mL) and DCM (30 mL). The organic phase was separated, dried over Na₂SO₄, filtered and concentrated under reduced pressure to afford (R)-N-(2-chloro-3-((5-chloro-3-methyl-4-oxo-3,4-dihydroquinazolin-6-yl)amino)-4-fluorophenyl)-3-(difluoromethoxy)pyrrolidine-1-sulfonamide (27.34 mg, 34%) as a white solid. ¹H NMR (400 MHz, CDCl₃) δ 7.93 (s, 1H), 7.59-7.53 (m, 1H), 7.50 (d, 1H), 7.15 (t, 1H), 6.98-6.94 (m, 1H), 6.77 (s, 1H), 6.46 (s, 1H), 6.35-5.97 (m, 1H), 4.88-4.81 (m, 1H), 3.63-3.44 (m, 7H), 2.17-2.10 (m, 2H); MS (apci, m/z)=552.0 (M+H).

Example 30

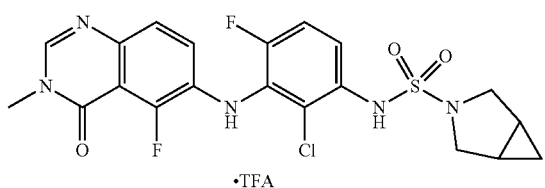 [SMILES: Cn1cnc2ccc(Nc3c(F)ccc(NS(=O)(=O)N4CC5CC5C4)c3Cl)c(F)c2c1=O]

·TFA

N-(2-chloro-4-fluoro-3-((5-fluoro-3-methyl-4-oxo-3,4-dihydroquinazolin-6-yl)amino)phenyl)-3-azabicyclo[3.1.0]hexane-3-sulfonamide trifluoroacetate A solution of 6-((3-amino-2-chloro-6-fluorophenyl)amino)-5-fluoro-3-methylquinazolin-4(3H)-one (30 mg, 0.09 mmol) and 3-azabicyclo[3.1.0]hexane-3-sulfonyl chloride (48 mg, 0.27 mmol) in pyridine (445 µL, 0.0891 mmol) was heated to 70° C. in a sealed vial for 24 hours. The solution was cooled to ambient temperature, concentrated and purified by reverse-phase chromatography (5-95% MeCN/water, 0.1% TFA). The product was lyophilized to give N-(2-chloro-4-fluoro-3-((5-fluoro-3-methyl-4-oxo-3,4-dihydroquinazolin-6-yl)amino)phenyl)-3-azabicyclo[3.1.0]hexane-3-sulfonamide trifluoroacetate (23.5 mg, 54.7%). $^1$H NMR (400 MHz, (CD$_3$)$_2$SO) δ 9.46 (s, 1H), 8.19 (s, 1H), 8.08 (s, 1H), 7.38-7.30 (m, 3H), 7.03-6.98 (t, 1H), 3.44 (s, 3H), 3.29 (s, 4H), 1.56-1.52 (m, 2H), 0.60-0.54 (m, 1H), 0.16-0.13 (m, 1H); MS (apci, m/z)=482.1 (M+H).

Example 31

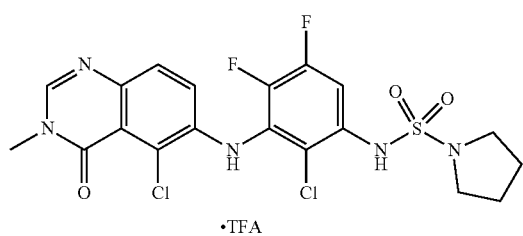 [SMILES: Cn1cnc2ccc(Nc3c(F)c(F)cc(NS(=O)(=O)N4CCCC4)c3Cl)c(Cl)c2c1=O]

·TFA

N-(2-chloro-3-((5-chloro-3-methyl-4-oxo-3,4-dihydroquinazolin-6-yl)amino)-4,5-difluorophenyl)pyrrolidine-1-sulfonamide trifluoroacetate A solution of 6-((3-amino-2-chloro-5,6-difluorophenyl)amino)-5-chloro-3-methylquinazolin-4(3H)-one (100 mg, 0.2694 mmol) and pyrrolidine-1-sulfonyl chloride (114.2 mg, 0.6735 mmol) in pyridine (1.35 mL) was heated at 70° C. for 18 hours. The reaction mixture was cooled to ambient temperature and partitioned between DCM (15 mL) and 10% aqueous CuSO$_4$ (15 mL). The organic phase was separated, dried over Mg$_2$SO$_4$, filtered, and concentrated. The reaction mixture was purified by reverse phase chromatography (5-95% ACN/water with 0.1% TFA). The desired fractions were collected and lyophilized to afford N-(2-chloro-3-((5-chloro-3-methyl-4-oxo-3,4-dihydroquinazolin-6-yl)amino)-4,5-difluorophenyl)pyrrolidine-1-sulfonamide trifluoroacetate (73.5 mg, 54%) as a white solid. $^1$H NMR (400 MHz, CDCl$_3$) δ 8.34 (s, 1H), 7.61 (d, 1H), 7.49-7.45 (m, 1H), 7.06-7.03 (m, 1H), 6.85 (s, 1H), 6.54 (s, 1H), 3.64 (s, 3H), 3.40-3.36 (m, 4H), 1.95-1.92 (m, 4H). MS (apci, m/z)=504.0 (M+H).

Example 32

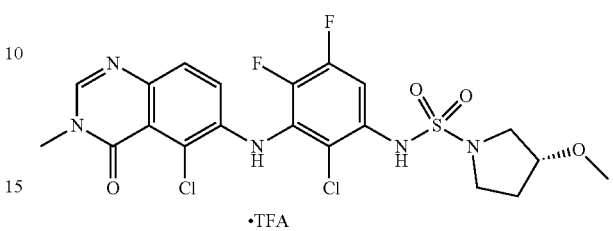

·TFA (R)-N-(2-chloro-3-((5-chloro-3-methyl-4-oxo-3,4-dihydroquinazolin-6-yl)amino)-4,5-difluorophenyl)-3-methoxypyrrolidine-1-sulfonamide trifluoroacetate A solution of 6-((3-amino-2-chloro-5,6-difluorophenyl)amino)-5-chloro-3-methylquinazolin-4(3H)-one (100 mg, 0.269 mmol) and (R)-3-methoxypyrrolidine-1-sulfonyl chloride (134.5 mg, 0.6735 mmol) in pyridine (1.35 mL) was sealed and heated at 70° C. for 18 hours. The reaction mixture was cooled to ambient temperature and diluted with DCM (15 mL) and washed with 10% aqueous CuSO$_4$ (15 mL). The DCM extract was dried over MgSO$_4$, concentrated and the residue was purified by reverse phase chromatography (5-95% ACN/water with 0.1% TFA) to provide (R)-N-(2-chloro-3-((5-chloro-3-methyl-4-oxo-3,4-dihydroquinazolin-6-yl)amino)-4,5-difluorophenyl)-3-methoxypyrrolidine-1-sulfonamide trifluoroacetate (144 mg, 60%). $^1$H NMR (400 MHz, CDCl$_3$) δ 8.34 (s, 1H), 7.60 (d, 1H), 7.53-7.48 (m, 1H), 7.07-7.04 (m, 2H), 6.54 (s, 1H), 4.00-3.98 (m, 1H), 3.64 (s, 3H), 3.56-3.43 (m, 4H), 3.29 (s, 3H), 2.18-2.12 (m, 1H), 2.04-1.94 (m, 1H). MS (apci, m/z)=534.1 (M+H).

Example 33

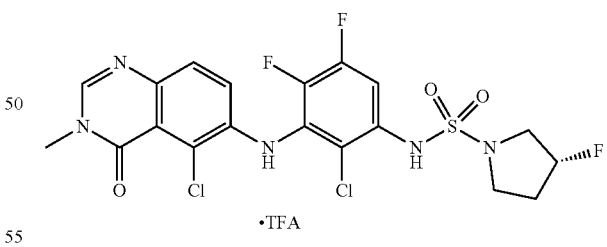

·TFA (R)-N-(2-chloro-3-((5-chloro-3-methyl-4-oxo-3,4-dihydroquinazolin-6-yl)amino)-4,5-difluorophenyl)-3-fluoropyrrolidine-1-sulfonamide trifluoroacetate A solution of 6-((3-amino-2-chloro-5,6-difluorophenyl)amino)-5-chloro-3-methylquinazolin-4(3H)-one (100 mg, 0.269 mmol) and (R)-3-fluoropyrrolidine-1-sulfonyl chloride (126.4 mg, 0.6735 mmol) in pyridine (1.35 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide (R)-N-(2-chloro-3-((5-chloro-3-methyl-4-oxo-3,4-dihydroquinazolin-6-yl)amino)-4,5-difluorophenyl)-3-fluoropyrrolidine-1-sulfonamide trifluoroacetate (141 mg, 43%). ¹H NMR (400 MHz, CDCl₃) δ 8.78 (s, 1H), 7.66 (d, 1H), 7.58-7.53 (m, 1H), 7.07-7.05 (m, 1H), 6.89 (s, 1H), 6.57 (s, 1H), 5.33-5.18 (m, 1H), 3.71 (s, 3H), 3.68-3.62 (m, 2H), 3.55-3.46 (m, 2H), 2.36-2.26 (m, 1H), 2.18-1.99 (m, 1H). MS (apci, m/z)=522.1 (M+H).

Example 34

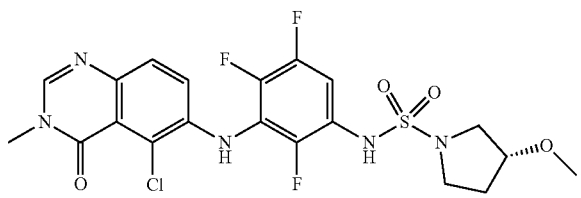

(R)-N-(3-((5-chloro-3-methyl-4-oxo-3,4-dihydroquinazolin-6-yl)amino)-2,4,5-trifluorophenyl)-3-methoxypyrrolidine-1-sulfonamide To a solution of 6-((3-amino-2,5,6-trifluorophenyl)amino)-5-chloro-3-methylquinazolin-4(3H)-one (15 mg, 0.042 mmol) in pyridine (211 μL, 0.042 mmol) was added (R)-3-methoxypyrrolidine-1-sulfonyl chloride (21 mg, 0.11 mmol) and the reaction mixture was heated in a sealed vial to 70° C. for 16 hours. The solution was cooled to ambient temperature, concentrated and purified by silica gel chromatography (1-15% MeOH/DCM, 1% NH₄OH) to give (R)-N-(3-((5-chloro-3-methyl-4-oxo-3,4-dihydroquinazolin-6-yl)amino)-2,4,5-trifluorophenyl)-3-methoxypyrrolidine-1-sulfonamide (12 mg, 55%). ¹H NMR (400 MHz, CDCl₃) δ 7.95 (s, 1H), 7.54 (d, 1H), 7.40-7.33 (m, 1H), 7.14-7.10 (m, 1H), 7.04 (s, br, 1H), 6.32 (s, br, 1H), 3.58 (s, 3H), 3.55-3.37 (m, 5H), 3.29 (s, 3H), 1.99-1.93 (m, 2H); MS (apci, m/z)=518.1 (M+H).

Example 35

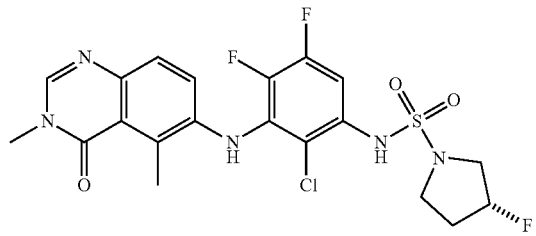 [SMILES: Cc1c(Nc2c(F)c(F)cc(NS(=O)(=O)N3CC[C@@H](F)C3)c2Cl)ccc2ncn(C)c(=O)c12]

(R)-N-(2-chloro-3-((3,5-dimethyl-4-oxo-3,4-dihydroquinazolin-6-yl)amino)-4,5-difluorophenyl)-3-fluoropyrrolidine-1-sulfonamide A solution of 6-((3-amino-2-chloro-5,6-difluorophenyl)amino)-3,5-dimethylquinazolin-4(3H)-one (125 mg, 0.35 mmol) and (R)-3-fluoropyrrolidine-1-sulfonyl chloride (334.3 mg, 1.78 mmol) in pyridine (3.6 mL) was heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na₂SO₄, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:APA and saturated aqueous NaHCO₃ (1×) and the organic layer was separated, dried over anhydrous Na₂SO₄, filtered, and concentrated to give (R)-N-(2-chloro-3-((3,5-dimethyl-4-oxo-3,4-dihydroquinazolin-6-yl)amino)-4,5-difluorophenyl)-3-fluoropyrrolidine-1-sulfonamide (50 mg, 28%) as an off-white solid. ¹H NMR (400 MHz, CDCl₃) δ 7.95 (s, 1H), 7.49-7.46 (d, 1H), 7.32-7.27 (m, 1H), 7.15-7.13 (m, 1H), 6.81 (s, 1H), 5.65 (s, 1H), 5.32-5.16 (m, 1H), 3.71-3.47 (m, 7H), 2.96 (s, 3H), 2.34-1.98 (m, 2H); MS (apci, m/z)=502.1, 504.1 (M+H).

Example 36

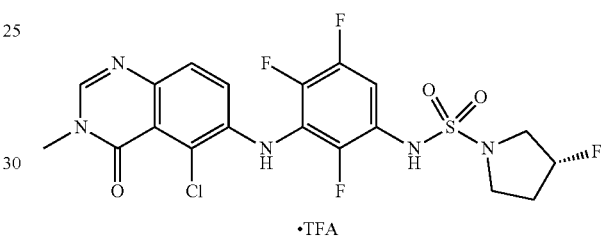

·TFA (R)-N-(3-((5-chloro-3-methyl-4-oxo-3,4-dihydroquinazolin-6-yl)amino)-2,4,5-trifluorophenyl)-3-fluoropyrrolidine-1-sulfonamide trifluoroacetate To a solution of 6-((3-amino-2,5,6-trifluorophenyl)amino)-5-chloro-3-methylquinazolin-4(3H)-one (13 mg, 0.037 mmol) in pyridine (183 μL, 0.037 mmol) was added (R)-3-fluoropyrrolidine-1-sulfonyl chloride (17 mg, 0.092 mmol) and the reaction mixture was heated in a sealed vial to 70° C. for 6 hours. The solution was cooled to ambient temperature, concentrated and purified by reverse-phase chromatography (5-95% MeCN/water, 0.1% TFA). The product was lyophilized to give (R)-N-(3-((5-chloro-3-methyl-4-oxo-3,4-dihydroquinazolin-6-yl)amino)-2,4,5-trifluorophenyl)-3-fluoropyrrolidine-1-sulfonamide trifluoroacetate (5 mg, 27% yield). ¹H NMR (400 MHz, CDCl₃) δ 8.55 (s, 1H), 7.64 (d, 1H), 7.45-7.38 (m, 1H), 7.16-7.12 (m, 1H), 6.65 (s, br, 1H), 6.40 (s, 1H), 5.25 (d, 1H), 3.69 (s, 3H), 3.66-3.44 (m, 4H), 2.35-2.00 (m, 2H); MS (apci, m/z)=506.1 (M+H).

Example 37

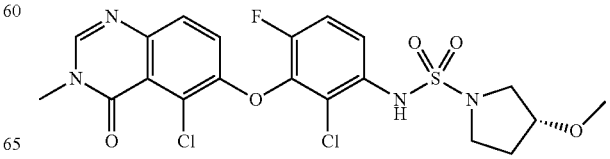

(R)-N-(2-chloro-3-((5-chloro-3-methyl-4-oxo-3,4-dihydroquinazolin-6-yl)oxy)-4-fluorophenyl)-3-methoxypyrrolidine-1-sulfonamide A solution of 6-(3-amino-2-chloro-6-fluorophenoxy)-5-chloro-3-methylquinazolin-4(3H)-one (96 mg, 0.2711 mmol) and (R)-3-methoxypyrrolidine-1-sulfonyl chloride (270.6 mg, 1.355 mmol) in pyridine (2.2 mL) was heated at 70° C. for 18 hours. The reaction mixture was cooled to ambient temperature, then partitioned between DCM (75 mL) and 10% aqueous CuSO₄ (75 mL). The organic phase was dried over Na₂SO₄, filtered, and concentrated under reduced pressure. The reaction mixture was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO₃ (30 mL) and DCM (15×3 mL). The organic phase was separated, dried over Na₂SO₄, filtered, and concentrated under reduced pressure to afford (R)-N-(2-chloro-3-((5-chloro-3-methyl-4-oxo-3,4-dihydroquinazolin-6-yl)oxy)-4-fluorophenyl)-3-methoxypyrrolidine-1-sulfonamide (38.53 mg, 27%) as a white solid. ¹H NMR (400 MHz, CDCl₃) δ 7.99 (s, 1H), 7.61-7.56 (m, 1H), 7.50 (d, 1H), 7.14 (t, 1H), 7.04-7.00 (m, 2H), 3.97-3.92 (m, 1H), 3.57 (s, 3H), 3.52-3.37 (m, 4H), 3.25 (s, 3H), 2.13-2.04 (m, 1H), 2.00-1.87 (m, 1H); MS (apci, m/z)=517.0 (M+H).

Example 38

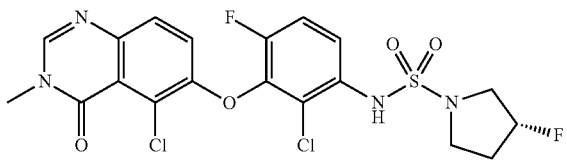 [SMILES: Cn1cnc2ccc(Oc3c(F)ccc(NS(=O)(=O)N4CC[C@@H](F)C4)c3Cl)c(Cl)c2c1=O]

(R)-N-(2-chloro-3-((5-chloro-3-methyl-4-oxo-3,4-dihydroquinazolin-6-yl)oxy)-4-fluorophenyl)-3-fluoropyrrolidine-1-sulfonamide A solution of 6-(3-amino-2-chloro-6-fluorophenoxy)-5-chloro-3-methylquinazolin-4(3H)-one (75 mg, 0.2118 mmol) and (R)-3-fluoropyrrolidine-1-sulfonyl chloride (119.2 mg, 0.6353 mmol) in pyridine (1.8 mL) was heated at 70° C. for 48 hours. The reaction mixture was cooled to ambient temperature and partitioned between DCM (50 mL) and 10% aqueous CuSO₄ (50 mL). The organic phase was dried over Na₂SO₄, filtered then concentrated under reduced pressure. The reaction mixture was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO₃ (15 mL) and DCM (30 mL). The organic phase was separated, dried over Na₂SO₄, filtered and concentrated under reduced pressure to afford (R)-N-(2-chloro-3-((5-chloro-3-methyl-4-oxo-3,4-dihydroquinazolin-6-yl)oxy)-4-fluorophenyl)-3-fluoropyrrolidine-1-sulfonamide (39.6 mg, 37%) as a white solid. ¹H NMR (400 MHz, CDCl₃) δ 8.00 (s, 1H), 7.63-7.58k (m, 1H), 7.50 (d, 1H), 7.15 (t, 1H), 7.03-6.99 (d, 1H), 6.89 (s, 1H), 5.30-5.13 (m, 1H), 3.68-3.42 (m, 7H), 2.32-2.18 (m, 1H), 2.13-1.93 (m, 1H); MS (apci, m/z)=505.0 (M+H).

Example 39

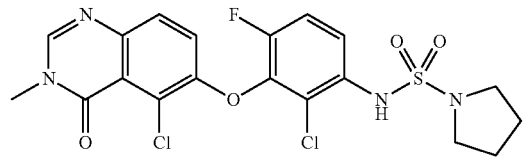 [SMILES: Cn1cnc2ccc(Oc3c(F)ccc(NS(=O)(=O)N4CCCC4)c3Cl)c(Cl)c2c1=O]

N-(2-chloro-3-((5-chloro-3-methyl-4-oxo-3,4-dihydroquinazolin-6-yl)oxy)-4-fluorophenyl)pyrrolidine-1-sulfonamide A solution of 6-(3-amino-2-chloro-6-fluorophenoxy)-5-chloro-3-methylquinazolin-4(3H)-one (50 mg, 0.141 mmol) and pyrrolidine-1-sulfonyl chloride (120 mg, 0.706 mmol) in pyridine (1.1 mL) was stirred at 70° C. for 48 hours. The reaction mixture was cooled to ambient temperature, then partitioned between DCM (50 mL) and 10% aqueous CuSO₄ (50 mL). The organic phase was dried over Na₂SO₄, filtered then concentrated under reduced pressure. The reaction mixture was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO₃ (15 mL) and DCM (30 mL). The organic phase was separated, dried over Na₂SO₄, filtered, and concentrated under reduced pressure to afford N-(2-chloro-3-((5-chloro-3-methyl-4-oxo-3,4-dihydroquinazolin-6-yl)oxy)-4-fluorophenyl)pyrrolidine-1-sulfonamide (45.6 mg, 66%) as a white solid. ¹H NMR (400 MHz, CDCl₃) δ 8.00 (s, 1H), 7.60-7.55 (m, 1H), 7.49 (d, 1H), 7.14 (t, 1H), 7.00 (d, 1H), 6.93 (s, 1H), 3.57 (s, 3H), 3.36-3.26 (m, 4H), 1.90-1.80 (m, 4H); MS (apci, m/z)=487.0 (M+H).

Example 40

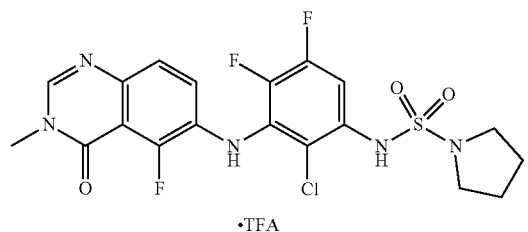 [SMILES: Cn1cnc2ccc(Nc3c(F)c(F)cc(NS(=O)(=O)N4CCCC4)c3Cl)c(F)c2c1=O]

N-(2-chloro-4,5-difluoro-3-((5-fluoro-3-methyl-4-oxo-3,4-dihydroquinazolin-6-yl)amino)phenyl)pyrrolidine-1-sulfonamide trifluoroacetate A solution of 6-((3-amino-2-chloro-5,6-difluorophenyl)amino)-5-fluoro-3-methylquinazolin-4(3H)-one (35 mg, 0.09867 mmol) and pyrrolidine-1-sulfonyl chloride (41.84 mg, 0.2467 mmol) in pyridine (0.49 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide N-(2-chloro- 4,5-difluoro-3-((5-fluoro-3-methyl-4-oxo-3,4-dihydroquinazolin-6-yl)amino)phenyl)pyrrolidine-1-sulfonamide trifluoroacetate (32.4 mg, 67%). ¹H NMR (400 MHz, CDCl₃) δ 8.55 (s, 1H), 7.54 (d, 1H), 7.46-7.41 (m, 1H), 7.19-7.13 (m, 1H), 6.85 (s, 1H), 6.05 (s, 1H), 3.68 (s, 3H), 3.40-3.36 (m, 4H), 1.95-1.92 (m, 4H). MS (apci, m/z)=488.1 (M+H).

Example 41

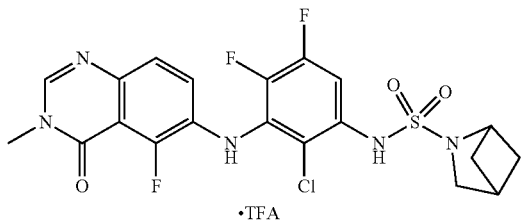 [SMILES: Cn1cnc2ccc(Nc3c(F)c(F)cc(NS(=O)(=O)N4CC5CC4C5)c3Cl)c(F)c2c1=O]

·TFA

N-(2-chloro-4,5-difluoro-3-((5-fluoro-3-methyl-4-oxo-3,4-dihydroquinazolin-6-yl)amino)phenyl)-2-azabicyclo[2.1.1]hexane-2-sulfonamide trifluoroacetate A solution of 6-((3-amino-2-chloro-5,6-difluorophenyl)amino)-5-fluoro-3-methylquinazolin-4(3H)-one (35 mg, 0.09867 mmol) and 2-azabicyclo[2.1.1]hexane-2-sulfonyl chloride (44.80 mg, 0.2467 mmol) in pyridine (0.49 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide N-(2-chloro-4,5-difluoro-3-((5-fluoro-3-methyl-4-oxo-3,4-dihydroquinazolin-6-yl)amino)phenyl)-2-azabicyclo[2.1.1]hexane-2-sulfonamide trifluoroacetate (16.4 mg, 33%). ¹H NMR (400 MHz, CDCl₃) δ 8.39 (s, 1H), 7.52-7.46 (m, 2H), 7.17-7.11 (m, 1H), 6.88 (s, 1H), 6.02 (s, 1H), 4.27 (d, 1H), 3.65 (s, 3H), 3.41 (s, 2H), 2.93-2.90 (m, 1H), 1.99-1.95 (m, 2H), 1.56-1.55 (m, 2H). MS (apci, m/z)=500.1 (M+H).

Example 42

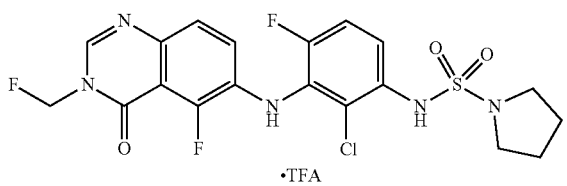 [SMILES: O=c1c2c(F)c(Nc3c(F)ccc(NS(=O)(=O)N4CCCC4)c3Cl)ccc2ncn1CF]

·TFA

N-(2-chloro-4-fluoro-3-((5-fluoro-3-(fluoromethyl)-4-oxo-3,4-dihydroquinazolin-6-yl)amino)phenyl)pyrrolidine-1-sulfonamide trifluoroacetate Step 1: Preparation of 6-bromo-5-fluoro-3-(fluoromethyl)quinazolin-4(3H)-one. 6-Bromo-5-fluoroquinazolin-4(3H)-one (0.512 g, 2.107 mmol) was dissolved in N,N-dimethylformamide (5.26 mL) and treated with iodofluoromethane (0.1566 mL, 2.317 mmol) and potassium carbonate (0.4367 g, 3.160 mmol). The reaction was maintained at ambient temperature for 16 hours. The crude reaction mixture was diluted with DCM (30 mL) and filtered through Celite®. The filtrate was washed with water (20 mL). The organic layer was collected, dried over MgSO₄, and concentrated to provide 6-bromo-5-fluoro-3-(fluoromethyl)quinazolin-4(3H)-one which was used in the next step without purification.

Step 2: Preparation of tert-butyl (5-fluoro-3-(fluoromethyl)-4-oxo-3,4-dihydroquinazolin-6-yl)carbamate. 6-Bromo-5-fluoro-3-(fluoromethyl)quinazolin-4(3H)-one (500 mg, 1.82 mmol) was dissolved in toluene (18 mL) and treated with tert-butyl carbamate (224 mg, 1.91 mmol), Tris(dibenzylideneacetone)dipalladium (0) (83.2 mg, 0.0909 mmol), Xantphos (158 mg, 0.273 mmol), and cesium carbonate (1777 mg, 5.45 mmol). The solution was sparged with argon for several minutes and then heated and stirred at 110° C. under an atmosphere of argon for 18 hours. The reaction mixture was cooled to ambient temperature and diluted with DCM (30 mL) and stirred for 15 minutes then filtered through Celite® and concentrated. The resulting residue was purified by silica gel chromatography (55-95% EtOAc/Hexanes) to provide (5-fluoro-3-(fluoromethyl)-4-oxo-3,4-dihydroquinazolin-6-yl)carbamate (270 mg, 47% over two-steps). MS (apci, m/z)=312.1 (M+H).

Step 3: Preparation of 6-amino-5-fluoro-3-(fluoromethyl)quinazolin-4(3H)-one. (5-Fluoro-3-(fluoromethyl)-4-oxo-3,4-dihydroquinazolin-6-yl)carbamate (267 mg, 0.858 mmol) was dissolved in 10 mL of a 1:1 TFA/DCM solution and the reaction mixture was stirred at ambient temperature for 15 minutes. The solvent was removed in vacuo. The resulting residue was dissolved in 4:1 DCM/IPA (10 mL) and washed with saturated aqueous NaHCO₃ (10 mL, ×3). The organic layer was dried over MgSO₄, filtered, and concentrated to provide 6-amino-5-fluoro-3-(fluoromethyl)quinazolin-4(3H)-one which was used with further purification. MS (apci, m/z)=212.1 (M+H).

Step 4: Preparation of tert-butyl (2-chloro-4-fluoro-3-((5-fluoro-3-(fluoromethyl)-4-oxo-3,4-dihydroquinazolin-6-yl)amino)phenyl)carbamate. 6-Amino-5-fluoro-3-(fluoromethyl)quinazolin-4(3H)-one (200 mg, 0.947 mmol) was dissolved in toluene (9 mL) and treated with tert-butyl (2-chloro-4-fluoro-3-iodophenyl)carbamate (370 mg, 0.994 mmol), tris(dibenzylideneacetone)dipalladium (0) (43.4 mg, 0.0474 mmol), Xantphos (82.2 mg, 0.142 mmol), and cesium carbonate (926 mg, 2.84 mmol). The solution was sparged with argon for several minutes and then heated and stirred at 110° C. under an atmosphere of argon for 6 hours. The reaction mixture was cooled to ambient temperature and diluted with DCM (15 mL) and stirred for 15 minutes then filtered through Celite and concentrated. The resulting residue was purified by silica gel chromatography (25-75% EtOAc/Hexanes) to provide tert-butyl (2-chloro-4-fluoro-3-((5-fluoro-3-(fluoromethyl)-4-oxo-3,4-dihydroquinazolin-6-yl)amino)phenyl)carbamate (332 mg, 75% over two-steps). MS (apci, m/z)=455.1 (M+H).

Step 5: Preparation of 6-((3-amino-2-chloro-6-fluorophenyl)amino)-5-fluoro-3-(fluoromethyl)quinazolin-4(3H)-one. Tert-butyl (2-chloro-4-fluoro-3-((5-fluoro-3-(fluoromethyl)-4-oxo-3,4-dihydroquinazolin-6-yl)amino)phenyl)carbamate (322 mg, 0.708 mmol) was dissolved in 10 mL of a 1:1 TFA/DCM solution and the reaction mixture was stirred at ambient temperature for 15 minutes. The solvent was removed in vacuo. The resulting residue was dissolved in 4:1 DCM/IPA (10 mL) and washed with saturated aqueous NaHCO₃ (10 mL, ×3). The organic layer was dried over MgSO₄, filtered, and concentrated to provide 6-((3-amino-2-chloro-6-fluorophenyl)amino)-5-fluoro-3-(fluoromethyl)quinazolin-4(3H)-one (96 mg, 38%) which was used with further purification. MS (apci, m/z)=355.1 (M+H).

Step 6: Preparation of N-(3-((5-chloro-3-methyl-4-oxo-3,4-dihydroquinazolin-6-yl)amino)-2,4,5-trifluorophenyl)pyrrolidine-1-sulfonamide trifluoroacetate. A solution of 6-((3-amino-2-chloro-6-fluorophenyl)amino)-5-fluoro-3-(fluoromethyl)quinazolin-4(3H)-one (20 mg, 0.05638 mmol) and pyrrolidine-1-sulfonyl chloride (23.91 mg, 0.1410 mmol), in pyridine (0.28 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide N-(2-chloro-4-fluoro-3-((5-fluoro-3-(fluoromethyl)-4-oxo-3,4-dihydroquinazolin-6-yl)amino)phenyl)pyrrolidine-1-sulfonamide trifluoroacetate (15.4 mg, 56%). ¹H NMR (400 MHz, CDCl₃) δ 8.28 (s, 1H), 7.58-7.54 (m, 1H), 7.48-7.46 (m, 1H), 7.16 (t, 1H), 7.09-7.04 (m, 1H), 6.77 (s, 1H), 6.05 (d, 2H), 6.00 (s, 1H), 3.37-3.34 (m, 4H), 1.91-1.88 (m, 4H). MS (apci, m/z)=488.1 (M+H).

Example 43

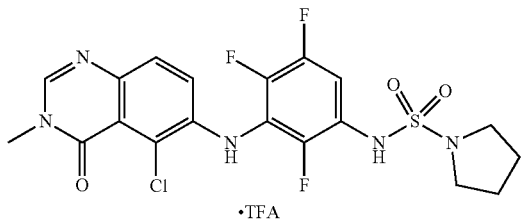 [SMILES: Cn1cnc2ccc(Nc3c(F)c(F)cc(NS(=O)(=O)N4CCCC4)c3F)c(Cl)c2c1=O]

N-(3-((5-chloro-3-methyl-4-oxo-3,4-dihydroquinazolin-6-yl)amino)-2,4,5-trifluorophenyl)pyrrolidine-1-sulfonamide trifluoroacetate To a solution of 6-((3-amino-2,5,6-trifluorophenyl)amino)-5-chloro-3-methylquinazolin-4(3H)-one (13 mg, 0.037 mmol) in pyridine (183 µL, 0.0366 mmol) was added pyrrolidine-1-sulfonyl chloride (10.5 µL, 0.0916 mmol) and the reaction mixture was heated in a sealed vial to 70° C. for 5 hours. The solution was concentrated and the residue was purified by reverse-phase chromatography (5-95% MeCN/water, 0.1% TFA). The product was lyophilized to give N-(3-((5-chloro-3-methyl-4-oxo-3,4-dihydroquinazolin-6-yl)amino)-2,4,5-trifluorophenyl)pyrrolidine-1-sulfonamide trifluoroacetate (9 mg, 50.3%). ¹H NMR (400 MHz, CDCl₃) δ 8.60 (s, 1H), 7.67 (d, 1H), 7.39-7.33 (m, 1H), 7.16-7.12 (m, 1H), 6.58 (s, br, 1H), 6.42 (s, 1H), 3.69 (s, 3H), 3.40-3.36 (m, 4H), 1.96-1.92 (m, 4H); MS (apci, m/z)=488.1 (M+H).

Example 44

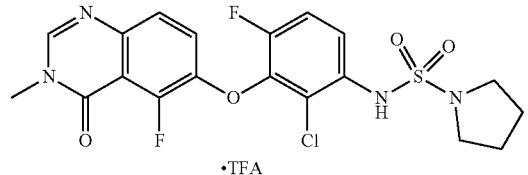 [SMILES: Cn1cnc2ccc(Oc3c(F)ccc(NS(=O)(=O)N4CCCC4)c3Cl)c(F)c2c1=O]

N-(2-chloro-4-fluoro-3-((5-fluoro-3-methyl-4-oxo-3,4-dihydroquinazolin-6-yl)oxy)phenyl)pyrrolidine-1-sulfonamide trifluoroacetate A solution of 6-(3-amino-2-chloro-6-fluorophenoxy)-5-fluoro-3-methylquinazolin-4(3H)-one (85 mg, 0.2517 mmol) and pyrrolidine-1-sulfonyl chloride (106.7 mg, 0.6292 mmol) in pyridine (1.26 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide N-(2-chloro-4-fluoro-3-((5-fluoro-3-methyl-4-oxo-3,4-dihydroquinazolin-6-yl)oxy)phenyl)pyrrolidine-1-sulfonamide trifluoroacetate (119 mg, 68%). ¹H NMR (400 MHz, CDCl₃) δ 8.31 (s, 1H), 7.60-4.56 (m, 1H), 7.31-7.27 (m, 1H), 7.14 (t, 1H), 6.77 (s, 1H), 3.63 (s, 3H), 3.35-3.32 (m, 4H), 1.91-1.87 (m, 4H). MS (apci, m/z)=471.1 (M+H).

Example 45

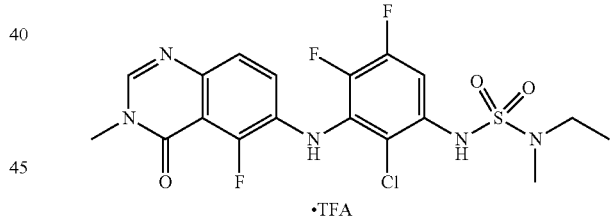

N-(2-chloro-4,5-difluoro-3-((5-fluoro-3-methyl-4-oxo-3,4-dihydroquinazolin-6-yl)phenyl)-(N-ethyl-N-methyl)-sulfamide trifluoroacetate A solution of 6-((3-amino-2-chloro-5,6-difluorophenyl)amino)-5-fluoro-3-methylquinazolin-4(3H)-one (30 mg, 0.08457 mmol) and N-ethyl-N-methylsulfamoyl chloride (33.32 mg, 0.2114 mmol), in pyridine (0.42 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide N-(2-chloro-4,5-difluoro-3-((5-fluoro-3-methyl-4-oxo-3,4-dihydroquinazolin-6-yl)phenyl)-(N-ethyl-N-methyl)-sulfamide trifluoroacetate (26.1 mg, 65%). ¹H NMR (400 MHz, CDCl₃) δ 8.38 (s, 1H), 7.52-7.50 (d, 1H), 7.39-7.34 (m, 1H), 7.18-7.12

(m, 1H), 6.78 (s, 1H), 6.03 (s, 1H), 3.66 (s, 3H), 3.34-3.29 (m, 2H), 2.88 (s, 3H), 1.20-1.16 (t, 3H); MS (apci, m/z)=476.1 (M+H).

Example 46

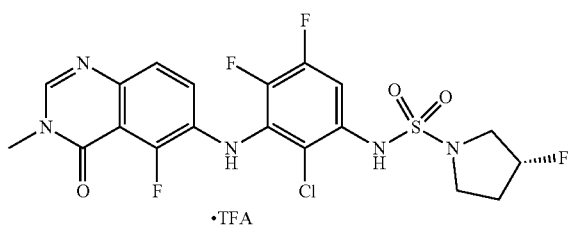 [SMILES: Cn1cnc2ccc(Nc3c(F)c(F)cc(NS(=O)(=O)N4CC[C@@H](F)C4)c3Cl)c(F)c2c1=O]
·TFA (R)-N-(2-chloro-4,5-difluoro-3-((5-fluoro-3-methyl-4-oxo-3,4-dihydroquinazolin-6-yl)amino)phenyl)-3-fluoropyrrolidine-1-sulfonamide trifluoroacetate. A solution of 6-((3-amino-2-chloro-5,6-difluorophenyl)amino)-5-fluoro-3-methylquinazolin-4(3H)-one (30 mg, 0.08457 mmol) and (R)-3-fluoropyrrolidine-1-sulfonyl chloride (39.67 mg, 0.2114 mmol) in pyridine (0.42 mL) was sealed and heated at 70° C. for 18 hours. The reaction mixture was cooled to ambient temperature and diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide (R)-N-(2-chloro-4,5-difluoro-3-((5-fluoro-3-methyl-4-oxo-3,4-dihydroquinazolin-6-yl)amino)phenyl)-3-fluoropyrrolidine-1-sulfonamide trifluoroacetate (24.1 mg, 56%). ¹H NMR (400 MHz, CDCl₃) δ 8.37 (s, 1H), 7.52-7.45 (m, 2H), 7.16-7.11 (m, 1H), 6.85 (s, 1H), 6.01 (s, 1H), 5.32-5.17 (m, 1H), 3.68-3.62 (m, 5H), 3.55-3.47 (m, 2H), 2.35-2.25 (m, 1H), 2.18-1.98 (m, 1H). MS (apci, m/z)=506.1 (M+H).

Example 47

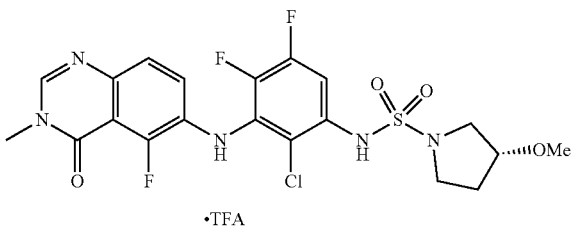 [SMILES: CO[C@@H]1CCN(S(=O)(=O)Nc2cc(F)c(F)c(Nc3ccc4ncn(C)c(=O)c4c3F)c2Cl)C1]
·TFA (R)-N-(2-chloro-4,5-difluoro-3-((5-fluoro-3-methyl-4-oxo-3,4-dihydroquinazolin-6-yl)amino)phenyl)-3-methoxypyrrolidine-1-sulfonamide trifluoroacetate A solution of 6-((3-amino-2-chloro-5,6-difluorophenyl)amino)-5-fluoro-3-methylquinazolin-4(3H)-one (30 mg, 0.08457 mmol) and (R)-3-methoxypyrrolidine-1-sulfonyl chloride (42.21 mg, 0.2114 mmol) in pyridine (0.42 mL) was sealed and heated at 70° C. for 18 hours. The reaction mixture was cooled to ambient temperature, diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide (R)-N-(2-chloro-4,5-difluoro-3-((5-fluoro-3-methyl-4-oxo-3,4-dihydroquinazolin-6-yl)amino)phenyl)-3-methoxypyrrolidine-1-sulfonamide trifluoroacetate (16.4 mg, 37%). ¹H NMR (400 MHz, CDCl₃) δ 8.42 (s, 1H), 7.53-7.44 (m, 2H), 7.17-7.12 (m, 1H), 7.03 (s, 1H), 6.03 (s, 1H), 4.00-3.98 (m, 1H), 3.66 (s, 3H), 3.59-3.43 (m, 4H), 3.29 (s, 3H), 2.18-2.12 (m, 1H), 2.03-1.94 (m, 1H). MS (apci, m/z)=518.1 (M+H).

Example 48

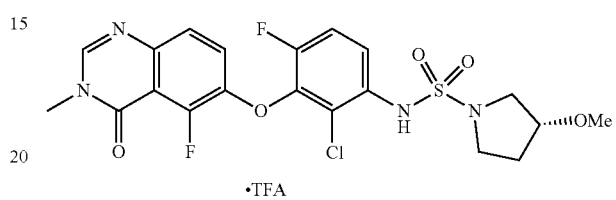
·TFA (R)-N-(2-chloro-4-fluoro-3-((5-fluoro-3-methyl-4-oxo-3,4-dihydroquinazolin-6-yl)oxy)phenyl)-3-methoxypyrrolidine-1-sulfonamide trifluoroacetate A solution of 6-(3-amino-2-chloro-6-fluorophenoxy)-5-fluoro-3-methylquinazolin-4(3H)-one (102 mg, 0.3020 mmol) and (R)-3-methoxypyrrolidine-1-sulfonyl chloride (150.8 mg, 0.7551 mmol) in pyridine (1.51 mL) was sealed and heated at 70° C. for 18 hours. The reaction mixture was cooled to ambient temperature, diluted with DCM (15 mL) and washed with 10% aqueous CuSO₄ (15 mL). The DCM extract was dried over MgSO₄, concentrated and the residue was purified by reverse phase chromatography (5-95% ACN/water with 0.1% TFA) to provide (R)-N-(2-chloro-4-fluoro-3-((5-fluoro-3-methyl-4-oxo-3,4-dihydroquinazolin-6-yl)oxy)phenyl)-3-methoxypyrrolidine-1-sulfonamide trifluoroacetate (78.3 mg, 52%). ¹H NMR (400 MHz, CDCl₃) δ 8.16 (s, 1H), 7.60-7.57 (m, 1H), 7.48-7.45 (m, 1H), 7.27-7.23 (m, 1H), 7.13 (t, 1H), 6.94 (s, 1H), 3.97-3.94 (m, 1H), 3.61 (s, 3H), 3.52-3.40 (m, 4H), 3.27 (s, 3H) 2.13-2.07 (m, 1H), 2.00-1.91 (m, 1H). MS (apci, m/z)=501.1 (M+H).

Example 49

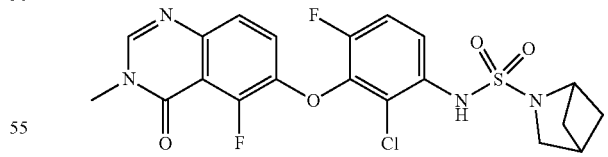

N-(2-chloro-4-fluoro-3-((5-fluoro-3-methyl-4-oxo-3,4-dihydroquinazolin-6-yl)oxy)phenyl)-2-azabicyclo[2.1.1]hexane-2-sulfonamide To a solution of 6-(3-amino-2-chloro-6-fluorophenoxy)-5-fluoro-3-methylquinazolin-4(3H)-one (15 mg, 0.044 mmol) in pyridine (222 µL, 0.044 mmol) was added 2-azabicyclo[2.1.1]hexane-2-sulfonyl chloride (24 mg, 0.13 mmol) and the reaction mixture was heated in a sealed vial to 70°

C. for 16 hours. The solution was concentrated and purified by reverse-phase chromatography (5-95% MeCN/water, 0.1% TFA). The product was partitioned between dichloromethane and saturated NaHCO$_3$. The combined organic layers were washed with brine, dried with Na$_2$SO$_4$, filtered, and concentrated to give N-(2-chloro-4-fluoro-3-((5-fluoro-3-methyl-4-oxo-3,4-dihydroquinazolin-6-yl)oxy)phenyl)-2-azabicyclo[2.1.1]hexane-2-sulfonamide (7 mg, 33%). $^1$H NMR (400 MHz, CDCl$_3$) δ 7.98 (s, 1H), 7.60-7.56 (m, 1H), 7.44-7.42 (m, 1H), 7.27-7.14 (m, 1H), 7.14-7.10 (t, 1H), 6.84 (s, br, 1H), 4.24-7.22 (m, 1H), 3.58 (s, 3H), 2.89-2.86 (m, 1H), 2.35 (s, 2H), 1.94-1.91 (m, 2H), 1.52-1.50 (m, 2H); MS (apci, m/z)=483.1 (M+H).

Example 50

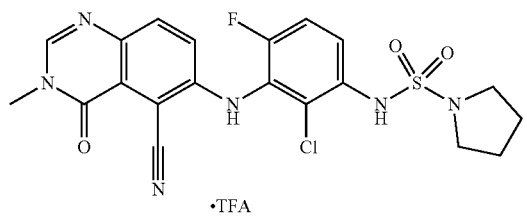 [SMILES: Cn1cnc2ccc(Nc3c(F)ccc(NS(=O)(=O)N4CCCC4)c3Cl)c(C#N)c2c1=O]

N-(2-chloro-3-((5-cyano-3-methyl-4-oxo-3,4-dihydroquinazolin-6-yl)amino)-4-fluorophenyl)pyrrolidine-1-sulfonamide trifluoroacetate N-(3-((5-bromo-3-methyl-4-oxo-3,4-dihydroquinazolin-6-yl)amino)-2-chloro-4-fluorophenyl)pyrrolidine-1-sulfonamide 2,2,2-trifluoroacetate (60 mg, 0.09305 mmol) and copper (1) cyanide (33.34 mg, 0.3722 mmol) in N,N-dimethylformamide (0.93 mL) was sealed in a vial and heated to 100° C. for 4 hours. The reaction was allowed to cool to ambient temperature. The crude solution was filtered through a 0.45 μm syringe filter and extracted between H$_2$O and 4:1 DCM/IPA. The combined organic layers were collected, dried over MgSO$_4$, and concentrated. The crude mixture was purified by reverse-phase chromatography (5-95% MeCN/water, 0.1% TFA) to provide N-(2-chloro-3-((5-cyano-3-methyl-4-oxo-3,4-dihydroquinazolin-6-yl)amino)-4-fluorophenyl)pyrrolidine-1-sulfonamide trifluoroacetate (10.8 mg, 24%). $^1$H NMR (400 MHz, CDCl$_3$) δ 8.21 (s, 1H), 7.78 (d, 1H), 7.68-7.65 (m, 1H), 7.19 (t, 1H), 6.78 (s, 1H), 6.69 (s, 1H), 3.68 (s, 3H), 3.37-3.34 (m, 4H), 1.92-1.89 (m, 4H). MS (apci, m/z)=477.1 (M+H).

Example 51

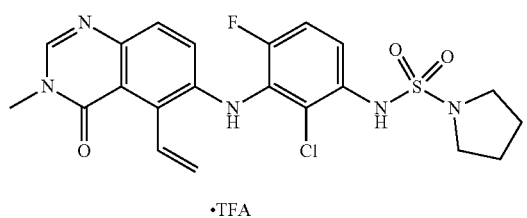 [SMILES: C=Cc1c(Nc2c(F)ccc(NS(=O)(=O)N3CCCC3)c2Cl)ccc2ncn(C)c(=O)c12]

N-(2-chloro-4-fluoro-3-((3-methyl-4-oxo-5-vinyl-3,4-dihydroquinazolin-6-yl)amino)phenyl)pyrrolidine-1-sulfonamide trifluoroacetate N-(3-((5-bromo-3-methyl-4-oxo-3,4-dihydroquinazolin-6-yl)amino)-2-chloro-4-fluorophenyl)pyrrolidine-1-sulfonamide 2,2,2-trifluoroacetate (100 mg, 0.155 mmol) and cesium carbonate (126 mg, 0.388 mmol) were dissolved in 3.2 mL dioxane and 1.0 mL water. To the solution were added vinylboronic acid pinacol cyclic ester (65.8 μl, 0.388 mmol) and dichloro[1,1'-bis(diphenylphosphino)ferrocene] palladium dichloromethane adduct (3.80 mg, 0.00465 mmol). The solution was heated to 80° C. for 16 hours. The reaction was allowed to cool to ambient temperature. The crude solution was filtered through a 0.45 μm syringe filter and extracted between H$_2$O (5 mL) and DCM (5 mL, ×2). The combined organic layers were collected, dried over MgSO$_4$, and concentrated. The crude mixture was purified by reverse-phase chromatography (5-95% MeCN/water, 0.1% TFA) to provide N-(2-chloro-4-fluoro-3-((3-methyl-4-oxo-5-vinyl-3,4-dihydroquinazolin-6-yl)amino)phenyl)pyrrolidine-1-sulfonamide trifluoroacetate (29.0 mg, 39%). $^1$H NMR (400 MHz, CDCl$_3$) δ 8.66 (s, 1H), 7.63 (d, 1H), 7.56-7.52 (m, 1H), 7.41-7.33 (m, 1H), 7.14 (t, 1H), 7.00-6.97 (m, 1H), 6.74 (s, 1H), 6.63 (s, 1H), 5.87-5.84 (m, 1H), 5.66-5.61 (m, 1H), 3.65 (s, 3H), 3.37-3.34 (m, 4H), 1.91-1.88 (m, 4H). MS (apci, m/z)=478.1 (M+H).

Example 52

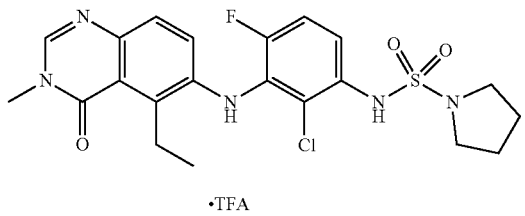 [SMILES: CCc1c(Nc2c(F)ccc(NS(=O)(=O)N3CCCC3)c2Cl)ccc2ncn(C)c(=O)c12]

N-(2-chloro-3-((5-ethyl-3-methyl-4-oxo-3,4-dihydroquinazolin-6-yl)amino)-4-fluorophenyl)pyrrolidine-1-sulfonamide trifluoroacetate To a solution of N-(2-chloro-4-fluoro-3-((3-methyl-4-oxo-5-vinyl-3,4-dihydroquinazolin-6-yl)amino)phenyl)pyrrolidine-1-sulfonamide 2,2,2-trifluoroacetate (11 mg, 0.0186 mmol) in methanol (372 μL) was added palladium on carbon (10% wt., 8 mg, 0.00752 mmol) and the reaction mixture was sparged with Ar for 5 minutes then stirred at ambient temperature under a balloon of hydrogen gas for 30 minutes. The reaction mixture was filtered through a 0.45 μm syringe filter, and the crude solution was purified by reverse phase chromatography (5-95 H$_2$O/ACN, 0.1% TFA) to provide N-(2-chloro-3-((5-ethyl-3-methyl-4-oxo-3,4-dihydroquinazolin-6-yl)amino)-4-fluorophenyl)pyrrolidine-1-sulfonamide trifluoroacetate (8.8 mg, 99%). $^1$H NMR (400 MHz, CDCl$_3$) δ 8.71 (s, 1H), 7.59 (d, 1H), 7.50-7.46 (m, 1H), 7.13 (t, 1H), 7.05-7.02 (m, 1H), 6.74 (s, 1H), 5.84 (s, 1H), 3.67 (s, 3H), 3.54-3.48 (m, 2H), 3.38-3.35 (m, 4H), 1.92-1.89 (m, 4H), 1.37 (t, 2H). MS (apci, m/z)=480.2 (M+H).

Example 53

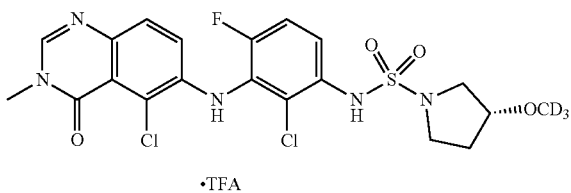

•TFA (R)-N-(2-chloro-3-((5-chloro-3-methyl-4-oxo-3,4-dihydroquinazolin-6-yl)amino)-4-fluorophenyl)-3-(methoxy-d3)pyrrolidine-1-sulfonamide trifluoroacetate Step 1: Preparation of (3R)-3-(methoxy-d3)pyrrolidine hydrochloride. Tert-butyl (R)-3-hydroxypyrrolidine-1-carboxylate (1.00 g, 5.34 mmol) was dissolved in N,N-dimethylformamide (26.7 mL, 5.34 mmol) and cooled to 0° C. Sodium hydride (0.214 g, 5.34 mmol) was added, and the resulting solution was warmed to ambient temperature and maintained for 10 minutes. Iodomethane-d3 (0.349 mL, 5.61 mmol) was added to the reaction, and allowed to stir at ambient temperature for one hour. The reaction was worked up by addition of 20 mL H$_2$O. The solution was extracted with DCM (2×20 mL) and the organic layer collected and concentrated. The crude product was purified by silica gel chromatography (0-10% MeOH in DCM). The desired fractions were collected and concentrated. The resulting pyrrolidine was dissolved in DCM (10 mL) and 3 mL of 5N HCl in isopropyl alcohol was added. The reaction was allowed to stir at ambient temperature overnight before the volatiles were concentrated to provide the desired product (605 mg, 81%) which was used as is in the following step.

Step 2: Preparation of (3R)-3-(methoxy-d3)pyrrolidine-1-sulfonyl chloride. A slurry of (3R)-3-(methoxy-d3)pyrrolidine hydrochloride (0.448 g, 4.30 mmol) and N-ethyl-N-isopropylpropan-2-amine (1.12 mL, 6.45 mmol) was stirred in DCM (14.3 mL) at ambient temperature until the mixture was fully dissolved. The reaction mixture was cooled to 0° C. and treated with sulfuryl chloride (0.70 mL, 8.60 mmol). The mixture was warmed to ambient temperature after 30 minutes and allowed to stir for 18 hours. The reaction mixture was diluted with additional DCM (20 mL) and washed with 1.0 M HCl (20 mL). The organic layer was separated, dried over anhydrous MgSO$_4$, filtered, and concentrated to provide crude (3R)-3-(methoxy-d3)pyrrolidine-1-sulfonyl chloride, which was used as is in the next step.

Step 3: Preparation of (R)-N-(2-chloro-3-((5-chloro-3-methyl-4-oxo-3,4-dihydroquinazolin-6-yl)amino)-4-fluorophenyl)-3-(methoxy-d3)pyrrolidine-1-sulfonamide trifluoroacetate. A solution of 6-((3-amino-2-chloro-6-fluorophenyl)amino)-5-chloro-3-methylquinazolin-4(3H)-one (25 mg, 0.07079 mmol) and (R)-3-(methoxy-d3)pyrrolidine-1-sulfonyl chloride (28.69 mg, 0.1416 mmol), in pyridine (0.35 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide (R)-N-(2-chloro-3-((5-chloro-3-methyl-4-oxo-3,4-dihydroquinazolin-6-yl)amino)-4-fluorophenyl)-3-(methoxy-d3)pyrrolidine-1-sulfonamide trifluoroacetate (18.7 mg, 51%). $^1$H NMR (400 MHz, CDCl$_3$) δ 8.22 (s, 1H), 7.61-7.52 (m, 2H), 7.15 (t, 1H), 7.00-6.97 (m, 1H), 6.93 (s, 1H), 6.49 (s, 1H), 3.97-3.95 (m, 1H), 3.62 (s, 3H), 3.53-3.42 (m, 4H), 2.14-2.07 (m, 1H), 2.01-1.92 (m, 1H). MS (apci, m/z)=519.1 (M+H).

Example 54

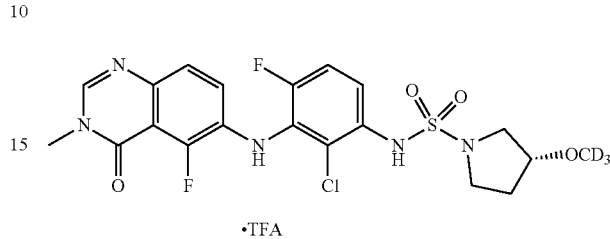

•TFA (R)-N-(2-chloro-4-fluoro-3-((5-fluoro-3-methyl-4-oxo-3,4-dihydroquinazolin-6-yl)amino)phenyl)-3-(methoxy-d3)pyrrolidine-1-sulfonamide trifluoroacetate A solution of 6-((3-amino-2-chloro-6-fluorophenyl)amino)-5-fluoro-3-methylquinazolin-4(3H)-one (25 mg, 0.07424 mmol) and (R)-3-(methoxy-d3)pyrrolidine-1-sulfonyl chloride (30.09 mg, 0.1485 mmol) in pyridine (0.37 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, filtered and concentrated, and the residue was purified by reverse phase chromatography (5-95% ACN/water with 0.1% TFA) to provide (R)-N-(2-chloro-4-fluoro-3-((5-fluoro-3-methyl-4-oxo-3,4-dihydroquinazolin-6-yl)amino)phenyl)-3-(methoxy-d3)pyrrolidine-1-sulfonamide trifluoroacetate (16.5 mg, 44%). $^1$H NMR (400 MHz, CDCl$_3$) δ 8.31 (s, 1H), 7.58-7.55 (m, 1H), 7.48-7.45 (m, 1H), 7.14 (t, 1H), 7.09-7.04 (m, 1H), 6.92 (s, 1H), 5.97 (s, 1H), 3.97-3.95 (m, 1H), 3.64 (s, 3H), 3.53-3.42 (m, 4H), 2.13-2.07 (m, 1H), 2.01-1.92 (m, 1H); MS (apci, m/z)=503.1 (M+H).

Example 55

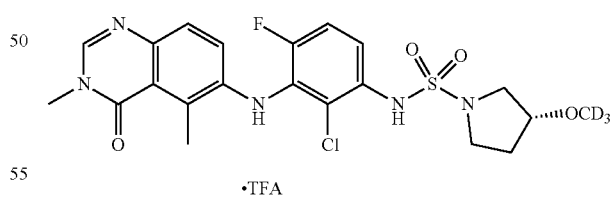

•TFA (R)-N-(2-chloro-3-((3,5-dimethyl-4-oxo-3,4-dihydroquinazolin-6-yl)amino)-4-fluorophenyl)-3-(methoxy-d3)pyrrolidine-1-sulfonamide trifluoroacetate A solution of 6-((3-amino-2-chloro-6-fluorophenyl)amino)-3,5-dimethylquinazolin-4(3H)-one (25 mg, 0.07513 mmol) and (R)-3-(methoxy-d3)pyrrolidine-1-sulfonyl chloride (30.45 mg, 0.1503 mmol) in pyridine (0.37 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide (R)-N-(2-chloro-3-((3,5-dimethyl-4-oxo-3,4-dihydroquinazolin-6-yl) amino)-4-fluorophenyl)-3-(methoxy-d3)pyrrolidine-1-sulfonamide trifluoroacetate (13.0 mg, 35%). $^1$H NMR (400 MHz, CDCl$_3$) δ 8.66 (s, 1H), 7.57 (d, 1H), 7.51-7.48 (m, 1H), 7.11 (t, 1H), 7.09-7.06 (m, 1H), 6.89 (s, 1H), 5.66 (s, 1H), 3.98-3.95 (m, 1H), 3.66 (s, 3H), 3.53-3.43 (m, 4H), 2.96 (s, 3H), 2.13-2.07 (m, 1H), 2.02-1.93 (m, 1H); MS (apci, m/z)=499.2 (M+H).

Example 56

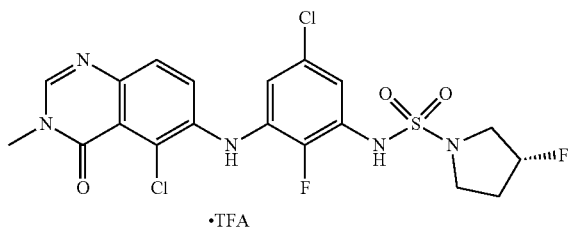

·TFA (R)-N-(5-chloro-3-((5-chloro-3-methyl-4-oxo-3,4-dihydroquinazolin-6-yl)amino)-2-fluorophenyl)-3-fluoropyrrolidine-1-sulfonamide trifluoroacetate To a solution of 6-((3-amino-5-chloro-2-fluorophenyl) amino)-5-chloro-3-methylquinazolin-4(3H)-one (20 mg, 0.057 mmol) in pyridine (283 µL, 0.057 mmol) was added (R)-3-fluoropyrrolidine-1-sulfonyl chloride (27 mg, 0.14 mmol) and the reaction mixture was heated in a sealed vial at 70° C. for 16 hours. The solution was cooled to ambient temperature, concentrated and purified by reverse-phase chromatography (5-95% MeCN/water, 0.1% TFA). The product was lyophilized to give (R)-N-(5-chloro-3-((5-chloro-3-methyl-4-oxo-3,4-dihydroquinazolin-6-yl)amino)-2-fluorophenyl)-3-fluoropyrrolidine-1-sulfonamide trifluoroacetate (11 mg, 39%). $^1$H NMR (400 MHz, CDCl$_3$) δ 8.51 (s, 1H), 7.70-7.61 (m, 2H), 7.34-7.32 (m, 1H), 7.03-7.00 (m, 1H), 6.72 (s, br, 1H), 6.55 (s, br, 1H), 5.25 (d, 1H), 3.73-3.49 (m, 7H), 2.36-2.00 (m, 2H); MS (apci, m/z)=504.1 (M+H).

Example 57

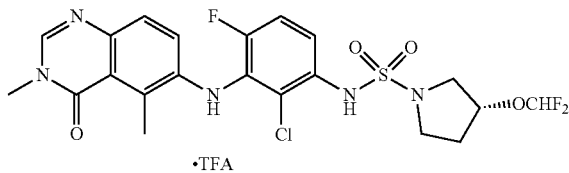 [SMILES: Cc1c(Nc2c(F)ccc(NS(=O)(=O)N3CC[C@@H](OC(F)F)C3)c2Cl)ccc2ncn(C)c(=O)c12]

·TFA (R)-N-(2-chloro-3-((3,5-dimethyl-4-oxo-3,4-dihydroquinazolin-6-yl)oxy)-4-fluorophenyl)-3-(difluoromethoxy)pyrrolidine-1-sulfonamide trifluoroacetate To a solution of 6-(3-amino-2-chloro-6-fluorophenoxy)-3,5-dimethylquinazolin-4(3H)-one (30 mg, 0.090 mmol) in pyridine (449 µL) was added (R)-3-(difluoromethoxy)pyrrolidine-1-sulfonyl chloride (64 mg, 0.27 mmol) and the reaction mixture was heated in a sealed vial at 70° C. for 16 hours. The solution was cooled to ambient temperature, concentrated and purified by reverse-phase chromatography (5-95% MeCN/water, 0.1% TFA). The product was lyophilized to give (R)-N-(2-chloro-3-((3,5-dimethyl-4-oxo-3,4-dihydroquinazolin-6-yl)oxy)-4-fluorophenyl)-3-(difluoromethoxy)pyrrolidine-1-sulfonamide trifluoroacetate (10 mg, 21%). $^1$H NMR (400 MHz, CDCl$_3$) δ 8.59 (s, 1H), 7.61-7.54 (m, 2H), 7.20-7.15 (t, 1H), 6.98 (d, 1H), 6.81 (s, br, 1H), 6.45-6.00 (m, 1H), 5.08-4.84 (m, 1H), 3.85-3.45 (m, 7H), 3.01 (s, 3H), 2.28-2.12 (m, 2H); MS (apci, m/z)=533.1 (M+H).

Example 58

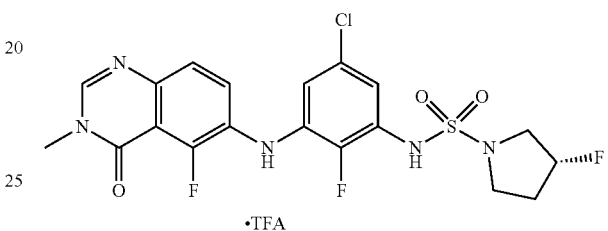

·TFA (R)-N-(5-chloro-2-fluoro-3-((5-fluoro-3-methyl-4-oxo-3,4-dihydroquinazolin-6-yl)amino)phenyl)-3-fluoropyrrolidine-1-sulfonamide trifluoroacetate To a solution of 6-((3-amino-5-chloro-2-fluorophenyl) amino)-5-fluoro-3-methylquinazolin-4(3H)-one (20 mg, 0.059 mmol) in pyridine (297 µL, 0.059 mmol) was added (R)-3-fluoropyrrolidine-1-sulfonyl chloride (28 mg, 0.15 mmol) and the reaction mixture was heated in a sealed vial at 70° C. for 16 hours. The solution was cooled to ambient temperature, concentrated and purified by reverse-phase chromatography (5-95% MeCN/water, 0.1% TFA). The product was lyophilized to give (R)-N-(5-chloro-2-fluoro-3-((5-fluoro-3-methyl-4-oxo-3,4-dihydroquinazolin-6-yl)amino)phenyl)-3-fluoropyrrolidine-1-sulfonamide trifluoroacetate (12 mg, 41%). %). $^1$H NMR (400 MHz, CDCl$_3$) δ 8.67 (s, 1H), 7.71-7.61 (m, 2H), 7.30-7.27 (m, 1H), 6.98-6.95 (m, 1H), 6.72 (s, br, 1H), 5.40-5.20 (m, 1H), 4.00-3.50 (m, 7H), 2.25-2.00 (m, 2H); MS (apci, m/z)=488.1 (M+H).

Example 59

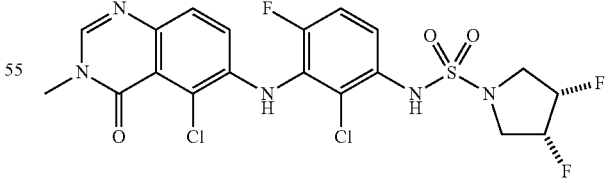

cis-N-(2-chloro-3-((5-chloro-3-methyl-4-oxo-3,4-dihydroquinazolin-6-yl)oxy)-4-fluorophenyl)-3,4-difluoropyrrolidine-1-sulfonamide A solution of 6-(3-amino-2-chloro-6-fluorophenoxy)-5-chloro-3-methylquinazolin-4(3H)-one (25 mg, 0.071 mmol)

and cis-3,4-difluoropyrrolidine-1-sulfonyl chloride (73 mg, 0.35 mmol) in pyridine (0.5 mL) was heated at 70° C. for 18 hours. The reaction mixture was cooled to ambient temperature then partitioned between DCM (25 mL) and saturated aqueous CuSO₄ (25 mL). The organic phase was separated and dried over Na₂SO₄, filtered and concentrated under reduced pressure. The reaction mixture was purified by silica gel chromatography (0-100% EtOAc hexanes) then reverse-phase chromatography (5-95% ACN water with 0.1% TFA). The desired fractions were diluted with saturated aqueous NaHCO₃ (15 mL) then extracted with DCM (30 mL). The organic phases were combined and dried over Na₂SO₄, filtered and concentrated to afford cis-N-(2-chloro-3-((5-chloro-3-methyl-4-oxo-3,4-dihydroquinazolin-6-yl)oxy)-4-fluorophenyl)-3,4-difluoropyrrolidine-1-sulfonamide (18 mg, 49%) as a white solid. $^1$H NMR (400 MHz, CDCl₃) δ 8.00 (s, 1H), 7.61-7.56 (m, 1H), 7.53 (d, 1H), 7.19 (t, 1H), 7.03 (d, 1H), 6.80 (s, 1H), 5.21-4.98 (m, 2H), 3.82-3.67 (m, 2H), 3.65-3.48 (m, 5H); MS (apci, m/z)=523.0 (M+H).

Example 60

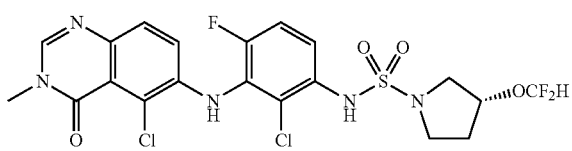

(R)-N-(2-chloro-3-((5-chloro-3-methyl-4-oxo-3,4-dihydroquinazolin-6-yl)oxy)-4-fluorophenyl)-3-(difluoromethoxy)pyrrolidine-1-sulfonamide Step 1: Preparation of (R)-3-(difluoromethoxy)pyrrolidine-1-sulfonyl chloride. To an ice-cold solution of (R)-3-(difluoromethoxy)pyrrolidine (107 mg, 0.780 mmol) and N-ethyl-N-isopropylpropan-2-amine (204 μL, 1.17 mmol) in DCM (6 mL) was added sulfuryl dichloride (189 μL, 2.34 mmol) and the reaction mixture was stirred at ambient temperature for 18 hours. The reaction mixture was diluted with DCM (20 mL) and washed with aqueous 1M HCl (10 mL). The organic phase was separated and dried over Na₂SO₄, filtered and concentrated under reduced pressure to afford (R)-3-(difluoromethoxy)pyrrolidine-1-sulfonyl chloride that was used directly in the next step without further purification. $^1$H NMR (400 MHz, CDCl₃) δ 6.47-6.09 (m, 1H), 5.00-4.95 (m, 1H), 3.73-3.58 (m, 4H), 2.30-2.20 (m, 2H).

Step 2: Preparation of (R)-N-(2-chloro-3-((5-chloro-3-methyl-4-oxo-3,4-dihydroquinazolin-6-yl)oxy)-4-fluorophenyl)-3-(difluoromethoxy)pyrrolidine-1-sulfonamide. A solution of 6-(3-amino-2-chloro-6-fluorophenoxy)-5-chloro-3-methylquinazolin-4(3H)-one (56 mg, 0.158 mmol) and (R)-3-(difluoromethoxy)pyrrolidine-1-sulfonyl chloride (186 mg, 0.791 mmol) in pyridine (0.800 mL) was heated at 70° C. for 18 hours. The reaction mixture was cooled to ambient temperature and partitioned between DCM (25 mL) and 10% aqueous CuSO₄ (25 mL). The organic phase was separated, dried over Na₂SO₄, filtered and concentrated under reduced pressure. The reaction mixture was purified by silica gel chromatography (hexanes/ethyl acetate 0-100%) followed by reverse phase chromatography (5-95% ACN/water with 0.1% TFA). The fractions containing the desired product were combined and partitioned between saturated aqueous NaHCO₃ (15 mL) and DCM (30 mL). The organic phase was separated, dried over Na₂SO₄, filtered and concentrated under reduced pressure to afford (R)-N-(2-chloro-3-((5-chloro-3-methyl-4-oxo-3,4-dihydroquinazolin-6-yl)oxy)-4-fluorophenyl)-3-(difluoromethoxy)pyrrolidine-1-sulfonamide (13.9 mg, 16%) as a white solid. $^1$H NMR (400 MHz, CDCl₃) δ 8.00 (s, 1H), 7.63-7.58 (m, 1H), 7.53 (d, 1H), 7.17 (t, 1H), 7.03 (d, 1H), 6.78 (s, 1H), 6.39-5.98 (m, 1H), 4.88-4.81 (m, 1H), 3.63-3.41 (m, 6H), 2.21-2.04 (m, 3H); MS (apci, m/z)=553.0 (M+H).

Example 61

N-(2-chloro-3-((5-chloro-3-methyl-4-oxo-3,4-dihydroquinazolin-6-yl)oxy)-4-fluorophenyl)-3,3-difluoropyrrolidine-1-sulfonamide A solution of 6-(3-amino-2-chloro-6-fluorophenoxy)-5-chloro-3-methylquinazolin-4(3H)-one (51 mg, 0.144 mmol) and 3,3-difluoropyrrolidine-1-sulfonyl chloride (148 mg, 0.720 mmol) in pyridine (0.500 mL) was heated at 70° C. for 18 hours. The reaction mixture was cooled to ambient temperature and partitioned between DCM (25 mL) and 10% aqueous CuSO₄ (25 mL). The organic phase was separated, dried over Na₂SO₄, filtered and concentrated under reduced pressure. The reaction mixture was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO₃ (15 mL) and DCM (30 mL). The organic phase was separated, dried over Na₂SO₄, filtered and concentrated under reduced pressure to afford N-(2-chloro-3-((5-chloro-3-methyl-4-oxo-3,4-dihydroquinazolin-6-yl)oxy)-4-fluorophenyl)-3,3-difluoropyrrolidine-1-sulfonamide (21.2 mg, 28%) as a white solid. $^1$H NMR (400 MHz, CDCl₃) δ 8.05 (s, 1H), 7.60-7.52 (m, 2H), 7.20-7.15 (t, 1H), 7.06-7.03 (d, 1H), 3.67-3.52 (m, 7H), 2.42-2.32 (m, 2H); MS (apci, m/z)=523.0 (M+H).

Example 62

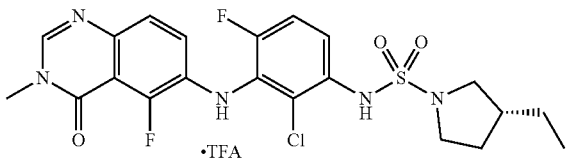 [SMILES: CC[C@@H]1CCN(S(=O)(=O)Nc2ccc(F)c(Nc3ccc4ncn(C)c(=O)c4c3F)c2Cl)C1]

(R)-N-(2-chloro-4-fluoro-3-((5-fluoro-3-methyl-4-oxo-3,4-dihydroquinazolin-6-yl)amino)phenyl)-3-ethylpyrrolidine-1-sulfonamide trifluoroacetate Step 1: Preparation of (3R)-3-ethylpyrrolidine-1-sulfonyl chloride. A slurry of (R)-3-ethylpyrrolidine hydrochloride (150 mg, 1.11 mmol) and N-ethyl-N-isopropylpropan-2-amine (0.289 mL, 1.66 mmol) was stirred in DCM (2.7 mL) at ambient temperature until the mixture was fully dissolved. The reaction mixture was cooled to 0° C. and treated with sulfuryl chloride (0.179 mL, 2.11 mmol). The mixture was warmed to ambient temperature after 30 minutes and allowed to stir for 18 hours. The reaction mixture was diluted with additional DCM (5 mL) and washed with 1.0 M HCl (5 mL). The organic layer was separated, dried over anhydrous MgSO$_4$, filtered, and concentrated to provide crude (3R)-3-ethylpyrrolidine-1-sulfonyl chloride, which was used as is in the next step.

Step 2: Preparation of (R)-N-(2-chloro-4-fluoro-3-((5-fluoro-3-methyl-4-oxo-3,4-dihydroquinazolin-6-yl)amino)phenyl)-3-ethylpyrrolidine-1-sulfonamide trifluoroacetate. A solution of 6-((3-amino-2-chloro-6-fluorophenyl)amino)-5-fluoro-3-methylquinazolin-4(3H)-one (20 mg, 0.05940 mmol) and (R)-3-ethylpyrrolidine-1-sulfonyl chloride (23.48 mg, 0.1188 mmol) in pyridine (0.30 mL) was sealed and heated at 70° C. for 18 hours. The reaction mixture was cooled to ambient temperature and diluted with DCM (15 mL) and washed with 10% aqueous CuSO$_4$. The DCM extract was dried over MgSO$_4$, concentrated and the residue was purified by reverse phase chromatography (5-95% ACN/water with 0.1% TFA) to provide (R)-N-(2-chloro-4-fluoro-3-((5-fluoro-3-methyl-4-oxo-3,4-dihydroquinazolin-6-yl)amino)phenyl)-3-ethylpyrrolidine-1-sulfonamide trifluoroacetate (18.1 mg, 61%). $^1$H NMR (400 MHz, CDCl$_3$) δ 8.28 (s, 1H), 7.56-7.52 (m, 1H), 7.48-7.45 (m, 1H), 7.15 (t, 1H), 7.08-7.03 (m, 1H), 6.75 (s, 1H), 5.97 (s, 1H), 3.64 (s, 3H), 3.55-3.43 (m, 2H), 3.34-3.28 (m, 1H), 2.94-2.89 (m, 1H), 2.11-2.00 (m, 2H), 1.40-1.32 (m, 2H), 0.89 (t, 3H). MS (apci, m/z)=498.2 (M+H).

Example 63

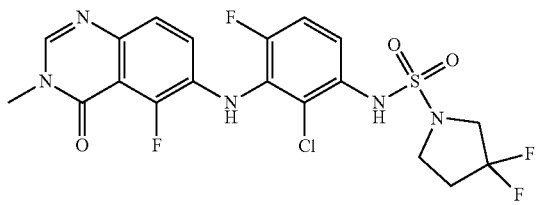 [SMILES: Cn1cnc2ccc(Nc3c(F)ccc(NS(=O)(=O)N4CCC(F)(F)C4)c3Cl)c(F)c2c1=O]

N-(2-chloro-4-fluoro-3-((5-fluoro-3-methyl-4-oxo-3,4-dihydroquinazolin-6-yl)oxy)phenyl)-3,3-difluoropyrrolidine-1-sulfonamide A solution of 6-(3-amino-2-chloro-6-fluorophenoxy)-5-fluoro-3-methylquinazolin-4(3H)-one (30 mg, 0.08 mmol) and 3,3-difluoropyrrolidine-1-sulfonyl chloride (91.3 mg, 0.44 mmol) was dissolved in pyridine (444 μL, 0.08 mmol) and heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na$_2$SO$_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:APA and saturated aqueous NaHCO$_3$ (1×) and the organic layer was separated, dried over anhydrous Na$_2$SO$_4$, filtered, and concentrated to give N-(2-chloro-4-fluoro-3-((5-fluoro-3-methyl-4-oxo-3,4-dihydroquinazolin-6-yl)oxy)phenyl)-3,3-difluoropyrrolidine-1-sulfonamide (18.1 mg, 40%) as an off-white solid. $^1$H NMR (400 MHz, CDCl$_3$) δ 7.98 (s, 1H), 7.58-7.51 (m, 1H), 7.48-7.41 (m, 1H), 7.30-7.21 (m, 1H), 7.20-7.10 (t, 1H), 6.75 (s, 1H), 3.69-3.61 (t, 2H), 3.60-3.53 (m, 5H), 2.45-2.30 (m, 2H); MS (apci, m/z)=507.1, 509.1 (M+H).

Example 64

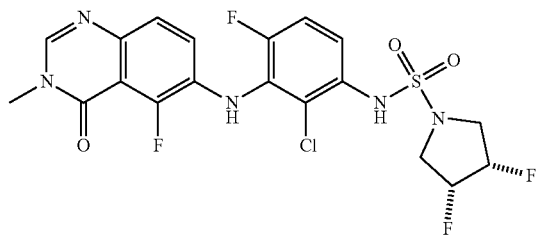 [SMILES: Cn1cnc2ccc(Nc3c(F)ccc(NS(=O)(=O)N4C[C@@H](F)[C@@H](F)C4)c3Cl)c(F)c2c1=O]

cis-N-(2-chloro-4-fluoro-3-((5-fluoro-3-methyl-4-oxo-3,4-dihydroquinazolin-6-yl)oxy)phenyl)-3,4-difluoropyrrolidine-1-sulfonamide A solution of 6-(3-amino-2-chloro-6-fluorophenoxy)-5-fluoro-3-methylquinazolin-4(3H)-one (30 mg, 0.08 mmol) and cis-3,4-difluoropyrrolidine-1-sulfonyl chloride (91.3 mg, 0.44 mmol) was dissolved in pyridine (444 μL, 0.08 mmol) and heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous Na$_2$SO$_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:IPA and saturated aqueous NaHCO$_3$ (1×) and the organic layer was separated, dried over anhydrous Na$_2$SO$_4$, filtered, and concentrated to give cis-N-(2-chloro-4-fluoro-3-((5-fluoro-3-methyl-4-oxo-3,4-dihydroquinazolin-6-yl)oxy)phenyl)-3,4-difluoropyrrolidine-1-sulfonamide (10.7 mg, 24%) as a white solid. $^1$H NMR (400 MHz, CDCl$_3$) δ 7.97 (s, 1H), 7.57-7.51 (m, 1H), 7.47-7.43 (m, 1H), 7.31-7.27 (d, 1H), 7.18-7.11 (t, 1H), 6.76 (s, 1H), 5.21-4.98 (m, 2H), 3.77-3.53 (m, 7H); MS (apci, m/z)=507.1, 509.1 (M+H).

Example 65

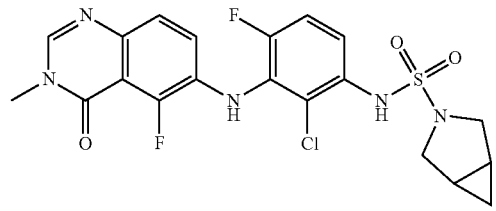 [SMILES: Cn1cnc2ccc(Nc3c(F)ccc(NS(=O)(=O)N4CC5CC5C4)c3Cl)c(F)c2c1=O]

N-(2-chloro-4-fluoro-3-((5-fluoro-3-methyl-4-oxo-3,4-dihydroquinazolin-6-yl)oxy)phenyl)-3-azabicyclo[3.1.0]hexane-3-sulfonamide A solution of 6-(3-amino-2-chloro-6-fluorophenoxy)-5-fluoro-3-methylquinazolin-4(3H)-one (30 mg, 0.08 mmol) and 3-azabicyclo[3.1.0]hexane-3-sulfonyl chloride (81 mg, 0.44 mmol) was dissolved in pyridine (444 µL, 0.08 mmol) and heated at 70° C. for 32 hours in a sealed vial. The reaction mixture was cooled to ambient temperature, diluted with ethyl acetate and washed with 10% citric acid (3×50 mL) and brine (1×25 mL), dried over anhydrous $Na_2SO_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:IPA and saturated aqueous $NaHCO_3$ (1×) and the organic layer was separated, dried over anhydrous $Na_2SO_4$, filtered, and concentrated to give N-(2-chloro-4-fluoro-3-((5-fluoro-3-methyl-4-oxo-3,4-dihydroquinazolin-6-yl)oxy)phenyl)-3-azabicyclo[3.1.0]hexane-3-sulfonamide (31 mg, 72%) as a white solid. $^1$H NMR (400 MHz, CDCl$_3$) δ 7.97 (s, 1H), 7.53-7.47 (m, 1H), 7.46-7.42 (m, 1H), 7.25-7.21 (d, 1H), 7.15-7.10 (t, 1H), 6.76 (s, 1H), 3.57 (s, 3H), 3.51-3.44 (d, 2H), 3.42-3.35 (d, 2H), 0.93-0.81 (m, 2H), 0.68-0.59 (m, 1H), 0.23-0.16 (m, 1H); MS (apci, m/z)=483.0, 485.0 (M+H).

Example 66

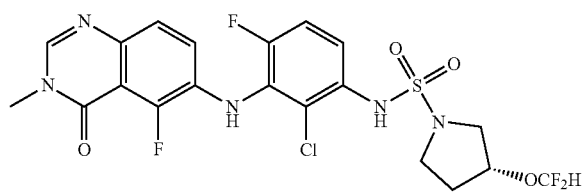

(R)-N-(2-chloro-4-fluoro-3-((5-fluoro-3-methyl-4-oxo-3,4-dihydroquinazolin-6-yl)oxy)phenyl) 3-(difluoromethoxy)pyrrolidine-1-sulfonamide A solution of 6-(3-amino-2-chloro-6-fluorophenoxy)-5-fluoro-3-methylquinazolin-4(3H)-one (30 mg, 0.08 mmol) and (R)-3-(difluoromethoxy)pyrrolidine-1-sulfonyl chloride (105 mg, 0.44 mmol) was dissolved in pyridine (444 µL, 0.08 mmol) and heated at 70° C. for 24 hours in a sealed vial. The reaction mixture was cooled to ambient temperature, diluted with ethyl acetate and washed with 10% citric acid (3×50 mL) and brine (1×25 mL), dried over anhydrous $Na_2SO_4$, filtered, and concentrated. The residue was purified by silica gel column chromatography (DCM/EtOAc) followed by reverse phase chromatography (water/ACN with 0.1% TFA). The desired fractions were combined and partitioned between 4:1 DCM:APA and saturated aqueous $NaHCO_3$ (1×). The organic layer was separated, dried over anhydrous $Na_2SO_4$, filtered, and concentrated to give (R)-N-(2-chloro-4-fluoro-3-((5-fluoro-3-methyl-4-oxo-3,4-dihydroquinazolin-6-yl)oxy)phenyl)-3-(difluoromethoxy)pyrrolidine-1-sulfonamide (3.5 mg, 7%) as a white solid. $^1$H NMR (400 MHz, CDCl$_3$) δ 7.97 (s, 1H), 7.61-7.55 (m, 1H), 7.48-7.43 (m, 1H), 7.30-7.27 (d, 1H), 7.17-7.09 (t, 1H), 6.77 (s, 1H), 6.40-6.00 (t, 1H), 4.88-4.82 (d, 1H), 3.59-3.45 (m, 7H), 2.16-2.10 (m, 2H); MS (apci, m/z)=537.0, 539.0 (M+H).

Example 67

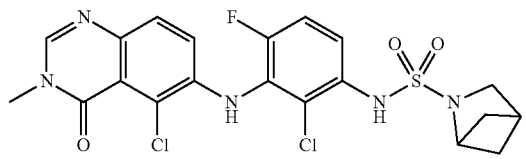 [SMILES: Cn1cnc2ccc(Nc3c(F)ccc(NS(=O)(=O)N4CC5CC4C5)c3Cl)c(Cl)c2c1=O]

N-(2-chloro-3-((5-chloro-3-methyl-4-oxo-3,4-dihydroquinazolin-6-yl)oxy)-4-fluorophenyl)-2-azabicyclo[2.1.1]hexane-2-sulfonamide A solution of 6-(3-amino-2-chloro-6-fluorophenoxy)-5-chloro-3-methylquinazolin-4(3H)-one (50 mg, and 0.1412 mmol), 2-azabicyclo[2.1.1]hexane-2-sulfonyl chloride (128.2 mg, 0.7059 mmol) in pyridine (0.700 mL) was heated at 70° C. for 18 hours. The reaction mixture was cooled to ambient temperature and partitioned between DCM (25 mL) and 10% aqueous CuSO$_4$ (25 mL). The organic phase was separated, dried over Na$_2$SO$_4$, filtered and concentrated under reduced pressure. The reaction mixture was purified by silica gel chromatography (hexanes/ethyl acetate 0-100%) followed by reverse phase chromatography (5-95% ACN/water with 0.1% TFA). The desired fractions were combined and partitioned between saturated aqueous NaHCO$_3$ (15 mL) and DCM (30 mL). The organic phase was separated, dried over Na$_2$SO$_4$, filtered and concentrated under reduced pressure to afford N-(2-chloro-3-((5-chloro-3-methyl-4-oxo-3,4-dihydroquinazolin-6-yl)oxy)-4-fluorophenyl)-2-azabicyclo[2.1.1]hexane-2-sulfonamide (18.4 mg, 26%) as a white solid. $^1$H NMR (400 MHz, CDCl$_3$) δ 7.99 (s, 1H), 7.64-7.58 (m, 1H), 7.53 (d, 1H), 7.16 (t, 1H), 7.03 (d, 1H), 6.82 (s, 1H), 4.27-4.22 (m, 1H), 3.58 (s, 3H), 3.38 (s, 2H), 2.92-2.86 (m, 1H), 1.98-1.89 (m, 2H), 1.56-1.50 (m, 2H); MS (apci, m/z)=499.1 (M+H).

Example 68

6-(2-Chloro-3-{[ethyl(methyl)sulfamoyl]amino}-6-fluorophenoxy)-3,5-dimethyl-3,4 dihydroquinazolin-4-one To a solution of 6-(3-amino-2-chloro-6-fluorophenoxy)-3,5-dimethylquinazolin-4(3H)-one (160.0 mg, 0.48 mmol) in DCM (10 mL) was added sequentially pyridine (0.19 mL, 2.39 mmol), ethyl(methyl)sulfamoyl chloride (378 mg, 2.39 mmol) and DMAP (5.8 mg, 0.048 mmol) and the reaction mixture was stirred at ambient temperature for 48 hours under nitrogen. The reaction mixture was concentrated under reduced pressure, diluted with water and extracted with ethyl acetate (2×50 mL). The combined organic layers were washed with water (2×25 mL) and brine (25 mL), dried over anhydrous Na$_2$SO$_4$, filtered and concentrated. The crude product was purified by reverse phase column chromatography (30-95% ACN/water with 20 mM ammonium bicarbonate) to provide 6-(2-chloro-3-{[ethyl(methyl)sulfamoyl]amino}-6-fluorophenoxy)-3,5-dimethyl-3,4-dihydroquinazolin-4-one as a pale white solid (23 mg, 10%). $^1$H NMR (400 MHz, Methanol-d$_4$) δ 8.18 (s, 1H), 7.56 (dd, 1H), 7.41 (d, 1H), 7.28 (t, 1H), 6.96 (d, 1H), 3.54 (s, 3H), 3.21 (m, 2H), 2.97 (s, 3H), 2.82 (s, 3H), 1.09 (t, 3H); MS (m/z)=455.1, 457.1 (M+H).

Example 69

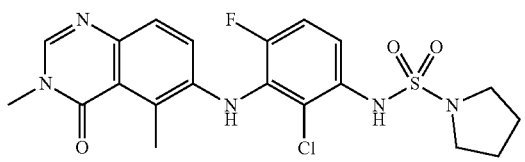 [SMILES: Cc1c(Nc2c(F)ccc(NS(=O)(=O)N3CCCC3)c2Cl)ccc2ncn(C)c(=O)c12]

N-(2-chloro-3-((3,5-dimethyl-4-oxo-3,4-dihydroquinazolin-6-yl)oxy)-4-fluorophenyl)pyrrolidine-1-sulfonamide To a solution of 6-(3-amino-2-chloro-6-fluorophenoxy)-3,5-dimethylquinazolin-4(3H)-one (130.0 mg, 0.39 mmol) in DCM (5 mL) was added Et$_3$N (0.75 mL, 5.83 mmol) and pyrrolidine-1-sulfonyl chloride (790 mg, 4.67 mmol) and the mixture was stirred for 16 hours at ambient temperature under nitrogen. The reaction mixture was concentrated under reduced pressure, diluted with water and extracted with ethyl acetate (2×50 mL). The combined organic layers were washed with water (2×25 mL) and brine (25 mL), dried over anhydrous Na$_2$SO$_4$, filtered and concentrated. The crude product was by reverse phase column chromatography (30-95% ACN/water with 20 mM ammonium bicarbonate) to provide N-(2-chloro-3-((3,5-dimethyl-4-oxo-3,4-dihydroquinazolin-6-yl)oxy)-4-fluorophenyl)pyrrolidine-1-sulfonamide as a white solid (23.4 mg, 13%). $^1$H NMR (400 MHz, Methanol-d$_4$) δ 8.18 (s, 1H), 7.60 (dd, 1H), 7.41 (d, 1H), 7.28 (t, 1H), 6.96 (d, 1H), 3.54 (s, 3H), 3.30 (m, 4H), 2.97 (s, 3H), 1.85 (m, 4H); MS (m/z)=467.3, 469.3 (M+H).

Example 70

(R)-N-(2-chloro-3-((3,5-dimethyl-4-oxo-3,4-dihydroquinazolin-6-yl)oxy)-4-fluorophenyl)-3-fluoropyrrolidine-1-sulfonamide To a solution of 6-(3-amino-2-chloro-6-fluorophenoxy)-3,5-dimethylquinazolin-4(3H)-one (119 mg, 0.357 mmol) in pyridine (2 mL) was added (R)-3-fluoropyrrolidine-1-sulfonyl chloride (147 mg, 0.784 mmol) and the reaction mixture was stirred at 65° C. for 48 hours. The reaction mixture was concentrated and the crude product was purified by reverse-phase column chromatography (5-95% MeCN/water with 0.1% TFA) to give (R)-N-(2-chloro-3-((3,5-dimethyl-4-oxo-3,4-dihydroquinazolin-6-yl)oxy)-4-fluorophenyl)-3-fluoropyrrolidine-1-sulfonamide (77 mg, 45%) as a white solid. $^1$H NMR (400 MHz, CDCl$_3$) δ 7.95 (s, 1H), 7.59-7.56 (m, 1H), 7.41 (d, 1H), 7.16-7.12 (t, 1H), 6.91-6.89 (m, 2H), 5.29-5.14 (m, 1H), 3.68-3.44 (m, 7H), 3.00 (s, 3H), 2.31-2.21 (m, 1H), 2.13-1.94 (m, 1H). MS (m/z)=485.1, 487.1 (M+H).

The compounds in Table 1 were prepared using a similar procedure described for the synthesis of (R)-N-(2-chloro-3-((3,5-dimethyl-4-oxo-3,4-dihydroquinazolin-6-yl)amino)-4-fluorophenyl)-3-methoxypyrrolidine-1-sulfonamide (Example 1) employing the following modifications: in Step 1, replacing (R)-3-methoxypyrrolidine hydrochloride with appropriate amine or amine hydrochloride and in Step 2, replacing 6-((3-amino-2-chloro-6-fluorophenyl)amino)-3,5-dimethylquinazolin-4(3H)-one and/or (R)-3-methoxypyrrolidine-1-sulfonyl chloride with appropriate quinazolin-4(3H)-one and/or sulfonyl chloride product from Step 1.

TABLE 1

| Ex# | structure and $^1$H NMR data | Chemical Name | MS (apci) m/z |
|---|---|---|---|
| 71 | 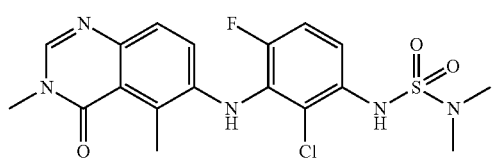<br>$^1$H NMR (400 MHz, CDCl$_3$) δ 7.92 (s, 1H), 7.46-7.44 (d, 1H), 7.40-7.36 (m, 1H), 7.10-7.03 (m, 2H), 6.65 (s, 1H), 5.58 (s, 1H), 3.54 (s, 3H), 2.97 (s, 3H), 2.87 (s, 6H). | N-(2-chloro-3-((3,5-dimethyl-4-oxo-3,4-dihydroquinazolin-6-yl)amino)-4-fluorophenyl)-(N,N-dimethyl)-sulfamide | 440.1 (M + H) |

TABLE 1-continued

| Ex# | structure and ¹H NMR data | Chemical Name | MS (apci) m/z |
|---|---|---|---|
| 72 | ¹H NMR (400 MHz, (CD₃)₂SO) δ 9.44 (s, 1H), 8.17 (s, 1H), 7.34-7.29 (m, 4H), 6.84-6.81 (d, 1H), 4.46-4.40 (m, 1H), 3.87-3.81 (m, 1H), 3.59-3.48 (m, 3H), 3.43 (s, 3H), 2.81 (s, 3H), 2.72 (s, 3H), 2.01-1.92 (m, 1H), 1.82-1.74 (m, 1H). | N-(2-chloro-3-((3,5-dimethyl-4-oxo-3,4-dihydroquinazolin-6-yl)amino)-4-fluorophenyl)-(N-methyl-N-(tetrahydrofuran-3-yl))-sulfamide | 496.1 (M + H) |
| 73 | ¹H NMR (400 MHz, CDCl₃) δ 7.92 (s, 1H), 7.46-7.39 (m, 2H), 7.09-7.03 (m, 2H), 6.79 (s, 1H), 5.58 (s, 1H), 3.55 (s, 3H), 2.97 (s, 3H), 2.92 (s, 3H), 2.38-2.33 (m, 1H), 0.74-0.73 (d, 4H). | N-(2-chloro-3-((3,5-dimethyl-4-oxo-3,4-dihydroquinazolin-6-yl)amino)-4-fluorophenyl)-(N-cyclopropyl-N-methyl)-sulfamide | 466.1 (M + H) |
| 74 | ¹H NMR (400 MHz, CDCl₃) δ 7.92 (s, 1H), 7.45-7.43 (d, 1H), 7.37-7.33 (m, 1H), 7.10-7.01 (m, 2H), 6.67 (s, 1H), 5.57 (s, 1H), 4.27-4.19 (m, 1H), 3.54 (s, 3H), 2.97 (s, 3H), 2.83 (s, 3H), 2.11-2.01 (m, 2H), 1.97-1.89 (m, 2H), 1.64-1.52 (m, 2H). | N-(2-chloro-3-((3,5-dimethyl-4-oxo-3,4-dihydroquinazolin-6-yl)amino)-4-fluorophenyl)-(N-cyclobutyl-N-methyl)-sulfamide | 480.1 (M + H) |
| 75 | •TFA<br>¹H NMR (400 MHz, CDCl₃) δ 8.68 (s, 1H), 7.59 (d, 1H), 7.46-7.43 (m, 1H), 7.12 (t, 1H), 7.07-7.04 (m, 1H), 6.67 (s, 1H), 5.66 (s, 1H), 3.66 (S, 3H), 3.49-3.43 (m, 2H), 3.38-3.34 (m, 1H), 3.33 (s, 3H), 3.23-3.17 (m, 2H), 2.97 (s, 3H), 1.89-1.82 (m, 2H), 1.68-1.60 (m, 2H). | N-(2-chloro-3-((3,5-dimethyl-4-oxo-3,4-dihydroquinazolin-6-yl)amino)-4-fluorophenyl)-4-methoxypiperidine-1-sulfonamide trifluoroacetate | 510.2 (M + H) |

TABLE 1-continued

| Ex# | structure and ¹H NMR data | Chemical Name | MS (apci) m/z |
|---|---|---|---|
| 76 |   ·TFA  ¹H NMR (400 MHz, CDCl₃) δ 8.62 (s, 1H), 7.58 (d, 1H), 7.47-7.43 (m, 1H), 7.13 (t, 1H), 7.08-7.05 (m, 1H), 6.74 (s, 1H), 5.66 (s, 1H), 3.68-3.63 (m, 4H), 3.50-3.42 (m, 3H), 3.01-2.93 (m, 4H), 2.25-2.16 (m, 1H), 2.13-2.04 (m, 1H). | N-(2-chloro-3-((3,5-dimethyl-4-oxo-3,4-dihydroquinazolin-6-yl)amino)-4-fluorophenyl)-3-(trifluoromethyl)pyrrolidine-1-sulfonamide trifluoroacetate | 534.1 (M + H) |
| 77 | 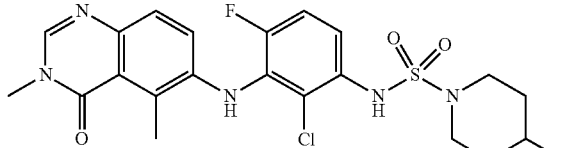  ·TFA  ¹H NMR (400 MHz, CDCl₃) δ 8.83 (s, 1H), 7.69 (d, 1H), 7.53-7.49 (m, 1H), 7.14 (t, 1H), 7.06-7.03 (m, 1H), 6.67 (s, 1H), 5.69 (s, 1H), 3.93-3.89 (m, 1H), 3.70 (s, 3H), 3.52-3.46 (m, 2H), 3.22-3.16 (m, 2H), 2.96 (s, 3H), 1.90-1.85 (m, 2H), 1.63-1.55 (m, 2H), 1.26 (s, 1H). | N-(2-chloro-3-((3,5-dimethyl-4-oxo-3,4-dihydroquinazolin-6-yl)amino)-4-fluorophenyl)-4-hydroxypiperidine-1-sulfonamide trifluoroacetate | 496.1 (M + H) |
| 78 | 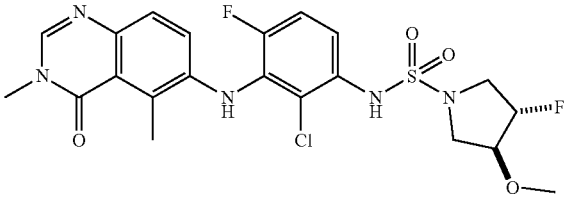  ¹H NMR (400 MHz, (CD₃)₂SO) δ 9.51 (s, 1H), 8.16 (s, 1H), 7.34-7.26 (m, 4H), 6.83-6.81 (d, 1H), 5.25-5.12 (m, 1H), 4.04-4.00 (m, 1H), 3.56-3.43 (m, 6H), 3.34-3.31 (m, 1H), 3.29 (s, 3H), 2.80 (s, 3H). | (trans)-N-(2-chloro-3-((3,5-dimethyl-4-oxo-3,4-dihydroquinazolin-6-yl)amino)-4-fluorophenyl)-3-fluoro-4-methoxypyrrolidine-1-sulfonamide | 514.1 (M + H) |
| 79 | 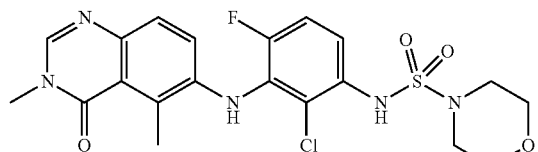  ¹H NMR (400 MHz, CDCl₃) δ 8.76 (s, 1H), 7.60 (d, 1H), 7.49-7.46 (m, 1H), 7.13 (t, 1H), 7.09-7.06 (m, 1H), 6.67 (s, 1H), 5.69 (s, 1H), 3.70 (t, 4H), 3.68 (s, 3H), 3.27 (t, 4H), 2.97 (s, 3H). | N-(2-chloro-3-((3,5-dimethyl-4-oxo-3,4-dihydroquinazolin-6-yl)amino)-4-fluorophenyl)morpholine-4-sulfonamide | 482.1 (M + H) |

TABLE 1-continued

| Ex# | structure and $^1$H NMR data | Chemical Name | MS (apci) m/z |
|---|---|---|---|
| 80 | 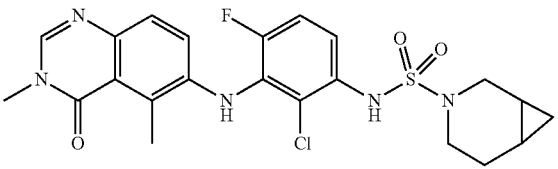 [SMILES: Cc1c(Nc2c(F)ccc(NS(=O)(=O)N3CCC4CC4C3)c2Cl)ccc2ncn(C)c(=O)c12]<br>$^1$H NMR (400 MHz, CDCl$_3$) δ 7.99 (s, 1H), 7.47-7.44 (d, 1H), 7.38-7.34 (m, 1H), 7.10-7.08 (d, 1H), 7.05-7.02 (m, 1H), 6.70 (s, 1H), 5.59 (s, 1H), 3.59-3.55 (m, 4H), 3.47-3.43 (m, 1H), 3.25-3.19 (m, 1H), 2.97 (s, 3H), 2.91-2.85 (m, 1H), 2.02-1.94 (m, 1H), 1.74-1.67 (m, 1H), 1.05-0.97 (m, 2H), 0.68-0.62 (m, 1H), 0.13-0.09 (m, 1H). | N-(2-chloro-3-((3,5-dimethyl-4-oxo-3,4-dihydroquinazolin-6-yl)amino)-4-fluorophenyl)-(N-isopropyl-N-methyl)-sulfamide | 492.1 (M + H) |
| 81 | 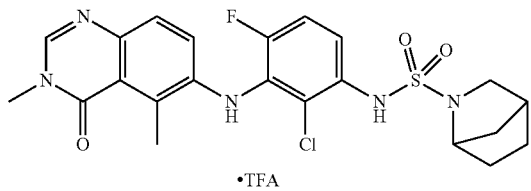 [SMILES: Cc1c(Nc2c(F)ccc(NS(=O)(=O)N3CC4CCC3C4)c2Cl)ccc2ncn(C)c(=O)c12]<br>•TFA<br>$^1$H NMR (400 MHz, CDCl$_3$) δ 8.95 (s, 1H), 7.62 (d, 1H), 7.49-7.45 (m, 1H), 7.13 (t, 1H), 7.07-7.04 (m, 1H), 6.75 (s, 1H), 5.69 (s, 1H), 4.20 (s, 1H), 3.71 (s, 3H), 3.29-3.25 (m, 1H), 3.04 (d, 1H), 2.96 (s, 3H), 2.62 (s, 1H), 1.79-1.55 (m, 4H), 1.49-1.42 (m, 2H). | N-(2-chloro-3-((3,5-dimethyl-4-oxo-3,4-dihydroquinazolin-6-yl)amino)-4-fluorophenyl)-2-azabicyclo[2.2.1]heptane-2-sulfonamide trifluoroacetate | 492.1 (M + H) |
| 82 | 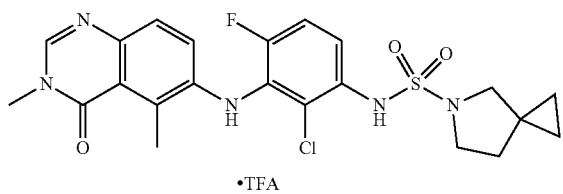 [SMILES: Cc1c(Nc2c(F)ccc(NS(=O)(=O)N3CCC4(CC4)C3)c2Cl)ccc2ncn(C)c(=O)c12]<br>•TFA<br>$^1$H NMR (400 MHz, CDCl$_3$) δ 8.65 (s, 1H), 7.58 (d, 1H), 7.51-7.48 (m, 1H), 7.12 (t, 1H), 7.08-7.05 (m, 1H), 6.73 (s, 1H), 5.67 (s, 1H), 3.66 (s, 3H), 3.53 (t, 2H), 3.25 (s, 2H), 2.96 (s, 3H), 1.81 (t, 2H), 0.60-0.53 (m, 4H). | N-(2-chloro-3-((3,5-dimethyl-4-oxo-3,4-dihydroquinazolin-6-yl)amino)-4-fluorophenyl)-5-azaspiro[2.4]heptane-5-sulfonamide trifluoroacetate | 492.1 (M + H) |
| 83 | 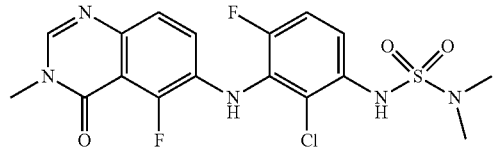<br>$^1$H NMR (400 MHz, CD$_3$)$_2$SO) δ 9.42 (s, 1H), 8.18 (s, 1H), 8.05 (s, 1H), 7.44-7.29 (m, 3H), 7.01 (t, 1H), 3.43 (s, 3H), 2.73 (s, 6H) | N-(2-chloro-4-fluoro-3-((5-fluoro-3-methyl-4-oxo-3,4-dihydroquinazolin-6-yl)amino)phenyl)-(N,N-dimethyl)-sulfamide | 444.1 (M + H) |

TABLE 1-continued

| Ex# | structure and ¹H NMR data | Chemical Name | MS (apci) m/z |
|---|---|---|---|
| 84 | 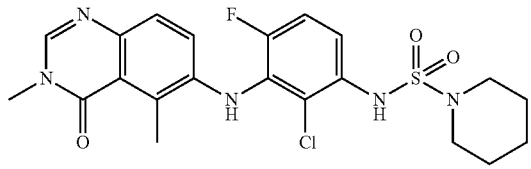 [SMILES: Cc1c(Nc2c(F)ccc(NS(=O)(=O)N3CCCCC3)c2Cl)ccc2ncn(C)c(=O)c12]<br>¹H NMR (400 MHz, (CD₃)₂SO) δ 9.36 (s, 1H), 8.16 (s, 1H), 7.36-7.27 (m, 4H), 6.81-6.79 (d, 1H), 3.43 (s, 3H), 3.11-3.09 (m, 4H), 2.81 (s, 3H), 1.50-1.44 (m, 6H). | N-(2-chloro-3-((3,5-dimethyl-4-oxo-3,4-dihydroquinazolin-6-yl)amino)-4-fluorophenyl)piperidine-1-sulfonamide | 480.1 (M + H) |
| 85 | 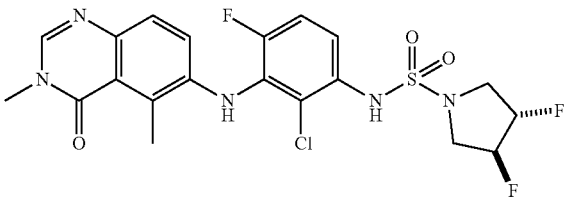 [SMILES: Cc1c(Nc2c(F)ccc(NS(=O)(=O)N3C[C@H](F)[C@@H](F)C3)c2Cl)ccc2ncn(C)c(=O)c12]<br>¹H NMR (400 MHz, (CD₃)₂SO) δ 9.66 (s, 1H), 8.16 (s, 1H), 7.32-7.26 (m, 4H), 6.83-6.80 (d, 1H), 5.43-5.28 (m, 2H), 3.67-3.54 (m, 4H), 3.43 (s, 3H), 2.80 (s, 3H). | (trans)-N-(2-chloro-3-((3,5-dimethyl-4-oxo-3,4-dihydroquinazolin-6-yl)amino)-4-fluorophenyl)-3,4-difluoropyrrolidine-1-sulfonamide | 502.1 (M + H) |
| 86 | 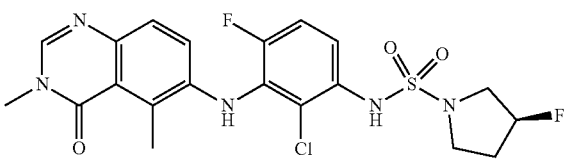<br>¹H NMR (400 MHz, CDCl₃) δ 8.80 (s, 1H), 7.59 (d, 1H), 7.54-7.51 (m, 1H), 7.13 (t, 1H), 7.54-7.51 (m, 1H), 6.76 (s, 1H), 5.66 (s, 1H), 5.31-5.16 (m, 1H), 3.68-3.59 (m, 5H), 3.54-3.44 (m, 2H), 2.96 (s, 3H), 2.32-2.23 (m, 1H), 2.15-1.95 (m, 1H). | (S)-N-(2-chloro-3-((3,5-dimethyl-4-oxo-3,4-dihydroquinazolin-6-yl)amino)-4-fluorophenyl)-3-fluoropyrrolidine-1-sulfonamide trifluoroacetate | 484.1 (M + H) |
| 87 | 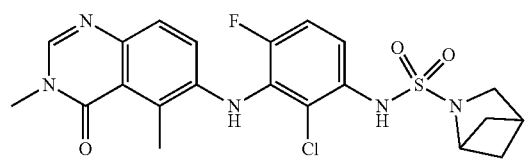<br>¹H NMR (400 MHz, CDCl₃) δ 8.83 (s, 1H), 7.60 (d, 1H), 7.54-7.51 (m, 1H), 7.12 (t, 1H), 7.07-7.04 (m, 1H), 6.80 (s, 1H), 5.68 (s, 1H), 4.27-4.24 (m, 1H), 3.69 (s, 3H), 3.40 (s, 2H), 2.96 (s, 3H), 2.92-2.89 (m, 1H), 1.96-1.93 (m, 2H), 1.55-1.53 (m, 2H). | N-(2-chloro-3-((3,5-dimethyl-4-oxo-3,4-dihydroquinazolin-6-yl)amino)-4-fluorophenyl)-2-azabicyclo[2.1.1]hexane-2-sulfonamide trifluoroacetate | 478.1 (M + H) |

TABLE 1-continued

| Ex# | structure and ¹H NMR data | Chemical Name | MS (apci) m/z |
|---|---|---|---|
| 88 |  ¹H NMR (400 MHz, CDCl₃) δ 7.93 (s, 1H), 7.45-7.43 (d, 1H), 7.35-7.31 (m, 1H), 7.10-7.08 (d, 1H), 7.05-7.02 (m, 1H), 6.79 (s, 1H), 5.59 (s, 1H), 3.54 (s, 3H), 3.47-3.41 (m, 3H), 3.21-3.19 (d, 1H), 2.97 (s, 3H), 1.27-1.20 (m, 4H), 0.52-0.49 (m, 1H), 0.37-0.35 (t, 1H). | N-(2-chloro-3-((3,5-dimethyl-4-oxo-3,4-dihydroquinazolin-6-yl)amino)-4-fluorophenyl)-(N-isopropyl-N-methyl)-sulfamide | 492.2 (M + H) |
| 89 | 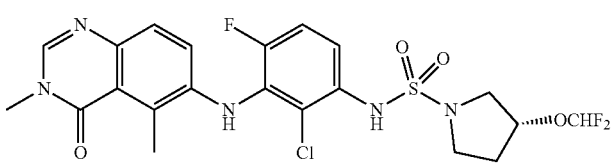 [SMILES: Cc1c(Nc2c(F)ccc(NS(=O)(=O)N3CC[C@@H](OC(F)F)C3)c2Cl)ccc2ncn(C)c(=O)c12] ¹H NMR (400 MHz, CDCl₃) δ 7.92 (s, 1H), 7.45-7.39 (m, 2H), 7.10-7.02 (m, 2H), 6.77 (s, 1H), 6.34-5.97 (t, 1H), 5.58 (s, 1H), 4.83-4.82 (m, 1H), 3.61-3.45 (m, 7H), 2.97 (s, 3H), 2.14-2.09 (m, 2H). | N-(2-chloro-3-((3,5-dimethyl-4-oxo-3,4-dihydroquinazolin-6-yl)amino)-4-fluorophenyl)-(N-isopropyl-N-methyl)-sulfamide | 532.1 (M + H) |
| 90 | 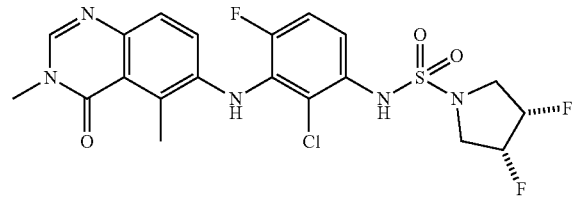 [SMILES: Cc1c(Nc2c(F)ccc(NS(=O)(=O)N3C[C@@H](F)[C@@H](F)C3)c2Cl)ccc2ncn(C)c(=O)c12] ¹H NMR (400 MHz, (CD₃)₂SO) δ 9.65 (s, 1H), 8.16 (s, 1H), 7.33-7.27 (m, 4H), 6.84-6.82 (d, 1H), 5.39-5.21 (m, 2H), 3.68-3.59 (m, 2H), 3.46-3.37 (m, 5H), 2.81 (s, 3H). | (cis)-N-(2-chloro-3-((3,5-dimethyl-4-oxo-3,4-dihydroquinazolin-6-yl)amino)-4-fluorophenyl)-3,4-difluoropyrrolidine-1-sulfonamide | 502.1 (M + H) |
| 91 | 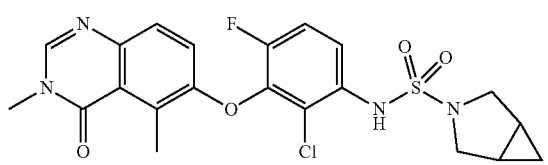 [SMILES: Cc1c(Oc2c(F)ccc(NS(=O)(=O)N3CC4CC4C3)c2Cl)ccc2ncn(C)c(=O)c12] ¹H NMR (400 MHz, CDCl₃) δ 7.95 (s, 1H), 7.51-7.47 (m, 1H), 7.45-7.42 (d, 1H), 7.17-7.12 (t, 1H), 6.92-6.90 (d, 1H), 6.78 (s, 1H), 3.56 (s, 3H), 3.49-3.47 (d, 2H), 3.40-3.38 (m, 2H), 3.02 (s, 3H), 1.54-1.50 (m, 2H), 0.66-0.60 (m, 1H), 0.21-0.18 (m, 1H). | N-(2-chloro-3-((3,5-dimethyl-4-oxo-3,4-dihydroquinazolin-6-yl)amino)-4-fluorophenyl)-(N-isopropyl-N-methyl)-sulfamide | 479.1 (M + H) |
| 92 | 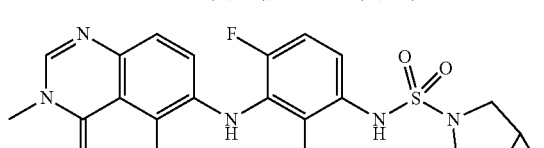 ¹H NMR (400 MHz, CDCl₃) δ 8.72 (s, 1H), 7.59 (d, 1H), 7.43-7.40 (m, 1H), 7.12 (t, 1H), 7.08-7.05 (m, 1H), 6.74 (s, 1H), 5.67 (s, 1H), 3.67 (s, 3H), 3.49 (d, 2H), 3.41 (d, 2H), 2.96 (s, 3H), 1.54-1.52 (m, 2H), 0.66-0.61 (m, 1H), 0.22-0.18 (m, 1H). | N-(2-chloro-3-((3,5-dimethyl-4-oxo-3,4-dihydroquinazolin-6-yl)amino)-4-fluorophenyl)-3-azabicyclo[3.1.0]hexane-3-sulfonamide | 478.1 (M + H) |

TABLE 1-continued

| Ex# | structure and ¹H NMR data | Chemical Name | MS (apci) m/z |
|---|---|---|---|
| 93 | 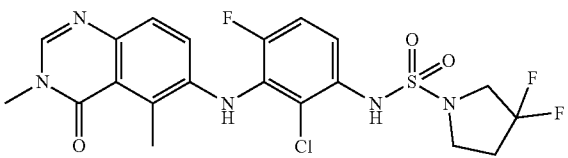 [SMILES: Cc1c(Nc2c(F)ccc(NS(=O)(=O)N3CCC(F)(F)C3)c2Cl)ccc2ncn(C)c(=O)c12]<br>¹H NMR (400 MHz, (CD₃)₂SO) δ 9.76 (s, 1H), 8.17 (s, 1H), 7.36-7.28 (m, 4H), 6.84-6.82 (d, 1H), 3.65-3.59 (t, 2H), 3.46-3.43 (m, 5H), 2.81 (s, 3H), 2.48-2.38 (m, 2H). | N-(2-chloro-3-((3,5-dimethyl-4-oxo-3,4-dihydroquinazolin-6-yl)amino)-4-fluorophenyl)-3,3-difluoropyrrolidine-1-sulfonamide | 502.1 (M + H) |
| 94 | 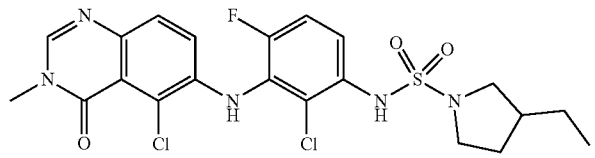<br>¹H NMR (400 MHz, CDCl₃) δ 8.68 (s, 1H), 7.64-7.57 (m, 2H), 7.18 (t, 1H), 7.01-6.98 (m, 1H), 6.97 (s, 1H), 6.56 (s, 1H), 3.70 (s, 3H), 3.55-3.44 (m, 2H), 3.35-3.28 (m, 1H), 2.93 (t, 1H), 2.12-2.01 (m, 2H), 1.58-1.48 (m, 1H), 1.40-1.33 (m, 2H), 0.90 (t, 3H). | N-(2-chloro-3-((5-chloro-3-methyl-4-oxo-3,4-dihydroquinazolin-6-yl)amino)-4-fluorophenyl)-3-ethylpyrrolidine-1-sulfonamide trifluoroacetate | 514.1 (M + H) |
| 95 | 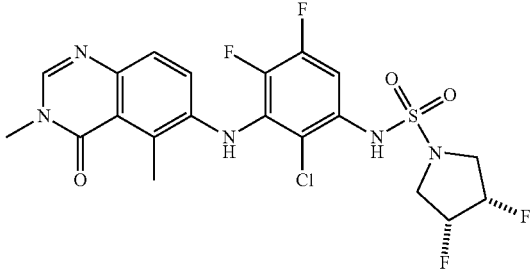 [SMILES: Cc1c(Nc2c(F)c(F)cc(NS(=O)(=O)N3C[C@@H](F)[C@@H](F)C3)c2Cl)ccc2ncn(C)c(=O)c12]<br>¹H NMR (400 MHz, CDCl₃) δ 7.95 (s, 1H), 7.49 (d, 1H), 7.29-7.21 (m, 1H), 7.18-7.14 (m, 1H), 6.80 (s, 1H), 5.67 (s, 1H), 5.21-5.01 (m, 2H), 3.84-3.58 (m, 4H), 3.55 (s, 3H), 2.96 (s, 3H). | cis-N-(2-chloro-3-((3,5-dimethyl-4-oxo-3,4-dihydroquinazolin-6-yl)amino)-4,5-difluorophenyl)-3,4-difluoropyrrolidine-1-sulfonamide | 520.1 (M + H) |
| 96 | 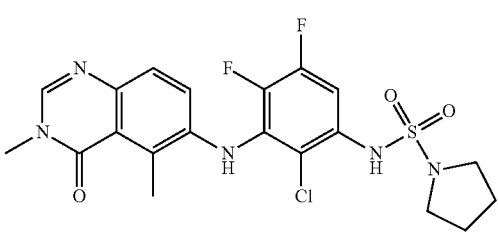 [SMILES: Cc1c(Nc2c(F)c(F)cc(NS(=O)(=O)N3CCCC3)c2Cl)ccc2ncn(C)c(=O)c12]<br>¹H NMR (400 MHz, CDCl₃) δ 8.07 (s, 1H), 7.50 (d, 1H), 7.31-7.27 (m, 1H), 7.17-7.12 (m, 1H), 6.79 (s, 1H), 5.67 (s, 1H), 3.57 (s, 3H), 3.40-3.35 (m, 4H), 2.96 (s, 3H), 1.95-1.90 (m, 4H). | N-(2-chloro-3-((3,5-dimethyl-4-oxo-3,4-dihydroquinazolin-6-yl)amino)-4,5-difluorophenyl)pyrrolidine-1-sulfonamide | 484.1 (M + H) |

TABLE 1-continued

| Ex# | structure and ¹H NMR data | Chemical Name | MS (apci) m/z |
|---|---|---|---|
| 97 | 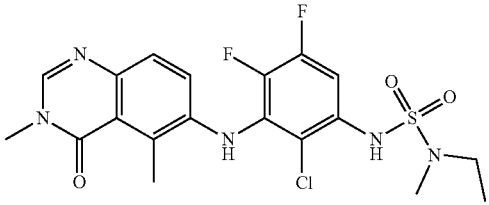 [SMILES: CCN(C)S(=O)(=O)Nc1cc(F)c(F)c(Nc2ccc3ncn(C)c(=O)c3c2C)c1Cl]<br>¹H NMR (400 MHz, CDCl₃) δ 7.95 (s, 1H), 7.48 (d, 1H), 7.23-7.12 (m, 2H), 6.74 (s, 1H), 5.66 (s, 1H), 3.55 (s, 3H), 3.35-3.27 (m, 2H), 2.96 (s, 3H), 2.88 (s, 3H), 1.17 (t, 3H). | N-(2-chloro-3-((3,5-dimethyl-4-oxo-3,4-dihydroquinazolin-6-yl)amino)-4,5-difluorophenyl)-(N-ethyl-N-methyl)-sulfamide | 472.1 (M + H) |
| 98 | 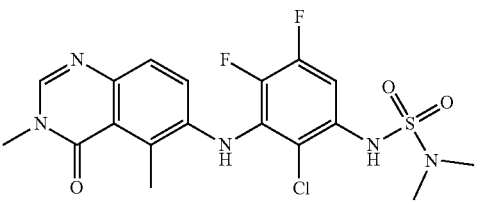<br>¹H NMR (400 MHz, CDCl₃) δ 7.95 (s, 1H), 7.48 (d, 1H), 7.25-7.21 (m, 1H), 7.18-7.13 (m, 1H), 6.71 (s, 1H), 5.66 (s, 1H), 3.55 (s, 3H), 2.96 (s, 3H), 2.90 (s, 6H). | N-(2-chloro-3-((3,5-dimethyl-4-oxo-3,4-dihydroquinazolin-6-yl)amino)-4,5-difluorophenyl)-(N,N-dimethyl)-sulfamide | 458.1 (M + H) |
| 99 | 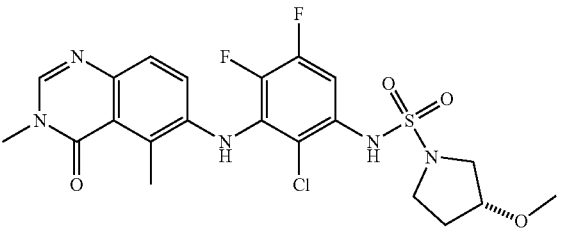<br>¹H NMR (400 MHz, CDCl₃) δ 7.95 (s, 1H), 7.48 (d, 1H), 7.33-7.27 (m, 1H), 7.19-7.12 (m, 1H), 6.94 (s, 1H), 5.65 (s, 1H), 4.01-3.95 (m, 1H), 3.55 (s, 3H), 3.54-3.42 (m, 4H), 3.29 (s, 3H), 2.96 (s, 3H), 2.16-1.93 (m, 2H). | (R)-N-(2-chloro-3-((3,5-dimethyl-4-oxo-3,4-dihydroquinazolin-6-yl)amino)-4,5-difluorophenyl)-3-methoxypyrrolidine-1-sulfonamide | 514.1 (M + H) |
| 100 | 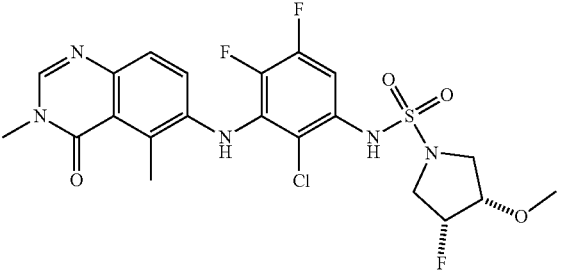<br>¹H NMR (400 MHz, CDCl₃) δ 7.97 (s, 1H), 7.48 (d, 1H), 7.29 (d, 1H), 7.18-7.13 (m, 1H), 6.81 (s, 1H), 5.66 (s, 1H), 5.22-5.04 (m, 1H), 3.83-3.75 (m, 1H), 3.70 (d, 1H), 3.65-3.60 (m, 1H), 3.56 (s, 3H), 3.48 (d, 1H), 3.46 (s, 3H), 3.33 (t, 1H), 2.96 (s, 3H). | cis-N-(2-chloro-3-((3,5-dimethyl-4-oxo-3,4-dihydroquinazolin-6-yl)amino)-4,5-difluorophenyl)-3-fluoro-4-methoxypyrrolidine-1-sulfonamide | 532.1 (M + H) |

| Ex# | structure and ¹H NMR data | Chemical Name | MS (apci) m/z |
|---|---|---|---|
| 101 | 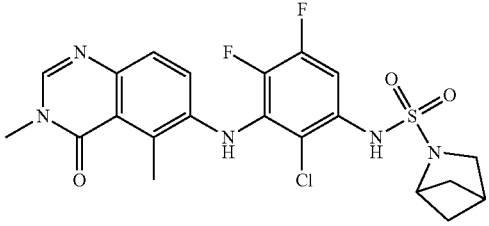 [SMILES: Cc1c(Nc2c(F)c(F)cc(NS(=O)(=O)N3CC4CC3C4)c2Cl)ccc2ncn(C)c(=O)c12]<br>¹H NMR (400 MHz, CDCl₃) δ 7.95 (s, 1H), 7.48 (d, 1H), 7.35-7.29 (m, 1H), 7.16-7.12 (m, 1H), 6.84 (s, 1H), 5.64 (s, 1H), 4.30-4.23 (m, 1H), 3.55 (s, 3H), 3.41 (s, 2H), 2.96 (s, 3H), 2.93-2.88 (m, 1H), 1.96 (d, 2H), 1.56-1.54 (m, 2H). | N-(2-chloro-3-((3,5-dimethyl-4-oxo-3,4-dihydroquinazolin-6-yl)amino)-4,5-difluorophenyl)-2-azabicyclo[2.1.1]hexane-2-sulfonamide | 496.2 (M + H) |
| 102 | 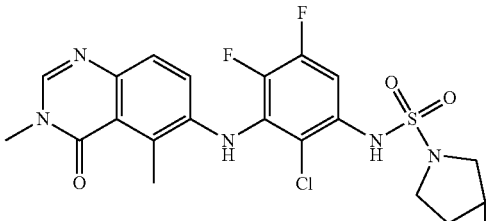<br>¹H NMR (400 MHz, CDCl₃) δ 7.95 (s, 1H), 7.48 (d, 1H), 7.24-7.18 (m, 1H), 7.17-7.13 (m, 1H), 6.79 (s, 1H), 5.66 (s, 1H), 3.55 (s, 3H), 3.51 (d, 2H), 3.42 (d, 2H), 2.96 (s, 3H), 1.57-1.54 (m, 2H), 0.71-0.61 (m, 1H), 0.29-0.22 (m, 1H). | N-(2-chloro-3-((3,5-dimethyl-4-oxo-3,4-dihydroquinazolin-6-yl)amino)-4,5-difluorophenyl)-3-azabicyclo[3.1.0]hexane-3-sulfonamide | 496.1 (M + H) |
| 103 | 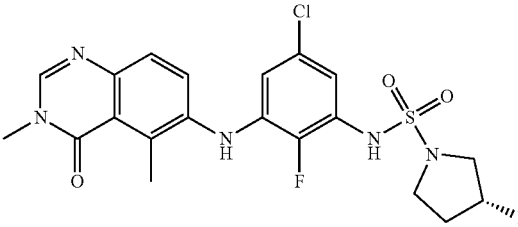<br>¹H NMR (400 MHz, CDCl₃) δ 8.05 (s, 1H), 7.59 (s, 2H), 7.05-7.01 (m, 1H), 6.61 (s, 1H), 6.44-6.39 (m, 1H), 5.67 (s, 1H), 5.33-5.17 (m, 1H), 3.71-3.50 (m, 7H), 2.83 (s, 3H), 2.38-2.23 (m, 1H), 2.17-1.97 (m, 1H). | (R)-N-(5-chloro-3-((3,5-dimethyl-4-oxo-3,4-dihydroquinazolin-6-yl)amino)-2-fluorophenyl)-3-fluoropyrrolidine-1-sulfonamide | 484.1 (M + H) |
| 104 | 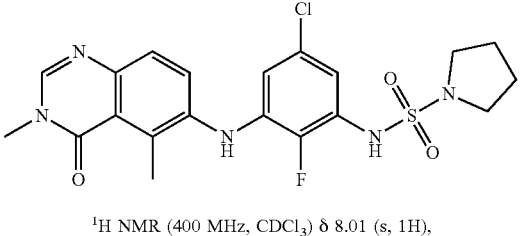<br>¹H NMR (400 MHz, CDCl₃) δ 8.01 (s, 1H), 7.59 (d, 2H), 7.03-6.98 (m, 1H), 6.60 (d, 1H), 6.42-6.36 (m, 1H), 5.66 (s, 1H), 3.56 (s, 3H), 3.40 (t, 4H), 2.84 (s, 3H), 1.98-1.88 (m, 4H). | N-(5-chloro-3-((3,5-dimethyl-4-oxo-3,4-dihydroquinazolin-6-yl)amino)-2-fluorophenyl)pyrrolidine-1-sulfonamide | 466.1 (M + H) |

TABLE 1-continued

| Ex# | structure and $^1$H NMR data | Chemical Name | MS (apci) m/z |
|---|---|---|---|
| 105 | 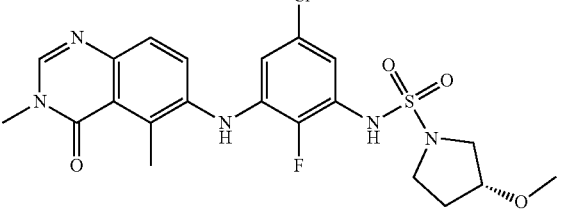<br>$^1$H NMR (400 MHz, CDCl$_3$) δ 8.01 (s, 1H), 7.59 (d, 2H), 7.08-7.03 (m, 1H), 6.84 (d, 1H), 6.43-6.37 (m, 1H), 5.65 (s, 1H), 4.01-3.96 (m, 1H), 3.63-3.43 (m, 7H), 3.31 (s, 3H), 2.84 (s, 3H), 2.18-1.94 (m, 2H). | (R)-N-(5-chloro-3-((3,5-dimethyl-4-oxo-3,4-dihydroquinazolin-6-yl)amino)-2-fluorophenyl)-3-methoxypyrrolidine-1-sulfonamide | 496.2 (M + H) |
| 106 | 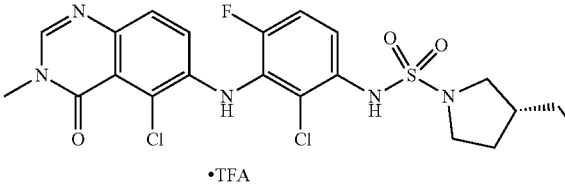<br>·TFA<br>$^1$H NMR (400 MHz, CDCl$_3$) δ 8.39 (s, 1H), 7.60-7.56 (m, 2H), 7.17 (t, 1H), 6.99-6.96 (m, 1H), 6.76 (s, 1H), 6.52 (s, 1H), 3.65 (s, 3H), 3.55-3.51 (m, 1H), 3.49-3.44 (m, 1H), 3.34-3.28 (m, 1H), 2.92 (t, 1H), 2.12-2.01 (m, 2H), 1.54-1.49 (m, 1H), 1.40-1.33 (m, 2H), 0.90 (t, 3H). | (R)-N-(2-chloro-3-((5-chloro-3-methyl-4-oxo-3,4-dihydroquinazolin-6-yl)amino)-4-fluorophenyl)-3-ethylpyrrolidine-1-sulfonamide trifluoroacetate | 514.2 (M + H) |

Example 107

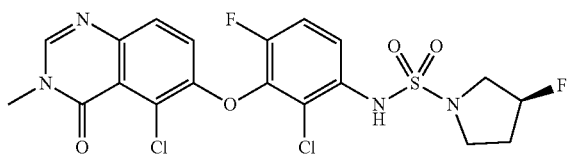 [SMILES: Cn1cnc2ccc(Oc3c(F)ccc(NS(=O)(=O)N4CC[C@H](F)C4)c3Cl)c(Cl)c2c1=O]

(S)-N-(2-chloro-3-((5-chloro-3-methyl-4-oxo-3,4-dihydroquinazolin-6-yl)oxy)-4-fluorophenyl)-3-fluoropyrrolidine-1-sulfonamide A solution of 6-(3-amino-2-chloro-6-fluorophenoxy)-5-chloro-3-methylquinazolin-4(3H)-one (51 mg, 0.144 mmol) and (S)-3-fluoropyrrolidine-1-sulfonyl chloride (135 mg, 0.720 mmol) in pyridine (0.50 mL) was heated at 70° C. for 18 hours. The reaction mixture was partitioned between DCM (25 mL) and 10% aqueous CuSO$_4$ (25 mL) and the organic phase was separated, dried over Na$_2$SO$_4$, filtered and concentrated. The reaction mixture was purified by silica gel chromatography (0-100% hexanes/ethyl acetate) followed by reverse phase chromatography (5-95% MeCN/water with 0.1% TFA). The fractions containing the desired product were combined and partitioned between saturated aqueous NaHCO$_3$ and DCM (30 mL). The organic phase was separated, dried over Na$_2$SO$_4$, filtered and concentrated to afford (S)-N-(2-chloro-3-((5-chloro-3-methyl-4-oxo-3,4-dihydroquinazolin-6-yl)oxy)-4-fluorophenyl)-3-fluoropyrrolidine-1-sulfonamide (23.5 mg, 32.3% yield). $^1$H NMR (400 MHz, CDCl$_3$) δ 8.00 (s, 1H), 7.64-7.59 (m, 1H), 7.52 (d, 1H), 7.16 (t, 1H), 7.03 (d, 1H), 6.79 (s, 1H), 5.30-5.14 (m, 1H), 3.70-3.56 (m, 5H), 3.53-3.43 (m, 2H), 2.33-2.21 (m, 1H), 2.15-1.93 (m, 1H); MS (apci, m/z)=505.0, 507.0 (M+H).

Example 108

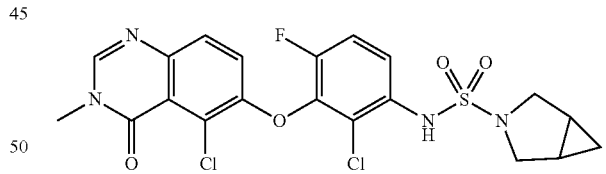

N-(2-chloro-3-((5-chloro-3-methyl-4-oxo-3,4-dihydroquinazolin-6-yl)oxy)-4-fluorophenyl)-3-azabicyclo[3.1.0]hexane-3-sulfonamide A solution of 6-(3-amino-2-chloro-6-fluorophenoxy)-5-chloro-3-methylquinazolin-4(3H)-one (30 mg, 0.085 mmol) and 3-azabicyclo[3.1.0]hexane-3-sulfonyl chloride (46 mg, 0.25 mmol) in pyridine (565 μL, 0.085 mmol) was heated to 70° C. for 16 hours in a sealed vial. The reaction mixture was cooled to ambient temperature, concentrated and purified by reverse-phase chromatography (5-95% MeCN/water, 0.1% TFA). The product was partitioned between dichloromethane and saturated NaHCO$_3$. The organic layer was washed with brine, dried with Na$_2$SO$_4$, filtered, and concentrated to give impure product. The impure product was purified by silica gel chromatography (5-95% EtOAc/DCM) and the product was partitioned between dichloromethane and saturated NaHCO$_3$. The organic layer was washed with brine, dried with Na$_2$SO$_4$, filtered, and concentrated to give N-(2-chloro-3-((5-chloro-3-methyl-4-oxo-3,4-dihydroquinazolin-6-yl)oxy)-4-fluorophenyl)-3-azabicyclo[3.1.0]hexane-3-sulfonamide (13 mg, 31% yield). $^1$H NMR (400 MHz, CDCl$_3$) δ 9.0 (s, 1H), 7.55-7.51 (m, 2H), 7.18-7.14 (t, 1H), 7.03 (d, 1H), 6.80 (s, 1H), 3.57 (s, 3H), 3.49-3.46 (m, 2H), 3.40-3.36 (m, 2H), 1.54-1.50 (m, 2H), 0.66-0.60 (m, 1H), 0.22-0.18 (m, 1H); MS (apci, m/z)=499.1, 501.1 (M+H).

Example 109

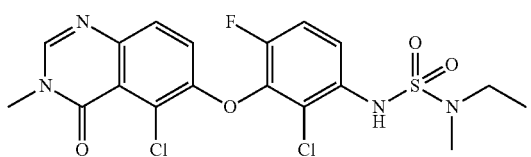 [SMILES: CCN(C)S(=O)(=O)Nc1ccc(F)c(Oc2ccc3ncn(C)c(=O)c3c2Cl)c1Cl]

N-(2-chloro-3-((5-chloro-3-methyl-4-oxo-3,4-dihydroquinazolin-6-yl)oxy)-4-fluorophenyl)-(N-ethyl-N-methyl)-sulfamide A solution of 6-(3-amino-2-chloro-6-fluorophenoxy)-5-chloro-3-methylquinazolin-4(3H)-one (50 mg, 0.141 mmol) and (N-ethyl-N-methyl)sulfamoyl chloride (86.9 µL, 0.706 mmol) in pyridine (0.5 mL) was heated at 70° C. for 8 hours. The reaction mixture was cooled to ambient temperature and partitioned between DCM (25 mL) and 10% aqueous CuSO$_4$ (25 mL). The organic phase was separated, dried over Na$_2$SO$_4$, filtered and concentrated under reduced pressure. The reaction mixture was purified by silica gel chromatography (0-100% hexanes/EtOAc) followed by HPLC reverse phase chromatography (5-95% MeCN/water with 0.1% TFA). The desired fractions were partitioned between saturated aqueous NaHCO$_3$ and DCM (20 mL). The organic phase was separated and dried over Na$_2$SO$_4$, filtered and concentrated to afford N-(2-chloro-3-((5-chloro-3-methyl-4-oxo-3,4-dihydroquinazolin-6-yl)oxy)-4-fluorophenyl)-(N-ethyl-N-methyl)-sulfamide (32.3 mg, 48.1% yield) as a white solid. $^1$H NMR (400 MHz, CDCl$_3$) δ 8.00 (s, 1H), 7.56-7.49 (m, 2H), 7.16 (t, 1H), 7.03 (d, 1H), 6.72 (s, 1H), 3.58 (s, 3H), 3.26 (m, 2H), 2.85 (s, 3H), 1.13 (t, 3H); MS (apci, m/z)=475.1, 477.1 (M+H).

Example 110

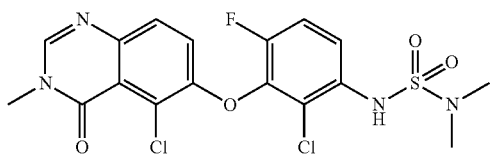

N-(2-chloro-3-((5-chloro-3-methyl-4-oxo-3,4-dihydroquinazolin-6-yl)oxy)-4-fluorophenyl)-(N,N-dimethyl)-sulfamide A solution of 6-(3-amino-2-chloro-6-fluorophenoxy)-5-chloro-3-methylquinazolin-4(3H)-one (50 mg, 0.1412 mmol) and dimethylsulfamoyl chloride (75.30 µl, 0.7059 mmol) in pyridine (0.5 mL) was heated at 70° C. for 18 hours. The reaction mixture was cooled to ambient temperature and partitioned between DCM (25 mL) and 10% aqueous CuSO$_4$ (25 mL). The organic phase was separated, dried over Na$_2$SO$_4$, filtered and concentrated under reduced pressure. The reaction mixture was purified by silica gel chromatography (0-100% EtOAc/hexanes) followed by HPLC reverse phase chromatography (5-95% ACN/water with 0.1% TFA). The desired fractions were partitioned between saturated aqueous NaHCO$_3$ and DCM (20 mL) and the organic phase was separated and dried over Na$_2$SO$_4$, filtered, and concentrated to afford N-(2-chloro-3-((5-chloro-3-methyl-4-oxo-3,4-dihydroquinazolin-6-yl)oxy)-4-fluorophenyl)-(N,N-dimethyl)-sulfamide (28.84 mg, 44.28% yield) as a white solid. $^1$H NMR (400 MHz, CDCl$_3$) δ 8.00 (s, 1H), 7.60-7.51 (m, 2H), 7.16 (t, 1H), 7.04 (d, 1H), 6.68 (s, 1H), 3.58 (s, 3H), 2.87 (s, 6H); MS (apci, m/z)=461.1, 463.1 (M+H).

Example 111

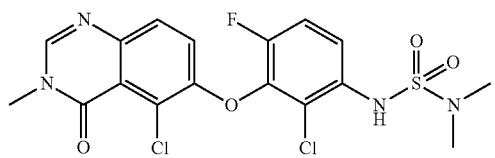

N-(2-chloro-4-fluoro-3-((5-fluoro-3-methyl-4-oxo-3,4-dihydroquinazolin-6-yl)oxy)phenyl)-(N,N-dimethyl)-sulfamide A solution of 6-(3-amino-2-chloro-6-fluorophenoxy)-5-fluoro-3-methylquinazolin-4(3H)-one (30 mg, 0.08 mmol) and (N,N-dimethyl)sulfamoyl chloride (47.7 µL, 0.44 mmol) in pyridine (0.88 mL) was heated at 60° C. for 3 days in a sealed vial. The reaction mixture was cooled to ambient temperature, diluted with EtOAc, and washed with 10% citric acid (3×50 mL) and brine (1×25 mL), then dried over anhydrous Na$_2$SO$_4$, filtered, and concentrated. The residue was purified by silica gel column chromatography (30-100% EtOAc/DCM) to give N-(2-chloro-4-fluoro-3-((5-fluoro-3-methyl-4-oxo-3,4-dihydroquinazolin-6-yl)oxy)phenyl)-(N,N-dimethyl)-sulfamide (21.3 mg, 54%) as an white solid. $^1$H NMR (400 MHz, CDCl$_3$) δ 7.97 (s, 1H), 7.56-7.51 (m, 1H), 7.48-7.43 (m, 1H), 7.29-7.22 (m, 1H), 7.17-7.08 (t, 1H), 6.67 (s, 1H), 3.57 (s, 3H), 2.86 (s, 6H); MS (apci, m/z)=445.0, 447.1 (M+H).

Example 112

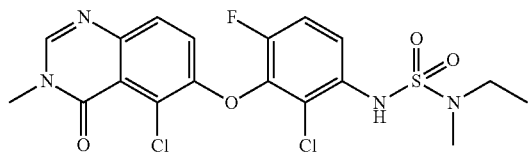 [SMILES: CCN(C)S(=O)(=O)Nc1ccc(F)c(Oc2ccc3ncn(C)c(=O)c3c2Cl)c1Cl]

N-(2-chloro-4-fluoro-3-((5-fluoro-3-methyl-4-oxo-3,4-dihydroquinazolin-6-yl)oxy)phenyl)-(N-ethyl-N-methyl)-sulfamide A solution of 6-(3-amino-2-chloro-6-fluorophenoxy)-5-fluoro-3-methylquinazolin-4(3H)-one (30 mg, 0.08 mmol) and (N-ethyl-N-methyl)sulfamoyl chloride (70 mg, 0.44 mmol) in pyridine (0.88 mL) was heated at 60° C. for 3 days in a sealed vial. The reaction mixture was cooled to ambient temperature, diluted with EtOAc, and washed with 10% citric acid (3×50 mL) and brine (1×25 mL), dried over anhydrous Na₂SO₄, filtered, and concentrated. The residue was purified by silica gel column chromatography (30-100% EtOAc/DCM) followed by reverse phase chromatography (5-95% MeCN/H₂O with 0.1% TFA). The desired fractions were combined and partitioned between 4:1 DCM: IPA and saturated aqueous NaHCO₃ (1×). The organic layer was separated, dried over anhydrous Na₂SO₄, filtered and concentrated to give N-(2-chloro-4-fluoro-3-((5-fluoro-3-methyl-4-oxo-3,4-dihydroquinazolin-6-yl)oxy)phenyl)-(N-ethyl-N-methyl)-sulfamide (7.1 mg, 17%) as a white solid. $^1$H NMR (400 MHz, CDCl₃) δ 7.97 (s, 1H), 7.53-7.48 (m, 1H), 7.47-4.42 (d, 1H), 7.25-7.20 (m, 1H), 7.16-7.08 (t, 1H), 6.70 (s, 1H), 3.57 (s, 3H), 3.31-3.22 (m, 2H), 2.85 (s, 3H), 1.15-1.10 (t, 3H); MS (apci, m/z)=459.0, 461.0 (M+H).

Example 113

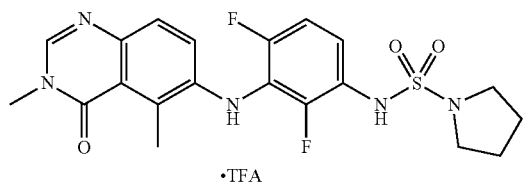 [SMILES: Cc1c(Nc2c(F)ccc(NS(=O)(=O)N3CCCC3)c2F)ccc2ncn(C)c(=O)c12]

N-(3-((3,5-dimethyl-4-oxo-3,4-dihydroquinazolin-6-yl)amino)-2,4-difluorophenyl)pyrrolidine-1-sulfonamide trifluoroacetate 6-((3-amino-2,6-difluorophenyl)amino)-3,5-dimethylquinazolin-4(3H)-one (22 mg, 0.06955 mmol), pyrrolidine-1-sulfonyl chloride (19.93 μL, 0.1739 mmol), and pyridine (347.8 μL, 0.06955 mmol) were added to a 3 mL vial and the reaction was sealed and heated to 70° C. for 16 hours. The reaction was cooled to ambient temperature and partitioned between DCM and saturated aqueous CuSO₄. The organic layer was concentrated, and the resulting residue was purified by reverse phase HPLC (5-95% MeCN/H₂O, 0.1% TFA). The desired fractions were lyophilized to provide N-(3-((3,5-dimethyl-4-oxo-3,4-dihydroquinazolin-6-yl)amino)-2,4-difluorophenyl)pyrrolidine-1-sulfonamide trifluoroacetate (23 mg, 74% yield). $^1$H NMR (400 MHz, CDCl₃) δ 8.56 (s, 1H), 7.58 (d, 1H), 7.36-7.30 (m, 1H), 7.16-7.13 (m, 1H), 7.02-6.97 (m, 1H), 6.43 (s, 1H), 5.48 (s, 1H), 3.64 (s, 3H), 3.37-3.30 (m, 4H), 2.95 (s, 3H), 1.93-1.88 (m, 4H). MS (apci, m/z)=450.1 (M+H).

Example 114

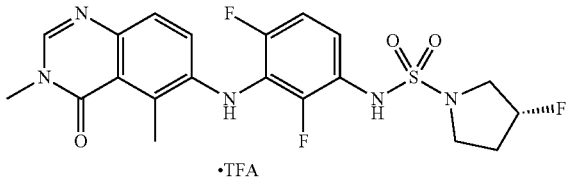 [SMILES: Cc1c(Nc2c(F)ccc(NS(=O)(=O)N3CC[C@@H](F)C3)c2F)ccc2ncn(C)c(=O)c12]

(R)-N-(3-((3,5-dimethyl-4-oxo-3,4-dihydroquinazolin-6-yl)amino)-2,4-difluorophenyl)-3-fluoropyrrolidine-1-sulfonamide trifluoroacetate 6-((3-Amino-2,6-difluorophenyl)amino)-3,5-dimethylquinazolin-4(3H)-one (8.0 mg, 0.0253 mmol), (R)-3-fluoropyrrolidine-1-sulfonyl chloride (11.9 mg, 0.0632 mmol), and pyridine (126 μl, 0.0253 mmol) were added to a 3 mL vial and the reaction was sealed and heated to 70° C. for 16 hours. The reaction was cooled to ambient temperature and partitioned between DCM and saturated aqueous CuSO₄. The organic layer was concentrated and the crude material was purified by reverse phase HPLC (5-95% MeCN/H₂O, 0.1% TFA). The desired fractions were lyophilized to provide (R)-N-(3-((3,5-dimethyl-4-oxo-3,4-dihydroquinazolin-6-yl)amino)-2,4-difluorophenyl)-3-fluoropyrrolidine-1-sulfonamide trifluoroacetate (4 mg, 32% yield). $^1$H NMR (400 MHz, CDCl₃) δ 8.66 (s, 1H), 7.59 (d, 1H), 7.40-7.35 (m, 1H), 7.18-7.15 (m, 1H), 7.02-6.97 (m, 1H), 6.44 (s, 1H), 5.48 (s, 1H), 5.31-5.17 (m, 1H), 3.66 (s, 3H), 3.49-3.10 (m, 2H), 2.94 (s, 3H), 2.32-2.22 (m, 2H), 2.16-1.98 (m, 2H). MS (apci, m/z)=468.1 (M+H).

Example 115

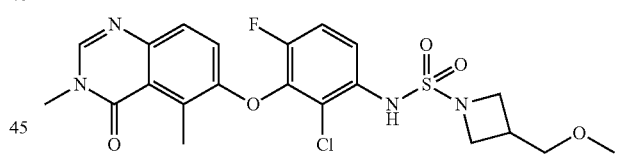

N-(2-chloro-3-((3,5-dimethyl-4-oxo-3,4-dihydroquinazolin-6-yl)oxy)-4-fluorophenyl)-3-(methoxymethyl)azetidine-1-sulfonamide Tert-butyl (2-chloro-3-((3,5-dimethyl-4-oxo-3,4-dihydroquinazolin-6-yl)oxy)-4-fluorophenyl)carbamate (30 mg, 0.07 mmol) was dissolved in THF (0.7 mL), cooled to 0° C., and treated with sodium hydride (5.5 mg, 0.14 mmol). The reaction was stirred for 10 minutes and then treated with 3-(methoxymethyl)azetidine-1-sulfonyl chloride (28 mg, 0.14 mmol) and then heated to 50° C. for 12 hours. The reaction mixture was cooled to ambient temperature and poured into 20 mL ice water and the aqueous layer was extracted with DCM (3×25 mL), dried over anhydrous Na₂SO₄, filtered, and concentrated. The resulting residue was dissolved in 1:1 DCM:TFA (5 mL) and stirred at ambient temperature for 30 minutes. The reaction mixture was concentrated, diluted with DCM, washed with saturated NaHCO₃ (3×50 mL) and brine (1×25 mL), dried over anhydrous Na₂SO₄, filtered, and concentrated. The residue was purified by reverse phase chromatography (5-95% water/ACN with 0.1% TFA) and the desired fractions were combined and partitioned between 4:1 DCM:IPA and saturated aqueous NaHCO₃ (1×). The organic layer was separated, dried over anhydrous Na₂SO₄, filtered and concentrated to give N-(2-chloro-3-((3,5-dimethyl-4-oxo-3,4-dihydroquinazolin-6-yl)oxy)-4-fluorophenyl)-3-(methoxymethyl)azetidine-1-sulfonamide (17 mg, 49%) as a white solid. ¹H NMR (400 MHz, (CD₃)₂SO) δ 9.72 (s, 1H), 8.28 (s, 1H), 7.55-7.43 (m, 3H), 6.98-6.94 (d, 1H), 3.90-3.83 (t, 2H), 3.61-3.55 (m, 2H), 3.46 (s, 3H), 3.43-3.40 (d, 2H), 3.23 (s, 3H), 2.91 (s, 3H), 2.81-2.70 (m, 1H); MS (apci, m/z)=497.1, 499.1 (M+H).

Example 116

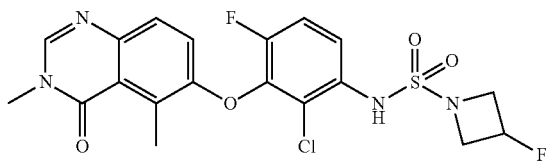 [SMILES: Cc1c(Oc2c(F)ccc(NS(=O)(=O)N3CC(F)C3)c2Cl)ccc2ncn(C)c(=O)c12]

N-(2-chloro-3-((3,5-dimethyl-4-oxo-3,4-dihydroquinazolin-6-yl)oxy)-4-fluorophenyl)-3-fluoroazetidine-1-sulfonamide Tert-butyl (2-chloro-3-((3,5-dimethyl-4-oxo-3,4-dihydroquinazolin-6-yl)oxy)-4-fluorophenyl)carbamate (30 mg, 0.07 mmol) was dissolved in THF (0.7 mL), cooled to 0° C., and treated with sodium hydride (5.5 mg, 0.14 mmol). The reaction was stirred for 10 minutes and then treated with 3-fluoroazetidine-1-sulfonyl chloride (24 mg, 0.14 mmol) and heated to 50° C. for 12 hours. The reaction mixture was cooled to ambient temperature and poured into 20 mL ice water. The aqueous layer was extracted with 4:1 DCM/IPA (3×25 mL), dried over anhydrous Na₂SO₄, filtered, and concentrated. The resulting residue was dissolved in 1:1 DCM:TFA (5 mL) and stirred at ambient temperature for 30 minutes. The reaction was concentrated, diluted with DCM, washed with saturated NaHCO₃ (3×50 mL) and brine (1×25 mL), dried over anhydrous Na₂SO₄, filtered, and concentrated. The residue was purified by reverse phase chromatography (5-95% water/ACN with 0.1% TFA) and the desired fractions were combined and partitioned between 4:1 DCM:IPA and saturated aqueous NaHCO₃. The organic layer was separated, dried over anhydrous Na₂SO₄, filtered, and concentrated to give N-(2-chloro-3-((3,5-dimethyl-4-oxo-3,4-dihydroquinazolin-6-yl)oxy)-4-fluorophenyl)-3-fluoroazetidine-1-sulfonamide (13 mg, 40%) as a white solid. ¹H NMR (400 MHz, (CD₃)₂SO) δ 9.96 (s, 1H), 8.28 (s, 1H), 7.52-7.42 (m, 3H), 6.99-6.94 (d, 1H), 5.46-5.24 (m, 1H), 4.20-4.08 (m, 2H), 4.01-3.89 (m, 2H), 3.46 (s, 3H), 2.91 (s, 3H); MS (apci, m/z)=471.0, 473.0 (M+H).

Example 117

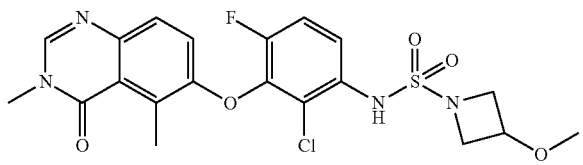

N-(2-chloro-3-((3,5-dimethyl-4-oxo-3,4-dihydroquinazolin-6-yl)oxy)-4-fluorophenyl)-3-methoxyazetidine-1-sulfonamide Tert-butyl (2-chloro-3-((3,5-dimethyl-4-oxo-3,4-dihydroquinazolin-6-yl)oxy)-4-fluorophenyl)carbamate (30 mg, 0.07 mmol) was dissolved in THF (0.7 mL), cooled to 0° C., and treated with sodium hydride (5.5 mg, 0.14 mmol). The reaction mixture was stirred for 10 minutes and treated with 3-methoxyazetidine-1-sulfonyl chloride (26 mg, 0.14 mmol) and heated to 50° C. for 24 hours. The reaction mixture was cooled to ambient temperature and poured into 20 mL ice water. The aqueous layer was extracted with DCM (2×25 mL), dried over anhydrous Na₂SO₄, filtered, and concentrated. The resulting residue was dissolved in 1:1 DCM:TFA (5 mL) and stirred at ambient temperature for 30 minutes. The reaction was concentrated, diluted with DCM, washed with saturated NaHCO₃ (3×50 mL) and brine (1×25 mL), dried over anhydrous Na₂SO₄, filtered, and concentrated. The residue was purified by reverse phase chromatography (5-95% water/ACN with 0.1% TFA) and the desired fractions were combined and partitioned between 4:1 DCM:IPA and saturated aqueous NaHCO₃ (1×). The organic layer was separated, dried over anhydrous Na₂SO₄, filtered and concentrated to give N-(2-chloro-3-((3,5-dimethyl-4-oxo-3,4-dihydroquinazolin-6-yl)oxy)-4-fluorophenyl)-3-methoxyazetidine-1-sulfonamide (13 mg, 39%) as an off-white solid. ¹H NMR (400 MHz, (CD₃)₂SO) δ 9.82 (s, 1H), 8.28 (s, 1H), 7.54-7.41 (m, 3H), 7.00-6.94 (d, 1H), 4.18-4.10 (m, 1H), 4.00-3.95 (m, 2H), 3.73-3.67 (m, 2H), 3.46 (s, 3H), 3.18 (s, 3H), 2.91 (s, 3H); MS (apci, m/z)=483.1, 485.1 (M+H).

Example 118

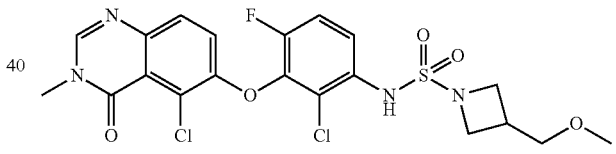

N-(2-chloro-3-((5-chloro-3-methyl-4-oxo-3,4-dihydroquinazolin-6-yl)oxy)-4-fluorophenyl)-3-(methoxymethyl)azetidine-1-sulfonamide A solution of tert-butyl (2-chloro-3-((5-chloro-3-methyl-4-oxo-3,4-dihydroquinazolin-6-yl)oxy)-4-fluorophenyl)carbamate (25 mg, 0.055 mmol) and sodium hydride (4.4 mg, 0.11 mmol) in THF (0.5 mL) was stirred at 0° C. for 10 minutes. 3-(Methoxymethyl)azetidine-1-sulfonyl chloride (22 mg, 0.11 mmol) was added and the reaction mixture was warmed to ambient temperature heated at 50° C. for 18 hours. The reaction mixture was cooled to ambient temperature and partitioned between water (25 mL) and 4:1 DCM:IPA (25 mL). The organic phase was dried over Na₂SO₄, filtered, and concentrated under reduced pressure. The reaction mixture was diluted in DCM (5 mL) and TFA (5 mL) was added. The reaction mixture was stirred at ambient temperature for 30 minutes, then concentrated and purified by HPLC reverse phase chromatography (5-95% acetonitrile:H₂O with 0.1% TFA). The fractions containing the desired product were combined and partitioned between saturated aqueous NaHCO₃ and DCM (25 mL). The organic phase was separated and dried over Na₂SO₄, filtered, and concentrated to afford N-(2-chloro-3-((5-chloro-3-methyl-4-oxo-3,4-dihydroquinazolin-6-yl)oxy)-4-fluorophenyl)-3-(methoxymethyl)azetidine-1-sulfonamide (7.7 mg, 27% yield) as a white solid. ¹H NMR (400 MHz, CDCl₃) δ 8.00 (s, 1H), 7.61-7.52 (m, 2H), 7.17 (t, 1H), 7.05 (d, 1H), 6.67 (s, 1H), 4.01 (t, 2H), 3.82-3.77 (m, 2H), 3.58 (s, 3H), 3.47 (d, 2H), 3.35 (s, 3H), 2.88-2.76 (m, 1H); MS (apci, m/z)=517.1, 519.1 (M+H).

Example 119

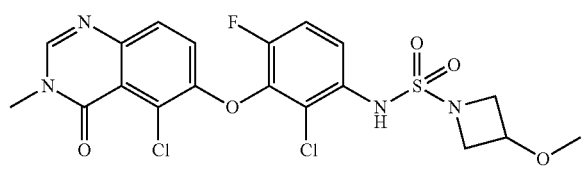

N-(2-chloro-3-((5-chloro-3-methyl-4-oxo-3,4-dihydroquinazolin-6-yl)oxy)-4-fluorophenyl)-3-methoxyazetidine-1-sulfonamide A solution of tert-butyl (2-chloro-3-((5-chloro-3-methyl-4-oxo-3,4-dihydroquinazolin-6-yl)oxy)-4-fluorophenyl)carbamate (0.674 ml, 0.0674 mmol) in THF (0.7 mL) and sodium hydride (5.39 mg, 0.135 mmol) was stirred at 0° C. for 10 minutes. 3-Methoxyazetidine-1-sulfonyl chloride (25.0 mg, 0.135 mmol) was added and the reaction mixture was warmed to ambient temperature then heated to 50° C. for 18 hours. The reaction mixture was cooled to ambient temperature and partitioned between water (25 mL) and 4:1 DCM:APA (25 mL). The organic phase was separated and dried over Na₂SO₄, filtered, and concentrated to afford a crude mixture that was taken up in DCM (5 mL) and trifluoroacetic acid (5 mL) and stirred at ambient temperature for 30 minutes. The reaction mixture was concentrated and purified by HPLC reverse phase chromatography (5-95% acetonitrile:H₂O with 0.1% TFA). The desired fractions were partitioned between with sat. aqueous NaHCO₃ and DCM (25 mL) and the organic phase was dried over Na₂SO₄, filtered, and concentrated to afford N-(2-chloro-3-((5-chloro-3-methyl-4-oxo-3,4-dihydroquinazolin-6-yl)oxy)-4-fluorophenyl)-3-methoxyazetidine-1-sulfonamide (8.3 mg, 24.5% yield). ¹H NMR (400 MHz, CDCl₃) δ 8.17 (s, 1H), 7.61-7.54 (m, 2H), 7.18 (t, 1H), 7.07 (d, 1H), 6.67 (s, 1H), 4.19-4.04 (m, 3H), 3.93-3.87 (m, 2H), 3.61 (s, 3H), 3.27 (s, 3H); MS (apci, m/z)=503.1, 505.1 (M+H).

Example 120

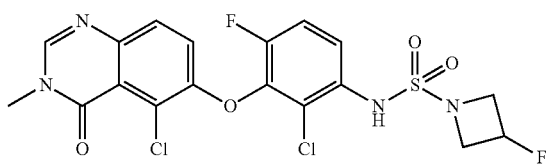 [SMILES: Cn1cnc2ccc(Oc3c(F)ccc(NS(=O)(=O)N4CC(F)C4)c3Cl)c(Cl)c2c1=O]

N-(2-chloro-3-((5-chloro-3-methyl-4-oxo-3,4-dihydroquinazolin-6-yl)oxy)-4-fluorophenyl)-3-fluoroazetidine-1-sulfonamide A solution of tert-butyl (2-chloro-3-((5-chloro-3-methyl-4-oxo-3,4-dihydroquinazolin-6-yl)oxy)-4-fluorophenyl)carbamate (0.605 ml, 0.0605 mmol) in THF (0.6 mL) and sodium hydride (4.84 mg, 0.121 mmol) was stirred at 0° C. for 10 minutes then 3-fluoroazetidine-1-sulfonyl chloride (21.0 mg, 0.121 mmol) was added and the reaction mixture was allowed to warm to ambient temperature then heated to 50° C. for 18 hours. The reaction mixture was cooled to ambient temperature and partitioned between water (25 mL) and 4:1 DCM:APA (25 mL). The organic phase was separated and dried over Na₂SO₄, filtered, and concentrated under reduced pressure and the reaction mixture was taken up in DCM (5 mL) and TFA (5 mL) and stirred at ambient temperature for 30 minutes. The reaction mixture was concentrated and purified by HPLC reverse phase chromatography (5-95% acetonitrile:H₂O with 0.1% TFA). The desired fractions were combined and partitioned between saturated aqueous NaHCO₃ and DCM (25 mL) and the organic phase was separated and dried over Na₂SO₄, filtered, and concentrated to afford N-(2-chloro-3-((5-chloro-3-methyl-4-oxo-3,4-dihydroquinazolin-6-yl)oxy)-4-fluorophenyl)-3-fluoroazetidine-1-sulfonamide (7.8 mg, 26.2% yield). ¹H NMR (400 MHz, CDCl₃) δ 8.00 (s, 1H), 7.59-7.51 (m, 2H), 7.18 (t, 1H), 7.05 (d, 1H), 6.68 (s, 1H), 5.35-5.14 (m, 1H), 4.26-4.08 (m, 4H), 3.59 (s, 3H); MS (apci, m/z)=491.0, 493.0 (M+H).

Example 121

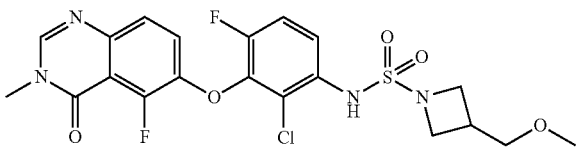

N-(2-chloro-4-fluoro-3-((5-fluoro-3-methyl-4-oxo-3,4-dihydroquinazolin-6-yl)oxy)phenyl)-3-(methoxymethyl)azetidine-1-sulfonamide Tert-butyl (2-chloro-4-fluoro-3-((5-fluoro-3-methyl-4-oxo-3,4-dihydroquinazolin-6-yl)oxy)phenyl)carbamate (25 mg, 0.06 mmol) was dissolved in THF (0.6 mL), cooled to 0° C. and treated with sodium hydride (4.6 mg, 0.11 mmol). The reaction was stirred for 10 minutes and treated with 3-(methoxymethyl)azetidine-1-sulfonyl chloride (23 mg, 0.11 mmol) and heated to 50° C. for 12 hours. The reaction was cooled to ambient temperature and poured into 20 mL ice water. The aqueous layer was extracted with 4:1 DCM/IPA (3×25 mL), dried over anhydrous Na₂SO₄, filtered, and concentrated. The resulting residue was dissolved in 1:1 DCM:TFA (5 mL) and stirred at ambient temperature for 30 minutes. The reaction mixture was concentrated, diluted with DCM, washed with saturated NaHCO₃ (3×50 mL) and brine (1×25 mL), dried over anhydrous Na₂SO₄, filtered, and concentrated. The residue was purified by silica gel column chromatography (0-100% DCM/EtOAc) followed by reverse phase chromatography (5-95% water/acetonitrile with 0.1% TFA). The desired fractions were combined and partitioned between 4:1 DCM:IPA and saturated aqueous NaHCO$_3$ (1×) and the organic layer was separated, dried over anhydrous Na$_2$SO$_4$, filtered, and concentrated to give N-(2-chloro-4-fluoro-3-((5-fluoro-3-methyl-4-oxo-3,4-dihydroquinazolin-6-yl)oxy)phenyl)-3-(methoxymethyl)azetidine-1-sulfonamide (10 mg, 35%) as an off-white solid. $^1$H NMR (400 MHz, CDCl$_3$) δ 8.02 (s, 1H), 7.58-7.54 (m, 1H), 7.47-7.43 (m, 1H), 7.29-7.22 (m, 1H), 7.17-7.11 (t, 1H), 6.67 (s, 1H), 4.04-3.97 (t, 2H), 3.82-3.76 (m, 2H), 3.58 (s, 3H), 3.49-3.45 (d, 2H), 3.35 (s, 3H), 2.88-2.77 (m, 1H); MS (apci, m/z)=501.0, 503.1 (M+H).

Example 122

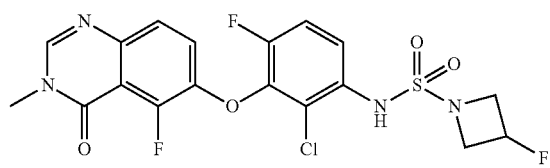

N-(2-chloro-4-fluoro-3-((5-fluoro-3-methyl-4-oxo-3,4-dihydroquinazolin-6-yl)oxy)phenyl)-3-fluoroazetidine-1-sulfonamide Tert-butyl (2-chloro-4-fluoro-3-((5-fluoro-3-methyl-4-oxo-3,4-dihydroquinazolin-6-yl)oxy)phenyl)carbamate (30 mg, 0.07 mmol) was dissolved in THF (0.6 mL), cooled to 0° C. and treated with sodium hydride (5.5 mg, 0.14 mmol). The reaction was stirred for 10 minutes and then treated with 3-fluoroazetidine-1-sulfonyl chloride (24 mg, 0.14 mmol). The reaction mixture was heated to 50° C. for 12 hours. The reaction was cooled to ambient temperature and poured into 20 mL ice water and the aqueous layer was extracted with DCM (3×25 mL), dried over anhydrous Na$_2$SO$_4$, filtered, and concentrated. The resulting residue was dissolved in 1:1 DCM:TFA (5 mL) and stirred at ambient temperature for 30 minutes. The reaction was concentrated, diluted with DCM, washed with saturated NaHCO$_3$ (3×50 mL) and brine (1×25 mL), dried over anhydrous Na$_2$SO$_4$, filtered, and concentrated. The residue was purified by silica gel column chromatography (0-100% DCM/EtOAc) followed by reverse phase chromatography (5-95% water/acetonitrile with 0.1% TFA). The desired fractions were combined and partitioned between 4:1 DCM:APA and saturated aqueous NaHCO$_3$ (1×) and the organic layer was separated, dried over anhydrous Na$_2$SO$_4$, filtered, and concentrated to give N-(2-chloro-4-fluoro-3-((5-fluoro-3-methyl-4-oxo-3,4-dihydroquinazolin-6-yl)oxy)phenyl)-3-fluoroazetidine-1-sulfonamide (14 mg, 43%) as a white solid. $^1$H NMR (400 MHz, (CD$_3$)$_2$SO) δ 9.99 (s, 1H), 8.33 (s, 1H), 7.55-7.43 (m, 3H), 7.36-7.29 (t, 1H), 5.45-5.25 (d, 1H), 4.20-4.08 (m, 2H), 3.99-3.88 (m, 2H), 3.46 (s, 3H); MS (apci, m/z)=475.1, 477.1 (M+H).

Example 123

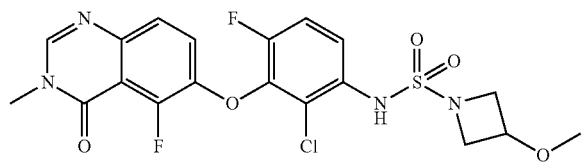

N-(2-chloro-4-fluoro-3-((5-fluoro-3-methyl-4-oxo-3,4-dihydroquinazolin-6-yl)oxy)phenyl)-3-methoxyazetidine-1-sulfonamide Tert-butyl (2-chloro-4-fluoro-3-((5-fluoro-3-methyl-4-oxo-3,4-dihydroquinazolin-6-yl)oxy)phenyl)carbamate (30 mg, 0.07 mmol) was dissolved in THF (0.6 mL), cooled to 0° C. and treated with sodium hydride (5.5 mg, 0.14 mmol). The reaction was stirred for 10 minutes and then treated with 3-methoxyazetidine-1-sulfonyl chloride (25 mg, 0.14 mmol) and heated to 50° C. for 12 hours. The reaction was cooled to ambient temperature and poured into 20 mL ice water. The aqueous layer was extracted with DCM (3×25 mL), dried over anhydrous Na$_2$SO$_4$, filtered, and concentrated. The resulting residue was dissolved in 1:1 DCM:TFA (5 mL) and stirred at ambient temperature for 30 minutes. The reaction was concentrated, diluted with DCM, washed with saturated NaHCO$_3$ (3×50 mL) and brine (1×25 mL), dried over anhydrous Na$_2$SO$_4$, filtered, and concentrated. The residue was purified by silica gel column chromatography (0-100% DCM/EtOAc) followed by reverse phase chromatography (5-95% water/acetonitrile with 0.1% TFA). The desired fractions were combined and partitioned between 4:1 DCM: IPA and saturated aqueous NaHCO$_3$ (1×). The organic layer was separated, dried over anhydrous Na$_2$SO$_4$, filtered and concentrated to give N-(2-chloro-4-fluoro-3-((5-fluoro-3-methyl-4-oxo-3,4-dihydroquinazolin-6-yl)oxy)phenyl)-3-methoxyazetidine-1-sulfonamide (14 mg, 42%) as a white solid. $^1$H NMR (400 MHz, (CD$_3$)$_2$SO) δ 9.85 (s, 1H), 8.33 (s, 1H), 7.55-7.43 (m, 3H), 7.35-7.28 (t, 1H), 4.18-4.10 (m, 1H), 4.00-3.93 (m, 2H), 3.73-3.66 (m, 2H), 3.46 (s, 3H), 3.17 (s, 3H); MS (apci, m/z)=487.1, 489.1 (M+H).

Example 124

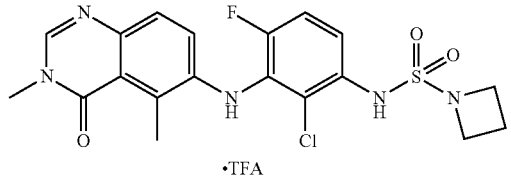 [SMILES: Cc1c(Nc2c(F)ccc(NS(=O)(=O)N3CCC3)c2Cl)ccc2ncn(C)c(=O)c12]

N-(2-chloro-3-((3,5-dimethyl-4-oxo-3,4-dihydroquinazolin-6-yl)amino)-4-fluorophenyl)azetidine-1-sulfonamide trifluoroacetate Step 1: Tert-butyl (azetidin-1-ylsulfonyl)(2-chloro-4-fluoro-3-iodophenyl)carbamate. To a solution of tert-butyl (2-chloro-4-fluoro-3-iodophenyl)carbamate (75 mg, 0.20 mmol) in tetrahydrofuran (2.0 mL) at 0° C. was added sodium hydride (60% in mineral oil, 12 mg, 0.30 mmol) and stirred for 10 minutes. Azetidine-1-sulfonyl chloride (63 mg, 0.40 mmol) was added and the solution was heated to 50° C. for 4 hours upon which the reaction stalled. The solution was partitioned between dichloromethane and saturated NaHCO$_3$ and the organic layer was washed with brine, dried over Na$_2$SO$_4$, filtered, concentrated, and purified by silica gel chromatography (5-95% DCM/hexanes then flushed with 80% EtOAc/hexanes) to give tert-butyl (azetidin-1-ylsulfonyl)(2-chloro-4-fluoro-3-iodophenyl)carbamate (64 mg, 65% yield).

Step 2: N-(2-chloro-3-((3,5-dimethyl-4-oxo-3,4-dihydroquinazolin-6-yl)amino)-4-fluorophenyl)azetidine-1-sulfonamide trifluoroacetate. A solution of 6-amino-3,5-dimethylquinazolin-4(3H)-one (25 mg, 0.13 mmol), tert-butyl (azetidin-1-ylsulfonyl)(2-chloro-4-fluoro-3-iodophenyl)carbamate (64 mg, 0.13 mmol), tris(dibenzylideneacetone) dipalladium (6 mg, 0.006 mmol), Xantphos (11 mg, 0.019 mmol), and cesium carbonate (86 mg, 0.26 mmol) in toluene (1320 µL) was sparged with argon and heated to 110° C. overnight in a sealed vial. The next morning the solution was filtered through Celite®, concentrated, and then stirred in 1 mL of DCM and 1 mL of TFA for 1 hour. The solution was concentrated and purified by reverse-phase chromatography (5-95% MeCN/water, 0.1% TFA) and the product was lyophilized to give N-(2-chloro-3-((3,5-dimethyl-4-oxo-3,4-dihydroquinazolin-6-yl)amino)-4-fluorophenyl)azetidine-1-sulfonamide trifluoroacetate (22 mg, 36% yield). $^1$H NMR (400 MHz, CDCl$_3$) δ 8.74 (s, 1H), 7.60 (d, 1H), 7.51-7.47 (m, 1H), 7.16-7.11 (t, 1H), 7.10-7.06 (m, 1H), 6.60 (s, br, 1H), 5.68 (s, br, 1H), 4.02-3.98 (t, 4H), 3.67 (s, 3H), 2.96 (s, 3H), 2.29-2.22 (m, 2H); MS (apci, m/z)=452.1, 454.1 (M+H).

Example 125

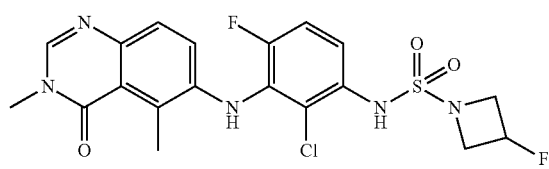 [SMILES: Cc1c(Nc2c(F)ccc(NS(=O)(=O)N3CC(F)C3)c2Cl)ccc2ncn(C)c(=O)c12]

N-(2-chloro-3-((3,5-dimethyl-4-oxo-3,4-dihydroquinazolin-6-yl)amino)-4-fluorophenyl)-3-fluoroazetidine-1-sulfonamide Step 1: Tert-butyl (2-chloro-4-fluoro-3-iodophenyl)((3-fluoroazetidin-1-yl)sulfonyl)carbamate. To a solution of tert-butyl (2-chloro-4-fluoro-3-iodophenyl)carbamate (100 mg, 0.269 mmol) in tetrahydrofuran (1790 µL) at 0° C. was added sodium hydride (60% in mineral oil, 16 mg, 0.40 mmol) and stirred for 10 minutes. 3-Fluoroazetidine-1-sulfonyl chloride (70 mg, 0.40 mmol) was added and the solution was heated to 50° C. for 5 hours. The solution was then partitioned between dichloromethane and saturated NaHCO$_3$ and then the organic layer was washed with brine, dried over Na$_2$SO$_4$, filtered, concentrated, and purified by silica gel chromatography (5-95% EtOAc/hexanes) to give tert-butyl (2-chloro-4-fluoro-3-iodophenyl)((3-fluoroazetidin-1-yl)sulfonyl)carbamate (60 mg, 44% yield).

Step 2: N-(2-chloro-3-((3,5-dimethyl-4-oxo-3,4-dihydroquinazolin-6-yl)amino)-4-fluorophenyl)-3-fluoroazetidine-1-sulfonamide. A solution of 6-amino-3,5-dimethylquinazolin-4(3H)-one (33 mg, 0.17 mmol), tert-butyl (2-chloro-4-fluoro-3-iodophenyl)((3-fluoroazetidin-1-yl)sulfonyl)carbamate (60 mg, 0.11 mmol), tris(dibenzylideneacetone) dipalladium (10 mg, 0.011 mmol), Xantphos (17 mg, 0.029 mmol), and cesium carbonate (76 mg, 0.23 mmol) in toluene (790 µL) was sparged with argon and heated to 110° C. overnight in a sealed vial. The solution was filtered through Celite®, concentrated, and the filtrate was stirred in 1 mL of DCM and 1 mL of TFA for 30 minutes. The solution was concentrated and purified by reverse-phase chromatography (5-95% MeCN/water, 0.1% TFA) and the product was partitioned between DCM and saturated NaHCO$_3$. The organic layer was washed with brine, dried over Na$_2$SO$_4$, filtered, and concentrated to give N-(2-chloro-3-((3,5-dimethyl-4-oxo-3,4-dihydroquinazolin-6-yl)amino)-4-fluorophenyl)-3-fluoroazetidine-1-sulfonamide (32 mg, 58% yield). $^1$H NMR (400 MHz, CDCl$_3$) δ 7.93 (s, 1H), 7.45 (d, 1H), 7.40-7.37 (m, 1H), 7.12-7.04 (m, 2H), 6.69 (s, br, 1H), 5.61 (s, br, 1H), 5.33-5.15 (m, 1H), 4.25-4.08 (m, 4H), 3.54 (s, 3H), 2.98 (s, 3H); MS (apci, m/z)=470.1, 472.1 (M+H).

Example 126

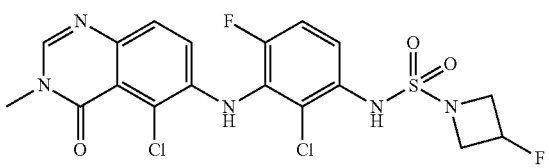 [SMILES: Cn1cnc2ccc(Nc3c(F)ccc(NS(=O)(=O)N4CC(F)C4)c3Cl)c(Cl)c2c1=O]

N-(2-chloro-3-((5-chloro-3-methyl-4-oxo-3,4-dihydroquinazolin-6-yl)amino)-4-fluorophenyl)-3-fluoroazetidine-1-sulfonamide A solution of 6-amino-5-chloro-3-methylquinazolin-4(3H)-one (90 mg, 0.42 mmol), tert-butyl (2-chloro-4-fluoro-3-iodophenyl)((3-fluoroazetidin-1-yl)sulfonyl)carbamate (218 mg, 0.429 mmol), tris(dibenzylideneacetone)dipalladium (39 mg, 0.042 mmol), Xantphos (62 mg, 0.10 mmol), and cesium carbonate (279 mg, 0.858 mmol) in toluene (2860 µL) was sparged with argon and heated to 110° C. overnight in a sealed vial. The solution was filtered through Celite®, concentrated, and the residue was stirred in 1 mL of DCM and 1 mL of TFA for 1 hour. The solution was concentrated and purified by reverse-phase chromatography (5-95% MeCN/water, 0.1% TFA) and the product was partitioned between DCM and saturated NaHCO$_3$. The organic layer was washed with brine, dried over Na$_2$SO$_4$, filtered, and concentrated to give N-(2-chloro-3-((5-chloro-3-methyl-4-oxo-3,4-dihydroquinazolin-6-yl)amino)-4-fluorophenyl)-3-fluoroazetidine-1-sulfonamide (78 mg, 37% yield). $^1$H NMR (400 MHz, CDCl$_3$) δ 7.94 (s, 1H), 7.56-7.52 (m, 1H), 7.51 (d, 1H), 7.19-7.14 (t, 1H), 6.99-6.95 (m, 1H), 6.72 (s, br, 1H), 6.47 (s, br, 1H), 5.35-5.15 (m, 1H), 4.25-4.10 (m, 4H), 3.57 (s, 3H); MS (apci, m/z)=490.1, 492.1 (M+H).

Example 127

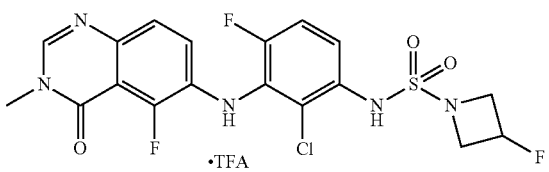 [SMILES: Cn1cnc2ccc(Nc3c(F)ccc(NS(=O)(=O)N4CC(F)C4)c3Cl)c(F)c2c1=O]

N-(2-chloro-4-fluoro-3-((5-fluoro-3-methyl-4-oxo-3,4-dihydroquinazolin-6-yl)amino)phenyl)-3-fluoroazetidine-1-sulfonamide trifluoroacetate A solution of 6-amino-5-fluoro-3-methylquinazolin-4(3H)-one (12 mg, 0.062 mmol), tert-butyl (2-chloro-4- fluoro-3-iodophenyl)((3-fluoroazetidin-1-yl)sulfonyl)carbamate (31 mg, 0.062 mmol), tris(dibenzylideneacetone)dipalladium (2 mg, 0.003 mmol), Xantphos (5 mg, 0.009 mmol), and cesium carbonate (40 mg, 0.12 mmol) in toluene (620 μL) was sparged with argon and heated to 110° C. in a sealed vial overnight. The solution was filtered through Celite, concentrated, and the residue was stirred in 1 mL of DCM and 1 mL of TFA for 1 hour. The solution was concentrated and purified by reverse-phase chromatography (5-95% MeCN/water, 0.1% TFA) and the product was lyophilized to give N-(2-chloro-4-fluoro-3-((5-fluoro-3-methyl-4-oxo-3,4-dihydroquinazolin-6-yl)amino)phenyl)-3-fluoroazetidine-1-sulfonamide trifluoroacetate (4 mg, 13% yield). $^1$H NMR (400 MHz, CDCl$_3$) δ 8.49 (s, 1H), 7.56-7.49 (m, 2H), 7.20-7.15 (t, 1H), 7.12-7.06 (m, 1H), 6.68 (s, br, 1H), 6.01 (s, br, 1H), 5.34-5.16 (m, 1H), 4.26-4.09 (m, 4H), 3.67 (s, 3H); MS (apci, m/z)=475.0, 477.0 (M+H).

Example 128

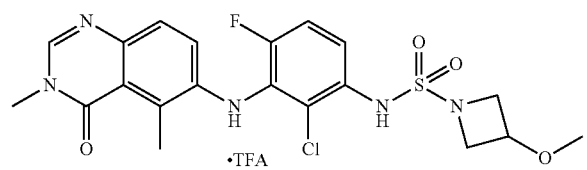

N-(2-chloro-3-((3,5-dimethyl-4-oxo-3,4-dihydroquinazolin-6-yl)amino)-4-fluorophenyl)-3-methoxyazetidine-1-sulfonamide trifluoroacetate Step 1: tert-butyl (2-chloro-4-fluoro-3-iodophenyl)((3-methoxyazetidin-1-yl)sulfonyl)carbamate. To a solution of tert-butyl (2-chloro-4-fluoro-3-iodophenyl)carbamate (40 mg, 0.11 mmol) in tetrahydrofuran (1070 μL) at 0° C. was added sodium hydride (60% in mineral oil, 6 mg, 0.2 mmol) and stirred for 10 minutes. 3-Methoxyazetidine-1-sulfonyl chloride (40 mg, 0.22 mmol) was added and the solution was heated to 50° C. for 2 hours. The solution was partitioned between dichloromethane and saturated NaHCO$_3$ and the organic layer was washed with brine, dried over Na$_2$SO$_4$, filtered, concentrated, and purified by silica gel chromatography (5-95% DCM/hexanes then flushed with 80% EtOAc/hexanes) to give tert-butyl (2-chloro-4-fluoro-3-iodophenyl)((3-methoxyazetidin-1-yl)sulfonyl)carbamate (49 mg, 87% yield).

Step 2: N-(2-chloro-3-((3,5-dimethyl-4-oxo-3,4-dihydroquinazolin-6-yl)amino)-4-fluorophenyl)-3-methoxyazetidine-1-sulfonamide trifluoroacetate. A solution of 6-amino-3,5-dimethylquinazolin-4(3H)-one (18 mg, 0.095 mmol), tert-butyl (2-chloro-4-fluoro-3-iodophenyl)((3-methoxyazetidin-1-yl)sulfonyl)carbamate (49 mg, 0.095 mmol), tris(dibenzylideneacetone)dipalladium (4 mg, 0.004 mmol), Xantphos (8 mg, 0.01 mmol), and cesium carbonate (61 mg, 0.19 mmol) in toluene (950 μL) was sparged with argon and heated to 110° C. in a sealed vial for 2 hours. The solution was filtered through Celite, concentrated, and the residue was stirred in 1 mL of DCM and 1 mL of TFA for 1 hour. The solution was concentrated and purified by reverse-phase chromatography (5-95% MeCN/water, 0.1% TFA) and the product was lyophilized to give N-(2-chloro-3-((3,5-dimethyl-4-oxo-3,4-dihydroquinazolin-6-yl)amino)-4-fluorophenyl)-3-methoxyazetidine-1-sulfonamide trifluoroacetate (12 mg, 26% yield). $^1$H NMR (400 MHz, CDCl$_3$) δ 8.68 (s, 1H), 7.58 (d, 1H), 7.50-7.46 (m, 1H), 7.11-7.06 (m, 2H), 6.63 (s, br, 1H), 5.66 (s, br, 1H), 4.19-4.13 (m, 1H), 4.11-4.07 (m, 2H), 3.93-3.89 (m, 2H), 3.66 (s, 3H), 3.26 (s, 3H), 2.97 (s, 3H); MS (apci, m/z)=482.1, 484.1 (M+H).

Example 129

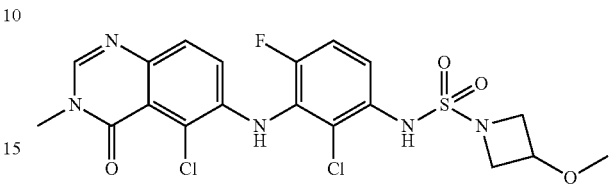

N-(2-chloro-3-((5-chloro-3-methyl-4-oxo-3,4-dihydroquinazolin-6-yl)amino)-4-fluorophenyl)-3-methoxyazetidine-1-sulfonamide 6-Amino-5-chloro-3-methylquinazolin-4(3H)-one (70 mg, 0.334 mmol), tert-butyl (2-chloro-4-fluoro-3-iodophenyl)((3-methoxyazetidin-1-yl)sulfonyl)carbamate (183 mg, 0.351 mmol), cesium carbonate (218 mg, 0.668 mmol), tris(dibenzylideneacetone)dipalladium(0) (30.6 mg, 0.0334 mmol), and (9,9-dimethyl-9H-xanthene-4,5-diyl)bis(diphenylphosphane) (48.3 mg, 0.0835 mmol) were dissolved in toluene (3.3 mL) and heated at 110° C. overnight in a sealed vial. The reaction mixture was allowed to cool to ambient temperature and the crude reaction mixture was diluted with DCM and filtered through Celite. The solvent was concentrated, then reconstituted in 1:1 DCM:TFA (10 mL) and allowed to stir at ambient temperature for 30 minutes. The crude reaction mixture was concentrated and purified by reverse phase chromatography (5-95%, MeCN/H$_2$O, 0.1% TFA). The desired product was extracted with DCM and saturated aqueous NaHCO$_3$ and the DCM layer was concentrated to provide the desired product (57 mg, 34% yield). $^1$H NMR (400 MHz, CDCl$_3$) δ 7.99 (s, 1H), 7.58-7.51 (m, 2H), 7.16 (t, 1H), 6.99-6.97 (m, 1H), 6.67 (s, 1H), 6.47 (s, 1H), 4.18-4.13 (m, 1H), 4.08 (t, 2H), 3.92-3.89 (m, 2H), 3.58 (s, 3H), 3.27 (s, 3H). MS (apci, m/z)=502.1, 504.1 (M+H).

Example 130

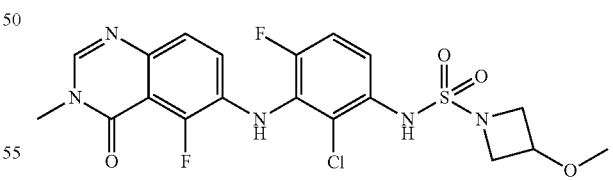

N-(2-chloro-4-fluoro-3-((5-fluoro-3-methyl-4-oxo-3,4-dihydroquinazolin-6-yl)amino)phenyl)-3-methoxyazetidine-1-sulfonamide 6-Amino-5-fluoro-3-methylquinazolin-4(3H)-one (84.44 mg, 0.4371 mmol), tert-butyl (2-chloro-4-fluoro-3-iodophenyl)((3-methoxyazetidin-1-yl)sulfonyl)carbamate (239 mg, 0.4590 mmol), cesium carbonate (284.8 mg, 0.8742 mmol), tris(dibenzylideneacetone)dipalladium(0) (40.03 mg, 0.04371 mmol), and (9,9-dimethyl-9H-xanthene-4,5-diyl)bis(diphenylphosphane) (63.23 mg, 0.1093 mmol) were dissolved in toluene (4.4 mL) and heated at 110° C. overnight in a sealed vial. The reaction mixture was allowed to cool to ambient temperature and the crude reaction mixture was diluted with DCM and filtered through Celite. The solvent was concentrated, then reconstituted in 1:1 DCM:TFA (10 mL) and allowed to stir at ambient temperature for 30 minutes. The crude reaction mixture was concentrated and purified by reverse phase chromatography (5-95%, MeCN/H$_2$O, 0.1% TFA). The desired product was extracted with DCM and saturated aqueous NaHCO$_3$ and the DCM layer was concentrated to provide the desired product (98 mg, 46% yield). $^1$H NMR (400 MHz, CDCl$_3$) δ 7.92 (s, 1H), 7.53-7.50 (m, 1H), 7.41-7.39 (m, 1H) 7.16-7.11 (m, 1H), 7.07-7.02 (m, 1H), 6.68 (s, 1H), 5.90 (s, 1H), 4.14 (t, 1H), 4.07 (t, 2H), 3.92-3.89 (m, 2H), 3.58 (s, 3H), 3.27 (s, 3H). MS (apci, m/z)=486.1, 488.1 (M+H).

Example 131

N-(2-chloro-3-((3,5-dimethyl-4-oxo-3,4-dihydroquinazolin-6-yl)amino)-4-fluorophenyl)-3-(methoxymethyl)azetidine-1-sulfonamide Step 1: 3-(methoxymethyl)azetidine-1-sulfonyl chloride. To a solution of 3-(methoxymethyl)azetidine hydrochloride (200 mg, 1.45 mmol) in DCM (3630 μL) was added sulfuryl dichloride (290 μL, 3.6 mmol) and Hunig's base (380 μL, 2.2 mmol) dropwise and the reaction was allowed to stir at ambient temperature for 48 hours. The reaction mixture was partitioned between DCM and 1 N HCl and the DCM layer was dried over Na$_2$SO$_4$, filtered, and concentrated to give 3-(methoxymethyl)azetidine-1-sulfonyl chloride (273 mg, 94.1% yield).

Step 2: tert-butyl (2-chloro-4-fluoro-3-iodophenyl)((3-(methoxymethyl)azetidin-1-yl)sulfonyl)carbamate. To a solution of tert-butyl (2-chloro-4-fluoro-3-iodophenyl)carbamate (300 mg, 0.807 mmol) in tetrahydrofuran (5380 μL) at 0° C. was added sodium hydride (60% in mineral oil, 48 mg, 1.2 mmol) and stirred for 10 minutes. 3-(Methoxymethyl)azetidine-1-sulfonyl chloride (242 mg, 1.21 mmol) was added and the solution was heated to 50° C. for 16 hours in a sealed vial. The solution was partitioned between DCM and saturated NaHCO$_3$ and the organic layer was washed with brine, dried over Na$_2$SO$_4$, filtered, concentrated, and purified by silica gel chromatography (5-95% EtOAc/hexanes) to give impure product. The impure product was concentrated and re-purified by reverse-phase chromatography (5-95% MeCN/water, 0.1% TFA). The product was partitioned between DCM and saturated NaHCO$_3$ and the organic layer was washed with brine, dried over Na$_2$SO$_4$, filtered, and concentrated to give tert-butyl (2-chloro-4-fluoro-3-iodophenyl)((3-(methoxymethyl)azetidin-1-yl)sulfonyl)carbamate (232 mg, 53.7% yield).

Step 3: N-(2-chloro-3-((3,5-dimethyl-4-oxo-3,4-dihydroquinazolin-6-yl)amino)-4-fluorophenyl)-3-(methoxymethyl)azetidine-1-sulfonamide. A solution of 6-amino-3,5-dimethylquinazolin-4(3H)-one (83 mg, 0.43 mmol), tert-butyl (2-chloro-4-fluoro-3-iodophenyl)((3-(methoxymethyl)azetidin-1-yl)sulfonyl)carbamate (234 mg, 0.438 mmol), tris(dibenzylideneacetone)dipalladium (40 mg, 0.043 mmol), Xantphos (63 mg, 0.10 mmol), and cesium carbonate (285 mg, 0.877 mmol) in toluene (2920 μL) was sparged with argon and heated to 110° C. for 16 hours in a sealed vial. The solution was filtered through Celite®, concentrated, and the residue was stirred in 1 mL of DCM and 1 mL of TFA for 1 hour. The solution was concentrated and purified by reverse-phase chromatography (5-95% MeCN/water, 0.1% TFA). The product was partitioned between DCM and saturated NaHCO$_3$ and the organic layer was washed with brine, dried over Na$_2$SO$_4$, filtered, and concentrated to give N-(2-chloro-3-((3,5-dimethyl-4-oxo-3,4-dihydroquinazolin-6-yl)amino)-4-fluorophenyl)-3-(methoxymethyl)azetidine-1-sulfonamide (165 mg, 75.8% yield). $^1$H NMR (400 MHz, CDCl$_3$) δ 7.93 (s, 1H), 7.46-7.39 (m, 2H), 7.12-7.04 (m, 2H), 6.68 (s, br, 1H), 5.60 (s, br, 1H), 4.03-3.99 (t, 2H), 3.80-3.76 (m, 2H), 3.54 (s, 3H), 3.48 (d, 2H), 3.34 (s, 3H), 2.97 (s, 3H), 2.85-2.77 (m, 1H); MS (apci, m/z)=496.2, 498.2 (M+H).

Example 132

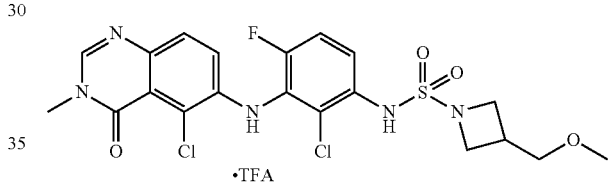

N-(2-chloro-3-((5-chloro-3-methyl-4-oxo-3,4-dihydroquinazolin-6-yl)amino)-4-fluorophenyl)-3-(methoxymethyl)azetidine-1-sulfonamide trifluoroacetate A solution of 6-amino-5-chloro-3-methylquinazolin-4(3H)-one (20 mg, 0.095 mmol), tert-butyl (2-chloro-4-fluoro-3-iodophenyl)((3-(methoxymethyl)azetidin-1-yl)sulfonyl)carbamate (76 mg, 0.14 mmol), tris(dibenzylideneacetone)dipalladium (4 mg, 0.004 mmol), Xantphos (8 mg, 0.01 mmol), and cesium carbonate (6 mg, 0.1 mmol) in toluene (950 μL) was sparged with argon and heated to 110° C. in a sealed vial for 16 hours. The solution was filtered through Celite®, concentrated, and the residue was stirred in 1 mL of DCM and 1 mL of TFA for 1 hour. The solution was concentrated and purified by reverse-phase chromatography (5-95% MeCN/water, 0.1% TFA) and the product was lyophilized to give N-(2-chloro-3-((5-chloro-3-methyl-4-oxo-3,4-dihydroquinazolin-6-yl)amino)-4-fluorophenyl)-3-(methoxymethyl)azetidine-1-sulfonamide trifluoroacetate (2.0 mg, 4.1% yield). $^1$H NMR (400 MHz, CDCl$_3$) δ 8.41 (s, 1H), 7.61-7.57 (m, 2H), 7.20-7.15 (t, 1H), 7.02-6.99 (m, 1H), 6.67 (s, br, 1H), 6.53 (s, br, 1H), 4.04-4.00 (t, 1H), 3.82-3.78 (m, 1H), 3.65 (s, 3H), 3.49 (d, 2H), 3.35 (s, 3H), 2.87-2.79 (m, 1H); MS (apci, m/z)=516.1, 518.1 (M+H).

Example 133

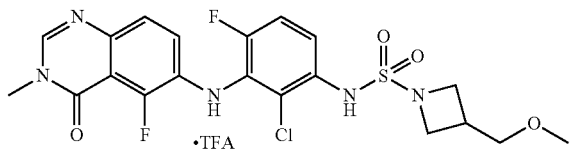

N-(2-chloro-4-fluoro-3-((5-fluoro-3-methyl-4-oxo-3,4-dihydroquinazolin-6-yl)amino)phenyl)-3-(methoxymethyl)azetidine-1-sulfonamide trifluoroacetate A solution of 6-amino-5-fluoro-3-methylquinazolin-4(3H)-one (20 mg, 0.10 mmol), tert-butyl (2-chloro-4-fluoro-3-iodophenyl)((3-(methoxymethyl)azetidin-1-yl)sulfonyl)carbamate (83 mg, 0.15 mmol), tris(dibenzylideneacetone)dipalladium (4 mg, 0.005 mmol), Xantphos (8 mg, 0.02 mmol), and cesium carbonate (67 mg, 0.20 mmol) in toluene (1030 µL) was sparged with argon and heated to 110° C. in a sealed vial for 16 hours. The solution was filtered through Celite®, concentrated, and the residue was stirred in 1 mL of DCM and 1 mL of TFA for 1 hour. The solution was concentrated and purified by reverse-phase chromatography (5-95% MeCN/water, 0.1% TFA) and the product was lyophilized to give N-(2-chloro-4-fluoro-3-((5-fluoro-3-methyl-4-oxo-3,4-dihydroquinazolin-6-yl)amino)phenyl)-3-(methoxymethyl)azetidine-1-sulfonamide trifluoroacetate (4.0 mg, 7.7% yield). $^1$H NMR (400 MHz, CDCl$_3$) δ 8.48 (s, 1H), 7.58-7.54 (m, 1H), 7.50 (d, 1H), 7.19-7.14 (t, 1H), 7.11-7.06 (m, 1H), 6.67 (s, br, 1H), 6.01 (s, br, 1H), 4.04-4.00 (t, 2H), 3.82-3.78 (m, 2H), 3.67 (s, 3H), 3.50-3.48 (d, 2H), 3.35 (s, 3H), 2.87-2.79 (m, 1H); MS (apci, m/z)=500.1, 502.1 (M+H).

Example 134

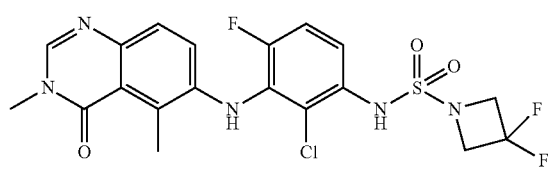 [SMILES: Cc1c(Nc2c(F)ccc(NS(=O)(=O)N3CC(F)(F)C3)c2Cl)ccc2ncn(C)c(=O)c12]

N-(2-chloro-3-((3,5-dimethyl-4-oxo-3,4-dihydroquinazolin-6-yl)amino)-4-fluorophenyl)-3,3-difluoroazetidine-1-sulfonamide Step 1: Tert-butyl (2-chloro-4-fluoro-3-iodophenyl)((3,3-difluoroazetidin-1-yl)sulfonyl)carbamate. Tert-butyl (2-chloro-4-fluoro-3-iodophenyl)carbamate (553.3 mg, 1.489 mmol) was dissolved in THF (15 mL) and treated with sodium hydride (60% in mineral oil, 178.7 mg, 4.467 mmol) and stirred at ambient temperature for 15 minutes. The reaction mixture was treated with 3,3-difluoroazetidine-1-sulfonyl chloride (855.8 mg, 4.467 mmol) and heated to 60° C. for 16 hours. The reaction mixture was cooled to ambient temperature and treated with water and extracted with EtOAc (2×) and the combined organic layer was washed with water (3×), brine (1×), and dried over Na$_2$SO$_4$, filtered, and concentrated. The resulting residue was purified by silica gel chromatography (Hexanes/EtOAc) to provide tert-butyl (2-chloro-4-fluoro-3-iodophenyl)((3,3-difluoroazetidin-1-yl)sulfonyl)carbamate (311.3 mg, 39.7% yield). $^1$H NMR (400 MHz, (CD$_3$)$_2$SO) δ 7.68-7.64 (m, 1H), 7.39-7.35 (m, 1H), 4.74-4.67 (t, 2H), 4.46-4.40 (t, 2H), 1.38 (s, 9H).

Step 2: N-(2-chloro-3-((3,5-dimethyl-4-oxo-3,4-dihydroquinazolin-6-yl)amino)-4-fluorophenyl)-3,3-difluoroazetidine-1-sulfonamide. 6-Amino-3,5-dimethylquinazolin-4(3H)-one (31.5 mg, 0.166475 mmol) was dissolved in toluene (1.7 mL) and treated with tert-butyl (2-chloro-4-fluoro-3-iodophenyl)((3,3-difluoroazetidin-1-yl)sulfonyl)carbamate (96.4493 mg, 0.183122 mmol), tris(dibenzylideneacetone)dipalladium (15.2446 mg, 0.0166475 mmol), 4,5-bis(diphenylphosphino)-9,9-dimethylxanthene (24.0819 mg, 0.0416187 mmol), and cesium carbonate (162.722 mg, 0.499424 mmol) then sparged with argon, sealed, and heated to 110° C. for 16 hours. The reaction mixture was cooled to ambient temperature and diluted with DCM then washed with water (1×) and dried over Na$_2$SO$_4$, filtered, and concentrated. The resulting residue was purified by silica gel chromatography (DCM/Acetone). The resulting residue was dissolved in 1:1 DCM:TFA (2.0 mL) and stirred at ambient temperature for 30 minutes. The reaction mixture was concentrated and purified by reverse phase C18 chromatography (water/ACN with 0.1% TFA) and the desired fractions were combined and partitioned between saturated aqueous NaHCO$_3$ and 4:1 DCM:IPA. The organic phase was separated, dried over Na$_2$SO$_4$, filtered, and concentrated under reduced pressure to provide N-(2-chloro-3-((3,5-dimethyl-4-oxo-3,4-dihydroquinazolin-6-yl)amino)-4-fluorophenyl)-3,3-difluoroazetidine-1-sulfonamide (33.0 mg, 40.6% yield). $^1$H NMR (400 MHz, (CD$_3$)$_2$SO) δ 10.04 (s, 1H), 8.17 (s, 1H), 7.35-7.31 (m, 4H), 6.86-6.84 (dd, 1H), 4.36-4.30 (t, 4H), 3.43 (s, 3H), 2.81 (s, 3H). MS (apci, m/z)=488.1, 490.1 (M+H).

Example 135

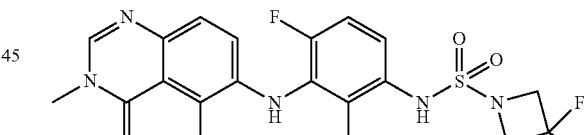

N-(2-chloro-3-((5-chloro-3-methyl-4-oxo-3,4-dihydroquinazolin-6-yl)amino)-4-fluorophenyl)-3,3-difluoroazetidine-1-sulfonamide 6-Amino-5-chloro-3-methylquinazolin-4(3H)-one (31.4 mg, 0.149786 mmol) was dissolved in toluene (1.5 mL) and treated with tert-butyl (2-chloro-4-fluoro-3-iodophenyl)((3,3-difluoroazetidin-1-yl)sulfonyl)carbamate (86.7802 mg, 0.164764 mmol), tris(dibenzylideneacetone)dipalladium (13.7164 mg, 0.0149786 mmol), 4,5-bis(diphenylphosphino)-9,9-dimethylxanthene (21.6677 mg, 0.0374464 mmol), and cesium carbonate (146.409 mg, 0.449357 mmol) then sparged with argon, sealed, and heated to 110° C. for 16 hours. The reaction mixture was cooled to ambient temperature and diluted with DCM and washed with water (1×) then dried over Na$_2$SO$_4$, filtered, and concentrated. The resulting residue was purified by silica gel chromatography (DCM/Acetone). The resulting residue was dissolved in 1:1 DCM:TFA (2.0 mL) and stirred at ambient temperature for 30 minutes. The reaction mixture was concentrated and purified by reverse phase C18 chromatography (water/ACN with 0.1% TFA) and the desired fractions were combined and partitioned between saturated aqueous NaHCO$_3$ and 4:1 DCM:IPA. The organic phase was separated, dried over Na$_2$SO$_4$, filtered, and concentrated under reduced pressure to provide N-(2-chloro-3-((5-chloro-3-methyl-4-oxo-3,4-dihydroquinazolin-6-yl)amino)-4-fluorophenyl)-3,3-difluoroazetidine-1-sulfonamide (29.0 mg, 38.1% yield). $^1$H NMR (400 MHz, (CD$_3$)$_2$SO) δ 10.14 (s, 1H), 8.21 (s, 1H), 7.79 (s, 1H), 7.53-7.49 (m, 1H), 7.45-7.38 (m, 2H), 6.79-6.76 (dd, 1H), 4.36-4.30 (t, 4H), 3.45 (s, 3H). MS (apci, m/z)=508.0, 510.0 (M+H).

Example 136

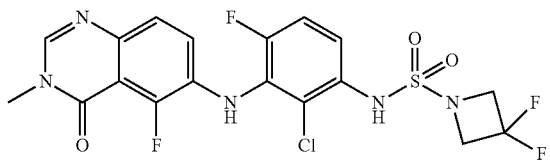 [SMILES: Cn1cnc2ccc(Nc3c(F)ccc(NS(=O)(=O)N4CC(F)(F)C4)c3Cl)c(Cl)c2c1=O]

N-(2-chloro-4-fluoro-3-((5-fluoro-3-methyl-4-oxo-3,4-dihydroquinazolin-6-yl)amino)phenyl)-3,3-difluoroazetidine-1-sulfonamide 6-Amino-5-fluoro-3-methylquinazolin-4(3H)-one (32.1 mg, 0.166165 mmol) was dissolved in toluene (1.7 mL) and treated with tert-butyl (2-chloro-4-fluoro-3-iodophenyl)((3,3-difluoroazetidin-1-yl)sulfonyl)carbamate (96.27 mg, 0.183 mmol), tris(dibenzylideneacetone)dipalladium (15.2163 mg, 0.0166 mmol), 4,5-bis(diphenylphosphino)-9,9-dimethylxanthene (24.0371 mg, 0.0415413 mmol), and cesium carbonate (162.419 mg, 0.498 mmol) then sparged with argon, sealed, and heated to 110° C. for 16 hours. The reaction mixture was cooled to ambient temperature and diluted with DCM and washed with water (1×) then dried over Na$_2$SO$_4$, filtered, and concentrated. The resulting residue was purified by silica gel chromatography (DCM/Acetone). The resulting residue was dissolved in 1:1 DCM:TFA (2.0 mL) and stirred at ambient temperature for 30 minutes. The reaction mixture was concentrated and purified by reverse phase C18 chromatography (water/acetonitrile with 0.1% TFA) and the desired fractions were combined and partitioned between saturated aqueous NaHCO$_3$ and 4:1 DCM:IPA. The organic phase was separated, dried over Na$_2$SO$_4$, filtered, and concentrated under reduced pressure to provide N-(2-chloro-4-fluoro-3-((5-fluoro-3-methyl-4-oxo-3,4-dihydroquinazolin-6-yl)amino)phenyl)-3,3-difluoroazetidine-1-sulfonamide (22.6 mg, 27.7% yield). $^1$H NMR (400 MHz, (CD$_3$)$_2$SO) δ 10.09 (s, 1H), 8.19 (s, 1H), 8.10 (s, 1H), 7.40-7.32 (m, 3H), 7.07-7.02 (t, 1H), 4.37-4.31 (t, 4H), 3.44 (s, 3H). MS (apci, m/z)=492.1, 494.1 (M+H).

Example 137

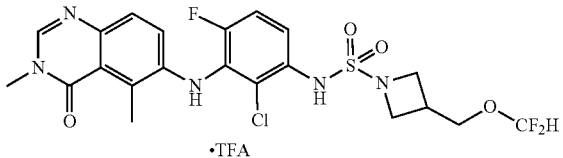 [SMILES: Cc1c(Nc2c(F)ccc(NS(=O)(=O)N3CC(COC(F)F)C3)c2Cl)ccc2ncn(C)c(=O)c12]

N-(2-chloro-3-((3,5-dimethyl-4-oxo-3,4-dihydroquinazolin-6-yl)amino)-4-fluorophenyl)-3-((difluoromethoxy)methyl)azetidine-1-sulfonamide trifluoroacetate Step 1: Preparation of 3-((difluoromethoxy)methyl)azetidine-1-sulfonyl chloride. 3-((difluoromethoxy)methyl)azetidine (200 mg, 1.46 mmol) was stirred with N-ethyl-N-isopropylpropan-2-amine (379 µL, 2.19 mmol) at ambient temperature in dichloromethane (3646 µL) for 5 minutes. The reaction mixture was cooled to -10° C. and sulfuryl dichloride (295 µL, 3.65 mmol) was then added as a neat liquid dropwise to the reaction. The reaction was allowed to warm to ambient temperature and stirred for 16 hours. The reaction mixture was diluted with DCM and washed with 1N aq. HCl. The DCM layer was dried over MgSO$_4$, concentrated, and used crude directly in the next step (345 mg, 100%).

Step 2: Preparation of tert-butyl (2-chloro-4-fluoro-3-iodophenyl)((3-((difluoromethoxy)-methyl)azetidin-1-yl)sulfonyl)carbamate. Tert-butyl (2-chloro-4-fluoro-3-iodophenyl)carbamate (105 mg, 0.283 mmol) was dissolved in tetrahydrofuran (1413 µL) and cooled to 0° C. Sodium hydride (60% in mineral oil, 17.0 mg, 0.424 mmol) was added and the resulting solution allowed to warm to ambient temperature then 3-((difluoromethoxy)-methyl)azetidine-1-sulfonyl chloride (99.9 mg, 0.424 mmol) was added, and the reaction mixture was heated to 60° C. for 16 hours. The crude reaction mixture was cooled to ambient temperature, concentrated, and purified by silica gel chromatography (Hexanes/EtOAc) to provide tert-butyl (2-chloro-4-fluoro-3-iodophenyl)((3-((difluoromethoxy)-methyl)azetidin-1-yl)sulfonyl)carbamate (98 mg, 61%).

Step 3: N-(2-chloro-3-((3,5-dimethyl-4-oxo-3,4-dihydroquinazolin-6-yl)amino)-4-fluorophenyl)-3-((difluoromethoxy)methyl)azetidine-1-sulfonamide trifluoroacetate. 6-amino-3,5-dimethylquinazolin-4(3H)-one (31 mg, 0.164 mmol), tert-butyl (2-chloro-4-fluoro-3-iodophenyl)((3-((difluoromethoxy)methyl)azetidin-1-yl)sulfonyl)carbamate (98.2 mg, 0.172 mmol), (9,9-dimethyl-9H-xanthene-4,5-diyl)bis(diphenylphosphane) (14.2 mg, 0.0246 mmol), cesium carbonate (107 mg, 0.328 mmol), and tris(dibenzylideneacetone)dipalladium(0) (7.50 mg, 0.00819 mmol) were dissolved in tolune (1.6 mL), sealed, and heated to 110° C. for 16 hours. The reaction mixture was allowed to cool to ambient temperature, filtered through Celite, concentrated, and the residue was reconstituted in 1:1 DCM:TFA (2 mL) and allowed to stir at ambient temperature for 30 minutes. The volatiles were removed in vacuo and the crude product was purified by reverse phase chromatography (5-95% MeCN/H$_2$O, 0.1% TFA). The desired fractions were lyophilized to provide N-(2-chloro-3-((3,5-dimethyl-4-oxo-3,4-dihydroquinazolin-6-yl)amino)-4-fluorophenyl)-3-((difluoromethoxy)methyl)azetidine-1-sulfonamide trifluoroacetate (38 mg, 44%). ¹H NMR (400 MHz, CDCl₃) δ 8.58 (s, 1H), 7.57 (d, 1H), 7.48-7.44 (m, 1H), 7.13 (t, 1H), 7.09-7.06 (m, 1H), 6.62 (s, 1H), 6.41-6.04 (m, 1H), 5.66 (s, 1H), 4.05 (t, 2H), 3.98-3.97 (d, 2H), 3.83-3.79 (m, 2H), 3.65 (s, 3H), 2.97 (s, 3H), 2.93-2.87 (m, 1H). MS (apci, m/z)=532.1, 534.1 (M+H).

Example 138

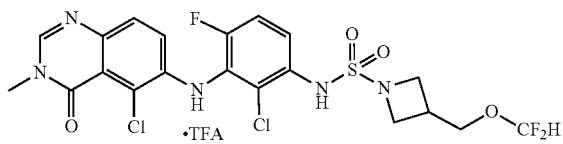 [SMILES: Cn1cnc2ccc(Nc3c(F)ccc(NS(=O)(=O)N4CC(COC(F)F)C4)c3Cl)c(Cl)c2c1=O]

N-(2-chloro-3-((5-chloro-3-methyl-4-oxo-3,4-dihydroquinazolin-6-yl)amino)-4-fluorophenyl)-3-((difluoromethoxy)methyl)azetidine-1-sulfonamide trifluoroacetate 6-Amino-5-chloro-3-methylquinazolin-4(3H)-one (28.1 mg, 0.1340 mmol), tert-butyl (2-chloro-4-fluoro-3-iodophenyl)((3-((difluoromethoxy)methyl)azetidin-1-yl)sulfonyl)carbamate (80.33 mg, 0.1407 mmol), cesium carbonate (87.35 mg, 0.2681 mmol), tris(dibenzylideneacetone)-dipalladium(0) (6.137 mg, 0.006702 mmol), and (9,9-dimethyl-9H-xanthene-4,5-diyl)bis-(diphenylphosphane) (9.307 mg, 0.01609 mmol) were dissolved in toluene (1.3 mL), sealed, and heated to 110° C. for 16 hours. The reaction mixture was allowed to cool to ambient temperature, filtered through Celite, concentrated, and the residue was reconstituted in 1:1 DCM:TFA (2 mL) and stirred at ambient temperature for 30 minutes. The volatiles were removed in vacuo, and the crude product purified by reverse phase chromatography (5-95% MeCN/H₂O, 0.1% TFA). The desired fractions were lyophilized to provide N-(2-chloro-3-((5-chloro-3-methyl-4-oxo-3,4-dihydroquinazolin-6-yl)amino)-4-fluorophenyl)-3-((difluoromethoxy)methyl)azetidine-1-sulfonamide trifluoroacetate (33 mg, 44%). ¹H NMR (400 MHz, CDCl₃) δ 8.50 (s, 1H), 7.61 (d, 1H), 7.60-7.57 (m, 1H), 7.19 (t, 1H), 7.02-6.99 (m, 1H), 6.66 (s, 1H), 6.53 (s, 1H), 6.41-6.04 (m, 1H), 4.05 (t, 2H), 3.99-3.97 (d, 2H), 3.83-3.80 (m, 2H), 3.67 (s, 3H), 2.96-2.86 (m, 1H). MS (apci, m/z)=552.1, 554.1 (M+H).

Example 139

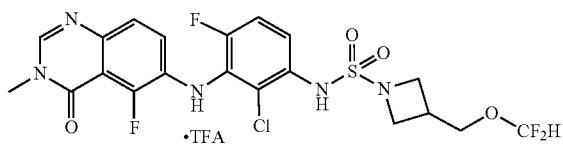 [SMILES: Cn1cnc2ccc(Nc3c(F)ccc(NS(=O)(=O)N4CC(COC(F)F)C4)c3Cl)c(F)c2c1=O]

N-(2-chloro-4-fluoro-3-((5-fluoro-3-methyl-4-oxo-3,4-dihydroquinazolin-6-yl)amino)phenyl)-3-((difluoromethoxy)methyl)azetidine-1-sulfonamide trifluoroacetate 6-Amino-5-fluoro-3-methylquinazolin-4(3H)-one (25.9 mg, 0.1341 mmol), tert-butyl (2-chloro-4-fluoro-3-iodophenyl)((3-((difluoromethoxy)methyl)azetidin-1-yl)sulfonyl)carbamate (80.35 mg, 0.1408 mmol), cesium carbonate (87.37 mg, 0.2681 mmol), tris(dibenzylideneacetone)-dipalladium(0) (6.139 mg, 0.006704 mmol), and (9,9-dimethyl-9H-xanthene-4,5-diyl)bis(diphenylphosphane) (9.309 mg, 0.01609 mmol) were dissolved in toluene (1.3 mL), sealed, and heated to 110° C. for 16 hours. The reaction mixture was allowed to cool to ambient temperature, filtered through Celite, concentrated, and the residue was reconstituted in 1:1 DCM/TFA (2 mL). The reaction was allowed to stir at ambient temperature for 30 minutes and the volatiles were removed in vacuo. The crude product purified by reverse phase chromatography (5-95% MeCN/H₂O, 0.1% TFA). The desired fractions were lyophilized to provide N-(2-chloro-4-fluoro-3-((5-fluoro-3-methyl-4-oxo-3,4-dihydroquinazolin-6-yl)amino)phenyl)-3-((difluoromethoxy)methyl)azetidine-1-sulfonamide trifluoroacetate (39 mg, 55%). ¹H NMR (400 MHz, CDCl₃) δ 8.54 (s, 1H), 7.57-7.50 (m, 2H), 7.17 (t, 1H), 7.12-7.07 (m, 1H), 6.65 (s, 1H), 6.41-6.04 (m, 1H), 6.01 (s, 1H), 4.05 (t, 2H), 3.98-3.97 (d, 2H), 3.83-3.79 (m, 2H), 3.68 (s, 3H), 2.96-2.85 (m, 1H). MS (apci, m/z)=536.1, 538.1 (M+H).

Example 140

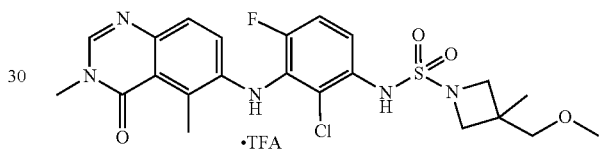

N-(2-chloro-3-((3,5-dimethyl-4-oxo-3,4-dihydroquinazolin-6-yl)amino)-4-fluorophenyl)-3-(methoxymethyl)-3-methylazetidine-1-sulfonamide trifluoroacetate Step 1: 3-(methoxymethyl)-3-methylazetidine-1-sulfonyl chloride. To a solution of 3-(methoxymethyl)-3-methylazetidine hydrochloride (230 mg, 1.52 mmol) and N-ethyl-N-isopropylpropan-2-amine (400 µL, 2 mmol) in dichloromethane (5060 µL) at 0° C. was added sulfuryl dichloride (300 µL, 3.8 mmol) and the reaction mixture was warmed to ambient temperature and stirred for 16 hours. The solution was diluted with DCM and washed with 1 N HCl (1×) and the DCM layer was dried over Na₂SO₄, filtered, and concentrated to give 3-(methoxymethyl)-3-methylazetidine-1-sulfonyl chloride (240 mg, 74% yield).

Step 2: tert-butyl (2-chloro-4-fluoro-3-iodophenyl)((3-(methoxymethyl)-3-methylazetidin-1-yl)sulfonyl)carbamate. To a solution of tert-butyl (2-chloro-4-fluoro-3-iodophenyl)carbamate (25 mg, 0.067 mmol) in tetrahydrofuran (340 µL) at 0° C. was added sodium hydride (60% in mineral oil, 4.0 mg, 0.10 mmol) and stirred for 10 minutes. 3-(Methoxymethyl)-3-methylazetidine-1-sulfonyl chloride (22 mg, 0.10 mmol) was added and the solution was heated to 50° C. in a sealed vial for 16 hours. The solution was partitioned between dichloromethane and saturated NaHCO₃ and the organic layer was washed with brine, dried over Na₂SO₄, filtered, concentrated, and purified by silica gel chromatography (5-95% EtOAc/hexanes) to give tert-butyl (2-chloro-4-fluoro-3-iodophenyl)((3-(methoxymethyl)-3-methylazetidin-1-yl)sulfonyl)carbamate (34 mg, 92% yield).

Step 3: N-(2-chloro-3-((3,5-dimethyl-4-oxo-3,4-dihydroquinazolin-6-yl)amino)-4-fluorophenyl)-3-(methoxymethyl)-3-methylazetidine-1-sulfonamide trifluoroacetate. A solution of 6-amino-3,5-dimethylquinazolin-4(3H)-one (12 mg, 0.063 mmol), tert-butyl (2-chloro-4-fluoro-3-iodophenyl)((3-(methoxymethyl)-3-methylazetidin-1-yl)sulfonyl)carbamate (34 mg, 0.063 mmol), tris(dibenzylideneacetone)dipalladium (5 mg, 0.006 mmol), Xantphos (9 mg, 0.01 mmol), and cesium carbonate (41 mg, 0.12 mmol) in toluene (420 µL) was sparged with argon and heated to 110° C. for 16 hours in a sealed vial. The solution was filtered through Celite®, concentrated, and stirred in 1 mL of DCM and 1 mL of TFA for 1 hour. The solution was concentrated and purified by reverse-phase chromatography (5-95% MeCN/water, 0.1% TFA) and the product was lyophilized to give N-(2-chloro-3-((3,5-dimethyl-4-oxo-3,4-dihydroquinazolin-6-yl)amino)-4-fluorophenyl)-3-(methoxymethyl)-3-methylazetidine-1-sulfonamide trifluoroacetate (6.0 mg, 19% yield). ¹H NMR (400 MHz, CDCl₃) δ 8.61 (s, 1H), 7.57 (d, 1H), 7.51-7.47 (m, 1H), 7.15-7.06 (m, 2H), 6.68 (s, br, 1H), 5.67 (s, br, 1H), 3.87 (d, 2H), 3.65 (s, 3H), 3.60 (d, 2H), 3.36 (s, 3H), 3.32 (s, 2H), 2.97 (s, 3H), 1.28 (s, 3H); MS (apci, m/z)=510.2, 512.2 (M+H).

Example 141

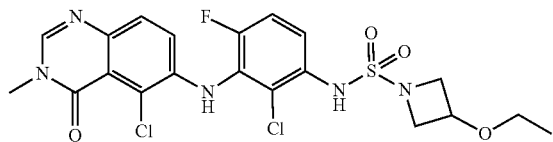

N-(2-chloro-3-((5-chloro-3-methyl-4-oxo-3,4-dihydroquinazolin-6-yl)amino)-4-fluorophenyl)-3-ethoxyazetidine-1-sulfonamide Step 1: tert-butyl 3-ethoxyazetidine-1-carboxylate. A solution of tert-butyl 3-hydroxyazetidine-1-carboxylate (63.5 ml, 12.7 mmol) in 1:1 DMF:THF (60 mL) and sodium hydride (0.762 g, 19.1 mmol) was stirred in the ice bath for 10 minutes. Iodoethane (3.05 ml, 38.1 mmol) was added and the reaction mixture was allowed to warm to ambient temperature and stirred for 18 hours. The reaction mixture was diluted with water (100 mL) and extracted with EtOAc (100 mL). The organic phase was dried over Na₂SO₄, filtered, and concentrated to provide tert-butyl 3-ethoxyazetidine-1-carboxylate (2.56 g, 100% yield) that was used directly in the next step without further purification.

Step 2: 3-ethoxyazetidine hydrochloride. A solution of tert-butyl 3-ethoxyazetidine-1-carboxylate (2.50 g, 12.4 mmol) in 1:1:3 THF:DMF:EtOAc (150 mL) was stirred at ambient temperature while a solution of 5N HCl (74.5 ml, 373 mmol) in IPA was added. The reaction mixture was stirred at ambient temperature then concentrated to afford 3-ethoxyazetidine hydrochloride (1.3 g, 76.1% yield) as a red oil that was used in the next steps without further purification. ¹H NMR (400 MHz, D₄.Methanol) δ 4.48-4.40 (m, 1H), 4.33-4.25 (m, 2H), 4.01-3.93 (m, 2H), 3.53 (m, 2H), 1.23 (t, 3H).

Step 3: 3-ethoxyazetidine-1-sulfonyl chloride. A solution of 3-ethoxyazetidine hydrochloride (500 mg, 3.63 mmol) in DCM (30 mL) was cooled to 0° C. and treated with N-ethyl-N-isopropylpropan-2-amine (949 µL, 5.45 mmol) followed by sulfuryl dichloride (881 µl, 10.9 mmol). The reaction mixture was warmed to ambient temperature and stirred for 18 hours then diluted with DCM (70 mL) and washed with 1N HCl (2×50 mL). The organic phases were combined and washed with brine (25 mL), then dried over Na₂SO₄, filtered and concentrated to afford 3-ethoxyazetidine-1-sulfonyl chloride (700 mg, 96.5% yield) as a yellow oil that was used without further purification. ¹H NMR (400 MHz, CDCl₃) δ 4.36-4.30 (m, 1H), 4.29-4.22 (m, 2H), 4.04-3.99 (m, 2H), 3.47 (m, 2H), 1.24 (t, 3H).

Step 4: tert-butyl (2-chloro-4-fluoro-3-iodophenyl)((3-ethoxyazetidin-1-yl)sulfonyl)carbamate. A solution of tert-butyl (2-chloro-4-fluoro-3-iodophenyl)carbamate (961 µl, 0.673 mmol) in THF (1 mL) was treated with sodium hydride (53.8 mg, 1.35 mmol, 60% dispersion in mineral oil) and stirred at 0° C. for 30 minutes. 3-ethoxyazetidine-1-sulfonyl chloride (269 mg, 1.35 mmol) was added and the reaction mixture was warmed to ambient temperature and heated at 50° C. for 96 hours. The reaction mixture was diluted with water (50 mL) and saturated aqueous NaHCO₃ (50 mL) and the aqueous layer was extracted with 4:1 DCM IPA (3×25 mL). The organic phases were combined and dried over Na₂SO₄, filtered, and concentrated to afford a brown oil that was purified by silica gel chromatography (0-50% hexanes:EtOAc) to afford tert-butyl (2-chloro-4-fluoro-3-iodophenyl)((3-ethoxyazetidin-1-yl)sulfonyl)carbamate (279 mg, 77.5% yield). ¹H NMR (400 MHz, CDCl₃) δ 7.40-7.35 (m, 1H), 7.07-7.01 (m, 1H), 4.40-4.28 (m, 3H), 4.26-4.18 (m, 2H), 3.46 (q, 2H), 1.43 (s, 9H), 1.23 (t, 3H).

Step 5: N-(2-chloro-3-((5-chloro-3-methyl-4-oxo-3,4-dihydroquinazolin-6-yl)amino)-4-fluorophenyl)-3-ethoxyazetidine-1-sulfonamide. A solution of 6-amino-5-chloro-3-methylquinazolin-4(3H)-one (30 mg, 0.143 mmol), tert-butyl (2-chloro-4-fluoro-3-iodophenyl)((3-ethoxyazetidin-1-yl)sulfonyl)carbamate (84.2 mg, 0.157 mmol), Pd₂(dba)₃ (13.1 mg, 0.0143 mmol), cesium carbonate (140 mg, 0.429 mmol) and (9,9-dimethyl-9H-xanthene-4,5-diyl)bis(diphenylphosphane) (20.7 mg, 0.0358 mmol) in toluene (0.9 mL) was sparged with argon for 5 minutes then heated at 100° C. for 18 hours. The reaction mixture was cooled to ambient temperature, then partitioned between water (25 mL) and EtOAc (50 mL). The organic phase was separated and washed with brine (25 mL) then dried over Na₂SO₄, filtered, and concentrated to a brown oil. The crude reaction mixture was dissolved in DCM (25 mL) and TFA (10 mL) and stirred for 20 minutes at ambient temperature then concentrated to afford a brown oil that was purified by HPLC (5-95% acetonitrile:H₂O with 0.1% TFA). The desired fractions were combined, and pH adjusted to 9 with saturated aqueous NaHCO₃. The aqueous was extracted with DCM (2×50 mL) and the organic phases were combined, dried over Na₂SO₄, filtered, and concentrated to afford N-(2-chloro-3-((5-chloro-3-methyl-4-oxo-3,4-dihydroquinazolin-6-yl)amino)-4-fluorophenyl)-3-ethoxyazetidine-1-sulfonamide (39.4 mg, 53.3% yield) as a beige solid. ¹H NMR (400 MHz, CDCl₃) δ 7.93 (s, 1H), 7.58-7.48 (m, 2H), 7.15 (t, 1H), 7.01-6.95 (m, 1H), 6.68 (s, 1H), 6.45 (s, 1H), 4.27-4.19 (m, 1H), 4.10-4.04 (m, 2H), 3.95-3.88 (m, 2H), 3.57 (s, 3H), 3.41 (m, 2H), 1.19 (t, 3H); MS (apci, m/z)=516.1, 518.1 (M+H).

Example 142

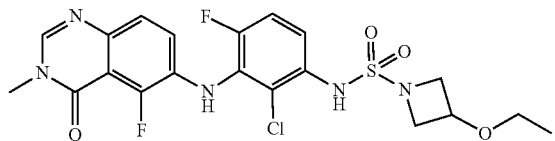 [SMILES: CCOC1CN(S(=O)(=O)Nc2ccc(F)c(Nc3ccc4ncn(C)c(=O)c4c3F)c2Cl)C1]

N-(2-chloro-4-fluoro-3-((5-fluoro-3-methyl-4-oxo-3,4-dihydroquinazolin-6-yl)amino)phenyl)-3-ethoxyazetidine-1-sulfonamide A solution of 6-amino-5-fluoro-3-methylquinazolin-4(3H)-one (30 mg, 0.155 mmol), tert-butyl (2-chloro-4-fluoro-3-iodophenyl)((3-ethoxyazetidin-1-yl)sulfonyl)carbamate (91.4 mg, 0.171 mmol), Pd$_2$(dba)$_3$ (14.2 mg, 0.0155 mmol), cesium carbonate (152 mg, 0.466 mmol) and (9,9-dimethyl-9H-xanthene-4,5-diyl)bis(diphenylphosphane) (22.5 mg, 0.0388 mmol) in toluene (0.9 mL) was sparged with argon for 5 minutes then heated at 100° C. for 18 hours. The reaction mixture was cooled to ambient temperature then partitioned between water (25 mL) and EtOAc (50 mL). The organic phase was separated and washed with brine (25 mL) then dried over Na$_2$SO$_4$, filtered, and concentrated to a brown oil. The crude reaction mixture was dissolved in DCM (25 mL) and TFA (10 mL) and stirred for 20 minutes at ambient temperature then concentrated to afford a brown oil that was purified by HPLC (5-95% acetonitrile:H$_2$O with 0.1% TFA). The desired fractions were combined and the pH was adjusted to 9 with saturated aqueous NaHCO$_3$. The aqueous was extracted with DCM (2×50 mL) and the organic phases were combined, dried over Na$_2$SO$_4$, filtered, and concentrated to afford N-(2-chloro-4-fluoro-3-((5-fluoro-3-methyl-4-oxo-3,4-dihydroquinazolin-6-yl)amino)phenyl)-3-ethoxyazetidine-1-sulfonamide (32.9 mg, 42.4% yield) as a beige solid. $^1$H NMR (400 MHz, CDCl$_3$) δ 7.90 (s, 1H), 7.54-7.48 (m, 1H), 7.43-7.38 (m, 1H), 7.14 (t, 1H), 7.08-7.02 (m, 1H), 6.64 (s, 1H), 5.92 (s, 1H), 4.27-4.19 (m, 1H), 4.10-4.03 (m, 2H), 3.94-3.89 (m, 2H), 3.57 (s, 3H), 3.42 (m, 2H), 1.19 (t, 3H); MS (apci, m/z)=500.1, 502.1 (M+H).

Example 143

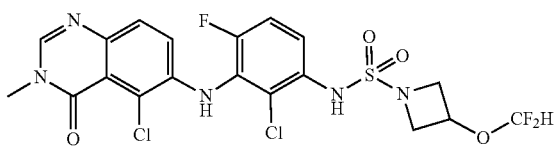 [SMILES: Cn1cnc2ccc(Nc3c(F)ccc(NS(=O)(=O)N4CC(OC(F)F)C4)c3Cl)c(Cl)c2c1=O]

N-(2-chloro-3-((5-chloro-3-methyl-4-oxo-3,4-dihydroquinazolin-6-yl)amino)-4-fluorophenyl)-3-(difluoromethoxy)azetidine-1-sulfonamide Step 1: Preparation of 3-(difluoromethoxy)azetidine-1-sulfonyl chloride. 3-(difluoromethoxy)azetidine hydrochloride (513 mg, 3.21 mmol) was suspended in DCM (15.7 mL) and to it added N,N-diisopropylethylamine (818.7 μL, 4.70 mmol) and stirred at ambient temperature until dissolved. The reaction mixture was cooled to 0° C. and treated with sulfuryl dichloride (0.77 mL, 9.64 mmol) dropwise and stirred at ambient temperature for 12 hours. The reaction mixture was diluted with DCM, washed with 10% HCl (3×25 mL), brine (1×25 mL), dried over anhydrous Na$_2$SO$_4$, filtered, and concentrated to give 3-(difluoromethoxy)azetidine-1-sulfonyl chloride (366 mg, 51%) as a yellow liquid that was used in the next step without purification. 1H NMR (400 MHz, CDCl$_3$) δ 6.48-6.08 (t, 1H), 5.08-5.01 (m, 1H), 4.41-4.35 (m, 2H), 4.21-4.16 (m, 2H).

Step 2: Preparation of tert-butyl (2-chloro-4-fluoro-3-iodophenyl)(3-(difluoromethoxy)azetidin-1-yl)sulfonyl)carbamate. Tert-butyl (2-chloro-4-fluoro-3-iodophenyl)carbamate (307 mg, 0.826 mmol) was dissolved in THF (4.1 mL) cooled to 0° C. and treated with sodium hydride (66.1 mg, 1.65 mmol). The reaction was stirred at ambient temperature for 15 minutes and treated with 3-(difluoromethoxy)azetidine-1-sulfonyl chloride (366 mg, 1.65 mmol) and then heated to 50° C. for 12 hours. The reaction mixture was cooled to ambient temperature and poured into 20 mL ice water. The aqueous layer was extracted with EtOAc (2×25 mL), dried over anhydrous Na$_2$SO$_4$, filtered, and concentrated. The residue was purified by reverse phase chromatography (5-95% water/ACN with 0.1% TFA) and the desired fractions were combined, partitioned between 4:1 DCM:IPA and saturated aqueous NaHCO$_3$ (1×). The organic layer was separated, dried over anhydrous Na$_2$SO$_4$, filtered, and concentrated to give tert-butyl (2-chloro-4-fluoro-3-iodophenyl)(3-(difluoromethoxy)azetidin-1-yl)sulfonyl)carbamate (228 mg, 50%) as an off-white semi-solid. $^1$H NMR (400 MHz, (CD$_3$)$_2$SO) δ 7.62-7.57 (m, 1H), 7.38-7.33 (m, 1H), 6.97-6.60 (t, 1H), 5.07-5.00 (m, 1H), 4.50-4.44 (m, 2H), 4.27-4.18 (m, 2H), 1.39 (s, 9H).

Step 3: Preparation of N-(2-chloro-3-((5-chloro-3-methyl-4-oxo-3,4-dihydroquinazolin-6-Yl)amino)-4-fluorophenyl)-3-(difluoromethoxy)azetidine-1-sulfonamide. Tert-butyl (2-chloro-4-fluoro-3-iodophenyl)(3-(difluoromethoxy)azetidine-1-yl)sulfonyl)carbamate (58.43 mg, 0.11 mmol), 6-amino-5-chloro-3-methylquinazolin-4(3H)-one (22 mg, 0.105 mmol), cesium carbonate (68.4 mg, 0.21 mmol), tris(dibenzylideneacetone)dipalladium (9.6 mg, 0.011 mmol) and (9,9-dimethyl-9H-xanthene-4,5-diyl)bis(diphenylphosphane) (15.2 mg, 0.026 mmol) were suspended in toluene (1.05 mL) and the reaction was sparged with argon for 15 minutes, sealed, and heated to 110° C. for 12 hours. The crude reaction was cooled to ambient temperature then diluted with DCM and filtered through a short Celite® pad and concentrated. The residue was dissolved in 1:1 DCM:TFA (5 mL) and stirred at ambient temperature for 30 minutes. The reaction was concentrated, diluted with DCM, washed with saturated NaHCO$_3$ (3×50 mL) and brine (1×25 mL), dried over anhydrous Na$_2$SO$_4$, filtered, and concentrated. The residue was purified by silica gel column chromatography (0-100% DCM/EtOAc) followed by reverse phase chromatography (5-95% water/acetonitrile with 0.1% TFA). The desired fractions were combined and partitioned between 4:1 DCM:IPA and saturated aqueous NaHCO$_3$ (1×) and the organic layer was separated, dried over anhydrous Na$_2$SO$_4$, filtered, and concentrated to give N-(2-chloro-3-((5-chloro-3-methyl-4-oxo-3,4-dihydroquinazolin-6-yl)amino)-4-fluorophenyl)-3-(difluoromethoxy)azetidine-1-sulfonamide (26 mg, 46%) as a light brown solid. $^1$H NMR (400 MHz, (CD$_3$)$_2$SO) δ 9.86 (s, 1H), 8.21 (s, 1H), 7.77 (s, 1H), 7.54-7.36 (m, 3H), 6.93-6.53 (m, 2H), 4.97-4.88 (m, 1H), 4.15-4.08 (m, 2H), 3.90-3.82 (m, 2H), 3.44 (s, 3H); MS (apci, m/z)=539.0, 541.0, 543.0 (M+H).

Example 144

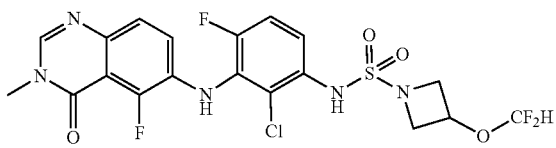 [SMILES: Cn1cnc2ccc(Nc3c(F)ccc(NS(=O)(=O)N4CC(OC(F)F)C4)c3Cl)c(F)c2c1=O]

N-(2-chloro-4-fluoro-3-((5-fluoro-3-methyl-4-oxo-3, 4-dihydroquinazolin-6-yl)amino)phenyl)-3-(difluoromethoxy)azetidine-1-sulfonamide Tert-butyl (2-chloro-4-fluoro-3-iodophenyl)(3-(difluoromethoxy)azetidin-1-yl)sulfonyl)carbamate (61.0 mg, 0.11 mmol), 6-amino-5-fluoro-3-methylquinazolin-4(3H)-one (21 mg, 0.11 mmol), cesium carbonate (71.0 mg, 0.22 mmol), tris(dibenzylideneacetone)dipalladium (10.0 mg, 0.011 mmol) and (9,9-dimethyl-9H-xanthene-4,5-diyl)bis(diphenylphosphane) (16 mg, 0.026 mmol) were suspended in toluene (1.08 mL) and the reaction was sparged with argon for 15 minutes, sealed, and heated to 110° C. for 12 hours. The crude reaction was cooled to ambient temperature then diluted with DCM and filtered through a short Celite® pad and concentrated. The residue was dissolved in 1:1 DCM:TFA (5 mL) and stirred at ambient temperature for 30 minutes. The reaction was concentrated, diluted with DCM, washed with saturated NaHCO₃ (3×50 mL) and brine (1×25 mL), dried over anhydrous Na₂SO₄, filtered, and concentrated. The residue was purified by silica gel column chromatography (0-100% DCM/EtOAc) followed by reverse phase chromatography (5-95% water/ACN with 0.1% TFA). The desired fractions were combined and partitioned between 4:1 DCM: IPA and saturated aqueous NaHCO₃ (1×) and the organic layer was separated, dried over anhydrous Na₂SO₄, filtered, and concentrated to give N-(2-chloro-4-fluoro-3-((5-fluoro-3-methyl-4-oxo-3,4-dihydroquinazolin-6-yl)amino)phenyl)-3-(difluoromethoxy)azetidine-1-sulfonamide (20 mg, 35%) as an off white solid. ¹H NMR (400 MHz, (CD₃)₂SO) δ 9.81 (s, 1H), 8.18 (s, 1H), 8.08 (s, 1H), 7.43-7.29 (m, 3H), 7.08-7.00 (t, 1H), 6.93-6.53 (t, 1H), 4.97-4.89 (m, 1H), 4.15-4.08 (m, 2H), 3.89-3.82 (m, 2H), 3.43 (s, 3H); MS (apci, m/z)=522.0, 524.0 (M+H).

Example 145

N-(2-chloro-3-((3,5-dimethyl-4-oxo-3,4-dihydroquinazolin-6-yl)amino)-4-fluorophenyl)-3-fluoro-3-(methoxymethyl)azetidine-1-sulfonamide trifluoroacetate Step 1: tert-butyl 3-fluoro-3-(methoxymethyl)azetidine-1-carboxylate. To a solution of tert-butyl 3-fluoro-3-(hydroxymethyl)azetidine-1-carboxylate (600 mg, 2.92 mmol) in tetrahydrofuran (14.6 mL) at 0° C. was added sodium hydride (60% in mineral oil, 175 mg, 4.39 mmol) and stirred at ambient temperature for 10 minutes. Iodomethane (364 µL, 5.85 mmol) was added and stirred at ambient temperature for 45 minutes. The solution was partitioned between saturated NaHCO₃ and DCM and the organic layer was washed with brine, dried over Na₂SO₄, filtered, concentrated, then purified by silica gel chromatography (5-75% EtOAc/hex) to give tert-butyl 3-fluoro-3-(methoxymethyl)azetidine-1-carboxylate (631 mg, 98.4% yield).

Step 2: 3-fluoro-3-(methoxymethyl)azetidine hydrochloride. A solution of tert-butyl 3-fluoro-3-(methoxymethyl)azetidine-1-carboxylate (631 mg, 2.88 mmol) in 4 M HCl in dioxane (5.76 mL) was stirred at ambient temperature overnight. The reaction mixture was concentrated to give 3-fluoro-3-(methoxymethyl)azetidine hydrochloride (440 mg, 98% yield).

Step 3: 3-fluoro-3-(methoxymethyl)azetidine-1-sulfonyl chloride. To a solution of 3-fluoro-3-(methoxymethyl)azetidine hydrochloride (440 mg, 2.83 mmol) and N-ethyl-N-isopropylpropan-2-amine (740 µL, 4.24 mmol) in dichloromethane (9.42 mL) at 0° C. was added sulfuryl dichloride (570 µL, 7.07 mmol) and warmed to ambient temperature and stirred for 16 hours. The solution was diluted with additional DCM and washed with 1 N HCl (1×) then dried over Na₂SO₄, filtered, and concentrated to give 3-fluoro-3-(methoxymethyl)azetidine-1-sulfonyl chloride (601 mg, 97.7% yield).

Step 4: N-(2-chloro-3-((3,5-dimethyl-4-oxo-3,4-dihydroquinazolin-6-yl)amino)-4-fluorophenyl)-3-fluoro-3-(methoxymethyl)azetidine-1-sulfonamide trifluoroacetate. 6-((3-amino-2-chloro-6-fluorophenyl)amino)-3,5-dimethylquinazolin-4(3H)-one (25 mg, 0.075 mmol), 3-fluoro-3-(methoxymethyl)azetidine-1-sulfonyl chloride (16 mg, 0.075 mmol), and calcium bis((trifluoromethyl)sulfonyl)amide (45 mg, 0.075 mmol) in toluene (190 µL) were heated to 100° C. for 16 hours in a sealed vial. The reaction mixture was cooled to ambient temperature then filtered, concentrated, and purified by reverse-phase chromatography (5-95% MeCN/water, 0.1% TFA). The product was concentrated to give N-(2-chloro-3-((3,5-dimethyl-4-oxo-3,4-dihydroquinazolin-6-yl)amino)-4-fluorophenyl)-3-fluoro-3-(methoxymethyl)azetidine-1-sulfonamide trifluoroacetate (6.0 mg, 16% yield). ¹H NMR (400 MHz, CDCl₃) δ 8.82 (s, 1H), 7.60 (d, 1H), 7.53-7.49 (m, 1H), 7.18-7.14 (t, 1H), 7.11-7.08 (m, 1H), 6.69 (s, br, 1H), 5.73 (s, br, 1H), 4.16-4.02 (m, 4H), 3.73 (s, 3H), 3.65 (d, 2H), 3.43 (s, 3H), 2.95 (s, 3H); MS (apci, m/z)=514.1, 516.1 (M+H).

Example 146

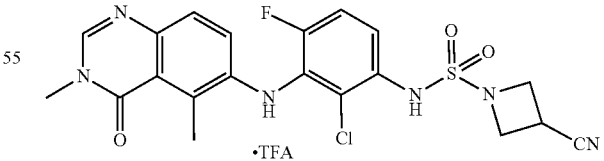

N-(2-chloro-3-((3,5-dimethyl-4-oxo-3,4-dihydroquinazolin-6-yl)amino)-4-fluorophenyl)-3-cyanoazetidine-1-sulfonamide trifluoroacetate 6-((3-Amino-2-chloro-6-fluorophenyl)amino)-3,5-dimethylquinazolin-4(3H)-one (25 mg, 0.0751 mmol), 3-cyanoazetidine-1-sulfonyl chloride (13.6 mg, 0.0751 mmol), and calcium bis((trifluoromethyl)sulfonyl)amide (45.1 mg, 0.0751 mmol) were suspended in toluene (150 μl) in a vial, sealed, and heated at 100° C. for 16 hours. The reaction was allowed to cool to ambient temperature and concentrated in vacuo. The crude reaction mixture was purified by reverse phase chromatography (5-95% MeCN/H₂O, 0.1% TFA). The desired fractions were combined and lyophilized to provide N-(2-chloro-3-((3,5-dimethyl-4-oxo-3,4-dihydroquinazolin-6-yl)amino)-4-fluorophenyl)-3-cyanoazetidine-1-sulfonamide trifluoroacetate (18 mg, 50% yield). ¹H NMR (400 MHz, CDCl₃) δ 8.67 (s, 1H), 7.61-7.58 (m, 1H), 7.15 (t, 1H), 7.12-7.09 (m, 1H), 6.63 (s, 1H), 5.69 (s, 1H), 4.27-4.18 (m, 4H), 3.66 (s, 3H), 3.50-3.43 (m, 1H), 2.97 (s, 3H). MS (apci, m/z)=477.1, 479.1 (M+H).

Example 147

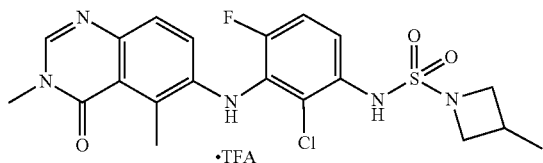

N-(2-chloro-3-((3,5-dimethyl-4-oxo-3,4-dihydroquinazolin-6-yl)amino)-4-fluorophenyl)-3-methylazetidine-1-sulfonamide trifluoroacetate Step 1: Preparation of 3-methylazetidine-1-sulfonyl chloride. 3-Methylazetidine hydrochloride (75 mg, 0.697 mmol) was stirred with N-ethyl-N-isopropylpropan-2-amine (181 μl, 1.05 mmol) at ambient temperature in dichloromethane (1743 μl) for 5 minutes. The reaction mixture was cooled to −10° C. (ice/acetone) and sulfuryl dichloride (141 μL, 1.74 mmol) was added as a neat liquid dropwise. The reaction mixture was allowed to warm to ambient temperature and stirred for 16 hours. The solution was diluted with additional DCM and washed with 1 N HCl (1×) then dried over Na₂SO₄, filtered, and concentrated to give 3-methylazetidine-1-sulfonyl chloride (118 mg, 100% yield) that was used directly in the next step.

Step 2: N-(2-chloro-3-((3,5-dimethyl-4-oxo-3,4-dihydroquinazolin-6-yl)amino)-4-fluorophenyl)-3-methylazetidine-1-sulfonamide trifluoroacetate. 6-((3-amino-2-chloro-6-fluorophenyl)amino)-3,5-dimethylquinazolin-4(3H)-one (20 mg, 0.0601 mmol), 3-methylazetidine-1-sulfonyl chloride (10.2 mg, 0.0601 mmol), and calcium bis((trifluoromethyl)sulfonyl)amide (36.1 mg, 0.0601 mmol) were suspended in toluene (120 μL) in a vial, sealed, and heated at 100° C. for 16 hours. The reaction was allowed to cool to ambient temperature and concentrated in vacuo. The crude reaction mixture was purified by reverse phase chromatography (5-95% MeCN/H₂O, 0.1% TFA). The desired fractions were combined and lyophilized to provide N-(2-chloro-3-((3,5-dimethyl-4-oxo-3,4-dihydroquinazolin-6-yl)amino)-4-fluorophenyl)-3-cyanoazetidine-1-sulfonamide trifluoroacetate (9.4 mg, 33% yield). ¹H NMR (400 MHz, CDCl₃) δ 8.95 (s, 1H), 7.63 (d, 1H), 7.55-7.51 (m, 1H), 7.16 (t, 1H), 7.11-7.08 (m, 1H), 6.62 (s, 1H), 5.73 (s, 1H), 4.03 (t, 2H), 3.73 (s, 3H), 3.61 (t, 2H), 2.96 (s, 3H), 2.74-2.65 (m, 1H) 1.23 (d, 3H). MS (apci, m/z)=466.1, 468.1 (M+H).

The following compounds were also prepared according to procedures described herein.

| Ex. No. | Structure | Chemical Name | ¹H NMR | MS (apci, m/z) |
|---|---|---|---|---|
| 148 | (Unequal mixture of diastereomers) | N-(2-chloro-3-((3,5-dimethyl-4-oxo-3,4-dihydroquinazolin-6-yl)amino)-4-fluorophenyl)-6-fluoro-3-azabicyclo[3.1.0]hexane-3-sulfonamide | (400 MHz, CDCl₃) δ 7.97-7.92 (m, 2H), 7.47-7.43 (m, 2H), 7.34-7.28 (m, 1H) 7.15-6.99 (m, 5H), 6.80 (s, 1H), 5.61 (s, 2H), 5.24 (s, 1H), 4.90-4.65 (m, 1 H), 4.32-4.08 (m, 1H), 3.70-3.65 (m, 1H), 3.60-3.52 (m, 8H), 3.47-3.29 (m, 4H), 3.02-2.92 (m, 6 H), 2.34-2.23 (m, 1H), 2.13-1.90 (m, 4H) | 496.1, 498.1 (M + H) |
| 149 | 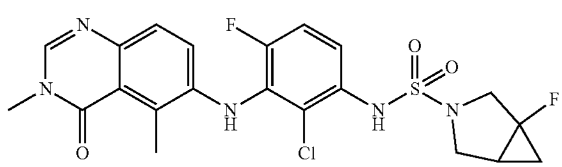 [SMILES: Cc1c(Nc2c(F)ccc(NS(=O)(=O)N3CC4CC4(F)C3)c2Cl)ccc2ncn(C)c(=O)c12] | N-(2-chloro-3-((3,5-dimethyl-4-oxo-3,4-dihydroquinazolin-6-yl)amino)-4-fluorophenyl)-1-fluoro-3-azabicyclo[3.1.0]hexane-3-sulfonamide | (400 MHz, CDCl₃) δ 7.93 (s, 1H), 7.46 (d, 1H), 7.35-7.30 (m, 1H), 7.12-7.03 (m, 2H), 6.75 (s, 1H), 3.92-3.86 (m, 1H), 3.72-3.64 (m, | 496.1, 498.1 (M + H) |

-continued

| Ex. No. | Structure | Chemical Name | ¹H NMR | MS (apci, m/z) |
|---|---|---|---|---|
| | | | 1H), 3.61-3.53 (m, 4H), 3.35-3.27 (m, 1H), 2.98 (s, 3H), 1.94-1.82 (m, 1H), 1.49-1.38 (m, 1H), 0.78-0.68 (m, 1H) | |
| 150 | 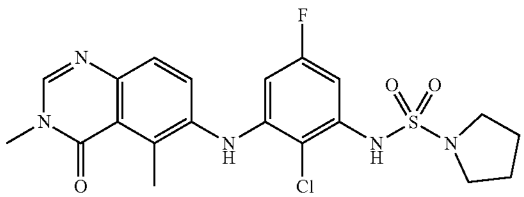 [SMILES: Cc1c(Nc2cc(F)cc(NS(=O)(=O)N3CCCC3)c2Cl)ccc2ncn(C)c(=O)c12] | N-(2-chloro-3-((3,5-dimethyl-4-oxo-3,4-dihydroquinazolin-6-yl)amino)-5-fluorophenyl) pyrrolidine-1-sulfonamide | (400 MHz, CDCl₃) δ 8.18 (s, 1H), 7.62 (s, 2H), 6.95 (s, 1H), 6.89-6.86 (m, 1H), 6.07-6.04 (m, 1H), 3.59 (s, 3H), 3.42-3.38 (m, 4H), 2.81 (s, 3H), 1.93-1.89 (m, 4H) | 466.1, 468.1 (M + H) |
| 151 | 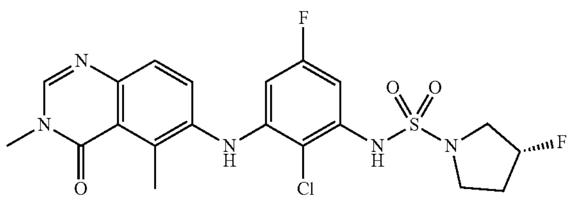 [SMILES: Cc1c(Nc2cc(F)cc(NS(=O)(=O)N3CC[C@@H](F)C3)c2Cl)ccc2ncn(C)c(=O)c12] | (R)-N-(2-chloro-3-((3,5-dimethyl-4-oxo-3,4-dihydroquinazolin-6-yl)amino)-5-fluorophenyl)-3-fluoropyrrolidine-1-sulfonamide | (400 MHz, CDCl₃) δ 8.70 (s, 1H), 7.70 (s, 2H), 7.06 (s, 1H), 7.01-6.90 (m, 2H), 6.16-6.07 (m, 2H), 5.34-5.15 (m, 1H), 3.84-3.48 (m, 6H), 2.82 (s, 3H), 2.36-1.85 (m, 2H) | 484.1, 486.1 (M + H) |
| 152 | 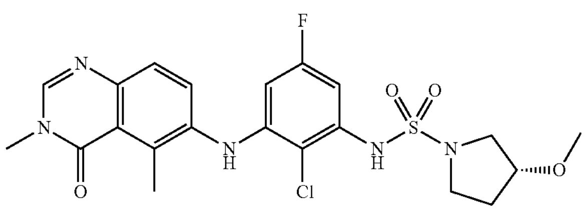 | (R)-N-(2-chloro-3-((3,5-dimethyl-4-oxo-3,4-dihydroquinazolin-6-yl)amino)-5-fluorophenyl)-3-methoxypyrrolidine-1-sulfonamide | (400 MHz, CDCl₃) δ 8.02 (s, 1H), 7.59 (s, 2H), 7.06 (s, 1H), 6.92-6.86 (m, 1H), 6.07-6.02 (m, 2H), 4.00-3.94 (m, 1H), 3.59-3.43 (m, 7H), 3.28 (s, 3H), 2.81 (s, 3H), 2.15-1.92 (m, 2H) | 496.1, 498.1 (M + H) |
| 153 | 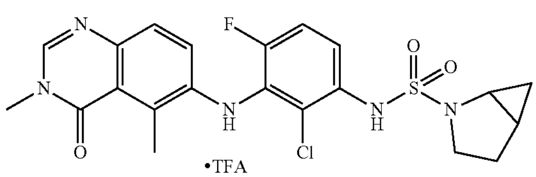 [SMILES: Cc1c(Nc2c(F)ccc(NS(=O)(=O)N3CCC4CC43)c2Cl)ccc2ncn(C)c(=O)c12] | N-(2-chloro-3-((3,5-dimethyl-4-oxo-3,4-dihydroquinazolin-6-yl)amino)-4-fluorophenyl)-2-azabicyclo[3.1.0] hexane-2-sulfonamide trifluoroacetate | (400 MHz, MeOH-d4) δ 9.07 (s, 1H), 7.60-7.56 (m 1H), 7.29 (d, 1H), 7.12 (t, 1H), 6.91-6.89 (m, 1H), 3.57 (s, 3H), 3.35-3.31 (m, 1H), 3.15-3.12 (m, 1H), 2.91-2.84 (m, 1H), 2.83 (s, 3H), 2.04-1.88 (m, 2H), 1.55-1.48 (m, 1H), 0.69-0.65 (m, 1H), 0.39-0.34 (m, 1H) | 478.1, 480.1 (M + H) |

-continued

| Ex. No. | Structure | Chemical Name | ¹H NMR | MS (apci, m/z) |
|---|---|---|---|---|
| 154 | 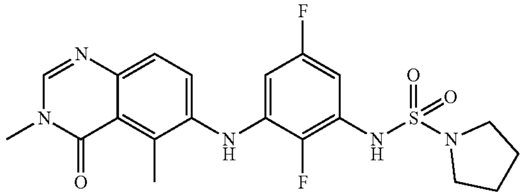 [SMILES: Cc1c(Nc2cc(F)cc(NS(=O)(=O)N3CCCC3)c2F)ccc2ncn(C)c(=O)c12] | N-(3-((3,5-dimethyl-4-oxo-3,4-dihydroquinazolin-6-yl)amino)-2,5-difluorophenyl)pyrrolidine-1-sulfonamide | (400 MHz, CDCl₃) δ 8.03 (s, 1H), 7.64-7.56 (m, 2H), 6.79-6.72 (m, 1H), 6.66 (s, 1H), 6.18-6.10 (m, 1H), 5.72 (s, 1H), 3.57 (s, 3H), 3.42-3.38 (m, 4H), 2.84 (s, 3H), 1.94-1.90 (m, 4H) | 450.1 (M + H) |
| 155 | 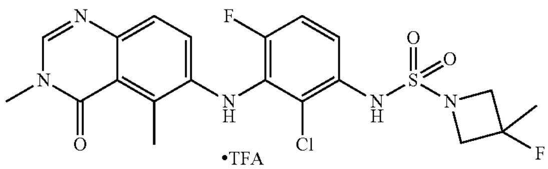 | N-(2-chloro-3-((3,5-dimethyl-4-oxo-3,4-dihydroquinazolin-6-yl)amino)-4-fluorophenyl)-3-fluoro-3-methylazetidine-1-sulfonamide trifluoroacetate | (400 MHz, CDCl₃) δ 8.72 (s, 1H), 7.59 (d, 1H), 7.50-7.46 (m, 1H), 7.16-7.12 (t, 1H), 7.10-7.06 (m, 1H), 6.65 (s, br, 1H), 5.67 (s, br, 1H), 4.21-4.13 (m, 2H), 3.95-3.86 (m, 1H), 3.66 (s, 3H), 2.96 (s, 3H), 1.66-1.61 (d, 3H) | 584.1, 586.1 (M + H) |
| 156 | 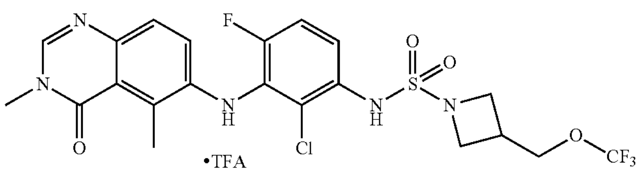 [SMILES: Cc1c(Nc2c(F)ccc(NS(=O)(=O)N3CC(COC(F)(F)F)C3)c2Cl)ccc2ncn(C)c(=O)c12] | N-(2-chloro-3-((3,5-dimethyl-4-oxo-3,4-dihydroquinazolin-6-yl)amino)-4-fluorophenyl)-3-((trifluoromethoxy)methyl)azetidine-1-sulfonamide trifluoroacetate | (400 MHz, CDCl₃) δ 8.68 (s, 1H), 7.59 (d, 1H), 7.47-7.44 (m, 1H), 7.16-7.11 (t, 1H), 7.09-7.06 (m, 1H), 6.62 (s, br, 1H), 5.68 (s, br, 1H), 4.12-4.07 (m, 4H), 3.82-3.78 (m, 2H), 3.66 (s, 3H), 2.97 (s, 3H), 2.99-2.92 (m, 1H) | 550.1, 552.1 (M + H). |
| 157 | 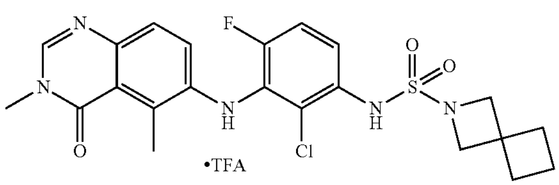 | N-(2-chloro-3-((3,5-dimethyl-4-oxo-3,4-dihydroquinazolin-6-yl)amino)-4-fluorophenyl)-2-azaspiro[3.3]heptane-2-sulfonamide trifluoroacetate | (400 MHz, CDCl₃) δ 8.83 (s, 1H), 7.61 (d, 1H), 7.50-7.47 (m, 1H), 7.13 (t, 1H), 7.09-7.06 (m, 1H), 6.59 (s, 1H), 5.68 (s, 1H), 3.92 (s, 4H), 3.69 (s, 3H), 2.96 (s, 3H), 2.15 (t, 4H), 1.87-1.80 (m, 2H) | 478.1, 480.1 (M + H) |
| 158 | 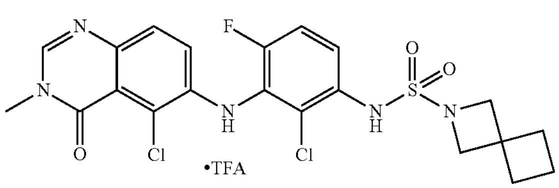 [SMILES: Cn1cnc2ccc(Nc3c(F)ccc(NS(=O)(=O)N4CC5(CCC5)C4)c3Cl)c(Cl)c2c1=O] | N-(2-chloro-3-((5-chloro-3-methyl-4-oxo-3,4-dihydroquinazolin-6-yl)amino)-4-fluorophenyl)-2-azaspiro[3.3]heptane-2- | (400 MHz, CDCl₃) δ 8.42 (s, 1H), 7.60-7.57 (m, 2H), 7.17 (t, 1H), 7.01-7.15 (m, 1H), 7.01-6.98 (m, 1H), 6.62 (s, 1H), | 512.1, 514.1 (M + H) |

| Ex. No. | Structure | Chemical Name | ¹H NMR | MS (apci, m/z) |
|---|---|---|---|---|
| | | sulfonamide trifluoroacetate | 6.52 (s, 1H), 3.92 (s, 4H), 3.65 (s, 3H), 2.15 (t, 4H), 1.87-1.79 (m, 2H) | |
| 159 | 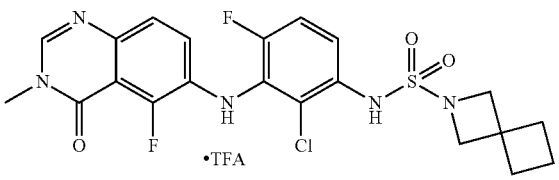 | N-(2-chloro-4-fluoro-3-((5-fluoro-3-methyl-4-oxo-3,4-dihydroquinazolin-6-yl)amino)phenyl)-2-azaspiro[3.3]heptane-2-sulfonamide trifluoroacetate | (400 MHz, CDCl₃) δ 8.30 (s, 1H), 7.56-7.54 (m, 1H), 7.48-7.45 (m, 1H), 7.15 (t, 1H), 7.09-7.04 (m, 1H), 6.61 (s, 1H), 5.97 (s, 1H), 3.91 (s, 4H), 3.64 (s, 3H), 2.15 (t, 4H), 1.87-1.79 (m, 2H) | 496.1, 498.1 (M + H) |
| 160 | 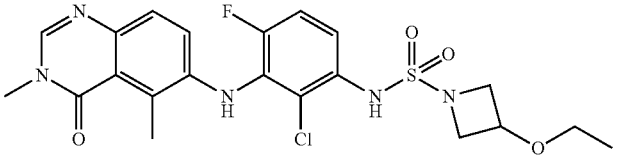 [SMILES: CCOC1CN(S(=O)(=O)Nc2ccc(F)c(Nc3ccc4ncn(C)c(=O)c4c3C)c2Cl)C1] | N-(2-chloro-3-((3,5-dimethyl-4-oxo-3,4-dihydroquinazolin-6-yl)amino)-4-fluorophenyl)-3-ethoxyazetidine-1-sulfonamide | (400 MHz, CDCl₃) δ 7.93 (s, 1H), 7.48-7.37 (m, 2H), 7.12-7.03 (m, 2H), 6.64 (s, 1H), 5.58 (s, 1H), 4.27-4.19 (m, 1H), 4.10-4.03 (m, 2H), 3.95-3.89 (m, 2H), 3.55 (s, 3H), 3.45-3.39 (m, 2H), 2.97 (s, 3H), 1.21-1.18 (t, 3H) | 496.1, 498.1 (M + H) |
| 161 | 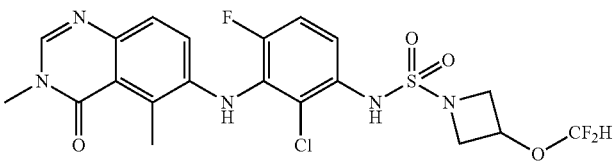 [SMILES: Cc1c(Nc2c(F)ccc(NS(=O)(=O)N3CC(OC(F)F)C3)c2Cl)ccc2ncn(C)c(=O)c12] | N-(2-chloro-3-((3,5-dimethyl-4-oxo-3,4-dihydroquinazolin-6-yl)amino)-4-fluorophenyl)-3-(difluoromethoxy)azetidine-1-sulfonamide | (400 MHz, (CD₃)₂SO) δ 9.76 (s, 1H), 8.17 (s, 1H), 7.37-7.26 (m, 4H), 6.93-6.53 (m, 2H), 4.97-488 (m, 1H), 4.13-4.07 (m, 2H), 3.86-3.83 (m, 2H), 3.43 (s, 3H), 2.81 (s, 3H) | MS (m/z) = 518.0, 520.0 (M + H) |
| 162 | 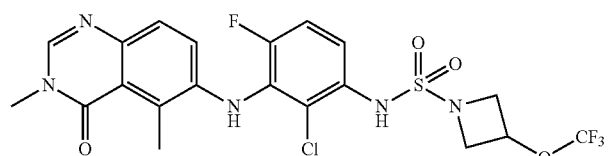 | N-(2-chloro-3-((3,5-dimethyl-4-oxo-3,4-dihydroquinazolin-6-yl)amino)-4-fluorophenyl)-3-(trifluoromethoxy)azetidine-1-sulfonamide | (400 MHz, (CD₃)₂SO) δ 9.84 (s, 1H), 8.17 (s, 1H), 7.37-7.27 (m, 4H), 6.87-6.83 (m, 1H), 5.21-5.14 (m, 1H), 4.23-4.16 (m, 2H), 3.98-3.92 (m, 2H), 3.43 (s, 3H), 2.81 (s, 3H) | 536.1, 538.1 (M + H). |

| Ex. No. | Structure | Chemical Name | ¹H NMR | MS (apci, m/z) |
|---|---|---|---|---|
| 163 | 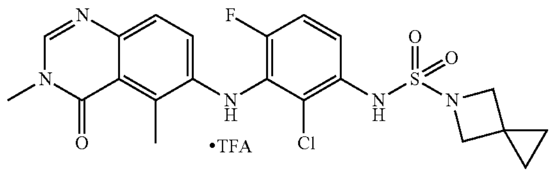 [SMILES: Cc1c(Nc2c(F)ccc(NS(=O)(=O)N3CC4(CC4)C3)c2Cl)ccc2ncn(C)c(=O)c12] | N-(2-chloro-3-((3,5-dimethyl-4-oxo-3,4-dihydroquinazolin-6-yl)amino)-4-fluorophenyl)-5-azaspiro[2.3]hexane-5-sulfonamide trifluoroacetate | (400 MHz, CDCl₃) δ 9.04 (s. 1H), 7.64 (d, 1H), 7.57-7.54 (m, 1H), 7.18-7.14 (t, 1H), 7.11-7.08 (m, 1H), 6.65 (s, br, 1H), 5.71 (s, br, 1H), 4.07 (s, 4H), 3.72 (s, 3H), 2.96 (s, 3H), 0.67 (s, 4H) | 478.1, 480.1 (M + H) |
| 164 | 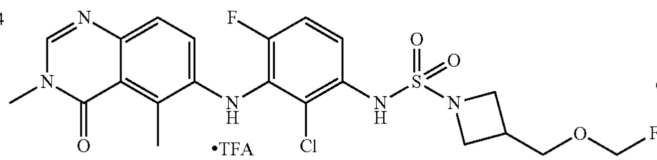 | N-(2-chloro-3-((3,5-dimethyl-4-oxo-3,4-dihydroquinazolin-6-yl)amino)-4-fluorophenyl)-3-((fluoromethoxy)methyl)azetidine-1-sulfonamide trifluoroacetate | (400 MHz, CDCl₃) δ 8.09 (s, 1H), 7.52 (d, 1H), 7.43-7.39 (m, 1H), 7.10 (t, 1H), 7.08-7.05 (m, 1H), 6.64 (s, 1H), 5.61 (s, 1H), 4.15-4.08 (m, 1H), 4.05-3.98 (m, 2H), 3.92-3.88 (m, 1H), 3.77-3.74 (m, 1H), 3.58 (s, 3H), 2.97 (s, 3H), 2.83-2.77 (m, 1H), 1.45 (d, 2H) | 514.1, 516.1 (M + H) |

What is claimed is:

1. A compound which is N-(2-chloro-3-((5-chloro-3-methyl-4-oxo-3,4-dihydroquinazolin-6-yl)amino)-4-fluorophenyl)-3-fluoroazetidine-1-sulfonamide having the structure:

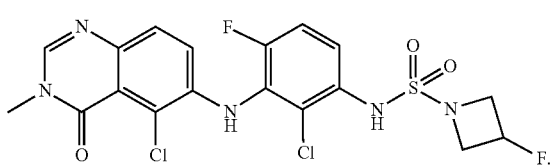 [SMILES: Cn1cnc2ccc(Nc3c(F)ccc(NS(=O)(=O)N4CC(F)C4)c3Cl)c(Cl)c2c1=O]

2. A pharmaceutically acceptable salt of the compound N-(2-chloro-3-((5-chloro-3-methyl-4-oxo-3,4-dihydroquinazolin-6-yl)amino)-4-fluorophenyl)-3-fluoroazetidine-1-sulfonamide, which has the structure:

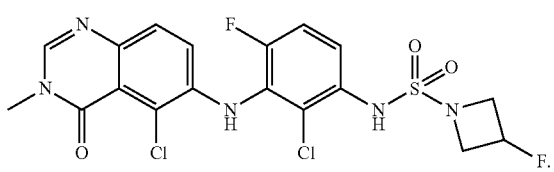 [SMILES: Cn1cnc2ccc(Nc3c(F)ccc(NS(=O)(=O)N4CC(F)C4)c3Cl)c(Cl)c2c1=O]

3. A compound which is N-(2-chloro-3-((5-chloro-3-methyl-4-oxo-3,4-dihydroquinazolin-6-yl)amino)-4-fluorophenyl)-3-fluoroazetidine-1-sulfonamide having the structure:

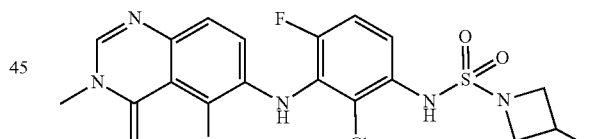

or a pharmaceutically acceptable salt thereof.

4. A pharmaceutical composition comprising a compound according to claim 3, and one or more pharmaceutically acceptable carriers.

5. A method of treating a BRAF-associated tumor in a subject in need thereof, comprising administering to the subject a therapeutically effective amount of a compound according to claim 3, wherein said BRAF-associated tumor is a cancer selected from lung cancer, melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, bladder carcinoma, plasma cell neoplasm, hepato-pancreato-biliary carcinoma, ovarian carcinoma, renal cell carcinoma, neuroendocrine cancer, cholangiocarcinoma and CNS cancers.

6. The method according to claim 5, wherein said tumor is a metastatic cancer.

7. The method according to claim 6, wherein said cancer is a metastatic CNS cancer.

8. The method according to claim 5, wherein said BRAF-associated tumor is a primary brain tumor.

9. The method according to claim 8, wherein said primary brain tumor is a Grade 2 glioma, a Grade 3 glioma, or a Grade 4 glioma.

10. The method according to claim 5, wherein said BRAF-associated tumor has a BRAF Class I mutation, wherein said BRAF-associated tumor is selected from melanoma, colorectal cancer, thyroid cancer, non-small cell lung cancer, ovarian cancer, renal cell carcinoma, and metastatic cancers thereof, and primary brain tumors.

11. The method according to claim 10, wherein said BRAF Class I mutation is BRAF V600E or BRAF V600K.

12. A method of treating a BRAF-associated tumor in a subject in need thereof, comprising administering to the subject a therapeutically effective amount of N-(2-chloro-3-((5-chloro-3-methyl-4-oxo-3,4-dihydroquinazolin-6-yl)amino)-4-fluorophenyl)-3-fluoroazetidine-1-sulfonamide or a pharmaceutically acceptable salt thereof, wherein said BRAF-associated tumor is a cancer selected from lung cancer, melanoma, colorectal cancer, breast cancer, pancreatic cancer, thyroid cancer, prostate cancer, adenoid cystic carcinoma, appendiceal cancer, small intestine cancer, head and neck squamous cell carcinoma, angiosarcoma, bladder carcinoma, plasma cell neoplasm, hepato-pancreato-biliary carcinoma, ovarian carcinoma, renal cell carcinoma, neuroendocrine cancer, cholangiocarcinoma and CNS cancers, wherein said BRAF-associated tumor has a BRAF Class II mutation.

13. The method according to claim 12, wherein said BRAF Class II mutation is a BRAF non-V600 mutation.

14. The method according to claim 13, wherein said BRAF non-V600 mutation is BRAF G469A or G469R.

15. The method according to claim 12, wherein said BRAF Class II mutation is a BRAF V600E splice variant.

16. The method according to claim 15, wherein said BRAF V600E splice variant is p61BRAF(V600E).

* * * * *